(12) United States Patent
Kim et al.

(10) Patent No.: US 11,066,700 B2
(45) Date of Patent: *Jul. 20, 2021

(54) NUCLEIC ACID COMPLEX PAIR, COMPETITIVE CONSTRUCT, AND PCR KIT USING THE SAME

(71) Applicant: Multilex, Inc., Seoul (KR)

(72) Inventors: Yong Tae Kim, Sejong-si (KR); Jun Hye Moon, Gyeonggi-do (KR)

(73) Assignee: MULTILEX, INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/752,277

(22) Filed: Jan. 24, 2020

(65) Prior Publication Data

US 2020/0232012 A1 Jul. 23, 2020

Related U.S. Application Data

(63) Continuation of application No. PCT/KR2018/008444, filed on Jul. 25, 2018.

(60) Provisional application No. 62/536,898, filed on Jul. 25, 2017, provisional application No. 62/580,335, filed on Nov. 1, 2017.

(30) Foreign Application Priority Data

Jan. 19, 2018 (KR) .......................... 10-2018-0007355
Feb. 6, 2018 (KR) .......................... 10-2018-0014739

(51) Int. Cl.
  *C12Q 1/686* (2018.01)
  *C12Q 1/6876* (2018.01)
  *C12Q 1/6853* (2018.01)

(52) U.S. Cl.
  CPC ........... *C12Q 1/686* (2013.01); *C12Q 1/6853* (2013.01); *C12Q 1/6876* (2013.01); *C12Q 2527/101* (2013.01); *C12Q 2565/1015* (2013.01); *C12Q 2565/60* (2013.01); *C12Q 2600/16* (2013.01); *C12Q 2600/166* (2013.01)

(58) Field of Classification Search
  CPC ........... C12Q 1/6853; C12Q 2525/161; C12Q 2525/186; C12Q 1/686; C12Q 1/6876; C12Q 2527/101; C12Q 2600/166
  See application file for complete search history.

(56) References Cited

U.S. PATENT DOCUMENTS

| 7,799,522 | B2 | 9/2010 | Li et al. |
|---|---|---|---|
| 2002/0197611 | A1 | 12/2002 | Chagovetz |
| 2007/0026429 | A1 | 2/2007 | Livak et al. |
| 2008/0064033 | A1 | 3/2008 | Haner et al. |
| 2010/0129792 | A1 | 5/2010 | Makrigiorgos |
| 2011/0207131 | A1 | 8/2011 | Fu |
| 2012/0052502 | A1 | 3/2012 | Li |
| 2013/0323738 | A1* | 12/2013 | Tanner ................. C12Q 1/6853 435/6.12 |

FOREIGN PATENT DOCUMENTS

| EP | 2789689 A1 | 10/2014 |
|---|---|---|
| GB | 2512631 A | 10/2014 |
| KR | 20120021262 A | 3/2012 |
| KR | 1020130008283 A | 1/2013 |
| WO | 2014135872 A1 | 9/2014 |
| WO | 2017106777 A1 | 6/2017 |

OTHER PUBLICATIONS

Li et al., Nature Protocol., 2(1):50-58, (Year: 2007).*
Notification of Reason for Refusal for Korean Patent Application No. 10-2018-0007355, dated Mar. 20, 2018, 13 pages.
Notification of Reason for Refusal for Korean Patent Application No. 10-2018-0014739, dated Mar. 20, 2018, 11 pages.
Grant of Patent for Korean Patent Application No. 10-2018-0007355, dated Jun. 26, 2018, 7 pages.
Grant of Patent for Korean Patent Application No. 10-2018-0014739, dated Jun. 26, 2018, 7 pages.
International Search Report for PCT Application No. PCT/KR2018/008444, dated Nov. 6, 2018, 3 pages.
Notification of Reason for Refusal for Korean Patent Application No. 10-2018-0086860, dated Aug. 16, 2019, 11 pages.
Notification of Reason for Refusal for Korean Patent Application No. 10-2018-0097144, dated Aug. 16, 2019, 10 pages.
Notification of Reason for Refusal for Korean Patent Application No. 10-2018-0097145, dated Aug. 18, 2019, 11 pages.
Notification of Reason for Refusal for Korean Patent Application No. 10-2018-0097146, dated Aug. 18, 2019, 10 pages.
Notification of Reason for Refusal for Korean Patent Application No. 10-2018-0097147, dated Aug. 19, 2019, 10 pages.
Hur et al., "Detection of generic variation using dual-labeled peptide nucleic acid (PNA) probe-based melting point analysis", Biological Procedures Online, 2015, 17:14.
Kandimalla et al., "'Cyclicons' as Hybridization-Based Fluorescent Primer-Probes: Synthesis, Properties and Application in Real-Time PCR", Bioorganic & Medicinal Chemistry, 8, 2000, pp. 1911-1916.
Navarro et al., "Real-time PCR detection chemistry", Clinica Chimica Acta, 2015, pp. 231-250.
Olivier, "The Invader assay for SNP genotyping", Mutation Research, 573, 2005, pp. 103-110.
Huang et al., "Multiplex Fluorescence Melting Curve Analysis for Mutation Detection with Dual-Labeled, Self-Quenched Probes", PloS One, 2011, vol. 6, 9 pages. Apr. 2011.
Notice of Allowance for Korean Patent Application No. 10-2018-0086860, dated Jun. 5, 2020, 3 pages.
Notice of Allowance for Korean Patent Application No. 10-2018-0097144, dated Jun. 5, 2020, 3 pages.

(Continued)

*Primary Examiner* — Cynthia B Wilder
(74) *Attorney, Agent, or Firm* — Perkins Coie LLP

(57) ABSTRACT

According to an exemplary embodiment of the present application, provided is a nucleic acid complex pair, which includes a first nucleic acid complex including a first determinant and a second tag; and a second nucleic acid complex including a second determinant and a second tag, wherein the first determinant includes a forward primer for first target DNA, the second determinant includes a reverse primer for the first target DNA, the first tag includes a base sequence complementary to the base sequence of the second tag, and the second tag includes a base sequence complementary to the base sequence of the first tag.

17 Claims, 61 Drawing Sheets

Specification includes a Sequence Listing.

(56) References Cited

OTHER PUBLICATIONS

Li, J. et al, "Anti-Primer Quenching-Based Real-Time PCR for Simplex or Multiplex DNA Quantification and Single-Nucleotide Polymorphism Genotyping", Nature Protocols 2(1): 50-58, 2007 (9 pages).
Notice of Final Rejection for Korean Patent Application No. 10-2018-0097146, dated Aug. 31, 2020 (3 pages).
Extended European Search Report dated Mar. 31, 2021 for European Patent Application No. 18839013.2 (9 pages).
Kim, Yong-Tae, et al., "Simultaneous Detection of Multiple Pathogenic Targets with Stem-Tagged Primer Sets", ChemBioChem, vol. 21, No. 8, pp. 1116-1120, 2020.
Kim, Yong-Tae, et al., "Simultaneous Genotyping of Multiple Somatic Mutations by Using a Clamping PNA and DNA Detection Probes", ChemBioChem, vol. 16, Issue 2, pp. 209-213, 2014.
Luo, Weihao, et al., "Melting temperature of molecular beacons as an indicator of the ligase detection reaction for multiplex detection of point mutations", Analytical Methods, vol. 7, No. 10, pp. 4225-4230, 2015.
Office Action dated Feb. 1, 2021 for Canadian Patent Application No. 3,071,088 (4 pages).
Grant of Patent dated Mar. 27, 2020 for Korean Patent Application No. 10-2018-0097145 (2 pages).
Grant of Patent dated Mar. 27, 2020 for Korean Patent Application No. 10-2018-0097147 (2 pages).
Non-Final Office Action dated May 27, 2020 for U.S. Appl. No. 16/045,566 (30 pages).
Final Office Action dated Nov. 13, 2020 for U.S. Appl. No. 16/045,566 (28 pages).

\* cited by examiner

FIG. 2
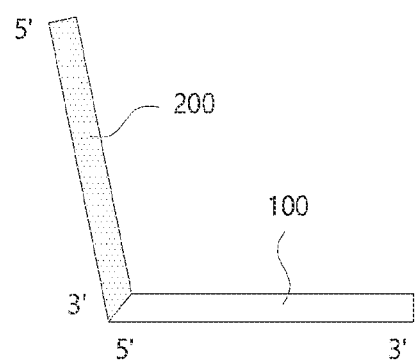
(a)
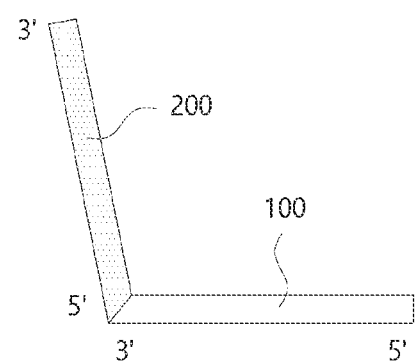
(b)

FIG. 4
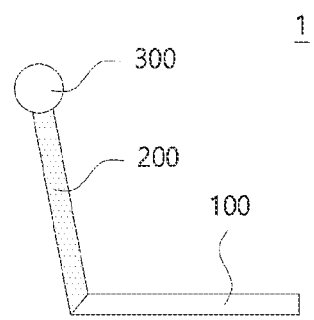
(a)
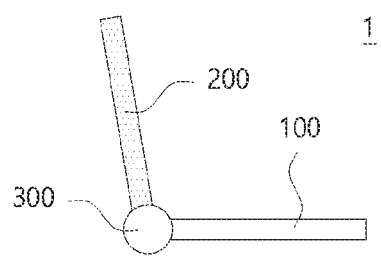
(b)
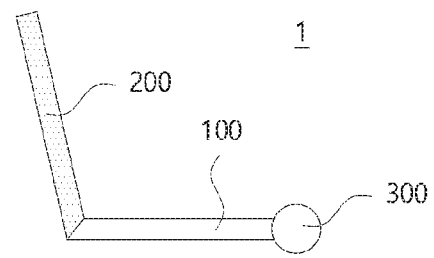
(c)

FIG. 8
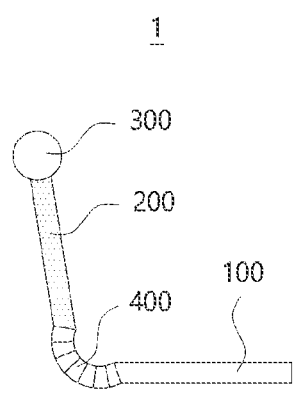
(a)
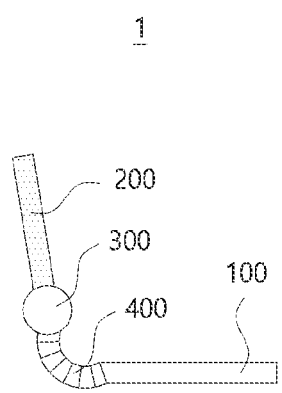
(b)
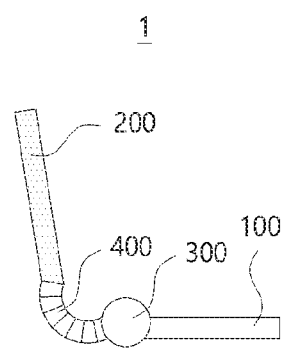
(c)
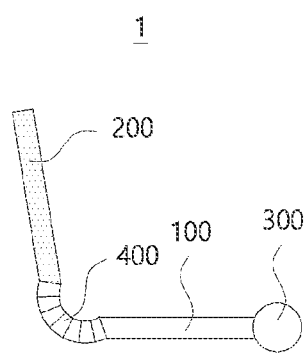
(d)

FIG. 12
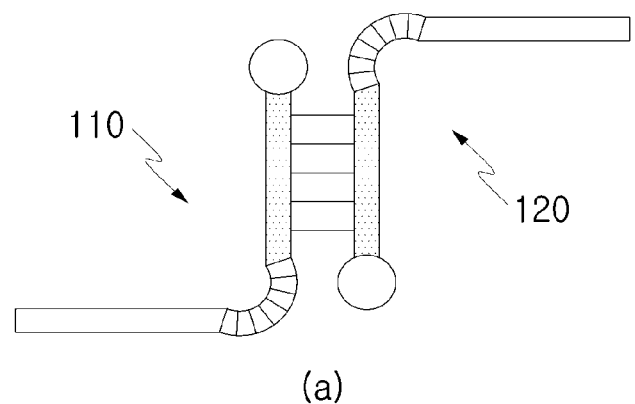
(a)
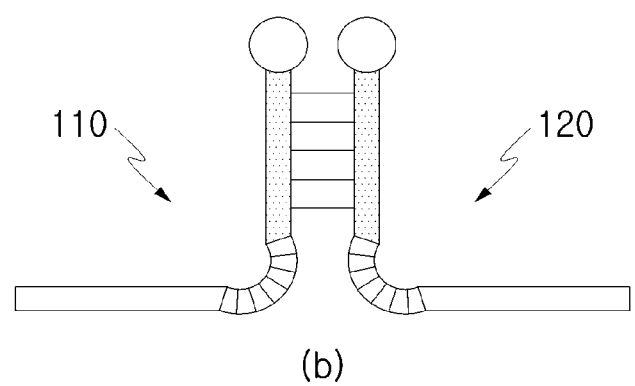
(b)

FIG. 14
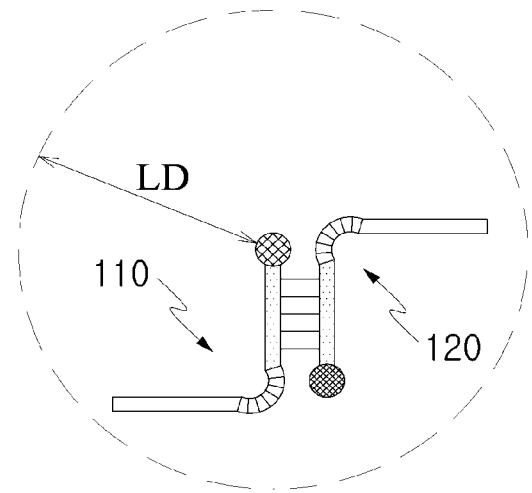
(a)
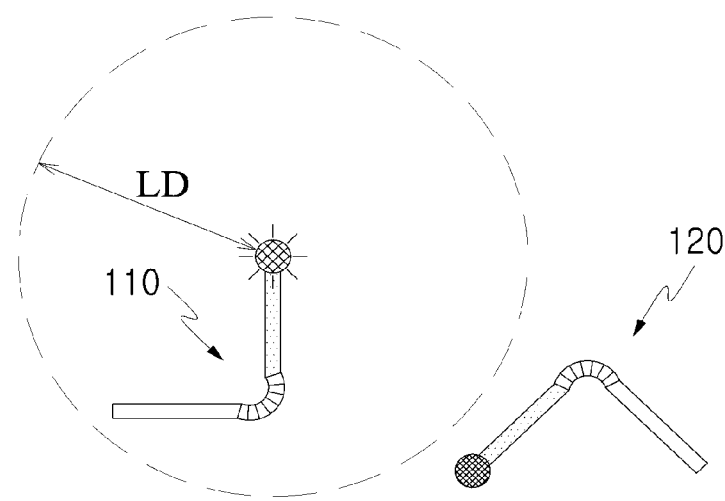
(b)
⬢ : FLUORESCENT        ⬢ : QUENCHER MOLECULE FIG. 15
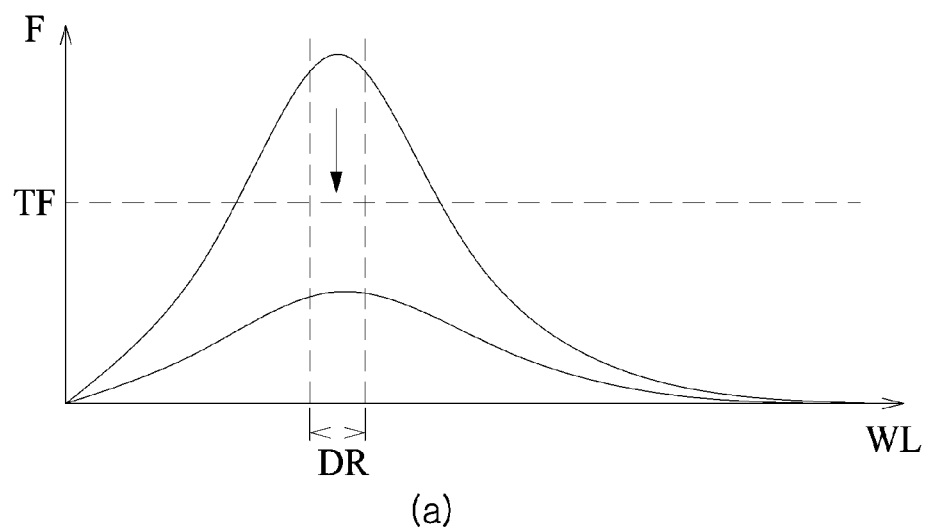
(a)
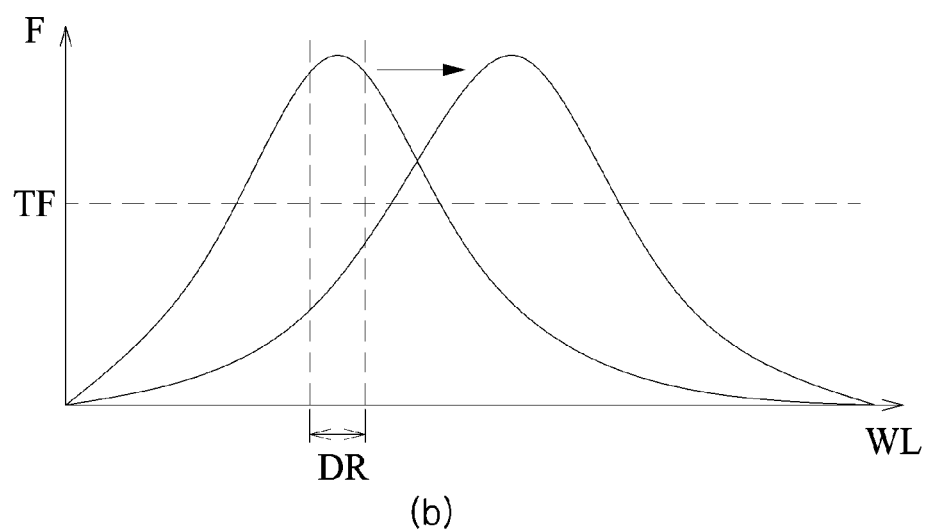
(b)

1

⬢ : FLUORESCENT    ⬢ : QUENCHER MOLECULE (a)

(b)

⊛ : FLUORESCENT    ● : QUENCHER MOLECULE

⊛ : FLUORESCENT      ⊛ : QUENCHER MOLECULE

FIG. 42
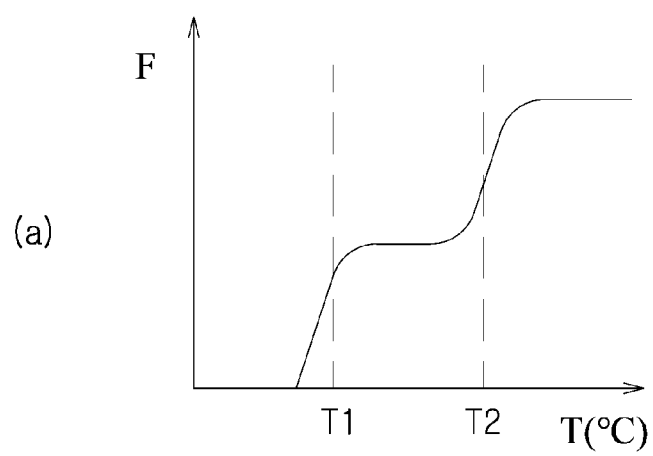
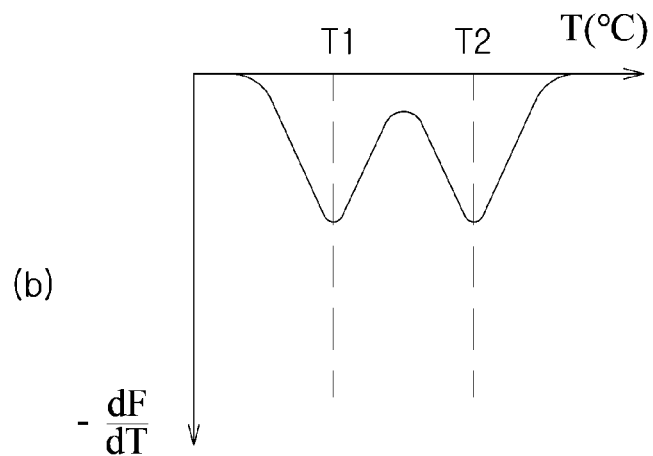

FIG. 44
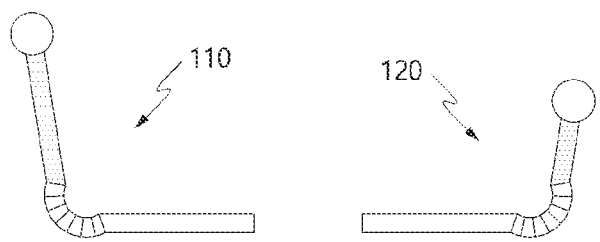
(a)
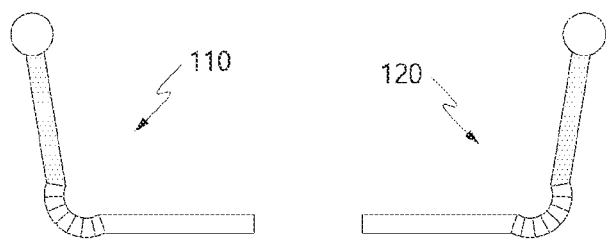
(b)

FIG. 45
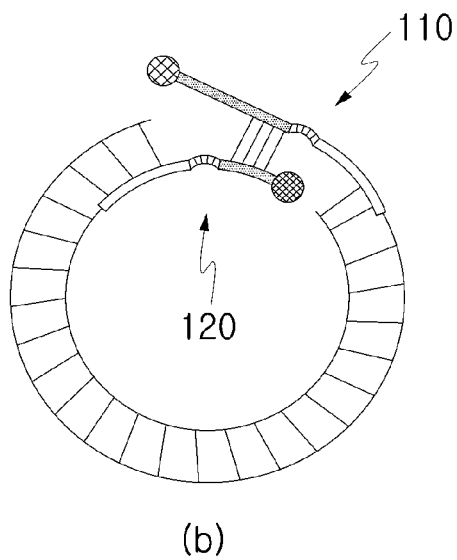
(b)
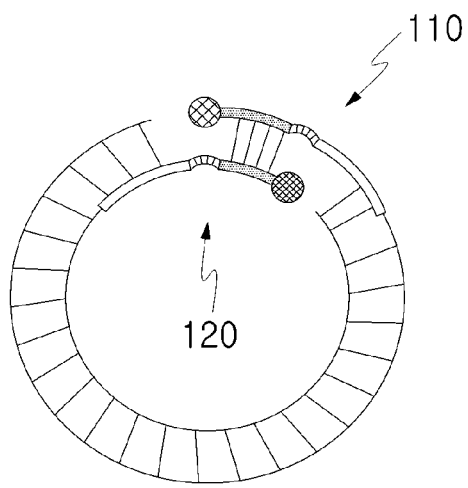
(b)

FIG. 51
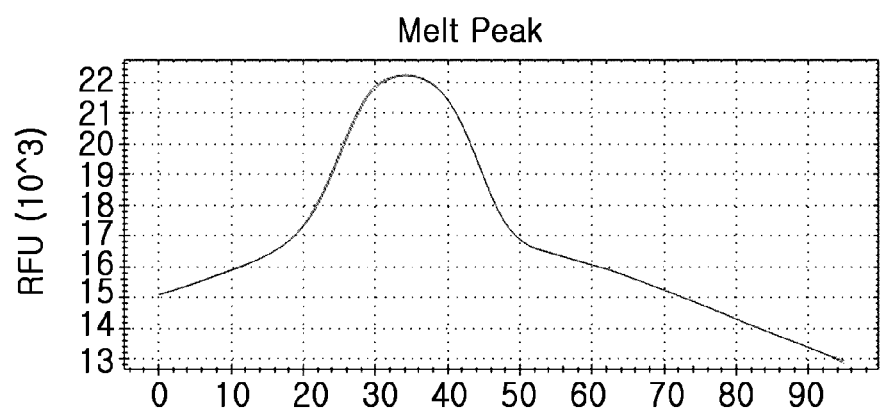
(a)
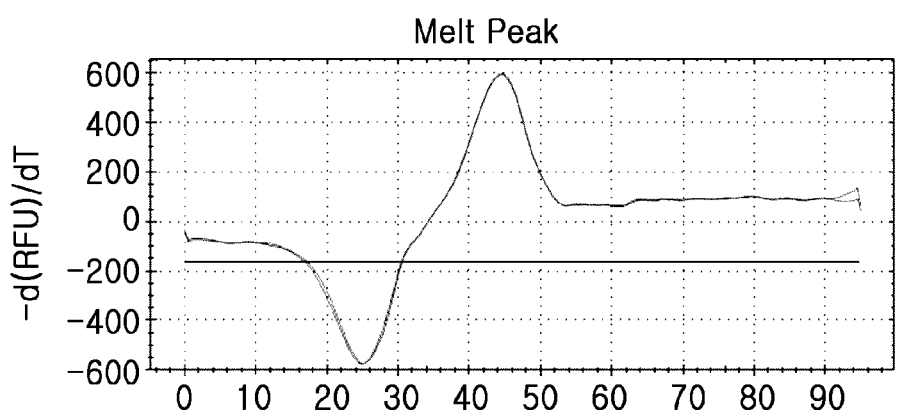
(b)

FIG. 57
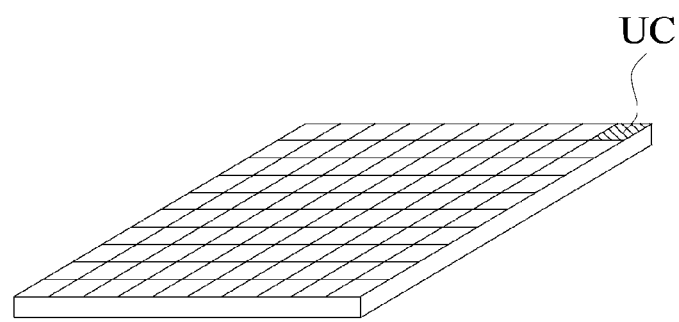
(a)
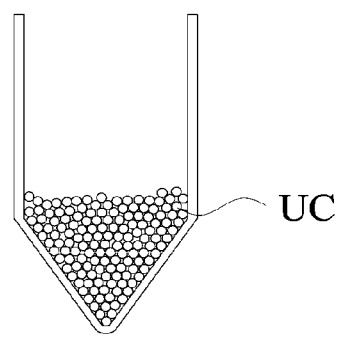
(b)

FIG. 59
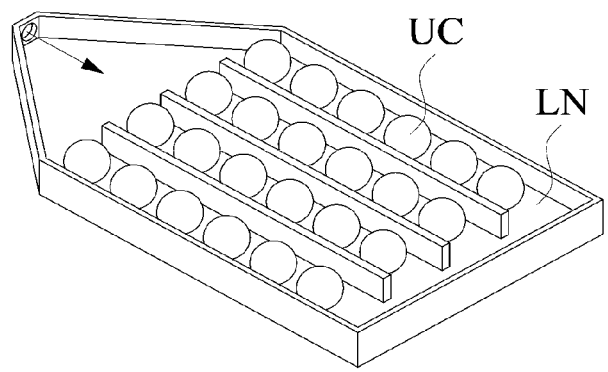
(a)
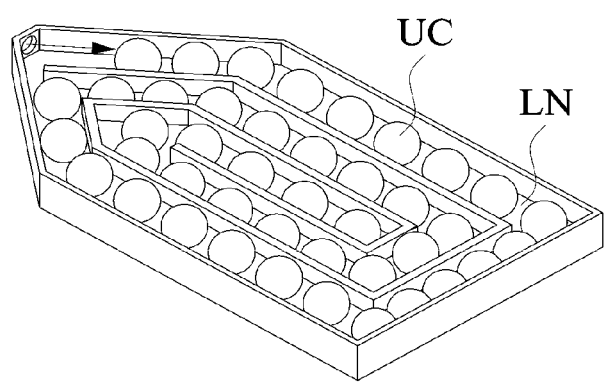
(b)

NUCLEIC ACID COMPLEX PAIR, COMPETITIVE CONSTRUCT, AND PCR KIT USING THE SAME

CROSS-REFERENCE TO RELATED APPLICATIONS

The present application is a continuation of PCT Application No. PCT/KR2018/008444 filed on Jul. 25, 2018, which claims priority to U.S. Patent Application No. 62/536,898 filed Jul. 25, 2017, U.S. Patent Application No. 62/580,335 filed Nov. 1, 2017, Korean Patent Application No. 10-2018-0007355 filed Jan. 19, 2018 and Korean Patent Application No. 10-2018-0014739 filed Feb. 6, 2018, the contents of which are hereby expressly incorporated by reference in their entirety.

REFERENCE TO SEQUENCE LISTING

The present application is being filed along with a Sequence Listing in electronic format. The Sequence Listing, created on Mar. 18, 2020, is provided as a file entitled 128205-8002_US00_SL.txt, which is 8,899 bytes in size. The information in the electronic format of the Sequence Listing is incorporated herein by reference in its entirety.

TECHNICAL FIELD

An exemplary embodiment relates to a nucleic acid complex pair.

An exemplary embodiment relates to a method of detecting a target using a nucleic acid complex pair.

An exemplary embodiment relates to a competitive construct used along with a nucleic acid complex pair.

An exemplary embodiment relates to a polymerase chain reaction (PCR) kit which includes a nucleic acid complex pair and a competitive construct.

BACKGROUND ART

Molecular diagnosis is a field for diagnosing a disease by analyzing genes, and currently shows the fastest growth in the field of in vitro diagnosis. Actually, with the rapid spread of new viruses assumed to be caused by rapid environmental pollution and climate change, much research has been conducted on molecular diagnosis, which has advantages of ensuring the highest accuracy of diagnosis in the field of the in vitro diagnosis and rapidly confirming infection in the case of an outbreak of new viruses.

In the field of molecular diagnosis, DNA sequencing and polymerase chain reaction (hereinafter, referred to as PCR) are generally used. Compared to a PCR assay, DNA sequencing still needs an expensive device, and cannot rapidly detect a target, and thus now in most of small and medium hospitals, large hospitals and health examination centers, a patient's disease is diagnosed by performing a PCR assay on a sample such as the blood of the patient.

According to a conventional PCR diagnosis method, one target is detected from one PCR tube, or a plurality of fluorescent channels are individually designed to emit light according to the presence or absence of a target using a probe, and multiple targets corresponding to the number of fluorescent channels may be simultaneously detected in one PCR tube using the probe.

However, the PCR method for detecting one target in one PCR tube has problems of wasting a large amount of reagents and considerably large amounts of time and labor costs. In addition, in the PCR method using probes designed to emit light in each of a plurality of fluorescent channels according to the presence or absence of a target, it was difficult to design probes and there was a problem of low reactivity.

Accordingly, a means for detecting multiple types of targets in one PCR tube at a time is required.

DISCLOSURE

Technical Problem

The present application is directed to providing a nucleic acid complex pair which is simply designed to be used for target detection in a sample.

The present application is also directed to providing a PCR kit which includes a nucleic acid complex pair capable of detecting multiple types of targets per fluorescent channel.

The problems to be solved by the present application are not limited to the above-described problems, and the problems not mentioned herein will be clearly understood to those of ordinary skill in the art with reference to the specification and the accompanying drawings.

Technical Solution

In one aspect, the present application may provide a competitive construct used in polymerase chain reaction (PCR) using a nucleic acid complex pair, which includes a first nucleic acid complex including a first determinant being a primer for a first target DNA, and a first tag; and a second nucleic acid complex including a second determinant being a primer for a second target DNA, and a second tag having a complementary sequence to the first tag, wherein the competitive construct includes a first additional sequence having a complementary sequence to at least a part of the base sequence of the first determinant, and a second additional sequence having a complementary sequence to at least a part of the base sequence of the first tag.

Advantageous Effects

A nucleic acid complex pair according to an embodiment can be used for target detection in a sample using the dissociation temperature of a tag complementarily bound with the target.

A PCR kit according to an embodiment includes a multiple types of nucleic acid complex pairs designed to have different dissociation temperatures of tags and thus can be used for detection of multiple types of targets per fluorescent channel.

The effect of the present application is not limited to the above-described effects, and effects that are not mentioned herein will be clearly understood by one of ordinary skill in the art with reference to the specification and the accompanying drawings.

DESCRIPTION OF DRAWINGS

FIG. 2 is a diagram illustrating a positional relationship between the determinant 100 and the tag 200 of a nucleic acid complex 1 according to an exemplary embodiment of the present application. FIG. 2(a) shows a specific example in which the 3' end of the tag 200 and the 5' end of the determinant 100 are directly connected. FIG. 2(*b*) shows a specific example in which the 5' end of the tag 200 and the 3' end of the determinant 100 are directly connected.

FIG. 4 is a diagram illustrating a positional relationship between the determinant 100, the tag 200 and the label 300 of a nucleic acid complex 1 according to an exemplary embodiment of the present application. FIG. 4(*a*) shows a specific example in which the tag 200 is located between the label 300 and the determinant 100. FIG. 4(*b*) shows a specific example in which the label 300 is located between the tag 200 and the determinant 100. FIG. 4(*c*) shows a specific example in which the determinant 100 is located between the tag 200 and the label 300.

FIG. 6(*a*) shows a specific example in which the 5' end of the determinant 100 is directly connected to linker 400 and the 3' end of the tag 200 is directly connected to linker 400. FIG. 6(*b*) shows a specific example in which the 3' end of the determinant 100 is directly connected to linker 400 and the 3' end of the tag 200 is directly connected to linker 400. FIG. 6(*c*) shows a specific example in which the 5' end of the determinant 100 is directly connected to linker 400 and the 5' end of the tag 200 is directly connected to linker 400. FIG. 6(*d*) shows a specific example in which the 3' end of the determinant 100 is directly connected to linker 400 and the 5' end of the tag 200 is directly connected to linker 400.

FIG. 8 is a diagram illustrating a positional relationship between the determinant 100, the tag 200, the label 300 and the linker 400 of a nucleic acid complex 1 according to an exemplary embodiment of the present application. FIG. 8(*a*) shows a specific example in which the label 300, the tag 200, the linker 400, and the determinant 100 are sequentially connected. FIG. 8(*b*) shows a specific example in which the tag 200, the label 300, the linker 400, and the determinant 100 are sequentially connected. FIG. 8(*c*) shows a specific example in which the tag 200, the linker 400, the label 300, and the determinant 100 are sequentially connected. FIG. 8(*d*) shows a specific example in which the tag 200, the linker 400, the determinant 100 and the label 300 are sequentially connected.

FIG. 10(*a*) shows a specific example in which a first tag 112 and a second tag 122 are toward the same side when the first determinant 111 and the second determinant 121 complementarily bind to the first target sequence and the second target sequence. FIG. 10(*b*) shows a specific example in which a first tag 112 and a second tag 122 are toward the different side when the first determinant 111 and the second determinant 121 are bound to the first target sequence and the second target sequence.

FIG. 11(*a*) shows a specific example in which the first determinant 111 complementarily bind to the first target base sequence, and the second determinant 121 complementarily bind to the second target base sequence included in any one strand including the first target base sequence. FIG. 11(*b*) shows a specific example in which the first determinant 111 complementarily bind to the first target base sequence included in one strand, and the second determinant 121 complementarily bind to the second target base sequence included in the other strand.

FIG. 12 is a diagram illustrating a direction to which the first nucleic acid complex 110 and the second nucleic acid complex 120 as shown in FIG. 9 are bonded according to an exemplary embodiment of the present application. FIG. 12(*a*) shows a specific example in which a first tag 112 complementary bind to a second tag 122 such that one region of the first tag 112 adjacent to a first determinant 111 complementarily binds to one region of the second tag 122 spaced apart from a second determinant 121. FIG. 12(*b*) shows a specific example in which a first tag 112 complementary bind to the second tag 122 such that one region of the first tag 112 adjacent to the first determinant 111 complementarily binds to one region of the second tag 122 adjacent to the second determinant 121.

FIG. 13(*a*) shows a specific example in which abound region 920 in which the first tag 112 and the second tag 122 form complementary bonds is relatively adjacent to a part in which the first tag 112 and the first determinant 111 are connected, compared to the non-bound region 910 in which there is no complementary bond between the first tag 112 and the second tag 122. FIG. 13(*b*) shows a specific example in which the bound region 920 in which the first tag 112 and the second tag 122 form complementary bonds is relatively spaced apart from the part in which the first tag 112 and the first determinant 111 are connected, compared to the non-bound region 910 in which there is no complementary bond between the first tag 112 and the second tag 122. FIG. 13(*c*) shows a specific example in which the bound region 920 in which the first tag 112 and the second tag 122 form complementary bonds is located between a first non-bound region 910 of the first tag 112 that does not complementarily bind to the second tag 122 and a second non-bound region 910 of the first tag 112 that does not bind to the second tag 122.

FIG. 14 is a diagram illustrating the operations of the first nucleic acid complex 110 and the second nucleic acid complex 120 as shown in FIG. 9 according to an exemplary embodiment of the present application. FIG. 14(a) shows a specific example in which a linked action occurs between the first label 113 and the second label 123 when the first label 113 is within an effective linkage distance (LD) from the second label 123. FIG. 14(b) shows a specific example in which a linked action does not occur between the first label 113 and the second label 123 when the first label 113 is separated from the second label 123 by an effective linkage distance (LD).

FIG. 15 is a graph of the fluorescence (F) per wavelength band (WL) according to the linked action between a first label 113 and a second label 123 according to an exemplary embodiment of the present application. TF, fluorescence threshold; DR, detection region; F, fluorescence; WL, wavelength band.

FIG. 18 shows the operation of a determinate 100 of a nucleic acid complex 1 in PCR steps. FIG. 19 shows the operation of a tag 200 of a nucleic acid complex 1 in PCR steps.

FIG. 23 diagrams illustrating the formation of a circle-like structure in which a first determinant 111 is bonded with a second determinant 121 such that a distance between a first label 113 and a second label 123 is longer than a distance between a first label 113 and a second linker 124 according to an exemplary embodiment of the present application. FIG. 24 diagrams illustrating the formation of a hairpin-like structure in which a first determinant 111 is bonded with a second determinant 121 such that a distance between a first label 113 and a second label 123 is longer than a distance between a first determinant 111 and a second determinant 121 according to an exemplary embodiment of the present application.

FIG. 25 shows the operation of a first determinant 111 and a second determinant 121 of a nucleic acid complex pair 10 in PCR steps according to an exemplary embodiment of the present application. FIG. 26 shows the operation of a first determinant 111 and a second determinant 121 of a nucleic acid complex pair 10 in PCR steps which is the next cycle of PCR steps of FIG. 25 according to an exemplary embodiment of the present application.

FIG. 27 shows the formation of circle-like structure of an amplicon from PCR steps including a first nucleic acid complex 110 and a second nucleic acid complex 120 according to an exemplary embodiment of the present application. FIG. 28 shows the formation of hairpin-like structure of an amplicon from PCR steps including a first nucleic acid complex 110 and a second nucleic acid complex 120 according to an exemplary embodiment of the present application.

FIG. 30 is a diagram illustrating the result for Probeless PCR amplicon T1 according to an exemplary embodiment of the present application, where the nucleic acid construct including a first nucleic acid complex pair has a mass of 180 bp.

FIG. 31(a) shows a specific embodiment in which a first tag 112 of one amplicon and a second tag 122 of another amplicon are bound to each other. FIG. 31(b) shows a specific embodiment in which a first tag 112 of amplicon and a second tag 122 of the same amplicon are bound to each other.

FIG. 38 shows the operation of a first determinant 111 and a second determinant 121 of a nucleic acid complex pair 10 in PCR steps according to an exemplary embodiment of the present application. FIG. 39 shows the operation of a first determinant 111 and a second determinant 121 of a nucleic acid complex pair 10 in PCR steps which is the next cycle of PCR steps of FIG. 38 according to an exemplary embodiment of the present application.

FIG. 40(a) shows a specific embodiment in which a second tag 122 which is not reacted with a second target base sequence complementary binds to first tag 112 of one amplicon. FIG. 40(b) shows a specific embodiment in which a second tag 122 which is not reacted with a second target base sequence complementary binds to the competitive construct 2 and a first tag 112 of amplicon and a second tag 122 of the same amplicon are bound to each other.

FIG. 42 shows a graph of between fluorescence value and temperature and a graph of between temperature and the negative rate of change in fluorescence with respect to temperature in one fluorescent channel according to an exemplary embodiment of the present application. F, fluorescence; T, temperature; dF/dT, the rate of change in fluorescence with respect to temperature; T1, dissociation peak value related to the first nucleic acid complex pair; T2, dissociation peak value related to the second nucleic acid complex pair.

FIGS. 44 and 45 are diagrams illustrating a usage of a nucleic acid complex pair 10 that includes a first nucleic acid complex 110 and a second nucleic acid complex 120 as shown in FIG. 32 according to a seventh exemplary embodiment of the present application. FIG. 44(a) shows a specific embodiment in which a length of the first tag 111 of the first nucleic acid complex 110 is different from a length of the second tag 121 of the second nucleic acid complex 120. FIG. 44(b) shows a specific embodiment in which a length of the first tag 111 of the first nucleic acid complex 110 and a length of the second tag 121 of the second nucleic acid complex 120 are the same. FIG. 45(a) shows the formation of circle-like structure of an amplicon from PCR steps including a first nucleic acid complex 110 and a second nucleic acid complex 120 according to FIG. 44(a). FIG. 45(b) shows the formation of circle-like structure of an amplicon from PCR steps including a first nucleic acid complex 110 and a second nucleic acid complex 120 according to FIG. 44(b).

FIG. 46(a) shows a specific embodiment in which the first determinant 111 of the first nucleic acid 110 is used as primer related to production of an amplification product including a probe-binding region (PR) to which a probe complex 600. FIG. 46(b) shows a specific embodiment in which a primer related to production of an amplification product including a probe-binding region (PR) to which the probe complex 600 binds is not a nucleic acid complex pair 10.

FIG. 48 shows the operation of a first determinant 111 and a second determinant 121 of a nucleic acid complex pair 10 and the determinant 611 of the probe complex 610 in PCR steps according to an exemplary embodiment of the present application. FIG. 49 shows the operation of a first determinant 111 and a second determinant 121 of a nucleic acid complex pair 10, and the determinant 611 of the probe complex 610 in PCR steps which is the next cycle of PCR steps of FIG. 47 according to an exemplary embodiment of the present application.

FIG. 51 is a set of graphs illustrating a result obtained by an experiment for confirming at least four kinds of target nucleic acids present in a unit cell (UC) according to an exemplary embodiment of the present application. RFU, relative fluorescence unit; RFU(10^3), RFU represented in units of 1000; d(RFU)/dT, the rate of change in RFU with respect to temperature.

FIG. 53 shows the operation of a first determinant 111 and a second determinant 121 of a nucleic acid complex pair 10 and a determinant 621 of a probe complex 620 in PCR steps according to an exemplary embodiment of the present application. FIG. 54 shows the operation of a first determinant 111 and a second determinant 121 of a nucleic acid complex pair 10 and a first pairing part 622 and a second pairing part 623 of a probe complex 620 in PCR steps which is the next cycle of PCR steps of FIG. 25 according to an exemplary embodiment of the present application.

FIG. 57 is a set of diagrams illustrating a unit cell (UC) in digital PCR according to an exemplary embodiment of the present application.

FIG. 59 is a set of diagrams illustrating a method of performing a dissociation curve detection step (S6000) in digital PCR according to an exemplary embodiment of the present application. UC, unit cell, LN, microfluidic lane.

MODES OF THE INVENTION

Figure 1:
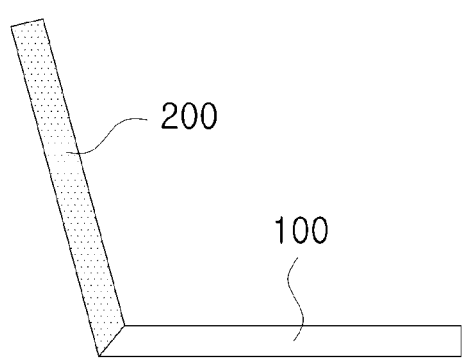
FIG. 1 is a diagram illustrating a nucleic acid complex 1 according to an exemplary embodiment of the present application that includes a determinant 100 and a tag 200.

The objects, features and advantages of the present application will be more apparent through the subsequent detailed description taken in conjunction with the accompanying drawings. However, the present application may be altered in various ways and have various embodiments, and specific embodiments are intended to be exemplified and illustrated in detail with reference to the drawings below.

In the drawings, the thicknesses of layers and regions are exaggerated for clarity, and when an element or layer is disposed on a different element or layer, it means that it may be disposed directly on a different element or layer, or a third layer or element is interposed between them. Throughout the specification, like reference numerals denote like elements in principle. In addition, elements having the same function within the scope of the same idea shown in the drawings of each embodiment will be described using the same reference numerals.

When detailed descriptions on known functions or configurations related to the present application are determined to unnecessarily obscure the subject matter of the present application, the detailed description will be omitted. In addition, numbers (e.g., first, second, etc.) used in the description of the specification are just identification symbols to distinguish one element from another element.

In addition, the suffixes "module" and "part" for elements used in the following description are given or mixed in consideration of the ease of specification, and do not have distinct meanings or roles.

According to an exemplary embodiment of the present application, in a nucleic acid complex pair including a first nucleic acid complex including a first determinant and a second tag, and a second nucleic acid complex including a second determinant and a second tag, the first determinant may include a forward primer for a first target DNA, the second determinant may include a reverse primer for the first target DNA, the first tag may include a base sequence complementary to the base sequence of the second tag, and the second tag may include a base sequence complementary to the base sequence of the first tag.

In the nucleic acid complex pair, the first determinant may consist of deoxyribonucleic acid (DNA), ribonucleic acid (RNA), peptide nucleic acid (PNA), locked nucleic acid (LNA), bridged nucleic acid (BNA), hexose nucleic acid (HNA), glycol nucleic acid (GNA), threose nucleic acid (TNA), cyclohexene nucleic acid (CeNA) or a combination thereof, and the second determinant may consist of DNA, RNA, PNA, LNA, BNA, HNA, GNA, TNA, CeNA or a combination thereof.

In the nucleic acid complex pair, the first tag may consist of DNA, RNA, PNA, LNA, BNA, HNA, GNA, TNA, CeNA or a combination thereof, and the second tag may consist of DNA, RNA, PNA, LNA, BNA, HNA, GNA, TNA, CeNA or a combination thereof.

In the nucleic acid complex pair, the first nucleic acid complex may include a first label, and the second nucleic acid complex may include a second label, wherein the first label may be configured to provide energy to the second label.

In the nucleic acid complex pair, the first label may include at least one of FAM, JOE, TET, HEX, VIC, Oregon Green®, TAMRA, ROX, Cyanine-3, Cyanine-3.5, Cyanine-5, Cyanine-5.5, Aequorin and a cyan fluorescent protein (CFP).

In the nucleic acid complex pair, the second label may be a material configured to accept a first light emitted from the first label and convert the first light to a second light or a material configured to absorb the first light emitted from the first label.

In the nucleic acid complex pair, when the first tag is complementarily bonded with the second tag, the first label may provide energy to the second label.

In the nucleic acid complex pair, the first tag may be located between the first determinant and the first label, and the second tag may be located between the second determinant and the second label.

In the nucleic acid complex pair, the first label may be located between the first determinant and the first tag, and the second tag may be located between the second determinant and the second label.

In the nucleic acid complex pair, a first linker may be located between the first determinant and the first tag, and a second linker may be located between the second determinant and the second tag.

In the nucleic acid complex pair, the first linker may include a PCR blocker for preventing an amplification product for the first tag from being produced, and the second linker may include a PCR blocker for preventing an amplification product for the second tag from being produced.

The nucleic acid complex pair may be used for PCR, which may be performed to amplify at least a part of the first target DNA sequence.

The nucleic acid complex pair may be used for a digital PCR.

In the nucleic acid complex pair, the length of the base sequence of the first tag may be shorter than a length of a base sequence of the second tag.

In the nucleic acid complex pair, a part of the base sequence of the first tag may be the same as a part of the base sequence of the first determinant or the second determinant.

A kit for PCR including the nucleic acid complex pair according to some embodiments of the present application may be provided.

The kit for PCR may further include at least one of a DNA polymerase, a coenzyme involved in PCR, and a buffer for adjusting pH and/or a salt concentration.

According to an exemplary embodiment of the present application, a competitive construct used for PCR using a nucleic acid complex pair, which includes a first nucleic acid complex including a first determinant being a primer for a first target DNA, and a first tag; and a second nucleic acid complex including a second determinant being a primer for second target DNA, and a second tag having a complementary sequence to the first tag, may be provided, wherein the competitive construct may include a first additional sequence having a complementary sequence to at least a part of the base sequence of the first determinant; and a second additional sequence having a complementary sequence to at least a part of the base sequence of the first tag.

In the competitive construct, the first determinant may be a forward primer for the first target DNA, and the second determinant may be a reverse primer for the first target DNA.

In the competitive construct, the first determinant may be a reverse primer for the first target DNA, and the second determinant may be a forward primer for the first target DNA.

In the competitive construct, the first additional sequence may consist of DNA, RNA, PNA, LNA, BNA, HNA, GNA, TNA, CeNA or a combination thereof.

In the competitive construct, the second additional sequence may consist of DNA, RNA, PNA, LNA, BNA, HNA, GNA, TNA, CeNA or a combination thereof.

In the competitive construct, the second nucleic acid complex may include a fluorescent molecule emitting a first light, and the first nucleic acid complex may include a quencher molecule, which accepts the first light and then emits second light, or absorbs the first light.

In the competitive construct, the first nucleic acid complex may include a fluorescent molecule emitting a first light, and the first nucleic acid complex may include a quencher molecule, which accepts the first light and then emits second light, or absorbs the first light.

In the competitive construct, a first light emitted from a tube including the first nucleic acid complex and the competitive construct after a complementary binding between the first nucleic acid complex and the competitive construct is induced may be stronger than a first light emitted from the tube including the first nucleic acid complex and the second nucleic acid complex after the complementary bond between the first nucleic acid complex and the second nucleic acid complex is induced.

In the competitive construct, the second additional sequence may have a base sequence complementary to a base sequence of the first tag, and the number of bases in the base sequence complementary to the base sequence of the first tag may be 50% or more of the number of base pairs complementarily binding between the first tag and the second tag.

In the competitive construct, the number of bases of the base sequence complementary to the base sequence of the first tag may be 75% or more of the number of base pairs complementarily binding between the first tag and the second tag.

In the competitive construct, the first additional sequence may have a base sequence complementary to a base sequence of the first determinant, and the base sequence complementary to the base sequence of the first determinant has an annealing temperature of 10 to 35° C.

In the competitive construct, the base sequence complementary to the base sequence of the first determinant may have an annealing temperature of 20 to 30° C.

A kit for PCR, which includes a first nucleic acid complex including a first determinant being a primer for first target DNA, and a first tag: a second nucleic acid complex including a second determinant being a primer for second target DNA, and a second tag having a complementary sequence to the first tag; and a first additional sequence having a sequence complementary to at least a part of the base sequence of the first determinant and a second additional sequence having a sequence complementary to at least a part of the base sequence of the first tag, may be provided.

In the kit for PCR, the first determinant may be a forward primer for the first target DNA, and the second determinant may be a reverse primer for the first target DNA.

In the kit for PCR, the second determinant may be a forward primer for the first target DNA, and the first determinant may be a reverse primer for the first target DNA.

In the kit for PCR, the first additional sequence may consist of DNA, RNA, PNA, LNA, BNA, HN A, GNA, TNA, CeNA or a combination thereof.

In the kit for PCR, the second additional sequence may consist of DNA, RNA, PNA, LNA, BNA, HNA, GNA, TNA, CeNA or a combination thereof.

In the kit for PCR, the second nucleic acid complex may include a fluorescent molecule emitting a first light, and the first nucleic acid complex may include a quencher molecule, which accepts the first light and then emits a second light, or absorbs the first light.

In the kit for PCR, the first nucleic acid complex may include a fluorescent molecule emitting a first light, and the second nucleic acid complex may include a quencher molecule, which accepts the first light and then emits a second light, or absorbs the first light.

In the kit for PCR, the total mass of at least one competitive construct included in the PCR kit may be larger than at least one of the total mass of at least one first nucleic acid complex included in the PCR kit and the total mass of at least one second nucleic acid complex included in the PCR kit.

In the kit for PCR, the total mass of at least one competitive construct included in the PCR kit may be two-fold or larger than at least one of the total mass of at least one first nucleic acid complex included in the PCR kit and the total mass of at least one second nucleic acid complex included in the PCR kit.

<Nucleic Acid Complex 1>

1. Nucleic Acid Complex 1

FIG. 1 is a diagram of a nucleic acid complex 1 according to an exemplary embodiment of the present application.

As shown in FIG. 1, the nucleic acid complex 1 according to an exemplary embodiment of the present application may include a determinant 100 and a tag 200.

1.1 Configuration of Nucleic Acid Complex 1
1.1.1 Determinant 100
1.1.1.1 Components of Determinant 100

According to an exemplary embodiment of the present application, the determinant 100 may include a nucleic acid and/or a nucleic acid analog. The determinant 100 may include a unit molecule of a nucleic acid. The determinant 100 may include a unit molecule of a nucleic acid analog. The determinant 100 may include a unit molecule of a nucleic acid and the unit molecule of a nucleic acid analog.

1.1.1.1.1 Unit Molecule of Nucleic Acid

The determinant 100 may include a unit molecule of a nucleic acid.

In one example, the determinant 100 may include the unit molecule of DNA which is a nucleic acid. The unit molecule of DNA may be a material represented by Formula 1 below.

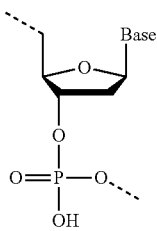

[Formula 1]

The base of Formula 1 may be adenine (A), guanine (G), thymine (T) or cytosine (C). Alternatively, the base of Formula 1 may be a purine or pyrimidine-based derivative such as hypoxanthine or xanthine.

In another example, the determinant 100 may include the unit molecule of RNA which is a nucleic acid. A unit molecule of RNA may be a material represented by Formula 2 below.

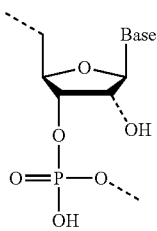

[Formula 2]

The base of Formula 2 may be adenine (A), guanine (G), cytosine (C) or uracil (U). Alternatively, the base of Formula 2 may be a purine or pyrimidine-based derivative such as hypoxanthine or xanthine.

According to an exemplary embodiment of the present application, the determinant 100 may include the unit molecule of a nucleic acid.

In one example, the determinant 100 may consist of the unit molecule of a nucleic acid. In a specific example, the determinant 100 may consist of the unit molecule of DNA. Alternatively, the determinant 100 may consist of the unit molecule of RNA.

In another example, the determinant 100 may consist of a polymer of the unit molecule of a nucleic acid. As a specific example, the determinant 100 may consist of a polymer of the unit molecule of DNA. Alternatively, the determinant 100 may consist of a polymer of the unit molecule of RNA.

According to an exemplary embodiment of the present application, the determinant 100 may include the unit molecule of a first nucleic acid and the unit molecule of a second nucleic acid. The determinant 100 may include at least a first nucleic acid and a second nucleic acid.

The first and second nucleic acids included in the determinant 100 may be directly connected to each other. In other words, the determinant 100 may be provided in the form in which one end of the unit molecule of a first nucleic acid (or a polymer of the unit molecule) and one end of the unit molecule of a second nucleic acid (or a polymer of the unit molecule) are directly connected to each other.

The first and second nucleic acids included in the determinant 100 may be connected by a specific compound. In other words, the determinant 100 may be provided in the form in which one end of the unit molecule of a first nucleic acid (or a polymer of the unit molecule) and one end of the unit molecule of a second nucleic acid (or a polymer of the unit molecule) are connected by a specific compound.

In one example, the determinant 100 may be provided in the form in which the unit molecule of a first nucleic acid and the unit molecule of a second nucleic acid are connected. As a specific example, the determinant 100 may be provided in the form in which the unit molecule of DNA and the unit molecule of RNA are connected. Alternatively, the determinant 100 may be provided in the form in which the unit molecule of DNA and the unit molecule of DNA are connected by a specific compound (e.g., a crosslinker). Alternatively, the determinant 100 may be provided in the form in which the unit molecule of RNA and the unit molecule of RNA are connected by a specific compound.

In another example, the determinant 100 may be provided in the form in which the unit molecule of a second nucleic acid and a polymer of the unit molecule of a first nucleic acid are connected. In a specific example, the determinant 100 may be configured in the form in which the unit molecule of RNA and a polymer of the unit molecule of DNA are connected. In addition, the determinant 100 may be configured in the form in which the unit molecule of DNA and a polymer of the unit molecule of RNA are connected. Alternatively, the determinant 100 may be configured in the form in which the unit molecule of DNA and a polymer of the unit molecule of DNA are connected by a specific compound. Alternatively, the determinant 100 may be configured in the form in which the unit molecule of RNA and a polymer of the unit molecule of RNA are connected by a specific compound.

In still another example, the determinant 100 may be configured in the form in which a polymer of the unit molecule of a first nucleic acid and a polymer of the unit molecule of a second nucleic acid are connected. In a specific example, the determinant 100 may be configured in the form in which a polymer of the unit molecule of DNA and a polymer of the unit molecule of RNA are connected. Alternatively, the determinant 100 may be configured in the form in which a polymer of the unit molecule of DNA and a polymer of the unit molecule of DNA are connected by a specific compound. Alternatively, the determinant 100 may be configured in the form in which a polymer of the unit molecule of RNA and a polymer of the unit molecule of RNA are connected by a specific compound.

1.1.1.1.2 Unit Molecule of Nucleic Acid Analog

The determinant 100 may include the unit molecule of a nucleic acid analog.

In one example, the determinant 100 may include the unit molecule of PNA which is a nucleic acid analog. The unit molecule of PNA may be a material represented by Formula 3 below.

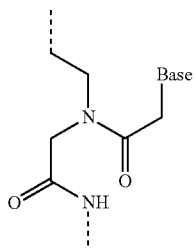

[Formula 3]

The base of Formula 3 may be adenine (A), guanine (G), thymine (T), cytosine (C) or uracil (U). Alternatively, the base of Formula 3 may be a purine or pyrimidine-based derivative such as hypoxanthine or xanthine.

In another example, the determinant 100 may include the unit molecule of LNA which is a nucleic acid analog. The unit molecule of LNA may be a material represented by Formula 4 below.

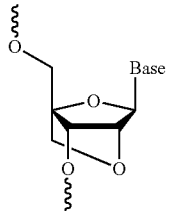

[Formula 4]

The base of Formula 4 may be adenine (A), guanine (G), thymine (T), cytosine (C) or uracil (U). Alternatively, the base of Formula 4 may be a purine or pyrimidine-based derivative such as hypoxanthine or xanthine.

In another example, the determinant 100 may include the unit molecule of BNA which is a nucleic acid analog. The unit molecule of BNA may be a material represented by Formula 5 below.

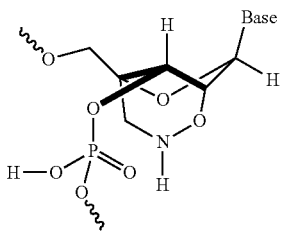

[Formula 5]

The base of Formula 5 may be adenine (A), guanine (G), thymine (T), cytosine (C) or uracil (U). Alternatively, the base of Formula 5 may be a purine or pyrimidine-based derivative such as hypoxanthine or xanthine.

In another example, the determinant 100 may include the unit molecule of HNA which is a nucleic acid analog. The unit molecule of HNA may be a material represented by Formula 6 below.

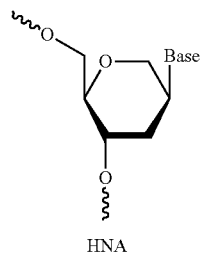

[Formula 6]

HNA

The base of Formula 6 may be adenine (A), guanine (G), thymine (T), cytosine (C) or uracil (U). Alternatively, the base of Formula 6 may be a purine or pyrimidine-based derivative such as hypoxanthine or xanthine.

In another example, the determinant 100 may include the unit molecule of GNA which is a nucleic acid analog. The unit molecule of GNA may be a material represented by Formula 7 below.

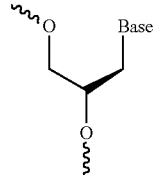

[Formula 7]

The base of Formula 7 may be adenine (A), guanine (G), thymine (T), cytosine (C) or uracil (U). Alternatively, the base of Formula 7 may be a purine or pyrimidine-based derivative such as hypoxanthine or xanthine.

In another example, the determinant 100 may include the unit molecule of TNA which is a nucleic acid analog. The unit molecule of TNA may be a material represented by Formula 8 below.

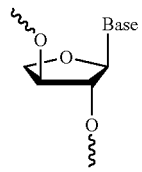

[Formula 8]

The base of Formula 8 may be adenine (A), guanine (G), thymine (T), cytosine (C) or uracil (U). Alternatively, the base of Formula 8 may be a purine or pyrimidine-based derivative such as hypoxanthine or xanthine.

In another example, the determinant 100 may include the unit molecule of CeNA which is a nucleic acid analog. The unit molecule of CeNA may be a material represented by Formula 9 below.

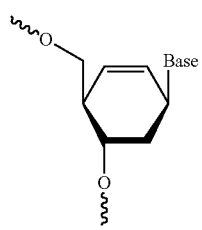

[Formula 9]

The base of Formula 9 may be adenine (A), guanine (G), thymine (T), cytosine (C) or uracil (U). Alternatively, the base of Formula 9 may be a purine or pyrimidine-based derivative such as hypoxanthine or xanthine.

According to an exemplary embodiment of the present application, the determinant 100 may include the unit molecule of a nucleic acid analog.

In one example, the determinant 100 may consist of the unit molecule of a nucleic acid analog. In a specific example, the determinant 100 may consist of the unit molecule of LNA.

In another example, the determinant 100 may consist of a polymer of the unit molecule of a nucleic acid analog. In a specific example, the determinant 100 may consist of a polymer of the unit molecule of PNA.

According to another exemplary embodiment of the present application, the determinant 100 may include the unit molecule of a first nucleic acid analog and the unit molecule of a second nucleic acid analog. The determinant 100 may include at least the first nucleic acid analog and the second nucleic acid analog.

The first nucleic acid analog and the second nucleic acid analog, which are included in the determinant 100, may be directly connected to each other. In other words, the determinant 100 may be provided in the form in which one end of the unit molecule (or a polymer of the unit molecule) of the first nucleic acid analog and one end of the unit molecule (or a polymer of the unit molecule) of the second nucleic acid analog are directly connected to each other.

The first nucleic acid analog and the second nucleic acid analog, which are included in the determinant 100, may be connected by a specific compound. In other words, the determinant 100 may be provided in the form in which one end of the unit molecule (or a polymer of the unit molecule) of the first nucleic acid analog and one end of the unit molecule (or a polymer of the unit molecule) of the second nucleic acid analog are connected by a specific compound.

In one example, the determinant 100 may be configured in the form in which the unit molecule of the first nucleic acid analog and the unit molecule of the second nucleic acid analog are connected. In a specific example, the determinant 100 may be configured in the form in which the unit molecule of PNA and the unit molecule of LNA are connected.

In another example, the determinant 100 may be configured in the form in which the unit molecule of the second nucleic acid analog and a polymer of the unit molecule of the first nucleic acid analog are connected. In a specific example, the determinant 100 may be configured in the form in which the unit molecule of GNA and a polymer of the unit molecule of TNA are connected. Alternatively, the determinant 100 may be configured in the form in which the unit molecule of CeNA and a polymer of the unit molecule of CeNA are connected by a specific compound.

In still another example, the determinant 100 may be configured in the form in which a polymer of the unit molecule of the first nucleic acid analog and a polymer of the unit molecule of the second nucleic acid analog are connected. In a specific example, the determinant 100 may be configured in the form in which a polymer of the unit molecule of BNA and a polymer of the unit molecule of HNA are connected. Alternatively, the determinant 100 may be configured in the form in which a polymer of the unit molecule of LNA and a polymer of the unit molecule of LNA are connected by a specific compound.

1.1.1.1.3 Combination of Unit Molecule of Nucleic Acid and Unit Molecule of Nucleic Acid Analog According to an exemplary embodiment of the present application, the determinant 100 may include the unit molecule of a nucleic acid and the unit molecule of a nucleic acid analog. The determinant 100 may include at least a first nucleic acid and a first nucleic acid analog.

The first nucleic acid and the first nucleic acid analog, which are included in the determinant 100 may be directly connected to each other. In other words, the determinant 100 may be provided in the form in which one end of the unit molecule (or a polymer of the unit molecule) of a first nucleic acid and one end of the unit molecule (or a polymer of the unit molecule) of a first nucleic acid analog may be directly connected to each other.

The first nucleic acid and the first nucleic acid analog, which are included in the determinant 100, may be connected by a specific compound. In other words, the determinant 100 may be provided in the form in which one end of the unit molecule (or a polymer of the unit molecule) of a first nucleic acid and one end of the unit molecule (or a polymer of the unit molecule) of a first nucleic acid analog may be connected by a specific compound.

In one example, the determinant 100 may be configured in the form in which the unit molecule of a nucleic acid and the unit molecule of a nucleic acid analog are connected. In a specific example, the determinant 100 may be configured in the form in which the unit molecule of DNA and the unit molecule of LNA are connected.

In another example, the determinant 100 may be configured in the form in which the unit molecule of a nucleic acid and a polymer of the unit molecule of a nucleic acid analog are connected. In a specific example, the determinant 100 may be configured in the form in which the unit molecule of RNA and a polymer of the unit molecule of PNA are connected.

In still another example, the determinant 100 may be configured in the form in which the unit molecule of a nucleic acid analog and a polymer of the unit molecule of a nucleic acid are connected. In a specific example, the determinant 100 may be configured in the form in which the unit molecule of GNA and a polymer of the unit molecule of DNA are connected.

In yet another example, the determinant 100 may be configured in which a polymer of the unit molecule of a nucleic acid and a polymer of the unit molecule of a nucleic acid analog are connected. In a specific example, the determinant 100 may be configured in the form in which a polymer of the unit molecule of RNA and a polymer of the unit molecule of CeNA are connected.

So far, the materials that can constitute the determinant 100 and the configuration thereof have been described in detail. However, specific embodiments are merely provided to help in understanding the determinant 100 according to the present application and it does not mean that the determinant 100 should be construed as limited to including the material disclosed herein.

In other words, the determinant 100 can be construed to include the unit molecule of a nucleic acid analog which is not disclosed in the specification. Here, the unit molecule of a nucleic acid analog may include a base, and have a form in which at least a part of the components except the base is chemically modified.

In addition, it can be interpreted that the determinant 100 may include a material in which at least one of Formulas 1 to 9 is chemically modified within a range easily designed and changed by one of ordinary skill in the art. For example, the determinant 100 may include deoxycytidine triphosphate (dCTP) in which cytosine (C) binds to the base of Formula 1, and two phosphoric acids further bind to the phosphoric acid of Formula 1.

Hereinafter, the operation and examples of the determinant 100 according to an exemplary embodiment of the present application will be described in detail. According to the material characteristics of the determinant 100 which are previously described and the operation and examples of the determinant 100 described below, the definition and function of the determinant 100 will be more clearly understood.

1.1.1.2 Operation of Determinant 100

The determinant 100 according to an exemplary embodiment of the present application may include a region complementarily binding to a specific base sequence. The determinant 100 may include a region specifically binding to a specific base sequence. For example, the specific base sequence may be a base sequence complementary to at least a part of the base sequence of the determinant 100.

The expression "the determinant 100 includes a region complementarily binding to a specific base sequence" may mean that at least one property of the electrical, chemical and physic al properties in at least a part of the regions of the determinant 100 corresponds to a specific base sequence.

In one example, the determinant 100 may include a region in which a chemical binding force with a specific base sequence may occur. In other words, the determinant 100 may include a region which is configured to form at least one bond of a covalent bond, a hydrogen bond, an ionic bond and a hydrophobic bond with a specific base sequence may occur.

According to an exemplary embodiment of the present application, the determinant 100 may have a unique base sequence. The determinant 100 may have a unique base sequence according to a base type (e.g., adenine, guanine, etc.) of the unit molecule of a nucleic acid included in the determinant 100 and/or the unit molecule of a nucleic acid analog.

According to an exemplary embodiment of the present application, the determinant 100 may complementarily bind to a specific base sequence. The determinant 100 may specifically bind to the specific base sequence which is complementary to at least a part of the unique base sequence of the determinant 100. The determinant 100 may complementarily bind to the specific base sequence by hydrogen bonding between at least a part of the unique base sequence of the determinant 100 and the specific base sequence.

According to an exemplary embodiment of the present application, the determinant 100 may determine a different material which can complementarily bind thereto. In other words, the determinant 100 may specifically bind to a specific base sequence, such that a binding target material of the determinant 100 may be determined to be a different material (e.g., ssDNA including the specific base sequence) including the specific base sequence.

1.1.1.3 Examples of Determinant 100

1.1.1.3.1 Single Strand Including Nucleic Acid and/or Nucleic Acid Analog

The determinant 100 according to an exemplary embodiment of the present application may be a single strand including a nucleic acid and/or a nucleic acid analog.

The determinant 100 may consist of at least one nucleic acid and/or nucleic acid analog. When the determinant 100 consists of a plurality of nucleic acids and/or nucleic acid analogs, the plurality of nucleic acids and/or nucleic acid analogs included in the determinant 100 may be connected to each other such that the determinant 100 is formed in a single strand.

According to an exemplary embodiment of the present application, the determinant 100 may specifically bind to a nucleic acid including a sequence complementary to the base sequence of the determinant 100. At least a part of the base sequence of the determinant 100 may specifically bind to a nucleic acid with a sequence complementary to the base sequence of the determinant 100.

In one example, all of the base sequence of the determinant 100 may specifically bind to a nucleic acid including a sequence complementary to the base sequence of the determinant 100. In a specific example, when the determinant 100 is 5'-AAACGGCTCAAATTT-3' (SEQ ID NO: 29), the determinant 100 may specifically bind to a nucleic acid including 5'-AAAAATTTGAGCCGTTT-3' (SEQ ID NO: 30). In another specific example, when the determinant 100 is 5'-AAACGGCTCAAATTTTT-3' (SEQ ID NO: 29), the determinant 100 may specifically bind to a nucleic acid including 5'-AAAAATTTGAG-3' (SEQ ID NO: 31).

According to an exemplary embodiment of the present application, the determinant 100 may include 1 to 100 mer of a nucleic acid and/or nucleic acid analog. Preferably, the determinant 100 may include a 5 to 50-mer nucleic acid and/or nucleic acid analog. Preferably, the determinant 100 may include a 15 to 30-mer nucleic acid and/or nucleic acid analog. When the determinant 100 includes at least a 15-mer nucleic acid and/or nucleic acid analog, the determinant 100 may be improved in reactivity with a target nucleic acid, compared to when having a 10-mer or less nucleic acid and/or nucleic acid analog.

1.1.1.3.2 Primers

The determinant 100 according to an exemplary embodiment of the present application may be a PCR primer.

The determinant 100 may specifically bind to a specific base sequence. The specific base sequence may a base sequence complementary to at least a part of the base sequence of the determinant 100.

When PCR is performed, the determinant 100 may bind to a target nucleic acid (e.g., target DNA including a specific base sequence), and a nucleotide is connected to the 3' end of the determinant 100, resulting in the elongation at the 3' end of the determinant 100. In other words, as PCR proceeds, the determinant 100 bound to a target nucleic acid may be elongated at the 3' end of the determinant 100 by a polymerase to connect a nucleotide (e.g., dNTP or ddNTP) to the 3' end of the determinant 100.

In a specific example, when the determinant 100 is 5'-AAACGGCTCAAATT-3' (SEQ ID NO: 29), the determinant 100 may specifically bind to a target nucleic acid including 5'-AAAAATTTGAGCCGTTT-3' (SEQ ID NO: 30), and the unit molecule of a nucleic acid (e.g., a nucleotide) having a base sequence complementary to bases in a region adjacent to the 5' end of the target nucleic acid may be connected to the 3' end of the determinant 100, resulting in the elongation at the 3' end of the determinant 100.

According to an exemplary embodiment of the present application, a nucleotide may be connected to the 3' end of the determinant 100 by a covalent bond. In one example, when the determinant 100 consists of a polymer of the unit molecule of DNA, a nucleotide may be connected to the 3' end of the determinant 100 by a covalent bond between a H group of a sugar at the 3' end of the determinant 100 and an OH group of a phosphate group of the nucleotide to be attached to the 3' end of the determinant 100.

According to an exemplary embodiment of the present application, the determinant 100 may include a 1 to 50-mer nucleic acid and/or nucleic acid analog. Preferably, the determinant 100 may include a 5 to 30-mer nucleic acid and/or nucleic acid analog. Preferably, the determinant 100 may include a 10 to 25-mer nucleic acid and/or nucleic acid analog. When the determinant 100 includes at least a 15-mer nucleic acid and/or nucleic acid analog, the determinant 100 may be improved in reactivity of the determinant 100 with the target nucleic acid, compared to when including a 10-mer or less nucleic acid and/or nucleic acid analog.

According to another embodiment of the present application, the determinant 100 may include at least two or more nucleic acids, and the first and second nucleic acids may be connected by a specific compound. The determinant 100 may include at least two unit molecules of nucleic acids, and the first nucleic acid (the unit molecule of a nucleic acid or a polymer of the unit molecule of a nucleic acid) and the second nucleic acid (the unit molecule of a nucleic acid or a polymer of the unit molecule of a nucleic acid) may be connected by a specific compound.

In one example, the determinant 100 may be configured in the form in which a first strand consisting of a polymer of the unit molecule of DNA and a second strand consisting of a polymer of the unit molecule of DNA are connected by a specific compound. In a more specific example, the determinant 100 may be provided in the form in which the first and second strands are connected by a polydeoxyinosine linker. In some cases, the determinant 100 in which the first strand and the second strand relatively shorter than the first strand are connected by a polydeoxyinosine linker may be provided.

1.1.2 Tag 200
1.1.2.1 Components of Tag 200
1.1.2.1.1 Compound

According to an exemplary embodiment of the present application, the tag 200 may include a compound including at least one of F, N, O and H to enable hydrogen bonding.

In one example, the tag 200 may be a polymer produced by polymerizing a monomer including at least one of F, N, O and H.

In a specific example, the tag 200 may consist of a polymer of the unit molecule of Formula 10 below.

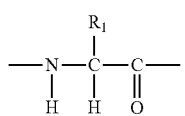

[Formula 10]

In another example, the tag 200 may have a form in which a first polymer produced by polymerizing a monomer including at least one of F, N, O and H and a second polymer produced by polymerizing a monomer including at least one of F, N, O and H are connected by a specific compound.

In still another example, the tag 200 may have a form in which a polymer produced by polymerizing a monomer including at least one of F, N, O and H and an arbitrary compound are connected.

1.1.2.1.2 Nucleic Acid and/or Nucleic Acid Analog

According to an exemplary embodiment of the present application, the tag 200 may include a nucleic acid and/or a nucleic acid analog. The tag 200 may include the unit molecule of a nucleic acid. The tag 200 may include the unit molecule of a nucleic acid analog. The tag 200 may include the unit molecule of a nucleic acid and the unit molecule of a nucleic acid analog.

1.1.2.1.2.1 Unit Molecule of Nucleic Acid

The tag 200 may include the unit molecule of a nucleic acid.

In one example, the tag 200 may include the unit molecule of DNA which is a nucleic acid. The unit molecule of DNA may be a material represented by Formula 1 described above.

In another example, the tag 200 may include the unit molecule of RNA which is a nucleic acid. The unit molecule of RNA may be a material represented by Formula 2 described above.

According to an exemplary embodiment of the present application, the tag 200 may include the unit molecule of a nucleic acid.

In one example, the tag 200 may consist of the unit molecule of a nucleic acid. In a specific example, the tag 200 may consist of the unit molecule of DNA. Alternatively, the tag 200 may consist of the unit molecule of RNA.

In another example, the tag 200 may consist of a polymer of the unit molecule of a nucleic acid. In a specific example, the tag 200 may consist of a polymer of the unit molecule of DNA. Alternatively, the tag 200 may consist of a polymer of the unit molecule of RNA.

According to another embodiment of the present application, the tag 200 may include the unit molecule of a first nucleic acid and the unit molecule of a second nucleic acid. The tag 200 may include at least the first and second nucleic acids.

The first and second nucleic acids included in the tag 200 may be directly connected to each other. In other words, the tag 200 may be provided in the form in which one end of the unit molecule (or a polymer of the unit molecule) of a first nucleic acid and one end of the unit molecule (or a polymer of the unit molecule) of a second nucleic acid are directly connected to each other.

The first and second nucleic acids included in the tag 200 may be connected by a specific compound. In other words, the tag 200 may be provided in the form in which one end of the unit molecule (or a polymer of the unit molecule) of a first nucleic acid and one end of the unit molecule (or a polymer of the unit molecule) of a second nucleic acid are connected by a specific compound.

In one example, the tag 200 may be configured in the form in which the unit molecule of a first nucleic acid and the unit molecule of a second nucleic acid are connected. In a specific example, the tag 200 may be configured in the form in which the unit molecule of DNA and the unit molecule of RNA are connected. Alternatively, the tag 200 may be configured in the form in which the unit molecule of DNA and the unit molecule of DNA are connected by a specific compound. Alternatively, the tag 200 may be configured in the form in which the unit molecule of RNA and the unit molecule of RNA are connected by a specific compound.

In another example, the tag 200 may be configured in the form in which the unit molecule of a second nucleic acid and a polymer of the unit molecule of a first nucleic acid are connected. In a specific example, the tag 200 may be configured in the form in which the unit molecule of RNA and a polymer of the unit molecule of DNA are connected. Alternatively, the tag 200 may be configured in the form in which the unit molecule of DNA and a polymer of the unit molecule of RNA are connected. Alternatively, the tag 200 may be configured in the form in which the unit molecule of DNA and a polymer of the unit molecule of DNA are connected by a specific compound. Alternatively, the tag 200 may be configured in the form in which the unit molecule of RNA and a polymer of the unit molecule of RNA are connected by a specific compound.

In still another example, the tag 200 may be configured in the form in which a polymer of the unit molecule of a first nucleic acid and a polymer of the unit molecule of a second nucleic acid are connected. In a specific example, the tag 200 may be configured in the form in which a polymer of the unit molecule of DNA and a polymer of the unit molecule of RNA are connected. Alternatively, the tag 200 may be configured in the form in which a polymer of the unit molecule of DNA and a polymer of the unit molecule of DNA are connected by a specific compound. Alternatively, the tag 200 may be configured in the form in which a polymer of the unit molecule of RNA and a polymer of the unit molecule of RNA are connected by a specific compound.

1.1.2.1.2.2 Unit Molecule of Nucleic Acid Analog

The tag 200 may include the unit molecule of a nucleic acid analog.

In one example, the tag 200 may include the unit molecule of PNA which is a nucleic acid analog. The unit molecule of PNA may be a material represented by Formula 3 described above.

In another example, the tag 200 may include the unit molecule of LNA which is a nucleic acid analog. The unit molecule of LNA may be a material represented by Formula 4 described above.

In still another example, the tag 200 may include the unit molecule of BNA which is a nucleic acid analog. The unit molecule of BNA may be a material represented by Formula 5 described above.

In yet another example, the tag 200 may include the unit molecule of HNA which is a nucleic acid analog. The unit molecule of HNA may be a material represented by Formula 6 described above.

In yet another example, the tag 200 may include the unit molecule of GNA which is a nucleic acid analog. The unit molecule of GNA may be a material represented by Formula 7 described above.

In yet another example, the tag 200 may include the unit molecule of TNA which is a nucleic acid analog. The unit molecule of TNA may be a material represented by Formula 8 described above.

In yet another example, the tag 200 may include the unit molecule of CeNA which is a nucleic acid analog. The unit molecule of CeNA may be a material represented by Formula 9 described above.

According to an exemplary embodiment of the present application, the tag 200 may include the unit molecule of a nucleic acid analog.

In one example, the tag 200 may consist of the unit molecule of a nucleic acid analog. In a specific example, the tag 200 may consist of the unit molecule of LNA.

In another example, the tag 200 may consist of a polymer of the unit molecule of a nucleic acid analog. In a specific example, the tag 200 may consist of a polymer of the unit molecule of PNA.

According to another embodiment of the present application, the tag 200 may include the unit molecule of a first nucleic acid analog and the unit molecule of a second nucleic acid analog. The tag 200 may include at least a first nucleic acid analog and a second nucleic acid analog.

The first nucleic acid analog and the second nucleic acid analog, which are included in the tag 200, may be directly connected to each other. In other words, the tag 200 may be provided in the form in which one end of the unit molecule (or a polymer of the unit molecule) of a first nucleic acid analog and one end of the unit molecule (or a polymer of the unit molecule) of a second nucleic acid analog are directly connected to each other.

The first nucleic acid analog and the second nucleic acid analog, which are included in the tag 200, may be connected by a specific compound. In other words, the tag 200 may be provided in the form in which one end of the unit molecule (or a polymer of the unit molecule) of a first nucleic acid analog and one end of the unit molecule (or a polymer of the unit molecule) of a second nucleic acid analog are connected by a specific compound.

In one example, the tag 200 may be configured in the form in which the unit molecule of a first nucleic acid analog and the unit molecule of a second nucleic acid analog are connected. In a specific example, the tag 200 may be configured in the form in which the unit molecule of PNA and the unit molecule of LNA are connected.

In another example, the tag 200 may be configured in the form in which the unit molecule of a second nucleic acid analog and a polymer of the unit molecule of a first nucleic acid analog are connected. In a specific example, the tag 200 may be configured in the form in which the unit molecule of GNA and a polymer of the unit molecule of TNA are connected. Alternatively, the tag 200 may be configured in the form in which the unit molecule of CeNA and a polymer of the unit molecule of CeNA are connected by a specific compound.

In still another example, the tag 200 may be configured in the form in which a polymer of the unit molecule of a first nucleic acid analog and a polymer of the unit molecule of a second nucleic acid analog are connected. In a specific example, the tag 200 may be configured in the form in which a polymer of the unit molecule of BNA and a polymer of the unit molecule of HNA are connected. Alternatively, the tag 200 may be configured in the form in which a polymer of the unit molecule of LNA and a polymer of the unit molecule of LN A are connected by a specific compound.

1.1.2.1.2.3 Combination of Unit Molecule of Nucleic Acid and Unit Molecule of a Nucleic Acid Analog According to an exemplary embodiment of the present application, the tag 200 may include the unit molecule of a nucleic acid and the unit molecule of a nucleic acid analog. The tag 200 may include at least a first nucleic acid and a first nucleic acid analog.

The first nucleic acid and the first nucleic acid analog, which are included in the tag 200, may be directly connected to each other. In other words, the tag 200 may be provided in the form in which one end of the unit molecule (or a polymer of the unit molecule) of a first nucleic acid and one end of the unit molecule (or a polymer of the unit molecule) of a first nucleic acid analog are directly connected to each other.

The first nucleic acid and the first nucleic acid analog included in the tag 200 may be connected by a specific compound. In other words, the tag 200 may be provided in the form in which one end of the unit molecule (or a polymer of the unit molecule) of a first nucleic acid and one end of the unit molecule (or a polymer of the unit molecule) of a first nucleic acid analog are connected by a specific compound.

In one example, the tag 200 may be configured in the form in which the unit molecule of a nucleic acid and the unit molecule of a nucleic acid analog are connected. In a specific example, the tag 200 may be configured in the form in which the unit molecule of DNA and the unit molecule of LNA are connected.

In another example, the tag 200 may be configured in the form in which a polymer of the unit molecule of a nucleic acid analog and the unit molecule of a nucleic acid are connected. In a specific example, the tag 200 may be configured in the form in which a polymer of the unit molecule of PNA and the unit molecule of RNA are connected.

In still another example, the tag 200 may be configured in the form in which a polymer of the unit molecule of a nucleic acid and the unit molecule of a nucleic acid analog are connected. In a specific example, the tag 200 may be configured in the form in which a polymer of the unit molecule of DNA and the unit molecule of GNA are connected.

In yet another example, the tag 200 may be configured in the form in which a polymer of the unit molecule of a nucleic acid and a polymer of the unit molecule of a nucleic acid analog are connected. In a specific example, the tag 200 may be configured in the form in which a polymer of the unit molecule of RNA and a polymer of the unit molecule of CeNA are connected.

So far, the materials that can constitute the tag 200 and the configuration thereof have been described in detail. However, specific embodiments are merely provided to help in understanding the tag 200 according to the present application and it does not mean that the tag 200 should be construed as limited to including the material disclosed herein.

In other words, it can be interpreted that the tag 200 includes a compound that is not disclosed herein.

In addition, the tag 200 may be interpreted to include the unit molecule of a nucleic acid analog which is not disclosed herein. Here, the unit molecule of a nucleic acid analog includes a base, and at least a part of the components except the base may be chemically modified, compared to a nucleotide.

In addition, the tag 200 may be interpreted to include a material in which at least one of Formulas 1 to 10 is chemically modified within a range that is easily designed and modified by one of ordinary skill in the art. For example, the tag 200 may include thymidine diphosphate (TDP) in which thymidine (T) binds to the base of Formula 2 and one phosphoric acid further binds to the phosphoric acid of Formula 2.

Hereinafter, the operation and examples of the tag 200 according to an exemplary embodiment of the present application will be described in detail. According to the material characteristics of the tag 200, which are described above, and the operation and examples of the tag 200, which will be described below, the definition and function of the tag 200 will be more clearly understood.

1.1.2.2 Operation of Tag 200

According to an exemplary embodiment of the present application, the tag 200 may include a region complementarily binding to a specific base sequence. The tag 200 may include a region specifically binding to the specific base sequence. In one example, the specific base sequence may be a base sequence which is complementary to at least a part of the base sequence of the tag 200.

The expression "the tag 200 includes a region complementarily binding to a specific base sequence" may mean that at least one property of electrical, chemical and physical properties in at least a part of the regions of the tag 200 corresponds to a specific base sequence.

In one example, the tag 200 may include a region in which a chemical binding force with a specific base sequence may occur. In other words, the tag 200 may include a region which is configured to form at least one bond of a covalent bond, a hydrogen bond, an ionic bond and a hydrophobic bond with a specific base sequence may occur.

According to an exemplary embodiment of the present application, the tag 200 may include a region complementarily binding to a different nucleic acid complex 1. The tag 200 may include a region complementarily binding to a tag 200 of the different nucleic acid complex 1.

In one example, when the tag 200 consists of the compound, the compound included in the tag 200 may have a unique chemical structure. The tag 200 may have a unique chemical structure according to a distance between elements of the compound included in the tag 200 and an element type of the compound included in the tag 200.

The tag 200 may complementarily bind to the tag 200 of a different nucleic acid complex 1 having a specific chemical structure. The tag 200 may complementarily bind to the tag 200 of a different nucleic acid complex 1 by hydrogen bonding with a specific chemical structure corresponding to the unique chemical structure of the tag 200.

In a specific example, when the tag 200 and the tag 200 of a different nucleic acid complex 1 have a polymer of the unit molecule of Formula 10, a hydrogen of the tag 200 may be bonded to a hydrogen of the tag 200 of a different nucleic acid complex 1 by a hydrogen bond, and a nitrogen of the tag 200 may be bonded to a hydrogen of the tag 200 of a different nucleic acid complex 1 by a hydrogen bond.

In another example, when the tag 200 includes a nucleic acid and/or the unit molecule of a nucleic acid analog, the tag 200 may have a unique base sequence. The tag 200 may have a unique base sequence according to a base type (e.g. adenine, guanine, etc.) of the unit molecule of a nucleic acid and/or the unit molecule of a nucleic acid analog, which are included in the tag 200.

The tag 200 may complementarily bind to a tag 200 of a different nucleic acid complex 1 including a specific base sequence. The tag 200 may complementarily bind to the tag 200 of a different nucleic acid complex 1 by hydrogen bonding with a specific base sequence corresponding to at least a part of the unique base sequence of the tag 200.

In a specific example, when the tag 200 and the tag 200 of a different nucleic acid complex 1 have a polymer of the unit molecule of DNA, cytosine (C) in the base sequence of the tag 200 may form a hydrogen bond with guanine (G) in the base sequence of the tag 200 of a different nucleic acid complex 1, and adenine (A) in the base sequence of the tag 200 may form a hydrogen bond with thymine (T) in the base sequence of the tag 200.

1.1.2.3 Examples of Tag 200

1.1.2.3.1 Single Strand Including Nucleic Acid and/or Nucleic Acid Analog

The tag 200 according to an exemplary embodiment of the present application may be a single strand including a nucleic acid and/or nucleic acid analog.

The tag 200 may consist of at least one nucleic acid and/or nucleic acid analog. When the tag 200 consists of a plurality of nucleic acids and/or nucleic acid analogs, the plurality of nucleic acids and/or nucleic acid analogs included in the tag 200 may be connected to each other such that the tag 200 is formed in a single strand.

According to an exemplary embodiment of the present application, the tag 200 may specifically bind to a tag 200 of a different nucleic acid complex 1 including a sequence complementary to the base sequence of the tag 200. At least a part of the base sequence of the tag 200 may specifically bind to the tag 200 of a different nucleic acid complex 1.

In one example, all of the base sequence of the tag 200 may specifically bind to the tag 200 of a different nucleic acid complex 1. In a specific example, when the tag 200 is AAAAAAAAAA (SEQ ID NO: 5), the tag 200 may specifically bind to the tag 200 of a different nucleic acid complex 1 including TTTTTTTTTT (SEQ ID NO: 7).

In another example, a part of the base sequence of the tag 200 may specifically bind to a tag 200 of a different nucleic acid complex 1. In a specific example, when the tag 200 is AAAAAAAAAA (SEQ ID NO: 5), the tag 200 may specifically bind to the tag 200 of a different nucleic acid complex 1 including TTTTTTTT (SEQ ID NO: 3). At least two bases (that is, AA) of the tag 200 may not participate in bonding.

The operation of the nucleic acid complex 1 according to an exemplary embodiment of the present application related to this will be described in detail in 2.2 (relating to Tag 200) and 2.4 (relating to the applications of a nucleic acid complex pair 10 according to Example 7).

According to an exemplary embodiment of the present application, the tag 200 may include a 1 to 50-mer nucleic acid and/or nucleic acid analog. Preferably, the tag 200 includes a 3 to 25-mer nucleic acid and/or nucleic acid analog. Preferably, the tag 200 includes a 5 to 20-mer nucleic acid and/or nucleic acid analog.

1.1.2.3.2 Probes for PCR Clamping

The tag 200 according to an exemplary embodiment of the present application may be a probe for PCR clamping. The tag 200 may be a single strand including a nucleic acid and/or nucleic acid analog, which has at least one different base sequence from a primer used in the PCR.

According to an exemplary embodiment of the present application, the tag 200 may be formed to have at least one different base sequence from the base sequence of the determinant 100. The tag 200 may specifically bind to a nucleic acid having a sequence similar to a specific base sequence binding to the determinant 100.

According to an exemplary embodiment of the present application, the tag 200 may prevent the determinant 100 from mismatch-binding to a similar sequence similar to a target base sequence of the determinant 100 (that is, a base sequence corresponding to at least a part of the base sequence of the determinant 100). The tag 200 may specifically bind to a similar sequence similar to the target base sequence to prevent the determinant 100 from mismatch-binding to the similar sequence similar to the target base sequence.

In a specific example, when the tag 200 is 5'-GAACGC-CATC-3' (SEQ ID NO: 32), the determinant 100 is 5'-TACGAATGCCATC-3' (SEQ ID NO: 33), and a target base sequence to which the determinant 100 specifically binds is 3'-ATGCTTACGGTAG-5' (SEQ ID NO: 34), the tag 200 may specifically bind to 5'-CTTGCGGTAG-3' (SEQ ID NO: 35) in 5'-ATGCTTGCGGTAG-3' (SEQ ID NO: 36) which is a similar sequence similar to the target base sequence. As a result, the tag 200 may prevent mismatch binding of the determinant 100 to the similar sequence.

According to an exemplary embodiment of the present application, the tag 200 may include a 1 to 50-mer nucleic acid and/or nucleic acid analog. Preferably, the tag 200 includes a 5 to 30-mer nucleic acid and/or nucleic acid analog. Preferably, the tag 200 includes a 10 to 25-mer nucleic acid and/or nucleic acid analog. When the tag 200 includes at least a 15-mer or more nucleic acid and/or nucleic acid analog, compared to when the tag 200 includes a 10-mer or less nucleic acid and/or nucleic acid analog, the reactivity of the tag 200 with the similar sequence may be improved.

So far, in the nucleic acid complex 1 including a determinant 100 and a tag 200, the material, operation and example of each element (that is, the determinant 100 and the tag 200) have been explained in detail.

Hereinafter, the positional relationship between elements of the nucleic acid complex 1 including the determinant 100 and the tag 200 will be described in detail.

1.2 Positional Relationship Between Elements of Nucleic Acid Complex 1

FIG. 2 is a diagram illustrating the positional relationship between components of a nucleic acid complex 1 according to an exemplary embodiment of the present application.

The nucleic acid complex 1 according to an exemplary embodiment of the present application may include a determinant 100 and a tag 200. The determinant 100 and tag 200 of the nucleic acid complex 1 may have a predetermined positional relation.

According to an exemplary embodiment of the present application, the determinant 100 and the tag 200 may be connected. In other words, one end of the determinant 100 and one end of the tag 200 may be directly connected to each other.

One end of the determinant 100 and one end of the tag 200 may be connected based on a chemical binding force. One end of the determinant 100 and one end of the tag 200 may be connected based on at least one of a covalent bond, a hydrogen bond, an ionic bond and a hydrophobic bond. In one example, the determinant 100 and the tag 200 may be connected by a covalent bond.

In a specific example, the determinant 100 and the tag 200 may be connected in the form in which the 3' end of the tag 200 and the 5' end of the determinant 100 are directly connected (see FIG. 2(*a*)). When each of the determinant 100 and the tag 200 consists of a polymer of the unit molecule of DNA, the determinant 100 and the tag 200 may be connected by a covalent bond of a H group of a sugar at the 3' end of the tag 200 and a OH group of a phosphate group at the 5' end of the determinant 100.

In another specific example, the determinant 100 and the tag 200 may be connected in the form in which the 5' end of the tag 200 and the 3' end of the determinant 100 are directly connected (see FIG. 2(*b*)). When each of the determinant 100 and the tag 200 consists of a polymer of the unit molecule of DNA, the determinant 100 and the tag 200 may be connected by a covalent bond of a H group of a sugar at the 3' end of the determinant 100 and a OH group of a phosphate group at the 5' end of the tag 200.

According to another embodiment of the present application, the determinant 100 and the tag 200 may be connected by a separate material. In one example, one end of the determinant 100 and one end of the tag 200 may be connected by a specific compound. The positional relationship between elements of a nucleic acid complex 1 (described in 4.2 below) will be described in detail with reference to specific examples related thereto.

In the above, the nucleic acid complex 1 according to an exemplary embodiment of the present application was described. The nucleic acid complex 1 according to the first exemplary embodiment to be described below is the same as the above-described nucleic acid complex 1, except that it includes a label 300. Therefore, to explain the first exemplary embodiment, the same reference numerals are assigned to the components common to those of the above-described embodiment, and detailed description thereof will be omitted.

2. Nucleic Acid Complex 1 According to First Exemplary Embodiment 2.1 Configuration of Nucleic Acid Complex 1 According to First Exemplary Embodiment FIG. 3 is a diagram illustrating a nucleic acid complex 1 according to a first exemplary embodiment of the present application.

Figure 3:
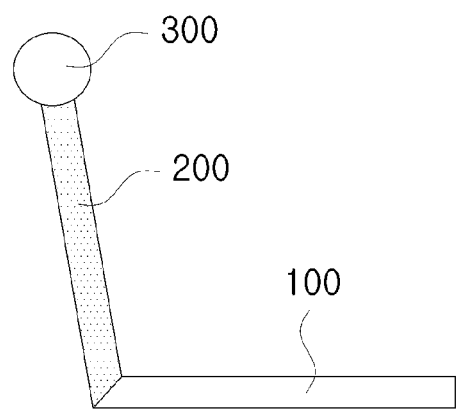
FIG. 3 is a diagram illustrating a nucleic acid complex 1 according to a first exemplary embodiment of the present application that includes a determinant 100, a tag 200 and a label 300.

As shown in FIG. 3, the nucleic acid complex 1 according to the first exemplary embodiment of the present application may include a determinant 100, a tag 200 and a label 300.

2.1.1 Label 300

2.1.1.1 Components of Label 300

2.1.1.1.1 Particle

According to an exemplary embodiment of the present application, the label 300 may include a small material having physical properties (e.g., size) and chemical properties (e.g., the change in chemical structure).

In one example, the label 300 may be a metal nanoparticle. The label 300 may include a transition metal, a post-transition metal, and/or a metalloid, or may be a particle with a size of several nanometers to several hundreds of nanometers (approximately $10^{-9}$ m).

In another example, the label 300 may be a magnetic nanoparticle. The label 300 may be a particle including an iron oxide ($Fe_2O_3$ or $Fe_3O_4$), ferrite (one Fe in $Fe_3O_4$ is changed to a different magnetic atom (e.g., $CoFe_2O_4$ or $MnFe_2O_4$)) and/or an alloy (alloyed with a noble metal for increased conductivity and stability and addressing oxidation problems caused by magnetic atoms, e.g., FePt or CoPt), and having a size of several nanometers to several hundreds of nanometers (approximately $10^{-9}$ m).

In still another example, the label 300 may be a latex bead. The label 300 may be a spherical polymer particle including an amorphous polymer (e.g., polystyrene), and having a colloidal size.

2.1.1.1.2 Energy Donor/Recipient

The label 300 may include particles donating energy. The label 300 may include particles accepting energy. The label 300 may include particles donating and accepting energy.

Energy donated from or accepted by the label 300 may include at least one of chemical energy, electrical energy, luminous energy and magnetic field energy.

According to an exemplary embodiment of the present application, the label 300 may include particles donating energy.

In one example, the label 300 may be a particle donating electron energy. In a specific example, the label 300 may be an oxidizing material that loses an electron.

In another example, the label 300 may be a particle donating fluorescence resonance energy. In a specific example, the label 300 may be a luminescent material. The label 300 may be a fluorescent molecule that emits light of its own wavelength when light is projected. As an example, the label 300 may be FAM, JOE, TET, HEX VIC, Oregon Green®, TAMRA, ROX, Cyanine-3, Cyanine-3.5, Cyanine-5, Cyanine-5.5, Aequorin or a cyan fluorescent protein (CFP).

According to an exemplary embodiment of the present application, the label 300 may include an energy-accepting particle.

In one example, the label 300 may be an electron energy-accepting particle. In a specific example, the label 300 may be a reducing material obtaining an electron.

In another example, the label 300 may be a particle accepting fluorescence resonance energy. In a specific example, the label 300 may be a quenching material. The label 300 may be a black hole quencher (BHQ). For example, the BHQ may be any one of Formulas 11 to 14 below.

[Formula 11]
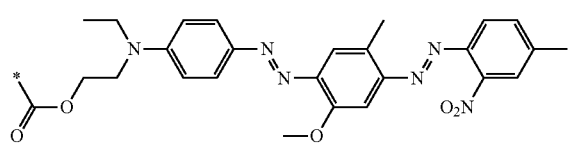

[Formula 12]
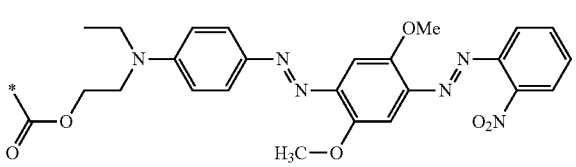

[Formula 13]
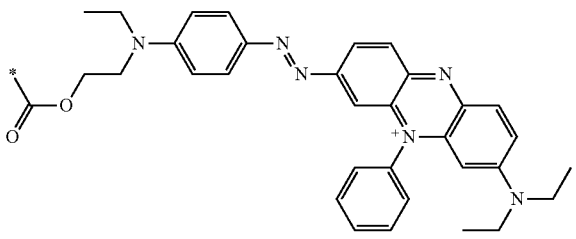

[Formula 14]
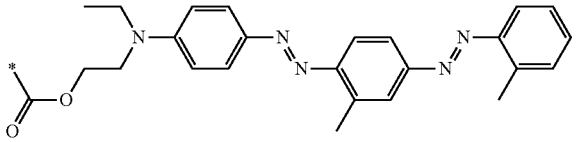

In another specific example, the label 300 may be a fluorescent conversion material. The label 300 may be a green fluorescent protein (GFP) emitting green fluorescence of 508 nm by accepting energy from Aequorin. Alternatively, the label 300 may be a yellow fluorescent protein (YFP) emitting yellow fluorescence of 535 nm by accepting energy from a cyan fluorescent protein (CFP).

So far, the materials constituting the label 300 have been described in detail. However, there are merely specific examples for helping in understanding the label 300 according to the present application and it does not mean that the label 300 should be construed as limited to including the material disclosed herein.

Hereinafter, an operation and examples of the label 300 according to an exemplary embodiment of the present application will be described in detail. According to the material characteristics of the label 300, which have been described above, and the operation and examples of the label 300, which will be described below, the definition and function of the label 300 will be understood in further detail.

2.1.1.2 Operation of Label 300

The label 300 according to an exemplary embodiment of the present application may be involved in labeling the nucleic acid complex 1. The label 300 may serve as a marker for confirming information on the nucleic acid complex 1. By confirming the information on the nucleic acid complex 1 including the label 300 according to the characteristics of the label 300, the nucleic acid complex 1 may be indicated by the label 300.

According to an exemplary embodiment of the present application, based on information on particles of the label 300 (e.g., the size, mobility, location, etc. of particles), the information on the nucleic acid complex 1 may be detected.

In a specific example, when the label 300 is a particle having physical properties, the presence or absence of the nucleic acid complex 1 may be confirmed depending on whether the label 300 is detected. In another specific example, when the label 300 is a particle having physical properties, the degree of aggregation of the nucleic acid complex 1 may be confirmed according to the position of the label 300. In still another specific example, when the label 300 is a particle having physical properties, according to the moving path of the label 300, whether the nucleic acid complex 1 moves or not and the information on the movement (e.g., speed) may be confirmed.

According to another exemplary embodiment of the present application, the information on the nucleic acid complex 1 including the label 300 may be detected in such a manner that at least one of chemical, electrical, optical and magnetic signals generated from the label 300 is detected.

In a specific example, when the label 300 is a material emitting energy, the presence or absence of the nucleic acid complex 1 and/or the distribution of the nucleic acid complex 1 may be confirmed based on the emitted energy (i.e., a signal).

In still another exemplary embodiment of the present application, the information on the nucleic acid complex 1 including the label 300 may be detected by detecting at least one of the chemical, electrical, optical and magnetic signals, which are generated by the label 300.

In a specific example, when the label 300 is a material accepting energy and emitting energy different from the accepted energy or a material absorbing energy, the information on the nucleic acid complex 1 may be confirmed according to the characteristics of the label 300 detected under a specific environmental condition.

2.1.1.3 Examples of Label 300

2.1.1.3.1 Gold Nanoparticles

A label 300 according to an exemplary embodiment of the present application may be a gold nanoparticle. The label 300 may be a particle including gold, and having a size of several nanometers to several hundreds of nanometers.

According to an exemplary embodiment of the present application, the nucleic acid complex 1 including the label 300 may be labeled in the manner in which the information on the particles of the label 300 (e.g., the size, mobility, location of particles, etc.) is detected.

In one example, the presence or absence of the label 300 may be confirmed depending on whether particles corresponding to the size of the label 300 are detected by an optical sensor or the like. Depending on whether the label 300 is detected, the presence or absence of the nucleic acid complex 1 may be confirmed.

In another example, by analyzing distribution by detecting the label 300, the degree of aggregation of the label 300 may be confirmed. According to the degree of the aggregation of the label 300, the degree of aggregation of the nucleic acid complex 1 may be confirmed.

In still another example, the movement of the nucleic acid complex 1 and the information thereof (e.g., speed) may be confirmed according to the moving path of the label 300.

According to another exemplary embodiment of the present application, the nucleic acid complex 1 including the label 300 may be labeled in the manner that information on the particle reactivity of the label 300 is detected.

In one example, by a method of analyzing a current detected according to applying a certain voltage to the label 300 (e.g., cyclic voltammetry), the presence or absence of particles of the label 300 may be confirmed. According to whether the label 300 is detected or not, the presence or absence of the nucleic acid complex 1 may be confirmed.

In another example, by a method of analyzing a current detected according to applying a certain voltage to the label 300 (e.g., cyclic voltammetry), the distribution of the label 300 may be confirmed. According to the distribution of the label 300, the distribution of the nucleic acid complex 1 may be confirmed.

2.1.1.3.2 Fluorescent Material

The label 300 according to an exemplary embodiment of the present application may be a fluorescent material. The label 300 may be a fluorescent molecule emitting light with a unique wavelength when the light is projected.

According to an exemplary embodiment of the present application, information on the nucleic acid complex 1 including the label 300 may be detected in the manner that at least one of the chemical, electrical, optical and magnetic signals generated from the label 300 is detected.

In one example, the presence or absence of particles of the label 300 may be confirmed by detecting an optical signal generated from the label 300. By detecting a signal in a specific wavelength band generated from the label 300, the presence or absence of the label 300 may be confirmed. By detecting whether a signal in a specific wavelength band generated from the label 300 exceeds a threshold, the presence or absence of particles of the label 300 may be confirmed. According to whether the label 300 is detected, the presence or absence of the nucleic acid complex 1 may be confirmed.

In another example, by detecting an optical signal generated from the label 300, distribution of the label may be confirmed. The distribution of the nucleic acid complex 1 may be confirmed according to the distribution of the label 300.

2.1.1.3.3 Quencher Material

The label 300 according to an exemplary embodiment of the present application may be a quencher material. The label 300 may be a quencher molecule absorbing energy, or maybe a material, when the energy in a specific wavelength band is projected, converting the projected energy in a specific wavelength band and emitting the converted energy.

According to an exemplary embodiment of the present application, at least one of the chemical, electrical, optical and magnetic signals generated by the label 300 may be detected, thereby detecting information on the nucleic acid complex 1 including the label 300.

In one example, by confirming whether the detected optical signal is affected by the label 300, the presence or absence of the label 300 may be confirmed. Compared to an optical signal generated from the label 300 before a specific environment condition (e.g., the input of the nucleic acid complex 1, etc.) is established, when an optical signal generated from the label 300 after a specific environment condition is established, the label 300 may be labeled based on whether there is a change or and/or the degree of change. According to labeling of the label 300, the nucleic acid complex 1 including the label 300 may be labeled.

So far, in the nucleic acid complex 1 including the determinant 100, the tag 200 and the label 300, the material, operation and example of each element (that is, the determinant 100, the tag 200 or the label 300) has been described in detail.

Hereinafter, the positional relationship between elements of the nucleic acid complex 1 including the determinant 100, the tag 200 and the label 300 will be described in detail.

2.2 Positional Relationship Between Elements of Nucleic Acid Complex 1

FIG. 4 is a diagram illustrating the positional relationship between components of a nucleic acid complex 1 according to an exemplary embodiment of the present application.

The nucleic acid complex 1 according to an exemplary embodiment of the present application may include a determinant 100, a tag 200 and a label 300. The determinant 100, the tag 200 and the label 300 of the nucleic acid complex 1 may have a predetermined positional relation.

According to an exemplary embodiment of the present application, the determinant 100, the tag 200 and the label 300 may be connected. The determinant 100, the tag 200 and the label 300 may be connected by a chemical binding force. The determinant 100, the tag 200 and the label 300 may be connected by at least one of a covalent bond, a hydrogen bond, an ionic bond, and a hydrophobic bond.

According to an exemplary embodiment of the present application, the tag 200 may be located between the determinant 100 and the label 300 (see FIG. 4(*a*)).

The determinant 100 may be connected to one end of the tag 200. One end of the determinant 100 may be connected to one end of the tag 200 by a chemical bond. One end of the determinant 100 may be directly connected with one end of the tag 200. Alternatively, one end of the tag 200 and one end of the determinant 100 may be connected by a specific compound.

The label 300 may be connected to the other end of the tag 200 (that is, an end different from one end of the tag 200). One end of the label 300 may be connected to the other end of the tag 200 by a chemical bond. The other end of the tag 200 and one end of the label 300 may be directly connected to each other. Alternatively, the other end of the tag 200 and one end of the label 300 may be connected by a specific compound.

According to an exemplary embodiment of the present application, in the nucleic acid complex 1 according to FIGS. 2(*a*) and 2(*b*), the label 300 may be further included, and the nucleic acid complex 1 which is configured such that the tag 200 is connected between the label 300 and the determinant 100 may be provided.

According to another exemplary embodiment of the present application, the label 300 may be located between the determinant 100 and the tag 200 (see FIG. 4(*b*)).

The determinant 100 may be connected to one end of the label 300. One end of the determinant 100 may be connected to one end of the label 300 by a chemical bond. One end of the label 300 and one end of the determinant 100 may be directly connected to each other. Alternatively, one end of the label 300 and one end of the determinant 100 may be connected by a specific compound.

The tag 200 may be connected to the other end (that is, an end different from one end of the label 300) of the label 300. One end of the tag 200 may be connected to the other end of the label 300 by a chemical bond. The other end of the label 300 and one end of the tag 200 may be directly connected to each other. The other end of the label 300 and one end of the tag 200 may be connected by a specific compound.

According to an exemplary embodiment of the present application, in the nucleic acid complex 1 of FIGS. 2(*a*) and 2(*b*), the label 300 may be further included, and the nucleic acid complex 1 which is configured such that the label 300 is connected between the determinant 100 and the tag 200 may be provided.

According to still another exemplary embodiment of the present application, the determinant 100 may be located between the tag 200 and the label 300 (see FIG. 4(*c*)).

The tag 200 may be connected to one end of the determinant 100. One end of the tag 200 may be connected to one end of the determinant 100 by a chemical bond. One end of the determinant 100 and one end of the tag 200 maybe directly connected to each other. Alternatively, one end of the determinant 100 and one end of the tag 200 may be connected by a specific compound.

The label 300 may be connected to the other end (that is, an end different from one end of the determinant 100) of the determinant 100. One end of the label 300 may be connected to the other end of the determinant 100 by a chemical bond. The other end of the determinant 100 and one end of the label 300 may be directly connected to each other. The other end of the determinant 100 and one end of the label 300 may be connected by a specific compound.

According to an exemplary embodiment of the present application, in the nucleic acid complex 1 according to FIGS. 2(*a*) and 2(*b*), the label 300 may be further included, and the nucleic acid complex 1 which is configured such that the determinant 100 is connected between the tag 200 and the label 300 may be provided.

In the above, the nucleic acid complex 1 according to the first exemplary embodiment of the present application has been described. A nucleic acid complex 1 according to a second exemplary embodiment to be described below is the same as that according to the first exemplary embodiment, except that it does not include a label 300, but further includes a linker 400. Therefore, to describe the second exemplary embodiment, components common to those of the above-described embodiment are denoted by the same reference numerals, and detailed description thereof will be omitted.

3. Nucleic Acid Complex 1 According to Second Exemplary Embodiment 3.1 Configuration of Nucleic Acid Complex 1 According to Second Exemplary Embodiment FIG. 5 is a diagram illustrating a nucleic acid complex 1 according to a second exemplary embodiment of the present application.

Figure 5:
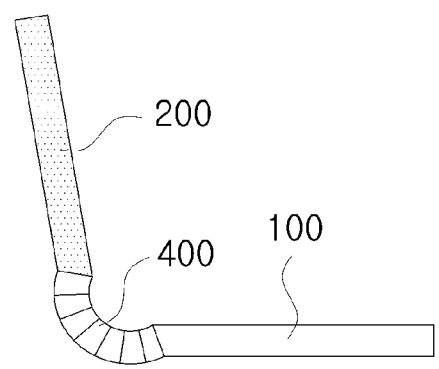
FIG. 5 is a diagram illustrating a nucleic acid complex 1 according to a second exemplary embodiment of the present application that includes a determinant 100, a tag 200 and a linker 400.

As shown in FIG. 5, the nucleic acid complex 1 according to an exemplary embodiment of the present application may include a determinant 100, a tag 200 and a linker 400.

3.1.1 Linker 400

3.1.1.1 Material of Linker 400

3.1.1.1.1 Compound

According to an exemplary embodiment of the present application, the linker 400 may be a compound including at least one of H, O, F, N, S, C and P. The linker 400 may have a predetermined length, and include a compound having at least one of H, O, F, N, S, C and P.

In one example, the linker 400 may include a carbon having at least one single bond. In a specific example, the linker 400 may include a compound of Formula 15 below. As an example, the linker 400 may be hexaethylene glycol.

[Formula 15]

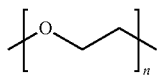

In another example, the linker 400 may include a carbon having a resonance structure. Alternatively, the linker 400 may include a carbon having at least one double bond. In a specific example, the linker 400 may include a basic Furan. For example, the linker 400 may include a compound of Formula 16 below.

[Formula 16]

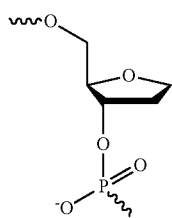

3.1.1.1.2 Nucleic Acid and/or Nucleic Acid Analog

According to an exemplary embodiment of the present application, the linker 400 may include a nucleic acid analog and/or a modified nucleic acid. The linker 400 may include the unit molecule of a modified nucleic acid. The linker 400 may include the unit molecule of a nucleic acid analog. The linker 400 may include the unit molecule of a modified nucleic acid and the unit molecule of a nucleic acid analog.

3.1.1.1.2.1 Unit Molecule of Modified Nucleic Acid

The linker 400 may include the unit molecule of the modified nucleic acid.

In one example, the unit molecule of the modified nucleic acid may be a molecule in which at least a part of the structure of the base of the unit molecule of DNA which is a nucleic acid is modified.

In another example, the unit molecule of the modified nucleic acid may be a molecule in which at least a part of the structure of the base of the unit molecule of RNA which is a nucleic acid is modified.

According to an exemplary embodiment of the present application, the linker 400 may include the unit molecule of the modified nucleic acid.

In one example, the linker 400 may consist of the unit molecule of the modified nucleic acid. In a specific example, the linker 400 may consist of the unit molecule of RNA in which a part of the base is modified.

In another example, the linker 400 may consist of a polymer of the unit molecule of the modified nucleic acid. In a specific example, the linker 400 may consist of a polymer of the unit molecule of DNA in which the base is completely modified.

According to another exemplary embodiment of the present application, the linker 400 may include the unit molecule of a first modified nucleic acid and the unit molecule of a second modified nucleic acid. The linker 400 may include at least a first modified nucleic acid and a second modified nucleic acid.

The first modified nucleic acid and the second modified nucleic acid, which are included in the linker 400, may be directly connected to each other. In other words, the linker 400 may be provided in the form in which one end of the unit molecule (or a polymer of the unit molecule) of the first modified nucleic acid and one end of the unit molecule (or a polymer of the unit molecule) of the second modified nucleic acid are directly connected.

The first modified nucleic acid and the second modified nucleic acid, which are included in the linker 400, may be connected by a specific compound. In other words, the linker 400 may be provided in the form in which one end of the unit molecule (or a polymer of the unit molecule) of the first modified nucleic acid and one end of the unit molecule (or a polymer of the unit molecule) of the second modified nucleic acid are connected by a specific compound.

In one example, the linker 400 may be configured in the form in which the unit molecule of the first modified nucleic acid and the unit molecule of the second modified nucleic acid are connected. In a specific example, the linker 400 may be configured in the form in which the unit molecule of DNA in which at least a part of the base is modified and the unit molecule of RNA in which at least a part of the base is modified are connected. Alternatively, the linker 400 may be configured in the form in which the unit molecule of RNA in which at least a part of the base is modified and the unit molecule of RNA in which at least a part of the base is modified are connected by a specific compound.

In another example, the linker 400 may be configured in the form in which a polymer of the unit molecule of the first modified nucleic acid and the unit molecule of the second modified nucleic acid are connected. In a specific example, the linker 400 may be configured in the form in which a polymer of the unit molecule of DNA in which at least a part of the base is modified and the unit molecule of RNA in which at least a part of the base is modified are connected. Alternatively, the linker 400 may be configured in the form in which a polymer of the unit molecule of DNA in which at least a part of the base is modified and the unit molecule of DNA in which at least a part of the base is modified are connected by a specific compound.

In still another example, the linker 400 may be configured in the form in which a polymer of the unit molecule of the first modified nucleic acid and a polymer of the unit molecule of the second modified nucleic acid are connected. In a specific example, the linker 400 may be configured in the form in which a polymer of the unit molecule of DNA in which at least a part of the base is modified and a polymer of the unit molecule of RNA in which at least a part of the base is modified are connected. Alternatively, the linker 400 may be configured in the form in which a polymer of the unit molecule of RNA in which at least a part of the base is modified and a polymer of the unit molecule of RNA in which at least a part of the base is modified are connected by a specific compound.

3.1.1.1.2.2 Unit Molecule of a Nucleic Acid Analog

The linker 400 may include the unit molecule of a nucleic acid analog.

In one example, the linker 400 may include the unit molecule of PNA which is a nucleic acid analog. The unit molecule of PNA may be a material represented by Formula 3 shown above.

In another example, the linker 400 may include the unit molecule of LNA which is a nucleic acid analog. The unit molecule of LNA may be a material represented by Formula 4 shown above.

In still another example, the linker 400 may include the unit molecule of BNA which is a nucleic acid analog. The unit molecule of BNA may be a material represented by Formula 5 shown above.

In yet another example, the linker 400 may include the unit molecule of HNA which is a nucleic acid analog. The unit molecule of HNA may be a material represented by Formula 6 shown above.

In yet another example, the linker 400 may include the unit molecule of GNA which is a nucleic acid analog. The unit molecule of GNA may be a material represented by Formula 7 shown above.

In yet another example, the linker 400 may include the unit molecule of TNA which is a nucleic acid analog. The unit molecule of TNA may be a material represented by Formula 8 shown above.

In yet another example, the linker 400 may include the unit molecule of CeNA which is a nucleic acid analog. The unit molecule of CeNA may be a material represented by Formula 9 shown above.

According to an exemplary embodiment of the present application, the linker 400 may include the unit molecule of a nucleic acid analog.

In one example, the linker 400 may consist of the unit molecule of a nucleic acid analog. In a specific example, the linker 400 may consist of the unit molecule of LNA.

In another example, the linker 400 may consist of a polymer of the unit molecule of a nucleic acid analog. In a specific example, the linker 400 may consist of a polymer of the unit molecule of PNA.

According to another exemplary embodiment of the present application, the linker 400 may include the unit molecule of a first nucleic acid analog and the unit molecule of a second nucleic acid analog. The linker 400 may include at least a first nucleic acid analog and a second nucleic acid analog.

The first nucleic acid analog and the second nucleic acid analog, which are included in the linker 400, may be directly connected to each other. In other words, the linker 400 may be provided in the form in which one end of the unit molecule (or a polymer of the unit molecule) of the first nucleic acid analog and one end of the unit molecule (or a polymer of the unit molecule) of the second nucleic acid analog are directly connected.

The first nucleic acid analog and the second nucleic acid analog, which are included in the linker 400, may be connected by a specific compound. In other words, the linker 400 may be provided in the form in which one end of the unit molecule (or a polymer of the unit molecule) of the first nucleic acid analog and one end of the unit molecule (or a polymer of the unit molecule) of the second nucleic acid analog are connected by a specific compound.

In one example, the linker 400 may be configured in the form in which the unit molecule of the first nucleic acid analog and the unit molecule of the second nucleic acid analog are connected. In a specific example, the linker 400 may be configured in the form in which the unit molecule of PNA and the unit molecule of LNA are connected.

In another example, the linker 400 may be configured in the form in which a polymer of the unit molecule of the first nucleic acid analog and the unit molecule of the second nucleic acid analog are connected. In a specific example, the linker 400 may be configured in which a polymer of the unit molecule of TNA and the unit molecule of GNA are connected. Alternatively, the linker 400 may be configured in the form in which a polymer of the unit molecule of CeNA and the unit molecule of CeNA are connected by a specific compound.

In still another example, the linker 400 may be configured in the form in which a polymer of the unit molecule of the first nucleic acid analog and a polymer of the unit molecule of the second nucleic acid analog are connected. In a specific example, the linker 400 may be configured in the form in which a polymer of the unit molecule of BNA and a polymer of the unit molecule of HNA are connected. Alternatively, the linker 400 may be configured in the form in which a polymer of the unit molecule of LNA and a polymer of the unit molecule of LNA are connected by a specific compound.

3.1.1.1.2.3 Combination of Unit Molecule of Nucleic Acid Analog and Unit Molecule of Modified Nucleic Acid According to an exemplary embodiment of the present application, the linker 400 may include the unit molecule of a nucleic acid analog and the unit molecule of a modified nucleic acid. The linker 400 may include at least a first nucleic acid analog and a first modified nucleic acid.

The first nucleic acid analog and the first modified nucleic acid, which are included in the linker 400, may be directly connected to each other. In other words, the linker 400 may be provided in the form in which one end of the unit molecule (or a polymer of the unit molecule) of the first nucleic acid analog and one end of the unit molecule (or a polymer of the unit molecule) of the first modified nucleic acid are directly connected.

The first nucleic acid analog and the first modified nucleic acid, which are included in the linker 400, may be connected by a specific compound. In other words, the linker 400 may be provided in the form in which one end of the unit molecule (or a polymer of the unit molecule) of the first nucleic acid analog and one end of the unit molecule (or a polymer of the unit molecule) of the first modified nucleic acid are connected by a specific compound.

In one example, the linker 400 may be configured in the form in which the unit molecule of a nucleic acid analog and the unit molecule of a modified nucleic acid are connected. In a specific example, the linker 400 may be configured in the form in which the unit molecule of DNA in which at least a part of the base is modified, and the unit molecule of LNA are connected.

In another example, the linker 400 may be configured in the form in which a polymer of the unit molecule of a nucleic acid analog and the unit molecule of the modified nucleic acid are connected. In a specific example, the linker 400 may be configured in the form in which the unit molecule of RNA in which at least a part of the base is modified, and a polymer of the unit molecule of PNA are connected.

In still another example, the linker 400 may be configured in the form in which a polymer of the unit molecule of the modified nucleic acid and the unit molecule of a nucleic acid analog are connected. In a specific example, the linker 400 may be configured in the form in which a polymer of the unit molecule of DNA in which at least a part of the base is modified, and the unit molecule of GNA are connected.

In yet another example, the linker 400 may be configured in the form in which a polymer of the unit molecule of a nucleic acid analog and a polymer of the unit molecule of the modified nucleic acid are connected. In a specific example, the linker 400 may be configured in the form in which a polymer of the unit molecule of RNA in which at least a part of the base is modified, and a polymer of the unit molecule of CeNA are connected.

So far, the materials for constituting the linker 400 and the configuration thereof have been described in detail. However, specific embodiments are merely provided to help in understanding the linker 400 according to the present application and it does not mean that the linker 400 should be construed as limited to including the material disclosed herein.

In other words, it may be construed that the linker 400 includes a compound that has not been disclosed herein.

In addition, it may be construed that the linker 400 includes the unit molecule of a nucleic acid analog, which has not been disclosed herein. Here, the unit molecule of a nucleic acid analog may include a base, and have a form in which at least a part of the materials except the base is chemically modified, compared to a nucleotide.

In addition, it may be construed that the linker 400 includes a material in which at least one of Formulas 1 to 10 and 15 and 16 is chemically modified in a range in which the linker 400 can be easily designed or modified by one of ordinary skill in the art.

The operation and examples of the linker 400 according to an exemplary embodiment of the present application will be described in detail below. According to the material characteristics of the linker 400 described above and the operation and examples of the linker 400 which will be described, the definition and function of the linker 400 will be understood more specifically.

3.1.1.2 Operation of Linker 400

According to an exemplary embodiment of the present application, the linker 400 may be used to connect the determinant 100 with the tag 200. The linker 400 may be disposed between the determinant 100 and the tag 200. The determinant 100 and the tag 200 may be connected by the linker 400.

The linker 400 may directly bind to one end of the determinant 100, or may be connected by a specific compound. The linker 400 may be connected with one end of the determinant 100 based on a chemical binding force. The linker 400 may be connected with one end of the determinant 100 based on at least one of a covalent bond, a hydrogen bond, an ionic bond and a hydrophobic bond.

The linker 400 may directly bind to one end of the tag 200, or may be connected by a specific compound. The linker 400 may be connected with one end of the tag 200 by a chemical binding force. The linker 400 may be connected with one end of the tag 200 based on at least one of a covalent bond, a hydrogen bond, an ionic bond and a hydrophobic bond.

According to an exemplary embodiment of the present application, the linker 400 may serve to space the determinant 100 from the tag 200. The linker 400 may serve to space one end of the determinant 100 from one end of the tag 200.

According to an exemplary embodiment of the present application, when the nucleic acid complex 1 is used in PCR, the linker 400 may space the determinant 100 from the tag 200 to block reading of the base sequence of the tag 200 by a DNA polymerase reading the base sequence of the determinant 100. This will be described in further detail in 3.1.1.3.1 (blocker for PCR) below.

3.1.1.3 Examples of Linker 400

3.1.1.3.1 Blocker for PCR

The linker 400 according to an exemplary embodiment of the present application may be a blocker for PCR.

The blocker for PCR may block information in one region connected with the blocker for PCR from being acquired by a different material (e.g., DNA polymerase). The blocker for PCR may prevent the production of an amplification product for the base sequence in any one region connected with the blocker for PCR. The blocker for PCR may prevent a DNA polymerase from acquiring information in any one region connected with the blocker for PCR.

Unless particularly defined otherwise, the "amplification product" used herein may be a material produced as a result of at least one cycle of PCR. The "amplification product" used herein may be a material produced by connecting at least two nucleotides by a covalent bond through PCR.

Unless particularly defined otherwise, the "amplification product for A" used herein may be a material produced to have a base sequence complementary to the base sequence of A. The "amplification product for A" used herein may be a nucleotide or polynucleotide produced to have a base sequence complementary to the base sequence of A. The polynucleotide may be produced by elongation in such a manner that a H group of the sugar of at least one nucleotide reacts with an OH group in a phosphate group of another nucleotide to form a covalent bond.

The linker 400 may prevent the production of an amplification product of the determinant 100 connected with the linker 400. In addition, the linker 400 may prevent the production of an amplification product of the tag 200 connected with the linker 400.

According to an exemplary embodiment of the present application, the linker 400 may have a predetermined length.

In one example, the linker 400 may be formed in a length exceeding at least 1 Å. Preferably, the linker 400 is formed in a length exceeding at least 3.4 Å. Preferably, the linker 400 is formed in a length exceeding at least 5 Å.

In another example, the linker 400 may be formed in a length exceeding at least one mer. Preferably, the linker 400 is formed in a length exceeding at least 3 mer. Preferably, the linker 400 is formed in a length exceeding at least 5 mer.

In a specific example, the linker 400 may include the unit molecule of a nucleic acid from which the base is removed. The linker 400 may be a polymer of the unit molecule of DNA from which the base is removed. The linker 400 may be a polymer of the unit molecule of RNA from which the base is removed.

In another specific example, the linker 400 may include the unit molecule of a nucleic acid in which the base is modified. The linker 400 may be a polymer of the unit molecule of DNA in which the base is modified. The linker 400 may be a polymer of the unit molecule of RNA in which the base is modified.

In still another specific example, the linker 400 may include the unit molecule of a nucleic acid analog. The linker 400 may be a polymer of the unit molecule of PNA. The linker 400 may be a polymer of the unit molecule of LNA.

In yet another specific example, the linker 400 may be a chain structure including a carbon. In a specific example, the linker 400 may be polyethylene glycol (PEG).

So far, in the nucleic acid complex 1 including the determinant 100, the tag 200 and the linker 400, the materials, operation and examples of each component (that is, the determinant 100, the tag 200 and the linker 400) have been described in detail.

Hereinafter, the positional relationship between components of the nucleic acid complex 1 including the determinant 100, the tag 200 and the linker 400 will be described in detail.

3.2 Positional Relationship Between Components of Nucleic Acid Complex 1

Figure 6:
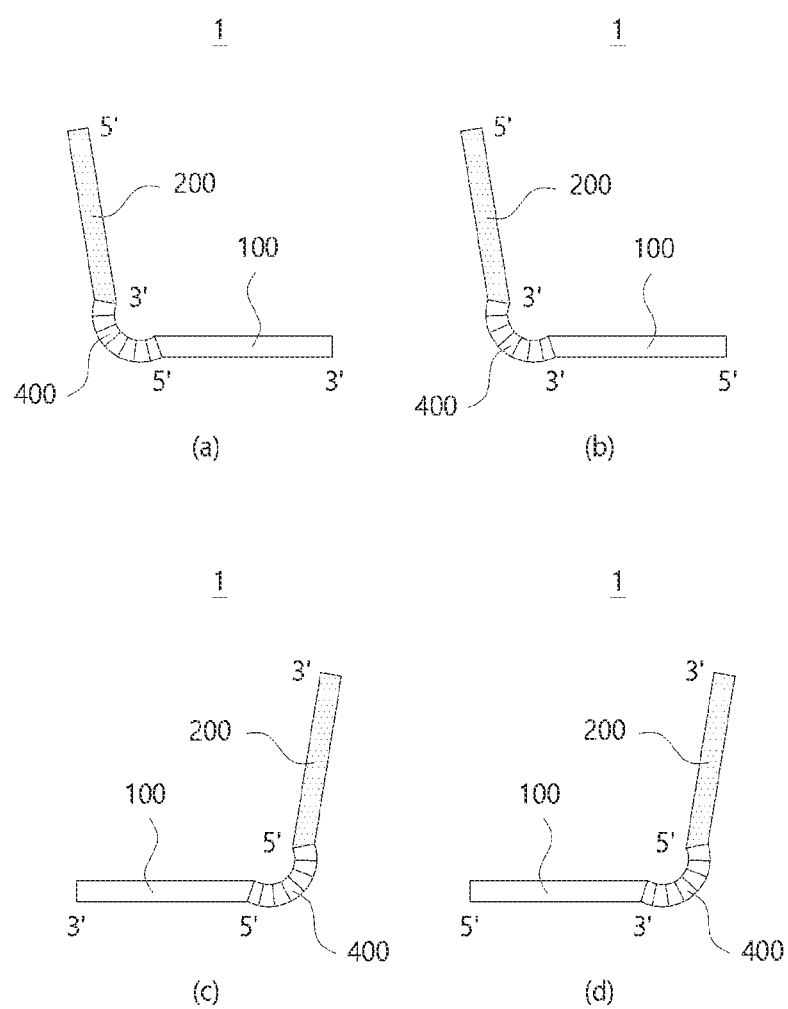
FIG. 6 is a diagram illustrating a positional relationship between the determinant 100, the tag 200 and the linker 400 of a nucleic acid complex 1 according to an exemplary embodiment of the present application in which the linker 400 is located between the label 300 and the determinant 100.

FIG. 6 is a diagram illustrating the positional relationship between components of a nucleic acid complex 1 according to an exemplary embodiment of the present application.

The nucleic acid complex 1 according to an exemplary embodiment of the present application may include the determinant 100, the tag 200 and the linker 400. The determinant 100, the tag 200 and the linker 400 of the nucleic acid complex 1 may have a predetermined positional relationship.

According to an exemplary embodiment of the present application, the determinant 100, the tag 200 and the linker 400 may be connected. A side of the linker 400 connected with the determinant 100 may be different from a side of the linker 400 connected with the tag 200. The linker 400 may be located between the determinant 100 and the tag 200.

One end of the determinant 100 and one end of the linker 400 may be directly connected, or connected by a specific compound. One end of the tag 200 and the other end of the linker 400 (an end different from one end of the linker 400) may be directly connected, or connected by a specific compound.

In one example, one end of the determinant 100 may be directly connected to one end of the linker 400 by a chemical bond, and one end of the tag 200 may be directly connected to the other end of the linker 400 by a chemical bond.

In another example, one end of the linker 400 may be directly connected with one end of the determinant 100, and the other end of the linker 400 may be connected with one end of the tag 200 by a specific compound.

In still another example, one end of the linker 400 may be connected with one end of the determinant 100 by a specific compound, and the other end of the linker 400 may be directly connected with one end of the tag 200.

In yet another example, one end of the linker 400 may be connected with one end of the determinant 100 by a specific compound, and the other end of the linker 400 may be connected with one end of the tag 200 by a specific compound.

In a specific example, the determinant 100, the tag 200 and the linker 400 may be connected in such a manner that the 3' end of the tag 200 is connected with one end of the linker 400, and the other end of the linker 400 (an end different from one end of the linker 400) is connected with the 5' end of the determinant 100 (see FIG. 6(a)).

In another specific example, the determinant 100, the tag 200 and the linker 400 may be connected in such a manner that the 3' end of the tag 200 and one end of the linker 400 are connected, and the other end of the linker 400 is connected with the 3' end of the determinant 100 (see FIG. 6(b)).

In still another specific example, the determinant 100, the tag 200 and the linker 400 may be connected in such a manner that the 5' end of the tag 200 and one end of the linker 400 are connected, and the other end of the linker 400 is connected with the 5' end of the determinant 100 (see FIG. 6(c)).

In yet another specific example, the determinant 100, the tag 200 and the linker 400 may be connected in such a manner that the 5' end of the tag 200 and one end of the linker 400 are connected, and the other end of the linker 400 is connected with the 3' end of the determinant 100 (see FIG. 6(d)).

In the above, the nucleic acid complex 1 according to the second exemplary embodiment of the present application has been described above. A nucleic acid complex 1 according to a third exemplary embodiment to be described below is the same as the above-described nucleic acid complex 1, except that a label 300 is further included. Therefore, in the description of the third exemplary embodiment, components common to those in the above-described exemplary embodiment are denoted by like reference numerals, and detailed description thereof is omitted.

4. Nucleic Acid Complex 1 According to Third Exemplary Embodiment

Figure 7:
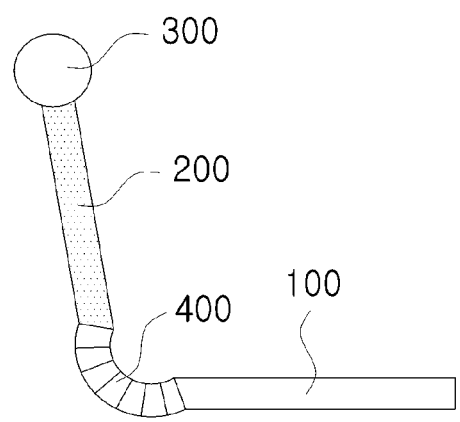
FIG. 7 is a diagram illustrating a nucleic acid complex 1 according to a third exemplary embodiment of the present application that includes a determinant 100, a tag 200, a label 300 and a linker 400.

4.1 Configuration of Nucleic Acid Complex 1 According to Third Exemplary Embodiment FIG. 7 is a diagram illustrating a nucleic acid complex 1 according to the third exemplary embodiment of the present application.

As shown in FIG. 7, the nucleic acid complex 1 according to an exemplary embodiment of the present application may include a determinant 100, a tag 200, a label 300 and a linker 400.

4.2 Positional Relationship Between Components of Nucleic Acid Complex 1

FIG. 8 is a diagram illustrating the positional relationship between components of a nucleic acid complex 1 according to an exemplary embodiment of the present application.

The nucleic acid complex 1 according to an exemplary embodiment of the present application may include a determinant 100, a tag 200, a label 300 and a linker 400. The determinant 100, the tag 200, the label 300 and the linker 400 may be connected by a chemical binding force. The determinant 100, the tag 200, the label 300 and the linker 400 may be connected based on at least one of a covalent bond, a hydrogen bond, an ionic bond and a hydrophobic bond.

The determinant 100, the tag 200, the label 300 and the linker 400 of the nucleic acid complex 1 may have a predetermined positional relationship.

According to an exemplary embodiment of the present application, a nucleic acid complex 1 in which the label 300, the tag 200, the linker 400 and the determinant 100 are sequentially connected may be provided (see FIG. 8(a)).

The label 300 may be connected to one end of the tag 200. One end of the label 300 may be connected to one end of the tag 200 by a chemical bond. One end of the tag 200 and one end of the label 300 may be directly connected to each other. Alternatively, one end of the tag 200 and one end of the label 300 may be connected by a specific compound.

The linker 400 may be connected to the other end of the tag 200 (that is, an end different from one end of the tag 200). One end of the linker 400 may be connected to the other end of the tag 200 by a chemical bond. The other end of the tag 200 and one end of the linker 400 may be directly connected to each other. Alternatively, the other end of the tag 200 and one end of the linker 400 may be connected by a specific compound.

The determinant 100 may be connected to the other end of the linker 400 (that is, an end different from one end of the linker 400). One end of the determinant 100 may be connected to the other end of the linker 400 by a chemical bond. The other end of the linker 400 and one end of the determinant 100 may be directly connected to each other. Alternatively, the other end of the linker 400 and one end of the determinant 100 may be connected by a specific compound.

According to an exemplary embodiment of the present application, a nucleic acid complex 1 like the nucleic acid complex 1 according to FIGS. 6(a) to 6(d) but further including a label 300 and configured such that a label 300, a tag 200, a linker 400 and a determinant 100 are sequentially connected may be provided.

According to an exemplary embodiment of the present application, a nucleic acid complex 1 in which a tag 200, a label 300, a linker 400 and a determinant 100 are sequentially connected may be provided (see FIG. 8(b)).

The tag 200 may be connected to one end of the label 300. One end of the tag 200 may be connected to one end of the label 300 by a chemical bond. One end of the label 300 and one end of the tag 200 may be directly connected to each other. Alternatively, one end of the label 300 and one end of the tag 200 may be connected by a specific compound.

The linker 400 may be connected to the other end (that is, an end different from one end of the label 300) of the label 300. One end of the linker 400 may be connected to the other end of the label 300 by a chemical bond. The other end of the label 300 and one end of the linker 400 may be directly connected to each other. Alternatively, the other end of the label 300 and one end of the linker 400 may be connected by a specific compound.

The determinant 100 may be connected to the other end (that is, an end different from one end of the linker 400) of the linker 400. One end of the determinant 100 may be connected to the other end of the linker 400 by a chemical bond. The other end of the linker 400 and one end of the determinant 100 may be directly connected to each other. Alternatively, the other end of the linker 400 and one end of the determinant 100 may be connected by a specific compound.

According to an exemplary embodiment of the present application, a nucleic acid complex 1 like the nucleic acid complex 1 according to FIGS. 6(a) to 6(d) but further including a label 300 and configured such that a tag 200, a label 300, a linker 400 and a determinant 100 are sequentially connected may be provided.

According to an exemplary embodiment of the present application, a nucleic acid complex 1 in which a tag 200, a linker 400, a label 300 and a determinant 100 are sequentially connected may be provided (see FIG. 8(c)).

The tag 200 may be connected to one end of the linker 400. One end of the tag 200 may be connected to one end of the linker 400 by a chemical bond. One end of the linker 400 and one end of the tag 200 may be directly connected to each other. Alternatively, one end of the linker 400 and one end of the tag 200 may be connected by a specific compound.

The label 300 may be connected to the other end (that is, an end different from one end of the linker 400) of the linker 400. One end of the label 300 may be connected to the other end of the linker 400 by a chemical bond. The other end of the linker 400 and one end of the label 300 may be directly connected to each other. Alternatively, the other end of the linker 400 and one end of the label 300 may be connected by a specific compound.

The determinant 100 may be connected to the other end (that is, an end different from one end of the label 300) of the label 300. One end of the determinant 100 may be connected to the other end of the label 300 by a chemical bond. The other end of the label 300 and one end of the determinant 100 may be directly connected to each other. Alternatively, the other end of the label 300 and one end of the determinant 100 may be connected by a specific compound.

According to an exemplary embodiment of the present application, a nucleic acid complex 1 like the nucleic acid complex 1 according to FIGS. 6(a) to 6(d) but further including a label 300 and configured such that a tag 200, a linker 400, a label 300 and a determinant 100 are sequentially connected may be provided.

According to an exemplary embodiment of the present application, a nucleic acid complex 1 in which a tag 200, a linker 400, a determinant 100 and a label 300 are sequentially connected may be provided (see FIG. 8(d)).

The tag 200 may be connected to one end of the linker 400. One end of the tag 200 may be connected to one end of the linker 400 by a chemical bond. One end of the linker 400 and one end of the tag 200 may be directly connected to each other. Alternatively, one end of the linker 400 and one end of the tag 200 may be connected by a specific compound.

The determinant 100 may be connected to the other end (that is, an end different from one end of the linker 400) of the linker 400. One end of the determinant 100 may be connected to the other end of the linker 400 by a chemical bond. The other end of the linker 400 and one end of the determinant 100 may be directly connected to each other. Alternatively, the other end of the linker 400 and one end of the determinant 100 may be connected by a specific compound.

The label 300 may be connected to the other end (that is, an end different from one end of the determinant 100) of the determinant 100. One end of the label 300 may be connected to the other end of the determinant 100 by a chemical bond. The other end of the determinant 100 and one end of the label 300 may be directly connected to each other. Alternatively, the other end of the determinant 100 and one end of the label 300 may be connected by a specific compound.

According to an exemplary embodiment of the present application, a nucleic acid complex 1 like the nucleic acid complex 1 according to FIGS. 6(a) to 6(d) but further including a label 300 and configured such that a tag 200, a linker 400, a determinant 100 and a label 300 are sequentially connected may be provided.

So far, the nucleic acid complexes 1 according to several exemplary embodiments of the present application have been described in detail. However, the nucleic acid complex 1 according to the present application may be embodied as a form excluding one of the above-described components, further including a separate component, having a plurality of specific components, and/or some modified elements.

Therefore, to construe the scope of the present application, the scope according to the present application should be determined according to the basic principles of interpreting the terms and claims described in the scope and should not be construed as limited to the configuration and form disclosed herein.

Hereinafter, the configuration and operation of a nucleic acid complex pair 10 including at least two nucleic acid complexes 1 will be described in detail.

<Nucleic Acid Complex Pair 10>

1. Configuration of Nucleic Acid Complex Pair 10

Figure 9:
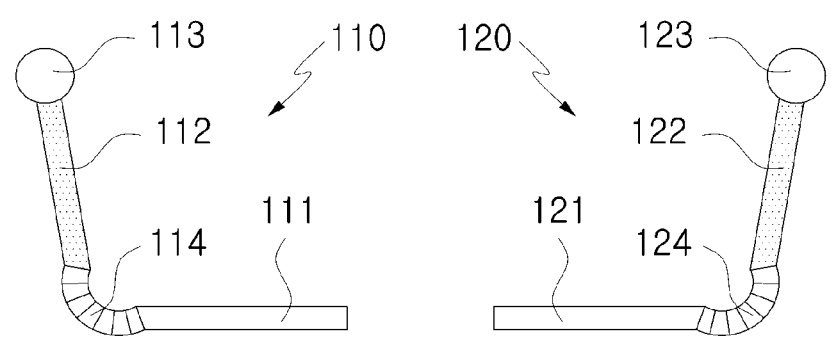
FIG. 9 is a diagram illustrating a nucleic acid complex pair 10 according to an exemplary embodiment of the present application that includes a first nucleic acid complex 110 including a first determinant 111, a first tag 112, a first label 113 and a first linker 114 and a second nucleic acid complex 120 including a second determinant 121, a second tag 122, a second label 123 and a second linker 124.

FIG. 9 is a diagram illustrating a nucleic acid complex pair 10 according to an exemplary embodiment of the present application.

The nucleic acid complex pair 10 according to an exemplary embodiment of the present application may include at least a first nucleic acid complex 110 and a second nucleic acid complex 120. The nucleic acid complex pair 10 may consist of a first nucleic acid complex 110 and a second nucleic acid complex 120. The nucleic acid complex pair 10 may be provided with a pair of the first nucleic acid complex 110 and the second nucleic acid complex 120.

The first nucleic acid complex 110 may be any one of the nucleic acid complexes 1 according to exemplary embodiments of the present application. The first nucleic acid complex 110 may include at least one component of a first determinant 111, a first tag 112, a first linker 114 and a first label 113. In one example, the first nucleic acid complex 110 may include a first determinant 111, a first tag 112, a first label 113 and a first linker 114. In another example, the first nucleic acid complex 110 may include a first determinant 111, a first tag 112 and a first label 113. In still another example, the first nucleic acid complex 110 may include a first determinant 111, a first tag 112 and a first linker 114. In yet another example, the first nucleic acid complex 110 may include a first determinant 111 and a first tag 112.

The second nucleic acid complex 120 may be any one of the nucleic acid complexes 1 according to exemplary embodiments of the present application. The second nucleic acid complex 120 may include at least one component of a second determinant 121, a second tag 122, a second linker 124 and a second label 123. In one example, the second nucleic acid complex 120 may include a second determinant 121, a second tag 122, a second label 123 and a second linker 124. In another example, the second nucleic acid complex 120 may include a second determinant 121, a second tag 122 and a second label 123. In still another example, the second nucleic acid complex 120 may include a second determinant 121, a second tag 122 and a second linker 124. In yet another example, the second nucleic acid complex 120 may include a second determinant 121 and a second tag 122.

Components of First Nucleic Acid Complex 110 and Second Nucleic Acid Complex 120

According to an exemplary embodiment of the present application, the first nucleic acid complex 110 may consist of the same components as the second nucleic acid complex 120.

In one example, when the first nucleic acid complex 110 consists of a first determinant 111 and a first tag 112, the second nucleic acid complex 120 may also consist of a second determinant 121 and a second tag 122.

In another example, when the first nucleic acid complex 110 consists of a first determinant 111, a first tag 112, a first label 113 and a first linker 114, the second nucleic acid complex 120 may also consist of a second determinant 121, a second tag 122, a second label 123 and a second linker 124.

According to another exemplary embodiment of the present application, the first nucleic acid complex 110 may consist of components different from those of the second nucleic acid complex 120.

In one example, when the first nucleic acid complex 110 consists of a first determinant 111, a first tag 112 and a first label 113, the second nucleic acid complex 120 may consist of a second determinant 121 and a second tag 122.

In another example, when the first nucleic acid complex 110 consists of a first determinant 111, a first tag 112 and a first linker 114, the second nucleic acid complex 120 may consist of a second determinant 121, a second tag 122, a second label 123 and a second linker 124.

1.1 Positional Relationship Between Components of First Nucleic Acid Complex 110 and Second Nucleic Acid Complex 120

According to an exemplary embodiment of the present application, the positional relationship between components of the first nucleic acid complex 110 may be the same as that of the second nucleic acid complex 120.

In one example, when the first nucleic acid complex 110 and the second nucleic acid complex 120 consist of the same components, the positional relationship between components of the first nucleic acid complex 110 may be the same as that of the second nucleic acid complex 120.

In a specific example, when the first nucleic acid complex 110 and the second nucleic acid complex 120 include a determinant 100, a tag 200 and a label 300, the first nucleic acid complex 110 and the second nucleic acid complex 120 may each have a form in which the determinant 100, the tag 200 and the label 300 are sequentially connected.

According to another exemplary embodiment of the present application, the positional relationship between components of the first nucleic acid complex 110 may be different from that of the second nucleic acid complex 120.

In one example, since the first nucleic acid complex 110 and the second nucleic acid complex 120 partly differ in constituent components, the positional relationship between components of the first nucleic acid complex 110 may be different from that of the second nucleic acid complex 120.

In a specific example, when the first nucleic acid complex 110 includes a first determinant 111, a first tag 112, a first label 113 and a first linker 114, and the second nucleic acid complex 120 includes a second determinant 121, a second tag 122 and a second label 123, the first nucleic acid complex 110 may have a form in which a first determinant 111, a first linker 114, a first tag 112 and a first label 113 are sequentially connected, and the second nucleic acid complex 120 may have a form in which second determinant 121, a second tag 122, and a second label 123 are sequentially connected.

In another example, when the first nucleic acid complex 110 has the same constituent components as the second nucleic acid complex 120, the positional relationship between components of the first nucleic acid complex 110 may be different from that of the second nucleic acid complex 120.

In a specific example, when the first nucleic acid complex 110 and the second nucleic acid complex 120 include a determinant 100, a tag 200, a label 300 and a linker 400, the first nucleic acid complex 110 may have a form in which a determinant 100, a linker 400, a tag 200 and a label 300 are sequentially connected, and the second nucleic acid complex 120 may have a form in which a determinant 100, a label 300, a linker 400 and a tag 200 are sequentially connected.

1.2 Function Between Components of First Nucleic Acid Complex 110 and Second Nucleic Acid Complex 120

According to an exemplary embodiment of the present application, the first nucleic acid complex 110 and the second nucleic acid complex 120 may have the same function between corresponding components.

Here, a component corresponding to the first determinant 111 may be a second determinant 121. A component corresponding to the first tag 112 may be a second tag 122. A component corresponding to the first label 113 may be a second label 123. A component corresponding to the first linker 114 may be a second linker 124.

In one example of the nucleic acid complex pair 10 having the same function between corresponding components between the first nucleic acid complex 110 and the second nucleic acid complex 120, the first determinant 111 and the second determinant 121 may serve as PCR primers, and the first label 113 and the second label 123 may serve to generate signals (e.g., to emit light or perform oxidation/reduction).

According to another exemplary embodiment of the present application, the first nucleic acid complex 110 and the second nucleic acid complex 120 may include components having different functions between corresponding components.

In one example, the first label 113 may serve to generate a specific signal (e.g., to emit light of a first wavelength band), and the second label 123 may serve to absorb the specific signal (e.g., to absorb light of a first wavelength band).

When the first nucleic acid complex 110 and the second nucleic acid complex 120 include at least one component with a different function from a corresponding one, the first nucleic acid complex 110 and the second nucleic acid complex 120 may include at least one component with the same function as a corresponding one.

In one example, the first label 113 may serve to generate a specific signal (e.g., to emit light of a first wavelength band), and the second label 123 may serve to absorb the specific signal (e.g., to absorb light of a first wavelength band). Here, the first determinant 111 and the second determinant 121 may serve as PCR primers.

Alternatively, when the first nucleic acid complex 110 and the second nucleic acid complex 120 include at least one component with a different function from a corresponding one, the first nucleic acid complex 110 and the second nucleic acid complex 120 may not include at least one component with the same function as a corresponding one.

In one example, the first label 113 may serve to generate a specific signal (e.g., to emit light of a first wavelength band), and the second label 123 may serve to absorb the specific signal (e.g., to absorb light of a first wavelength band). Here, the first tag 112 may serve as a probe for PCR clamping, and the second tag 122 may not serve as a probe for PCR clamping.

1.3 Materials for First Nucleic Acid Complex 110 and Second Nucleic Acid Complex 120

According to an exemplary embodiment of the present application, corresponding constituent components between the first nucleic acid complex 110 and the second nucleic acid complex 120 may consist of the same material.

In one example, the first determinant 111 and the second determinant 121 (the component corresponding to the first determinant 111) may consist of a polymer of the unit molecule of DNA, and the first tag 112 and the second tag 122 (the component corresponding to the first tag 112) may consist of a polymer of Formula 10 shown above.

According to another exemplary embodiment of the present application, corresponding constituent components between the first nucleic acid complex 110 and the second nucleic acid complex 120 may consist of different materials.

In one example, the first determinant 111 may consist of a polymer of the unit molecule of DNA, and the second determinant 121 (the component corresponding to the first determinant 111) may consist of a polymer of the unit molecule of PNA.

When the first nucleic acid complex 110 and the second nucleic acid complex 120 include at least one component consisting of a different material from a corresponding one, the first nucleic acid complex 110 and the second nucleic acid complex 120 may include at least one component consisting of the same material as a corresponding one.

In one example, the first determinant 111 may consist of a polymer of the unit molecule of DNA, and the second determinant 121 (the component corresponding to the first determinant 111) may consist of a polymer of the unit molecule of LNA. Here, the first tag 112 and the second tag 122 may consist of Formula 10 shown above.

Alternatively, when the first nucleic acid complex 110 and the second nucleic acid complex 120 include at least one component consisting of a different material from a corresponding one, the first nucleic acid complex 110 and the second nucleic acid complex 120 may not include at least one component consisting of the same material as a corresponding one.

In one example, the first determinant 111 may consist of a polymer of the unit molecule of DNA, and the second determinant 121 (the component corresponding to the first determinant 111) may consist of a polymer of the unit molecule of LNA. Here, the first tag 112 may consist of a polymer of the unit molecule of DNA, and the second tag 122 may consist of a polymer of the unit molecule of PNA. Here, the first label 113 may consist of a fluorescent molecule, and the second label 123 may consist of a quencher molecule.

1.4 Physical Properties of First Nucleic Acid Complex 110 and Second Nucleic Acid Complex 120

According to an exemplary embodiment of the present application, the first nucleic acid complex 110 and the second nucleic acid complex 120 may have the same physical properties between corresponding components. In addition, the first nucleic acid complex 110 and the second nucleic acid complex 120 may have different physical properties between corresponding components.

When the first nucleic acid complex 110 and the second nucleic acid complex 120 have different physical properties between corresponding components, the first nucleic acid complex 110 and the second nucleic acid complex 120 may include at least one component having the same physical property as a corresponding one.

Alternatively, when the first nucleic acid complex 110 and the second nucleic acid complex 120 have different physical properties between corresponding components, the first nucleic acid complex 110 and the second nucleic acid complex 120 may not include at least one component having the same physical property as a corresponding one.

As an example, the physical properties may include physical length, weight, optical properties (e.g., wavelength band, intensity, etc.), binding force with a specific material, color, thermal conductivity and/or strength.

Hereinafter, in relation to the length among the various physical properties, specific embodiments of the first nucleic acid complex 110 and the second nucleic acid complex 120 will be described.

For simplicity, the descriptions on specific embodiments of the first nucleic acid complex 110 and the second nucleic acid complex 120 relating to other properties among the physical properties will be omitted, but the first nucleic acid complex 110 and the second nucleic acid complex 120, which may have the same properties or different properties, may be easily understood by one of ordinary skill in the art, and thus, in interpreting the scope of the specification, physical properties should not be limited to length.

According to an exemplary embodiment of the present application, the first nucleic acid complex 110 and the second nucleic acid complex 120 may have the same physical length between corresponding components. In a specific example, when the first determinant 111 is a single-stranded nucleic acid (e.g., DNA) with a length of 10 mer, the second determinant 121 may also be a single-stranded nucleic acid (e.g., DNA) with a length of 10 mer.

According to another exemplary embodiment of the present application, the first nucleic acid complex 110 and the second nucleic acid complex 120 may have different physical lengths of corresponding components. In a specific example, the first tag 112 may have a single-stranded nucleic acid (e.g., DNA) with a length of 10 mer, and the second tag 122 may have a single-stranded nucleic acid (e.g., DNA) with a length of 7 mer.

When the first nucleic acid complex 110 and the second nucleic acid complex 120 include at least one corresponding component with a different physical length, the first nucleic acid complex 110 and the second nucleic acid complex 120 may include at least one component with the same physical length as a corresponding one.

In one example, when the first tag 112 is a single-stranded nucleic acid (e.g., PNA) with a length of 10 mer, the second tag 122 may be a single-stranded nucleic acid (e.g., PNA) with a length of 7 mer. Here, when the first determinant 111 is a single-stranded nucleic acid (e.g., DNA) with a length of 10 mer, the second determinant 121 may be a single-stranded nucleic acid (e.g., DNA) with a length of 10mer.

Alternatively, when the first nucleic acid complex 110 and the second nucleic acid complex 120 include at least one component having a different physical length from a corresponding one, the first nucleic acid complex 110 and the second nucleic acid complex 120 may not include at least one component having the same physical length as a corresponding one.

In one example, when the first tag 112 is a single-stranded nucleic acid (e.g., PNA) with a length of 10 mer, the second tag 122 may be a single-stranded nucleic acid (e.g., PNA) with a length of 7 mer. Here, when the first determinant 111 is a single-stranded nucleic acid (e.g., DNA) with a length of 17 mer, the second determinant 121 may be a single-stranded nucleic acid (e.g., DNA) with a length of 15 mer.

So far, the configurations of the first nucleic acid complex 110 and the second nucleic acid complex 120, which are included in the nucleic acid complex pair 10, have been described in detail.

Specific embodiments are merely provided to help in understanding the nucleic acid complex pair 10 according to the present application, and it does not mean that the nucleic acid complex pair 10 should be construed as limited to the configuration disclosed herein.

Specifically, the nucleic acid complex pair 10 according to the present application may be provided in the form in which an additional nucleic acid complex 1 is included as well as the first nucleic acid complex 110 and the second nucleic acid complex 120.

In addition, the first nucleic acid complex 110 and the second nucleic acid complex 120 included in the nucleic acid complex pair 10 may have characteristics other than those described above, or the first nucleic acid complex 110 and the second nucleic acid complex 120 may have at least two or more distinguishing characteristics among the above-described characteristics.

Hereinafter, the operation and examples of the nucleic acid complex pair 10 according to an exemplary embodiment of the present application will be described in detail. According to the configuration of the nucleic acid complex pair 10 described above and the operation and examples thereof, which will be described below, the definition and function of the nucleic acid complex pair will be more clearly understood.

However, for convenience of description, unless separately noted otherwise as needed, it is assumed that the nucleic acid complex pair 10 consists of a first nucleic acid complex 110 and a second nucleic acid complex 120, the first nucleic acid complex 110 includes a first determinant 111, a first linker 114, a first tag 112 and a first label 113, and the second nucleic acid complex 120 includes a second determinant 121, a second linker 124, a second tag 122 and a second label 123.

This is to prevent exemplary embodiments from being unnecessarily and repeatedly described in each case, and it does not mean that nucleic acid complex pairs 10 used in various exemplary embodiments described below should be construed in a limited way according to the above-described assumption.

2. Operation of Nucleic Acid Complex Pair 10

2.1 Determinant 100

The first determinant 111 according to an exemplary embodiment of the present invention may complementarily bind to a first target base sequence. The "first target base sequence" used herein may mean a base sequence complementary to at least a part of the base sequence of the first determinant 111.

The complementary bond between the first determinant 111 and the first target base sequence may mean that they are associated with each other in correspondence with at least one of electrical, chemical and physical properties. In one example, by hydrogen bonding between at least one base of the first determinant 111 and the first target base sequence, the first determinant 111 and the first target base sequence may complementarily bind to each other.

The binding force between the first determinant 111 and the first target base sequence may be determined in association with at least one of the type of the unit molecule of the first target base sequence, the type of a base of the unit molecule of the first target base sequence, and the number of bases involved in the complementary binding with the first determinant 111.

The binding force between the first determinant 111 and the first target base sequence may be determined in association with at least one of the type of the unit molecule of the first determinant 111, the type of a base of the unit molecule of the first determinant 111, and the number of bases involved in the complementary binding with the first target base sequence.

In one example, when the unit molecule of the first determinant 111 binding with the first target base sequence consists of the unit molecule of PNA, compared to when the unit molecule of the first determinant 111 binding with the first target base sequence consists of the unit molecule of DNA, the binding force between the first target base sequence and the first determinant 111 may be higher.

In another example, when bases included in at least a partial region of the first determinant 111 binding with the first target base sequence have a higher cytosine (C)-guanine (G) content, compared to when the bases included in at least a partial region of the first determinant 111 binding with the first target base sequence have a lower C-G content, the binding force between the first target base sequence and the first determinant 111 may be higher.

In still another example, when there are 10-bp bases in at least a partial region of the first determinant 111 binding with the first target base sequence, compared to when there are 5-bp bases in at least a partial region of the first determinant 111 binding with the first target base sequence, the binding force between the first target base sequence and the first determinant 111 may be higher.

A second determinant 121 according to an exemplary embodiment of the present application may complementarily bind to a second target base sequence. The "second target base sequence" used herein may mean a base sequence complementary to at least a part of the base sequence of the second determinant 121.

The complementary bond between the second determinant 121 and the second target base sequence may mean that they are associated with each other in correspondence with at least one of electrical, chemical and physical properties. In one example, by hydrogen bonding between at least one base of the second determinant 121 and the second target base sequence, the second determinant 121 and the second target base sequence may complementarily bind to each other.

The binding force between the second determinant 121 and the second target base sequence may be determined in association with at least one of the type of the unit molecule of the second target base sequence, the type of a base of the unit molecule of the second target base sequence, and the number of bases involved in the complementary binding with the second determinant 121.

The binding force between the second determinant 121 and the second target base sequence may be determined in association with at least one of the type of the unit molecule of the second determinant 121, the type of a base of the unit molecule of the second determinant 121, and at least one of bases involved in the complementary binding with the second target base sequence.

In one example, when the unit molecule of the second determinant 121 bonded with the second target base sequence consists of the unit molecule of PNA, compared to when the unit molecule of the second determinant 121 bonded with the second target base sequence consists of the unit molecule of DNA, the binding force between the second target base sequence and the second determinant 121 may be higher.

In another example, when the bases included in at least a partial region of the second determinant 121 bonded with the second target base sequence have a higher C-G content, compared to when the bases included in at least a partial region of the second determinant 121 bonded with the second target base sequence have a lower C-G content, the binding force between second target base sequence and the second determinant 121 may be higher.

In still another example, when there are 10-bp bases included in at least a partial region of the second determinant 121 bonded with the second target base sequence, compared to when there are 5-bp bases included in at least a partial region of the second determinant 121 bonded with the second target base sequence, the binding force between the second target base sequence and the second determinant 121 may be higher.

According to an exemplary embodiment of the present application, the first determinant 111 and the second determinant 121 may specifically bind to a related material. A first target nucleic acid including a first target base sequence complementarily binding to the first determinant 111 may be associated with a second target nucleic acid including a second target base sequence complementarily binding to the second determinant 121. The first nucleic acid complex 110 and the second nucleic acid complex 120 may act on related materials, respectively. The first determinant 111 and the second determinant 121 may be associated with each other afterward.

In one example, the first determinant 111 and the second determinant 121 may specifically bind to the same nucleic acid. The first target nucleic acid and the second target nucleic acid may be the same.

Here, a first target base sequence and a second target base sequence may be included in a single-stranded nucleic acid.

Alternatively, the first target base sequence and the second target base sequence may be included in a double-stranded nucleic acid, wherein the first target base sequence and the second target base sequence may be any one strand of the double strands.

Alternatively, the first target base sequence and the second target base sequence may be included in a double-stranded nucleic acid, wherein the first target base sequence may be included in one strand of the double strands, and the second target base sequence may be included in the other strand of the double strands.

Figure 10:
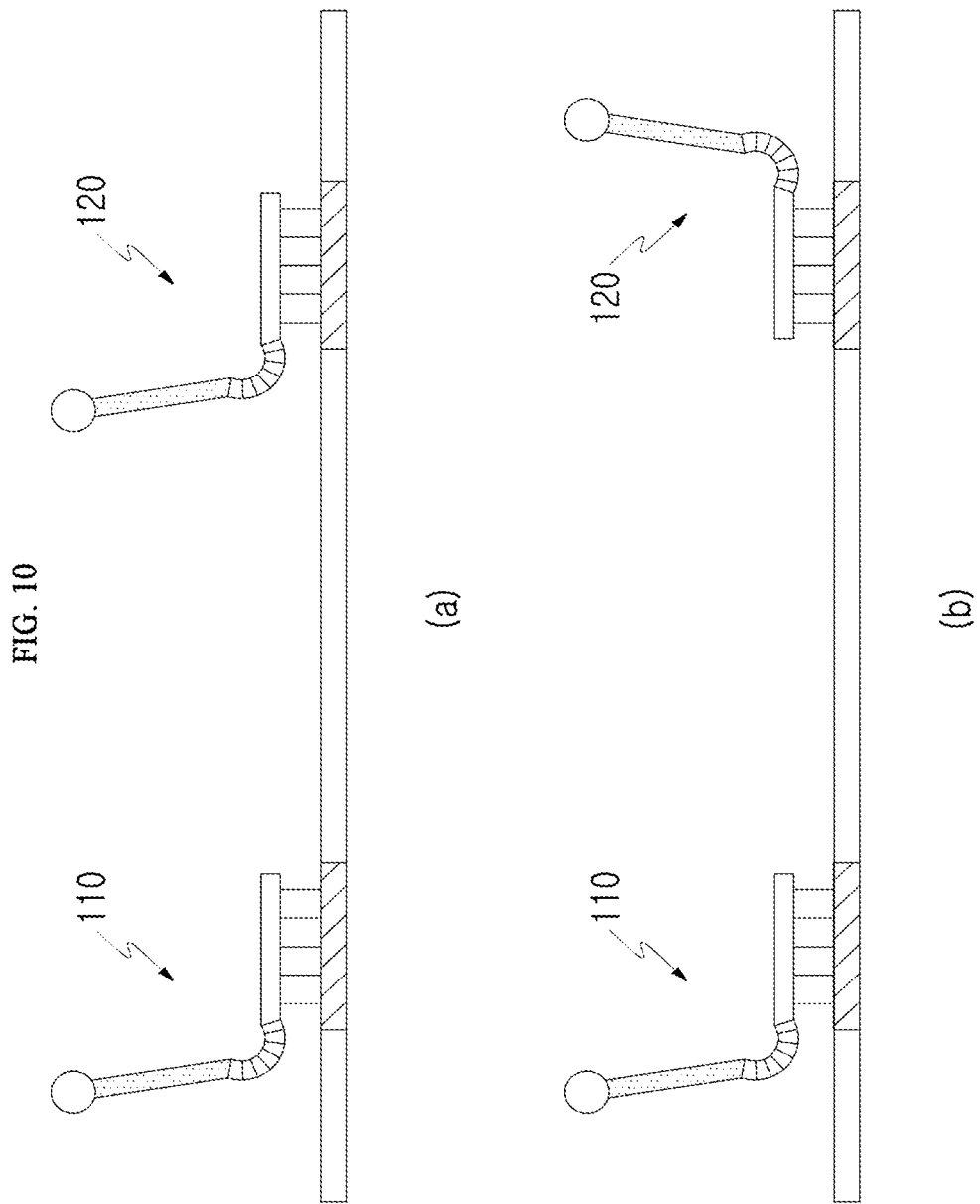
FIG. 10 is diagram illustrating operations of the first nucleic acid complex 110 and the second nucleic acid complex 120 as shown in FIG. 9 according to an exemplary embodiment of the present application that a first target base sequence and a second target base sequence are included in a single-stranded nucleic acid, and the first determinant 111 and the second determinant 121 complementarily bind to the first target sequence and the second target sequence.
Figure 11:
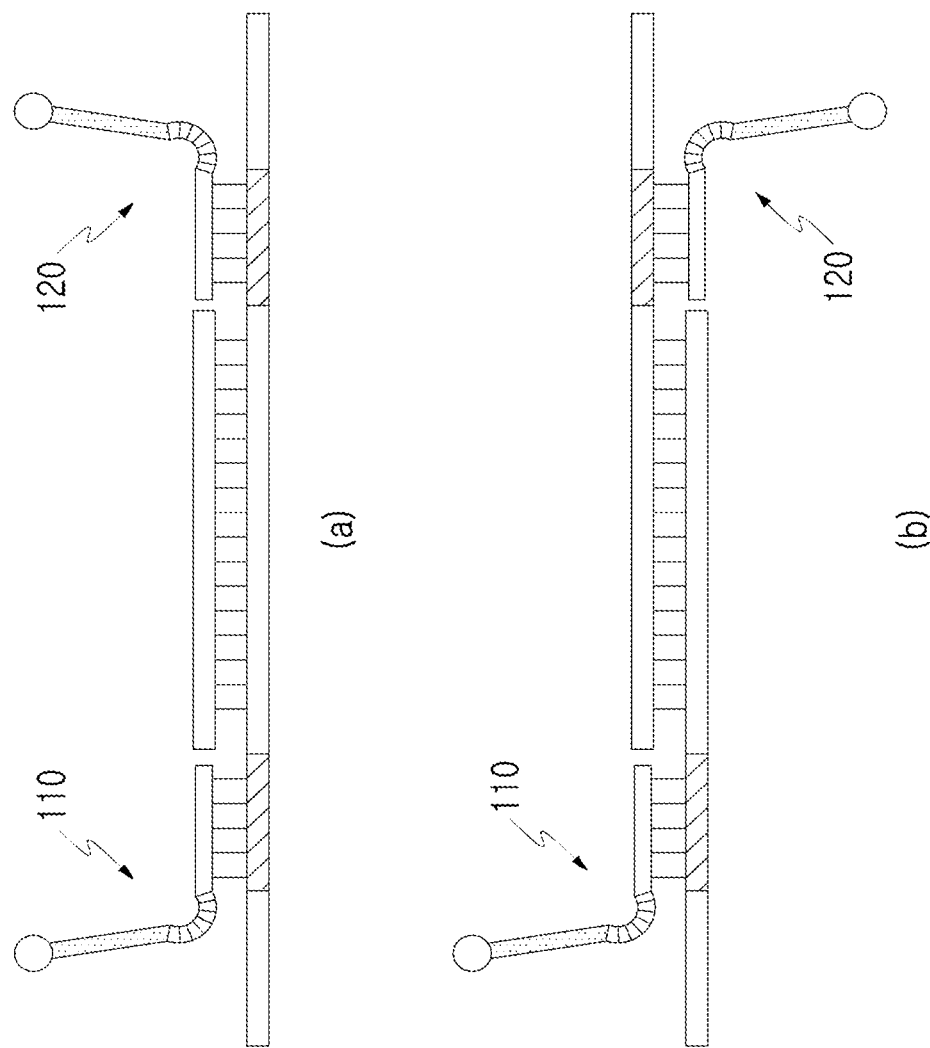
FIG. 11 is diagram illustrating operations of the first nucleic acid complex 110 and the second nucleic acid complex 120 as shown in FIG. 9 according to an exemplary embodiment of the present application that a first target base sequence and a second target base sequence are included in any one strand of the double strands, and the first determinant 111 and the second determinant 121 complementarily binds to the first target sequence and the second target sequence.

FIGS. 10 and 11 are diagrams illustrating operations of the first determinant 111 and the second determinant 121 according to an exemplary embodiment of the present application The first determinant 111 and the second determinant 121 may complementarily bind to related materials, respectively. The first determinant 111 and the second determinant 121 may complementarily bind to the same nucleic acid. Here, the same nucleic acid may be a single-stranded nucleic acid including the first target base sequence and the second target base sequence.

When the first target base sequence and the second target base sequence are included in the single-stranded nucleic acid, the first determinant 111 may complementarily bind to the first target base sequence, and the second determinant 121 may complementarily bind to the second target base sequence in a region different from the first target base sequence. Here, the first tag 112 connected with the first determinant 111 and the second tag 122 connected with the second determinant 121 may be disposed on the same side based on the first determinant 111 and the second determinant 121, respectively (see FIG. 10(a)).

Alternatively, when the first target base sequence and the second target base sequence are included in a single-stranded nucleic acid, the first determinant 111 may complementarily bind to the first target base sequence, and the second determinant 121 may complementarily bind to the second target base sequence in a region different from the first target base sequence. Here, the first tag 112 connected with the first determinant 111 and the second tag 122 connected with the second determinant 121 may be disposed on opposite sides based on the first determinant 111 and the second determinant 121, respectively (see FIG. 10(b)).

The first determinant 111 and the second determinant 121 may complementarily bind to related materials. The first determinant 111 and the second determinant 121 may complementarily bind to the same nucleic acid. Here, the first target base sequence and the second target base sequence may be included in a double-stranded nucleic acid, wherein the first target base sequence and the second target base sequence may be included in any one strand of the double strands.

The first determinant 111 may complementarily bind to the first target base sequence, and the second determinant 121 may complementarily bind to the second target base sequence included in any one strand including the first target base sequence (see FIG. 11(a)).

The first determinant 111 and the second determinant 121 may complementarily bind to related materials. The first determinant 111 and the second determinant 121 may complementarily bind to the same nucleic acid. Here, the first target base sequence and the second target base sequence may be included in the double-stranded nucleic acid, wherein the first target base sequence may be included in one strand of the double strands, and the second target base sequence may be included in the other strand of the double strands. One region of the nucleic acid corresponding to the first target base sequence and one region of the nucleic acid corresponding to the second target base sequence may be present in the form of a single strand.

The first determinant 111 may complementarily bind to the first target base sequence included in one strand, and the second determinant 121 may complementarily bind to the second target base sequence included in the other strand (see FIG. 11(b)).

As shown in FIG. 11, although not shown specifically, as described in FIG. 10, the first tag 112 connected with the first determinant 111 and the second tag 122 connected with the second determinant 121 may be disposed on the same side based on the first determinant 111 and the second determinant 121, respectively.

According to another exemplary embodiment of the present application, the first target nucleic acid including the first target base sequence to which the first determinant 111 specifically binds and the second target nucleic acid including the second target base sequence to which the second determinant 121 specifically binds may be associated with each other afterward.

In one example, when the nucleic acid complex pair 10 according to an exemplary embodiment of the present application is used in PCR, the first determinant 111 specifically binds to a first target base sequence, and a nucleotide may be elongated at the 3' end of the determinant 100 to have a sequence complementary to the first target base sequence. Here, the base sequence of the polynucleotide formed by elongation may include the second target nucleic acid. In other words, the second target base sequence may be included in the polynucleotide formed by being elongated at the 3' end of the first determinant 111.

In such a configuration, the first target nucleic acid and the second target nucleic acid may be associated with each other afterward. In a specific exemplary embodiment related thereto, this will be understood in detail with reference to FIGS. 27 and 28 to be described below.

2.2 Tag 200

The first tag 112 according to an exemplary embodiment of the present application may complementarily bind to another nucleic acid complex 1 (that is, a nucleic acid complex 1 other than the first nucleic acid complex 110).

In one example, the first tag 112 may complementarily bind to the second tag 122 of the second nucleic acid complex 120.

In a specific example, the first tag 112 may include a compound having a chemical structure complementary to that of the second tag 122. The second tag 122 may include a compound having a chemical structure complementary to that of the first tag 112.

In another specific example, the first tag 112 may include a base sequence complementary to the base sequence of the second tag 122. The first tag 112 may include a nucleic acid and/or nucleic acid complex 1, which includes a base sequence complementary to the base sequence of the second tag 122. The second tag 122 may include a base sequence complementary to that of the first tag 112. The second tag 122 may include a nucleic acid and/or nucleic acid complex 1, which includes a base sequence complementary to that of the first tag 112.

According to an exemplary embodiment of the present application, depending on the binding directions of the first tag 112 and the second tag 122, the binding directions of the first nucleic acid complex 110 and the second nucleic acid complex 120 may vary.

In one example, according to the arrangement of elements (that is, a distance between elements, the type of element or the like) exposed at the outside of the first tag 112 and the second tag 122, the binding directions of the first nucleic acid complex 110 and the second nucleic acid complex 120 may vary. In another example, depending on the base sequences of the first tag 112 and the second tag 122, the binding directions of the first nucleic acid complex 110 and the second nucleic acid complex 120 may vary.

In a specific example, according to the relationship between the base sequence in the 5' to 3' direction of the first tag 112 and the base sequence in the 5' to 3' direction of the second tag 122, the binding directions of the first nucleic acid complex 110 and the second nucleic acid complex 120 may vary.

FIG. 12 is a diagram illustrating the direction in which a first nucleic acid complex 110 and a second nucleic acid complex 120 are bonded according to an exemplary embodiment of the present application.

Referring to FIG. 12(a), a first tag 112 may include a sequence complementary to a second tag 122 such that one region of the first tag 112 adjacent to a first determinant 111 complementarily binds to one region of the second tag 122 spaced apart from a second determinant 121. The second tag 122 may include a sequence complementary to the first tag 112 such that one region of the second tag 122 adjacent to the second determinant 121 complementarily binds to one region of the first tag 112 spaced apart from the first determinant 111.

In a specific example, the first nucleic acid complex 110 and the second nucleic acid complex 120 may be embodied in the form in which a determinant 100, a linker 400, a tag 200 and a label 300 are sequentially connected. The first tag 112 may have the base sequence of CCCCCAAAA, enumerating a base sequence of the first tag 112 adjacent to a first linker 114. The second tag 122 may have the base sequence of TTTTGGGGG, enumerating a base sequence of the second tag 122 adjacent to a second linker 124.

Preferably, the first tag 112 has the base sequence of 5'-CCCCCAAAA-3', enumerating a base sequence of the first tag 112 adjacent to the first linker 114. The second tag 122 may have the base sequence of 5'-TTTTGGGGG-3', enumerating a base sequence of the second tag 122 adjacent to the first linker 124.

Alternatively, preferably, the first tag 112 has the base sequence of 3'-CCCCCAAAA-5', enumerating a base sequence of the first tag 112 adjacent to the first linker 114. The second tag 122 may have the base sequence of 3'-TTTTGGGGG-5', enumerating a base sequence of the second tag 122 adjacent to the second linker 124.

When the nucleic acid complex pair 10 is embodied such that one region of the second tag 122 adjacent to the second determinant 121 complementarily binds to one region of the first tag 112 spaced apart from the first determinant 111, the first determinant 111 may be disposed on one side based on the first tag 112 and the second tag 122, and the second determinant 121 may be disposed on the opposite side based on the first tag 112 and the second tag 122.

When the nucleic acid complex pair 10 is embodied such that one region of the second tag 122 adjacent to the second determinant 121 complementarily binds to one region of the first tag 112 spaced apart from the first determinant 111, the part in which the first determinant 111 is connected with the first tag 112 may be disposed on a first side based on an imaginary surface passing through the first tag 112 and the second tag 122, and the part in which the second determinant 121 is connected with the second tag 122 may be disposed on a second side based on an imaginary surface passing through the first tag 112 and the second tag 122. The first and second sides may be opposite to each other based on the imaginary surface.

Referring to FIG. 12(b), the first tag 112 may include a sequence complementary to the second tag 122 such that one region of the first tag 112 adjacent to the first determinant 111 complementarily binds to one region of the second tag 122 adjacent to the second determinant 121. The second tag 122 may include a sequence complementary to the first tag 112 such that one region of the second tag 122 adjacent to the second determinant 121 complementarily binds to one region of the first tag 112 adjacent to the first determinant 111.

In a specific example, the first nucleic acid complex 110 and the second nucleic acid complex 120 may be embodied in the form in which a determinant 100, a linker 400, a tag 200 and a label 300 are sequentially connected. The first tag 112 may have the base sequence of CCCCCAAAA, enumerating a base sequence of the first tag 112 adjacent to the first linker 114. The second tag 122 may have the base sequence of GGGGGTTTT, enumerating a base sequence of the second tag 122 adjacent to the second linker 124.

The first tag 112 preferably has the base sequence of 5'-CCCCCAAAA-3', enumerating a base sequence of the first tag 112 adjacent to the first linker 114. The second tag 122 may have the base sequence of 3'-GGGGGTTTT-5', enumerating a base sequence of the second tag 122 adjacent to the second linker 124.

Alternatively, the first tag 112 preferably has the base sequence of 3'-CCCCCAAAA-5', enumerating a base sequence of the first tag 112 adjacent to the first linker 114. The second tag 122 may have the base sequence of 5'-GGGGGTTTT-3', enumerating a base sequence of the second tag 122 adjacent to the second linker 124.

When a nucleic acid complex pair 10 is embodied such that one region of the second tag 122 adjacent to the second determinant 121 complementarily binds to one region of the first tag 112 adjacent to the first determinant 111, the first determinant 111 may be disposed on one side based on the first tag 112 and the second tag 122, and the second determinant 121 may be disposed on the one side based on the first tag 112 and the second tag 122.

When a nucleic acid complex pair 10 is embodied such that one region of the second tag 122 adjacent to the second determinant 121 complementarily binds to one region of the first tag 112 adjacent to the first determinant 111, the part in which the first determinant 111 is connected with the first tag 112 may be disposed on a first side based on an imaginary surface passing through the first tag 112 and the second tag 122, and the part in which the second determinant 121 is connected with the second tag 122 may be disposed on a second side based on an imaginary surface passing through the first tag 112 and the second tag 122. The first side and the second side may be on the same side based on the imaginary surface.

According to an exemplary embodiment of the present application, according to the base sequences of the first tag 112 and the second tag 122, the shapes of other materials related to the first nucleic acid complex 110 and the second nucleic acid complex 120 may be changed. Depending on the base sequences of the first tag 112 and the second tag 122, the shape of at least one target nucleic acid including the first target base sequence and the second target base sequence may be changed. In this regard, this will be described in detail in 1.2 Formation of secondary structure below.

Hereinafter, unless separately described otherwise, to explain the complementary bond between the first tag 112 and the second tag 122, it is assumed that one region of the second tag 122 adjacent to the second determinant 121 complementarily binds to one region of the first tag 112 spaced apart from the first determinant 111.

This is to prevent unnecessary repetitive description, and it will be obvious that it is not assumed that the complementary bond between the first tag 112 and the second tag 122 does not include the complementary bond between one region of the second tag 122 adjacent to the second determinant 121 and one region of the first tag 112 adjacent to the first determinant 111.

According to an exemplary embodiment of the present application, the first tag 112 may include a region complementarily binding to the second tag 122. The first tag 112 may complementarily bind to at least a partial region of the second tag 122.

In one example, the first tag 112 may complementarily bind to the entire region of the second tag 122. In a specific example, a base sequence of the first tag 112 may complementarily bind to the entire base sequence of the second tag 122. The first tag 112 may not have abase not binding to the second tag 122. A base sequence of the second tag 122 may complementarily bind to the entire base sequence of the first tag 112. The second tag 122 may not have a base not binding to the base sequence of the first tag 112.

In another example, the first tag 112 may have a base sequence complementary to the base sequence of the second tag 122, and the base sequence of the first tag 112 and the base sequence of the second tag 122 may differ by at least one base. The second tag 122 may have a base sequence complementary to the base sequence of the first tag 112, and the base sequence of the second tag 122 and the base sequence of the first tag 112 may differ by at least one base. Here, the first tag 112 and the second tag 122 may be mismatched and bonded to each other based on bond between complementary base sequences included in the first tag 112 and the second tag 122.

In still another example, the first tag 112 may complementarily bind to a partial region of the second tag 122. In a specific example, the base sequence of the first tag 112 may complementarily bind to a part of the base sequence of the second tag 122. The first tag 112 may not have a base that does not bind to the second tag 122. The second tag 122 may include a base that does not bind to the base sequence of the first tag 112.

Figure 13:
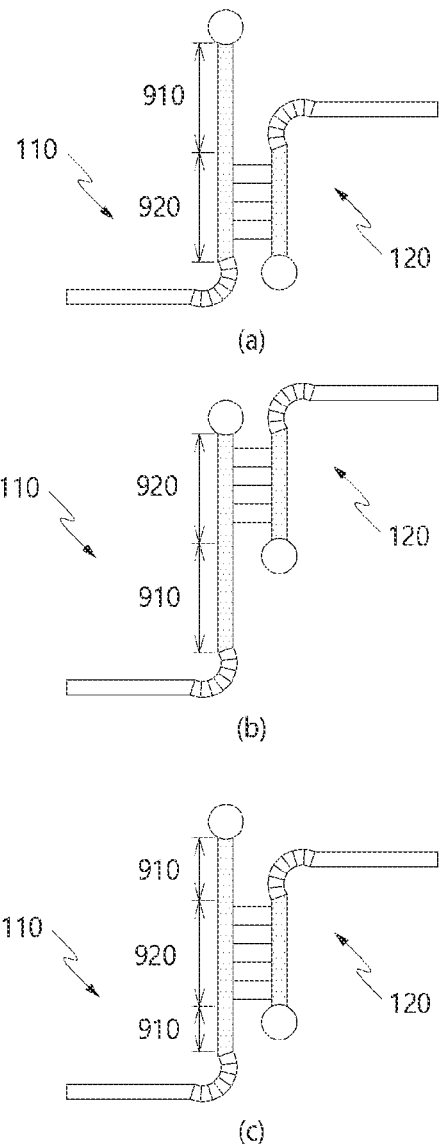
FIG. 13 is a diagram illustrating the bond between the first nucleic acid complex 110 and the second nucleic acid complex 120 as shown in FIG. 9, between a first tag 112 and a second tag 122 at which a non-bound region 910 in which there is no complementary bond exists according to an exemplary embodiment of the present application.

FIG. 13 is a diagram illustrating the bond between a first tag 112 and a second tag 122 according to an exemplary embodiment of the present application.

The first tag 112 may complementarily bind to a partial region of the second tag 122. The base sequence of the first tag 112 and the base sequence of the second tag 122 may have regions complementarily binding to each other, and the first tag 112 may further include a region that does not complementarily bind to the base sequence of the second tag 122.

The bound region 920 in which the first tag 112 and the second tag 122 form complementary bonds may be relatively adjacent to a part in which the first tag 112 and the first determinant 111 are connected, compared to a non-bound region 910 in which there is no complementary bond between the first tag 112 and the second tag 122. A base of the first tag 112 complementarily binding to the second tag 122 may be adjacent to the first determinant 111, compared to a base of the first tag 112 not complementarily binding to the second tag 122 (see FIG. 13(a)).

The bound region 920 in which the first tag 112 and the second tag 122 form complementary bonds may be relatively spaced apart from the part in which the first tag 112 and the first determinant 111 are connected, compared to the non-bound region 910 in which there is no complementary bond between the first tag 112 and the second tag 122. A base of the first tag 112 complementarily binding to the second tag 122 may be spaced apart from the first determinant 111, compared to a base of the first tag 112 not complementarily binding to the second tag 122 (see FIG. 13(b)).

The bound region 920 in which the first tag 112 and the second tag 122 form complementary bonds may be located between a first non-bound region 910 of the first tag 112 that does not complementarily bind to the second tag 122 and a second non-bound region 910 of the first tag 112 that does not bind to the second tag 122. The first tag 112 may include a first target base sequence that does not complementarily bind to the second tag 122, a second target base sequence that complementarily binds to the second tag 122, and a third base sequence that does not complementarily bind to the second tag 122. The first tag 112 may be formed by sequentially connecting a first target base sequence that does not complementarily bind to the second tag 122, a second target base sequence that complementarily binds to the second tag 122, and a third base sequence that does not complementarily bind to the second tag 122 (see FIG. 13(c)).

In some cases, when the first tag 112 further includes a base sequence that does not complementarily bind to a base sequence of the second tag 122, the second tag 122 may further include a base sequence that does not complementarily bind to the base sequence of the first tag 112.

In one example, a base of the second tag 122, which does not complementarily bind to the first tag 112 may be formed in a first direction (e.g., a 5' to 3' direction based on the second tag 122) of a region in which the first tag 112 complementarily binds to the second tag 122.

In another example, a base of the second tag 122, which does not complementarily bind to the first tag 112, may be formed in a second direction (e.g., a 3' to 5' direction based on the second tag 122) of a region in which the first tag 112 complementarily binds to the second tag 122.

In still another example, a base of the second tag 122, which does not complementarily bind to the first tag 112, may be formed in a first direction (e.g., a 5' to 3' direction based on the second tag 122) of a region in which the first tag 112 complementarily binds to the second tag 122 and a second direction (e.g., a 3' to 5' direction based on the second tag 122) of a region in which the first tag 112 complementarily binds to the second tag 122.

2.3 Label 300

According to an exemplary embodiment of the present application, a first label 113 and a second label 123 may be involved in labeling of a nucleic acid complex pair 10. In one example, the first label 113 may be involved in labeling of the nucleic acid complex pair 10 due to an action associated with the second label 123. The second label 123 may be involved in labeling of the nucleic acid complex pair 10 through a linked action with the first label 113.

According to an exemplary embodiment of the present application, the first label 113 may be associated with the second label 123. When the first label 113 and the second label 123 are disposed close enough to perform a linked action, the linked action (hereinafter, a linked action) between the first label 113 and the second label 123 may occur.

In one example, the linked action between the first label 113 and the second label 123 may occur through complementary binding between the first tag 112 and the second tag 122.

In another example, when there is an association between a first target base sequence to which a first determinant 111 binds and a second target base sequence to which a second determinant 121 binds, the linked action between the first label 113 and the second label 123 may occur.

According to an exemplary embodiment of the present application, the linked action may be performed in the form in which energy delivery between the first label 113 and the second label 123 occurs.

As an aspect of energy delivery, the first label 113 may provide energy to the second label 123, and the second label 123 may receive energy from the first label 113. As another aspect of energy delivery, the second label 123 may provide energy to the first label 113, and the first label 113 may receive energy from the second label 123. As still another aspect of energy delivery, the first label 113 may provide energy to the second label 123, and receive energy from the second label 123. The second label 123 may provide energy to the first label 113, and receive energy from first label 113.

According to whether energy delivery occurs between the first label 113 and the second label 123, a physical property generated by the linked action between the first label 113 and the second label 123 may vary. The physical property may be at least one of chemical, electrical, optical and magnetic properties. In a specific example, according to whether energy delivery occurs between the first label 113 and the second label 123, an optical property detected from an unit cell (UC) including the first label 113 and the second label 123 may vary. The varying optical property may be a change in intensity of light or a change in wavelength range of light.

According to an exemplary embodiment of the present application, based on the physical property varying according to whether a linked action between the first label 113 and the second label 123 occurs, the association between the first label 113 and the second label 123 may be confirmed. As a result, a nucleic acid complex pair 10 may be labeled in such a manner that information of the nucleic acid complex pair 10 is confirmed according to whether the first label 113 and the second label 123 are associated.

Hereinafter, operations of the first label 113 and the second label 123 will be described in further detail.

However, to help in understanding the present application, it is assumed that the first label 113 is a fluorescent molecule emitting light of a first wavelength range when light is incident, and the second label 123 is a blackhole quencher molecule absorbing light when light of a first wavelength range is incident.

FIG. 14 is a diagram illustrating the operations of a first label 113 and a second label 123 according to an exemplary embodiment of the present application.

A nucleic acid complex pair 10 according to an exemplary embodiment of the present application will be defined by "effective linkage distance (LD)" between the first label 113 and the second label 123.

Here, the "effective linkage distance (LD)" may refer to a reference distance from a first label 113 or a second label 123, in which a linked action may occur between the first label 113 and the second label 123. Here, the "effective linkage distance (LD)" may refer to the critical distance between the first label 113 and the second label 123, in which a linked action may occur between the first label 113 and the second label 123. Here, the "effective linkage distance (LD)" may refer to the critical distance of spacing between the second label 123 and the first label 113, in which a linked action may occur between the first label 113 and the second label 123.

The effective linkage distance (LD) may be determined based on properties of the first label 113 and the second label 123. In other words, when the first label 113 is a fluorescent molecule, and the second label 123 is a quencher molecule, the effective linkage distance (LD) may be determined according to characteristics between the fluorescent molecule and the quencher molecule. In one example, when a distance between the quencher molecule and the fluorescent molecule is 100 Å (angstrom) and the linked action is performed, the effective linkage distance (LD) may be 100 Å.

When the first label 113 and the second label 123 are disposed adjacent to each other such that the distance between the first label 113 and the second label 123 is within the effective linkage distance (LD), the first label 113 and the second label 123 may perform a linked action (see FIG. 14(a)).

When the first label 113 and the second label 123 perform a linked action, the first label 113 may emit light of a first wavelength band, and the second label 123 may absorb light of the first wavelength band. As a result, when light of a unit cell (UC) including the first label 113 and the second label 123 is detected using an optical device, the light of the first wavelength band may not be detected from the unit cell (UC). Alternatively, as a result, when light of the unit cell (UC) including the first label 113 and the second label 123 is detected using an optical device, the intensity of light of the first wavelength band detected from the unit cell (UC) may be reduced.

When the first label 113 and the second label 123 are spaced such that the distance between the first label 113 and the second label 123 exceeds the effective linkage distance (LD), the first label 113 and the second label 123 may not perform a linked action (see FIG. 14(b)).

When the first label 113 and the second label 123 does not perform the linked action, the first label 113 may emit light of the first wavelength band, and the second label 123 may not emit light of the first wavelength band. As a result, when light of the unit cell (UC; e.g., a tube) including the first label 113 and the second label 123 is detected using an optical device, the light of the first wavelength band may be detected from the unit cell (UC).

According to an exemplary embodiment of the present application, the distance between the first label 113 and the second label 123 may be changed based on whether the first tag 112 and the second tag 122 are bonded. The distance between the first label 113 and the second label 123 may be determined based on whether the first tag 112 and the second tag 122 are bonded.

In a specific example, when the first tag 112 and the second tag 122 are bonded, the first label 113 and the second label 123 may be disposed adjacent to each other. When the first tag 112 and the second tag 122 are complementarily bonded, the first label 113 connected to the first tag 112 and the second label 123 connected to the second tag 122 may be disposed adjacent to each other.

In addition, when the first tag 112 and the second tag 122 are not bonded, the first label 113 and the second label 123 may be spaced apart from each other. When the first tag 112 and the second tag 122 are not complementarily bonded to each other, the first label 113 connected to the first tag 112 and the second label 123 connected to the second tag 122 may be disposed spaced apart from each other.

Therefore, according to an exemplary embodiment of the present application, whether the linked action between the first label 113 and the second label 123 is performed or not may be determined based on whether the first tag 112 and the second tag 122 are bonded.

FIG. 15 is a graph of the fluorescence (F) per wavelength band (WL) according to the linked action between the first label 113 and the second label 123 according to an exemplary embodiment of the present application.

The linked action between the first label 113 and the second label 123 according to an exemplary embodiment of the present application may cause a change in optical characteristics. The optical characteristics of the unit cell (UC) including the first label 113 and the second label 123 before the linked action between the first label 113 and the second label 123 may be different from those of the unit cell (UC) including the first label 113 and the second label 123 after the linked action between the first label 113 and the second label 123.

In one example, when light of the unit cell (UC) including the first label 113 and the second label 123 is detected using an optical device, the linked action between the first label 113 and the second label 123 may lead to a change in the wavelength band of the detected signal (e.g., the wavelength band of light).

In another example, when light of the unit cell (UC) including the first label 113 and the second label 123 is detected using an optical device, the linked action between the first label 113 and the second label 123 may lead to a change in the intensity of a signal in a specific wavelength band.

In still another example, when light of the unit cell (UC) including the first label 113 and the second label 123 is detected using an optical device, the linked action between the first label 113 and the second label 123 may lead to a change of a signal between on/off due to the setting or limit of the optical device.

In a specific example, in the detection of light of the unit cell (UC) including the first label 113 and the second label 123 using an optical device, when the linked action of the first label 113 and the second label 123 occurs in a state in which the detection value of the unit cell (UC) exceeds the fluorescence threshold (TF) of the optical device, the detection value of the unit cell (UC) may decrease to less than the fluorescence threshold (TF) (see FIG. 15(a)).

Here, the fluorescence threshold (TF) may be the lowest fluorescence value that can be detected using the optical device, determined by the setting or limit of the optical device.

When the detection value of the unit cell (UC) decreases to less than the fluorescence threshold (TF) from an initial state (i.e., the detection value of the unit cell (UC) exceeds the fluorescence threshold (TF) of the optical device) by a linked action, a signal of the optical device may be changed from "on" state to "off" state.

Alternatively, a signal of the optical device continuously detect a fluorescence value of the unit cell (UC) and then may be changed to "off" state when the detection value of the unit cell (UC) is reduced to less than the fluorescence threshold (TF) from the initial state by the linked action.

In a specific example, in detection of light of the unit cell (UC) including the first label 113 and the second label 123 using an optical device, when the linked action of the first label 113 and the second label 123 in a state in which the detection value of the unit cell (UC) exceeds the fluorescence threshold (TF) in a detection region (DR), a detection value of the unit cell (UC) may decrease to less than the fluorescence threshold (TF) in the detection region (DR) (see FIG. 15(b)).

Here, the detection region (DR) may be a wavelength band range that can detect a fluorescence value using the optical device, determined by the setting or limit of the optical device.

Here, the fluorescence threshold (TF) may be the lowest fluorescence value that can detect a fluorescence value using the optical device, determined by the setting or limit of the optical device.

From an initial state (i.e., the detection value of the unit cell (UC) exceeds the fluorescence threshold (TF) of the optical device), when the detection value of the unit cell (UC) decreases to less than the fluorescence threshold (TF) according to a linked action, a signal of the optical device may be changed from "on" state to "off" state.

From the initial state, when the detection value of the unit cell (UC) is reduced to less than the fluorescence threshold (TF) according to the linked action, a signal of the optical device may continuously detect a fluorescence value of the unit cell (UC) and then be changed to "off" state.

2.4 Linker 400

According to an exemplary embodiment of the present application, when a PCR is performed, the first linker 114 may prevent the production of an amplification product for the first tag 112. In addition, when a PCR is performed, the second linker 124 may prevent the production of an amplification product for the second tag 122.

After the PCR was performed, the first linker 114 and the second linker 124 may allow the first tag 112 and the second tag 122 to be maintained in a single-stranded nucleic acid. The first tag 112 and the second tag 122, which are single-stranded nucleic acids, may complementarily bind in specific environmental conditions.

The first linker 114 and the second linker 124 according to an exemplary embodiment of the present invention may allow the length of the amplification product produced in association with the nucleic acid complex pair 10 through PCR to have a constant length. In this regard, it will be described in further detail in 1. Application of nucleic acid complex pair 10 #1-PCR.

The structure and general operation of the nucleic acid complex pair 10 disclosed in the present application have been disclosed.

The nucleic acid complex pair 10 according to the present application may be used in various fields using a nucleic acid.

For example, the nucleic acid complex pair 10 may be used in synthesis of a plasmid, manufacture of a DNA chip, and as a primer for DNA sequencing. In another example, the nucleic acid complex pair 10 may be used to prevent amplification of a specific base sequence in PCR. In still another example, the nucleic acid complex pair 10 may be used to confirm the presence or absence of a target nucleic acid in a sample.

Hereinafter, specific embodiments of the use of the nucleic acid complex 1 and the nucleic acid complex pair 10 will be described in detail.

However, for convenience of description, unless separately described as needed, it is assumed that the first determinant 111 is a forward primer, and the second determinant 121 is a reverse primer, the first linker 114 and the second linker 124 are PCR blockers, the first tag 112 and the second tag 122 are single strands consisting of DNA, the first label 113 is a fluorescent molecule, and the second label 123 is a quencher molecule.

This is to prevent unnecessary repetitive description, and the first determinant 111, the first linker 114, the first tag 112, the first label 113, the second determinant 121, the second linker 124, the second tag 122 and the second label 123 should be reasonably interpreted based on the above-described materials, configurations, examples, and the spirit of the specification, and the first determinant 111, the first linker 114, the first tag 112, the first label 113, the second determinant 121, the second linker 124, the second tag 122 and the second label 123 should not be construed as limited to the above-described assumptions.

<Application of Nucleic Acid Complex 1>

1. Application of Nucleic Acid Complex 1 #1-PCR Clamping 1.1 Configuration of Nucleic Acid Complex 1

Figure 16:
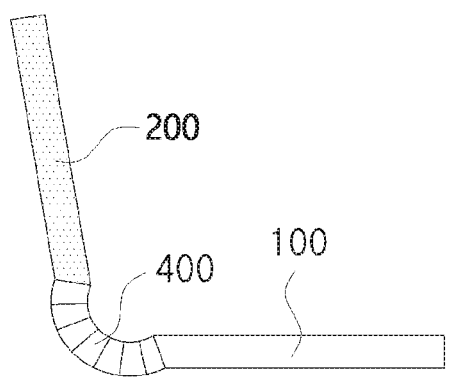
FIG. 16 is a diagram illustrating a nucleic acid complex 1 that includes a determinant 100, a tag 200 and a blocker 400 which can be used for PCR clamping according to an exemplary embodiment of the present application.

FIG. 16 is a diagram illustrating a nucleic acid complex 1 which can be used for PCR clamping according to an exemplary embodiment of the present application.

According to an exemplary embodiment of the present application, the nucleic acid complex 1 which can perform PCR clamping may include at least a determinant 100 and a tag 200. The nucleic acid complex 1 according to an exemplary embodiment of the present application may include a determinant 100, a tag 200 and a linker 400.

The determinant 100 may be a forward primer or reverse primer which initiates PCR. The detailed description thereof has been shown in 1.1.1.3.2 (Primer), and overlapping content will be omitted.

The tag 200 may be a single-stranded body including a nucleic acid and/or a nucleic acid analog. The tag 200 may be a probe for PCR clamping. The base sequence of the tag 200 and the base sequence of the determinant 100 may differ by at least one base. The detailed description thereof has been shown in 1.1.2.3.2 (Probe for PCR clamping), and overlapping content will be omitted.

The linker 400 may be a compound having a predetermined length. The linker 400 may be a blocker for PCR. The detailed description thereof has been shown in 3.1.1.3.1 (blocker for PCR), and overlapping content will be omitted.

1.2 Operation of Nucleic Acid Complex 1

1.2.1 General of PCR

The nucleic acid complex 1 according to an exemplary embodiment of the present application may be used in PCR.

Figure 17:
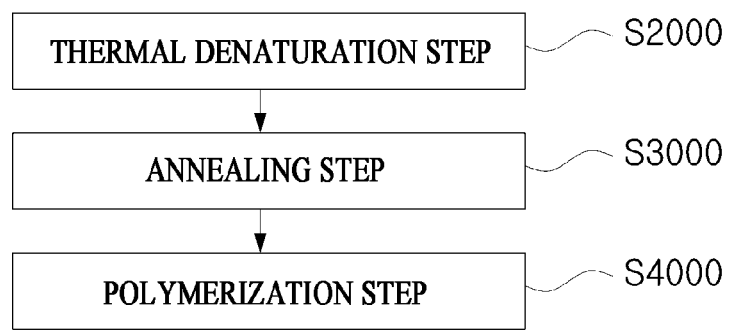
FIG. 17 is a diagram illustrating the PCR steps according to an exemplary embodiment of the present application that includes a thermal denaturation step S2000, an annealing step S3000 and a polymerization step S4000.

FIG. 17 is a diagram illustrating the PCR steps according to an exemplary embodiment of the present application.

The PCR may include a thermal denaturation step (S2000), an annealing step (S3000) and a polymerization step (S4000).

According to an exemplary embodiment of the present application, PCR steps for the unit cell (UC) including the nucleic acid complex 1 may be performed. The unit cell (UC) including the nucleic acid complex 1 may be a unit cell (UC) in which a temperature is changed to perform a PCR reaction. The unit cell (UC) including the nucleic acid complex 1 may be a unit cell (UC) to which a plurality of samples are provided to perform a PCR reaction. In one example, the unit cell (UC) may be a tube in which a PCR reaction is performed.

At least one sample may be provided to the unit cell (UC). The unit cell (UC) may be provided with at least one sample used in the PCR steps. For example, in the unit cell (UC), the nucleic acid complex 1 may be included. In the unit cell (UC), at least one of an enzyme involved in polymerization (e.g., polymerase), a base fragment (e.g., deoxynucleotide triphosphate (dNTP)), a coenzyme involved in PCR (e.g., $MgCl_2$ or $MgSO_4$), a buffer for providing optimized pH and/or salt concentration for PCR.

The PCR steps for the unit cell (UC) may include, generally, 1) a thermal denaturation step (S2000, denaturation step) for separating double-stranded DNA by adjusting the temperature of a unit cell (UC), 2) an annealing step (S3000) for allowing a primer to bind to a target nucleic acid (e.g., separated single-stranded DNA) including a specific base sequence by adjusting a temperature of the unit cell (UC), and 3) a polymerization step (S4000, extension step) for producing an amplification product for the target nucleic acid at one end of the primer binding to the target nucleic acid by adjusting the temperature of the unit cell (UC).

The above-described thermal denaturation step (S2000), annealing step (S3000) and polymerization step (S4000) may be sequentially performed repeatedly.

The temperature adjusted in the thermal denaturation step (S2000) may be a temperature at which double-stranded DNA is separated. Preferably, the temperature of the unit cell (UC) in the thermal denaturation step (S2000) is maintained over 80° C. Preferably, the temperature of the unit cell (UC) in the thermal denaturation step (S2000) is maintained over 90° C. Preferably, the temperature of the unit cell (UC) in the thermal denaturation step (S2000) is maintained over 95° C. Preferably, the temperature of the unit cell (UC) in the thermal denaturation step (S2000) is maintained at 95° C.

The temperature adjusted in the annealing step (S3000) may be a temperature at which a primer binds to a target nucleic acid. Preferably, the temperature of the unit cell (UC) in the annealing step (S3000) is maintained at approximately 40 to 60° C. Preferably, the temperature of the unit cell (UC) in the annealing step (S3000) is maintained at approximately 45 to 55° C. Preferably, the temperature of the unit cell (UC) in the annealing step (S3000) is maintained at approximately 50° C.

The temperature adjusted in the polymerization step (S4000) may be a temperature for producing an amplification product for the target nucleic acid from one end of a primer binding to the target nucleic acid. Preferably, the temperature of the unit cell (UC) in the polymerization step (S4000) is maintained at approximately 50 to 70° C. Preferably, the temperature of the unit cell (UC) in the polymerization step (S4000) is maintained at approximately 55 to 65° C. Preferably, the temperature of the unit cell (UC) in the polymerization step (S4000) is maintained at approximately 60° C.

Hereinafter, when the nucleic acid complex 1, which can perform PCR clamping, according to an exemplary embodiment of the present application is provided to the unit cell (UC; e.g., tube), the schematic diagram of the nucleic acid complex 1 as PCR is performed will be described in detail.

1.2.2 Operation of Nucleic Acid Complex 1

Figure 18:
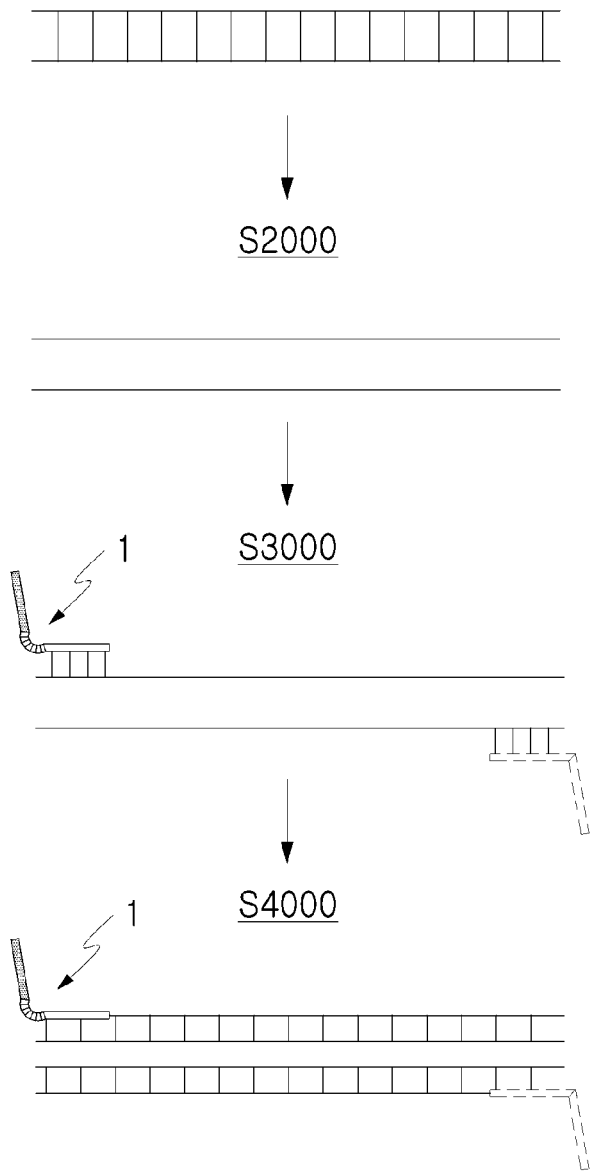
FIGS. 18 and 19 are diagrams illustrating the operations of a nucleic acid complex 1 as shown in FIG. 16 that includes a determinant 100, a tag 200 and a blocker 400 which can be used for PCR clamping according to an exemplary embodiment of the present application.
Figure 19:
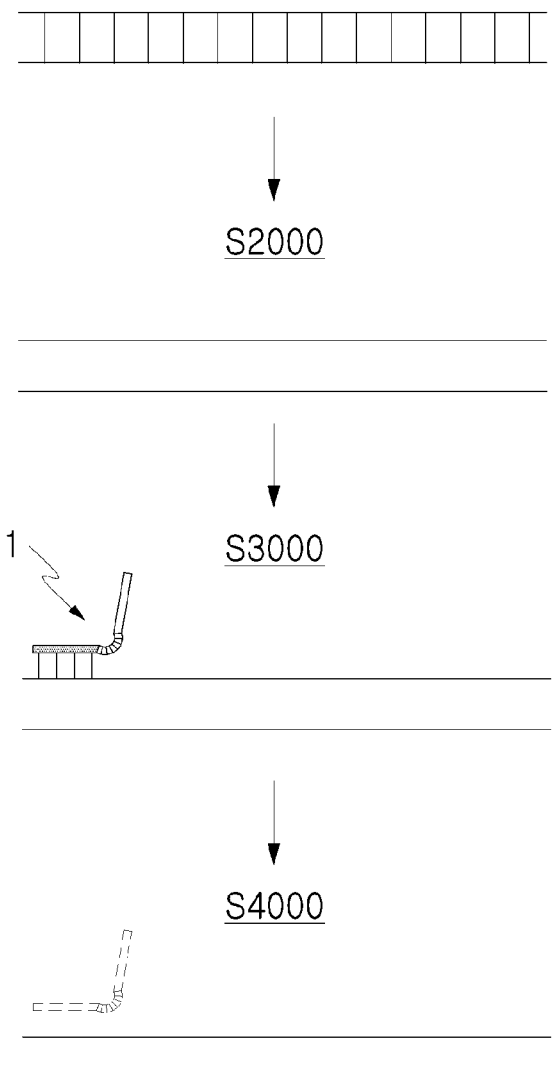

FIGS. 18 and 19 are diagrams illustrating the operations of a nucleic acid complex 1, which can be used for PCR clamping, according to an exemplary embodiment of the present application.

Referring to FIG. 18, in the thermal denaturation step (S2000), double-stranded DNA present in the unit cell (UC) may be denatured to single-stranded DNA. In the thermal denaturation step (S2000), the double-stranded DNA may be separated into two of single-stranded DNAs. In the thermal denaturation step (S2000), double-stranded DNA formed by the hydrogen bonding of two single stranded DNAs may be separated into two of single-stranded DNAs.

At least one single-stranded DNA separated in the thermal denaturation step (S2000) may include a target base sequence (i.e., base sequence complementary to at least part of the base sequence of the determinant 100). The at least one single-stranded DNA present in the unit cell (UC) may include a target base sequence.

In the annealing step (S3000), after the thermal denaturation step (S2000), the determinant 100 may bind to a target nucleic acid including a target base sequence of a single-stranded DNA present in the unit cell (UC). The determinant 100 may complementarily bind to the target base sequence of a single-stranded DNA present in the unit cell (UC). The determinant 100 may complementarily bind to the target base sequence, and initiate the production of an amplification product for at least a partial region of the target nucleic acid including the target base sequence.

When the determinant 100 (i.e., the determinant 100 of the nucleic acid complex 1) is a forward primer, a separate reverse primer may be provided to the unit cell (UC). The reverse primer may be the nucleic acid complex 1. The reverse primer may not be the nucleic acid complex 1.

In the annealing step (S3000), the reverse primer may bind to single-stranded DNA having a complementary sequence to the base sequence of the reverse primer. The reverse primer may complementarily bind to single-stranded DNA having a complementary sequence to the base sequence of the reverse primer.

When the determinant 100 is a reverse primer, a separate forward primer may be provided in the unit cell (UC). The forward primer may be the nucleic acid complex 1. The forward primer may not be the nucleic acid complex 1.

In the annealing step (S3000), the forward primer may bind to single-stranded DNA having a complementary sequence to the base sequence of the forward primer. The forward primer may complementarily bind to single-stranded DNA having a complementary sequence to the base sequence of the forward primer.

In the polymerization step (S4000), using the determinant 100 as a starting point, an amplification product for at least a part of a target nucleic acid to which the determinant 100 binds may be produced. In the polymerization step (S4000), an amplification product for at least a part of a target nucleic acid may be extended from the 3' end of the determinant 100.

In the polymerization step (S4000), using the reverse primer as a starting point, an amplification product for at least a part of single-stranded DNA to which the reverse primer binds may be produced. In the polymerization step (S4000), an amplification product for at least a part of single-stranded DNA to which the reverse primer binds may be extended at the 3' end of the reverse primer.

According to an exemplary embodiment of the present application, when the forward primer and the reverse primer are the nucleic acid complexes 1, when at least two cycles of PCR are done, a construct in which a first tag 112 is located at one side of double-stranded DNA and a second tag 122 is located at the other side (a side different from one side of the double-stranded DNA) of the double-stranded DNA may be produced. In other words, when the forward primer and the reverse primer are nucleic acid complexes 1, when at least two cycles of PCR are done, a construct in which a first tag 112 is located at the 5' end of the forward primer, and a second tag 122 is located at the 5' end of the reverse primer may be produced.

This will be described in further detail in 1.2 Formation of secondary structure below.

Referring to FIG. 19, in the thermal denaturation step (S2000), double-stranded DNA present in the unit cell (UC) may be denatured into single-stranded DNA. In the thermal denaturation step (S2000), double-stranded DNA including the target base sequence may be denatured to single-stranded DNA. In the thermal denaturation step (S2000), the double-stranded DNA including the target base sequence may be separated into two of single-stranded DNA.

There may be a similar base sequence in which at least one base sequence is different from the target base sequence in the unit cell (UC). There may be single-stranded DNA and/or single-stranded DNA including a similar base sequence in the unit cell (UC). A similar base sequence may mean a base sequence in which a partial base sequence is omitted or substituted, compared to the target base sequence.

In the thermal denaturation step (S2000), double-stranded DNA including a similar base sequence may be denatured into single-stranded DNA. In the thermal denaturation step (S2000), the double-stranded DNA including a similar base sequence may be separated into two of single-stranded DNA.

The similar base sequence and the target base sequence may be included in the same nucleic acid. In a specific example, the similar base sequence and the target base sequence may be included in the same strand of DNA. The similar base sequence and the target base sequence may be included in different nucleic acids. In a specific example, the similar base sequence and the target base sequence may be included in different strands of DNA.

In the annealing step (S3000), after the thermal denaturation step (S2000), the determinant 100 may bind to a target nucleic acid including a target base sequence of single-stranded DNA present in the unit cell (UC). The determinant 100 may complementarily bind to the target base sequence of the single-stranded DNA of the unit cell (UC).

In the annealing step (S3000), after the thermal denaturation step (S2000), the tag 200 may bind to a nucleic acid including a similar base sequence of the single-stranded DNA present in the unit cell (UC). The tag 200 may complementarily bind to the similar base sequence of the single-stranded DNA in the unit cell (UC).

When the tag 200 complementarily binds to the similar base sequence, the tag 200 may prevent the determinant 100 from being mismatched and bonded to the similar base sequence. When the tag 200 complementarily binds to the similar base sequence, the tag 200 may prevent the determinant 100 from non-specifically binding to the similar base sequence.

In the polymerization step (S4000), using the determinant 100 as a starting point, an amplification product for at least a part of the target nucleic acid to which the determinant 100 binds may be produced. In the polymerization step (S4000), an amplification product for at least a part of the target nucleic acid may be extended from the 3' end of the determinant 100.

In the polymerization step (S4000), the production of an amplification product for single-stranded DNA including the similar base sequence using the tag 200 as a starting point may be prevented.

In one example, the tag 200 may be connected with the linker 400. The production of an amplification product for single-stranded DNA including the similar base sequence with the tag 200 as a starting point may be prevented by connecting the tag 200 with a linker 400. The production of an amplification product for single-stranded DNA including the similar base sequence may be prevented by connecting the tag 200 with the linker 400.

Because a H group of a sugar at the 3' end of the tag 200 is used in the connection with the linker 400, and the production of an amplification product for single-stranded DNA including the similar base sequence in the 3'end direction of the tag 200 may be prevented.

In a specific example, when the linker 400 is polyethylene glycol (PEG), the tag 200 may be connected with the linker 400 in such a manner that a H group of the tag 200 reacts with an OH group of the linker 400 to form a covalent bond. As a result, the production of a amplification product for single-stranded DNA including the similar base sequence in the 3' end direction of the tag 200 may be prevented by previously involving a H group of a sugar at the 3' end of the tag 200 at which the nucleotide is extended in the reaction.

In some cases, in the polymerization step (S4000), the tag 200 may be dissociated from the similar base sequence. According to the binding force of the tag 200 determined based on the type and length of the base sequence of the tag 200, and the composition of the tag 200, in the polymerization step (S4000), the bond between the tag 200 and the similar base sequence may be dissociated.

As described above, when the nucleic acid complex 1 according to an exemplary embodiment of the present invention is used in PCR, an amplification product for a nucleic acid related to a target base sequence can be produced, and the production of an amplification product for a nucleic acid related to a similar base sequence can be prevented. Therefore, when the nucleic acid complex 1 according to an exemplary embodiment of the present application is used in PCR, the advantage that desired DNA can be more accurately amplified may be derived.

According to another exemplary embodiment of the present application, a nucleic acid complex 1 that can perform PCR clamping may include a determinant 100 and a tag 200.

The determinant 100 may be a forward primer or reverse primer, which initiates a PCR reaction. The determinant 100 may initiate the production of an amplification product for at least a partial region of a nucleic acid including a target base sequence.

The tag 200 may include a nucleic acid analog. In a specific example, the tag 200 may consist of a polymer of the unit molecule of PNA. The tag 200 may have a base sequence in which at least a partial region is different from the determinant 100. The tag 200 may have a base sequence in which a partial sequence of the base sequence of the determinant 100 is deleted or a partial sequence is substituted.

The tag 200 may bind to a similar base sequence. The tag 200 may bind to a similar base sequence to prevent binding of the determinant 100 to the similar base sequence.

The tag 200 may bind to a similar base sequence to prevent the amplification of single-stranded DNA including the similar base sequence. In one example, the tag 200 may consist of the unit molecule of a nucleic acid analog, and may not be extended by a DNA polymerase. As a result, the tag 200 may prevent the amplification of single-stranded DNA including the similar base sequence.

<Application of Nucleic Acid Complex Pair 10>

1. Application of Nucleic Acid Complex Pair 10 #1-PCR 1.1 Application of Nucleic Acid Complex Pair 10 for Providing Primer Pair 1.1.1 Configuration of Nucleic Acid Complex Pair 10

Figure 20:
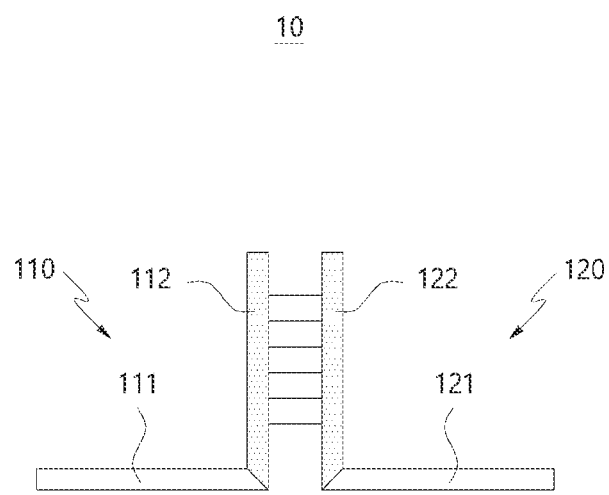
FIG. 20 is a diagram illustrating a nucleic acid complex pair 10 that includes a first nucleic acid complex 110 including a first determinant 111 and a first tag 112 and a second nucleic acid complex 120 including a second determinant 121 and a second tag 122 according to an exemplary embodiment of the present application.

FIG. 20 is a diagram illustrating a nucleic acid complex pair 10 according to an exemplary embodiment of the present application.

The nucleic acid complex pair 10 according to an exemplary embodiment of the present application may include a first nucleic acid complex 110 and a second nucleic acid complex 120. The first nucleic acid complex 110 may include at least a first determinant 111 and a first tag 112. The second nucleic acid complex 120 may include at least a second determinant 121 and a second tag 122.

The first determinant 111 may be a forward primer or a reverse primer. When the first determinant 111 is a forward primer, the second determinant 121 may be a reverse primer. When the first determinant 111 is a reverse primer, the second determinant 121 may be a forward primer.

In a specific example, the first determinant 111 may complementarily bind to a first target base sequence related to a specific disease, and the second determinant 121 may complementarily bind to a second target base sequence related to the same specific disease.

The first tag 112 may complementarily bind to the second tag 122. In one example, the second tag 122 may include a base sequence complementarily binding to the first tag 112. In another example, the second tag 122 may include a compound complementarily binding to the first tag 112.

1.1.2 Operation of Nucleic Acid Complex Pair 10

The nucleic acid complex pair 10 according to an exemplary embodiment of the present application may be used in PCR. The nucleic acid complex pair 10 may be used in PCR to serve as a forward primer and a reverse primer. The first nucleic acid complex 110 may be used as a forward primer, and the second nucleic acid complex 120 may be used as a reverse primer. Alternatively, the first nucleic acid complex 110 may be used as a reverse primer, and the second nucleic acid complex 120 may be used as a forward primer.

When the nucleic acid complex pair 10 is used in PCR, the nucleic acid complex pair 10 may be provided to a unit cell (UC) to be subjected to PCR.

When the nucleic acid complex pair 10 is provided to the unit cell (UC), the nucleic acid complex pair 10 may have a state in which the first tag 112 and the second tag 122 complementarily bind to each other. The nucleic acid complex pair 10 in which the first tag 112 and the second tag 122 complementarily bind to each other may be provided to the unit cell (UC). This is because the nucleic acid complex pair 10 may be synthesized in a form in which the first tag 112 and the second tag 122 complementarily bind to each other.

Alternatively, after the nucleic acid complex pair 10 is provided to the unit cell (UC), the first tag 112 and the second tag 122 may complementarily bind to each other.

Figure 21:
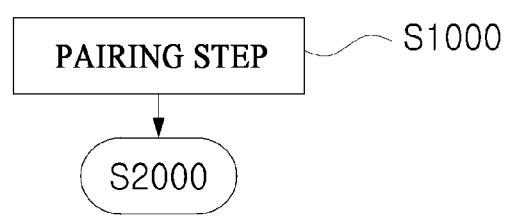
FIG. 21 is a diagram illustrating the pairing operation of a nucleic acid complex pair 10 according to an exemplary embodiment of the present application.

FIG. 21 is a diagram illustrating the pairing operation of a nucleic acid complex pair 10 according to an exemplary embodiment of the present application.

Before the performance of PCR, a pairing step (S1000) may be performed. Before a thermal denaturation step (S2000), a pairing step (S1000) may be performed.

The pairing step (S1000) may be a step of inducing the complementary binding of the first tag 112 and the second tag 122. In other words, the complementary bond between the first tag 112 and the second tag 122 of the nucleic acid complex pair 10 included in the unit cell (UC) may be induced by adjusting a temperature of the unit cell (UC).

The temperature adjusted in the pairing step (S1000) may be a temperature at which the first tag 112 and the second tag 122 complementarily bind to each other. Preferably, the temperature adjusted in the pairing step (S1000) is an annealing temperature of a region in which the first tag 112 and the second tag 122 complementarily bind to each other.

According to an exemplary embodiment of the present application, after the pairing step (S1000), the nucleic acid complex pair 10 may be used for PCR. After the pairing step (S1000), the nucleic acid complex pair 10 may undergo a thermal denaturation step (S2000). After the pairing step (S1000), the nucleic acid complex pair 10 may be subjected to PCR in the sequence of a thermal denaturation step (S2000), an annealing step (S3000), and a polymerization step (S4000). After the pairing step (S1000), the nucleic acid complex pair 10 may be subjected to at least one cycle of PCR including a thermal denaturation step (S2000), an annealing step (S3000), and a polymerization step (S4000).

According to another exemplary embodiment of the present application, after a pairing step (S1000), a solution of a unit cell (UC) containing the nucleic acid complex pair 10 may be distributed. After a pairing step (S1000), a solution of a unit cell (UC) containing the nucleic acid complex pair 10 may be distributed into a smaller unit (e.g., a tube or well). This will be described in detail in 4. Application of nucleic acid complex pair 10 #4-digital PCR below.

Figure 22:
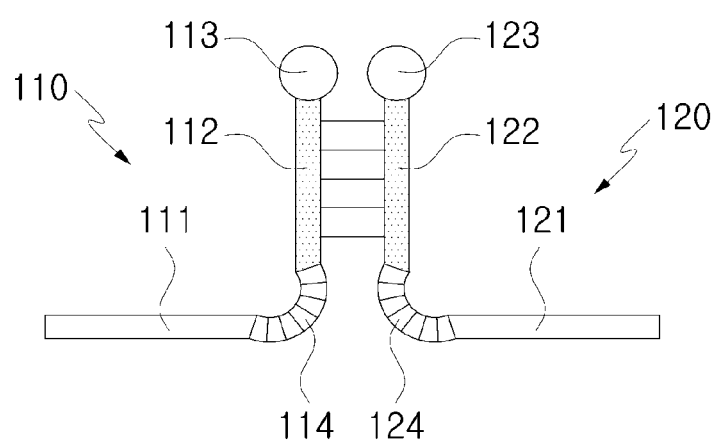
FIG. 22 is a diagram illustrating a nucleic acid complex pair 10 that includes a first nucleic acid complex 110 including a first determinant 111, a first tag 112, a first label 113 and a first linker 114 and a second nucleic acid complex 120 including a second determinant 121, a second tag 122, a second label 123 and a second linker 124 according to an exemplary embodiment of the present application.

1.1.3 Application of Nucleic Acid Complex Pair 10 According to Fourth Exemplary Embodiment FIG. 22 is a diagram illustrating a nucleic acid complex pair 10 according to an exemplary embodiment of the present application.

The nucleic acid complex pair 10 according to an exemplary embodiment of the present application may include a first nucleic acid complex 110 and a second nucleic acid complex 120. The first nucleic acid complex 110 may include at least a first determinant 111, a first tag 112 and a first label 113. The second nucleic acid complex 120 may include at least a second determinant 121, a second tag 122 and a second label 123.

The first determinant 111 may be a forward primer or a reverse primer. When the first determinant 111 is a forward primer, the second determinant 121 may be a reverse primer. When the first determinant 111 is a reverse primer, the second determinant 121 may be a forward primer.

In a specific example, the first determinant 111 may complementarily bind to a first target base sequence related to a specific disease, and the second determinant 121 may complementarily bind to a second target base sequence related to the same disease.

The first tag 112 may complementarily bind to the second tag 122. In one example, the second tag 122 may include a base sequence complementarily binding to the first tag 112. In another example, the second tag 122 may include a compound complementarily binding to the first tag 112.

The first label 113 and the second label 123 may perform a linked action. In one example, when the first label 113 is a fluorescent molecule, the second label 123 may be a quencher molecule for absorbing or converting light emitted from the first label 113.

The linked action between the first label 113 and the second label 123 may be associated with binding between the first tag 112 and the second tag 122. In one example, the linked action between the first label 113 and the second label 123 may be determined by binding between the first tag 112 and the second tag 122.

Like the above-described exemplary embodiment, after a pairing step (S1000), a solution of a unit cell (UC) containing the nucleic acid complex pair 10 may be distributed. After the pairing step (S1000), the solution of a unit cell (UC) containing the nucleic acid complex pair 10 may be distributed into a smaller unit.

A temperature of the distributed solution of a smaller unit cell (UC) may be adjusted. By adjusting the temperature of the distributed solution of a smaller unit cell (UC), the nucleic acid complex pair 10 distributed into a smaller unit cell (UC) may induce or dissociate the bond between the first tag 112 and the second tag 122 according to an adjusted temperature. Preferably, the nucleic acid complex pair 10 distributed into a smaller unit cell (UC) dissociates the bond between the first tag 112 and the second tag 122 by increasing a temperature of the distributed solution of a smaller unit cell (UC).

According to the dissociation of the bond between the first tag 112 and the second tag 122, physical properties of the smaller unit cell (UC) before the temperature adjustment may be different from physical properties of the smaller unit cell (UC) after the temperature adjustment. In one example, when optical properties of the smaller unit cell (UC) are detected using an optical device, a detection value obtained before the temperature of the unit cell (UC) is adjusted to increase may be smaller than a detection value obtained after the temperature of the unit cell (UC) is adjusted to increase.

1.2 Formation of Secondary Structure 1.2.1 Formation of Secondary Structure

In a nucleic acid complex pair 10 according to an exemplary embodiment of the present application, a first determinant 111 and a second determinant 121 may specifically bind to a related material.

In one example, the nucleic acid complex pair 10 may specifically bind to a nucleic acid (i.e., a related material) including a first target base sequence complementarily binding to the first determinant 111 and a second target base sequence complementarily binding to the second determinant 121. The first determinant 111 and the second determinant 121 may specifically bind to a nucleic acid including a first target base sequence and a second target base sequence.

In the nucleic acid complex pair 10 according to an exemplary embodiment of the present application, the first tag 112 and the second tag 122 may complementarily bind to each other. In one example, according to the complementary bond between the first tag 112 and the second tag 122, the shape of the construct in which the first determinant 111 and the second determinant 121 are connected may be changed.

According to an exemplary embodiment of the present application, according to the complementary bond between the first tag 112 and the second tag 122, the construct in which the first determinant 111 and the second determinant 121 are connected may have a secondary structure. As an example, according to the complementary bond between the first tag 112 and the second tag 122, a construct in which the first determinant 111 and the second determinant 121 are connected may have a hairpin-like structure.

According to an exemplary embodiment of the present application, the shape of a secondary structure formed by complementary binding between the first tag 112 and the second tag 122 may vary according to a binding direction of the first tag 112 and the second tag 122. The binding operation between the first tag 112 and the second tag 122 has been described in detail in 2.2 Tag 200 described above, and duplicate descriptions will be omitted.

Figure 23:
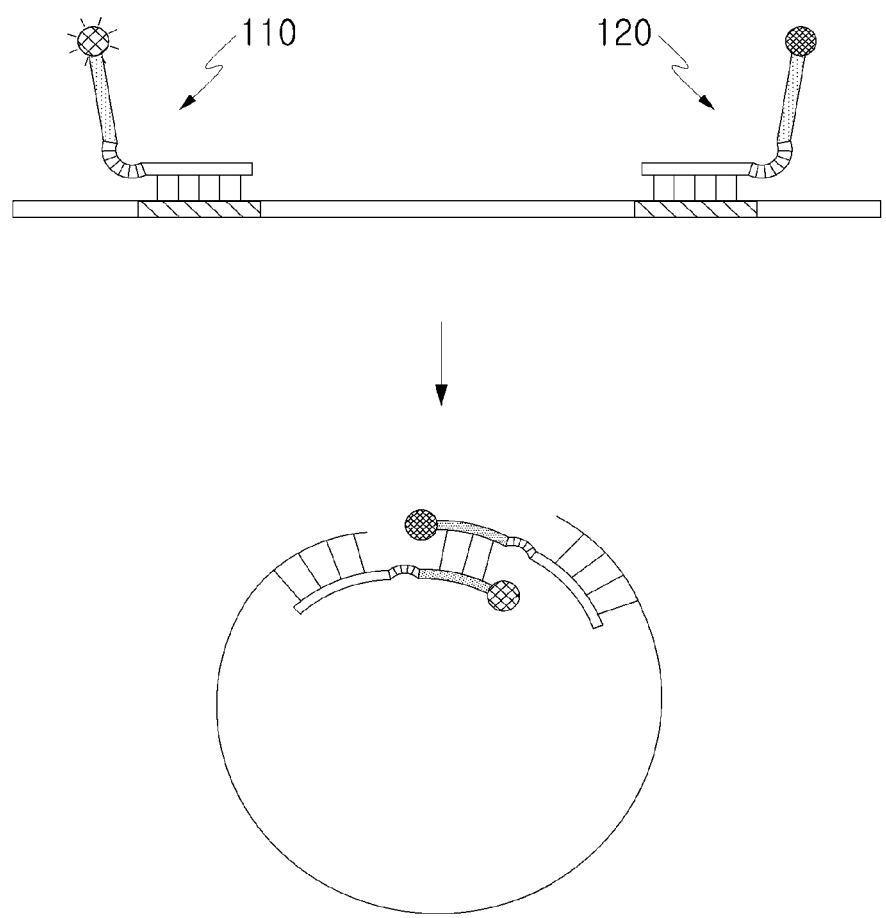
FIGS. 23 and 24 are diagrams illustrating the formation of a secondary structure of a construct between the first nucleic acid complex 110 and the second nucleic acid complex as shown in FIG. 22 in which a first determinant 111 is bonded with a second determinant 121 according to an exemplary embodiment of the present application.
Figure 24:
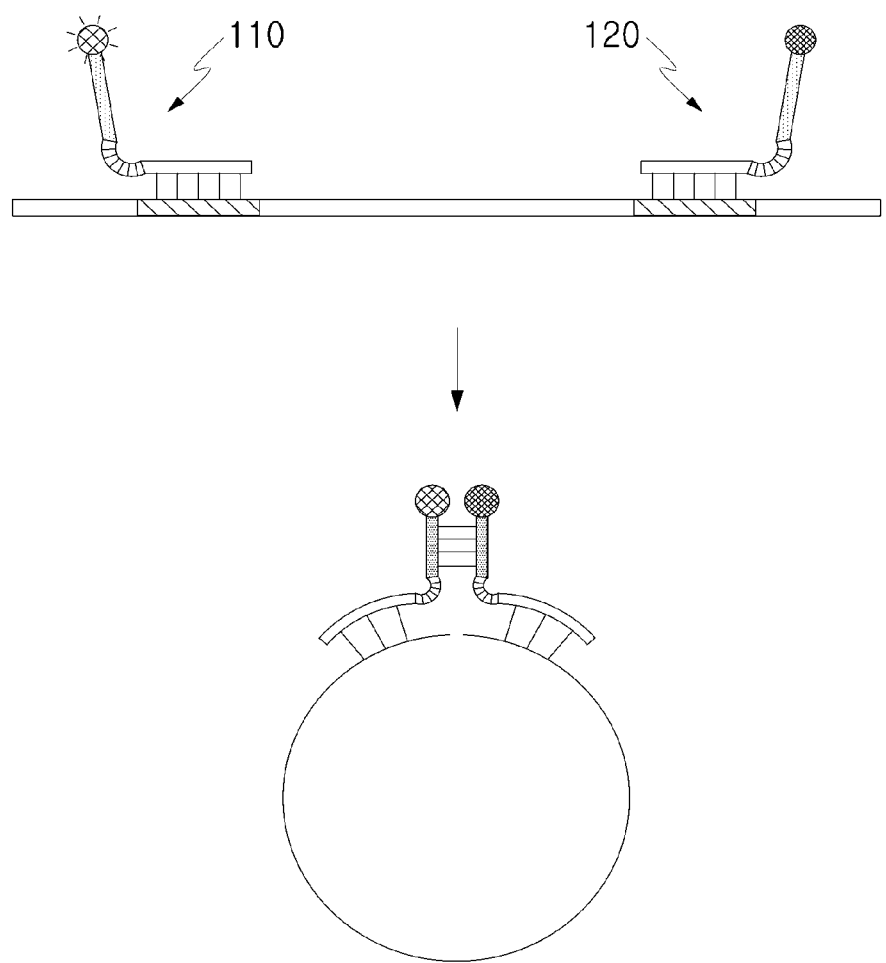

FIGS. 23 and 24 are diagrams illustrating the formation of the secondary structure of a construct in which a first determinant 111 is bonded with a second determinant 121 according to an exemplary embodiment of the present application.

Referring to FIG. 23, the first determinant 111 may bind to a nucleic acid including a first target base sequence. The second determinant 121 may bind to a nucleic acid including a second target base sequence. The first determinant 111 and the second determinant 121 may bind to a nucleic acid including a first target base sequence and a second target base sequence.

The first tag 112 may complementarily bind to the second tag 122. The first tag 112 and the second tag 122 may have base sequences which allow complementary bonds between base sequences of the first tag 112 which are adjacent to the first determinant 111 and base sequences of the second tag 122 which are spaced apart from the second determinant 121 to be formed. The first tag 112 and the second tag 122 may have base sequences which allow complementary bonds between base sequences of the first tag 112 which are adjacent to the first linker 114 and base sequences of the second tag 122 which are spaced apart from the second linker 124 to be formed. In one example, the first tag 112 and the second tag 122 may have base sequences that can bind to each other as shown in FIG. 12(a).

According to an exemplary embodiment of the present application, a nucleic acid including a first target base sequence and a second target base sequence may form a circle-like structure. The nucleic acid including the first target base sequence and the second target base sequence may complementarily bind to the first determinant 111 and the second determinant 121. When the first tag 112 and the second tag 122 complementarily bind to each other, the nucleic acid including the first target base sequence and the second target base sequence which are connected to the first determinant 111 and the second determinant 121, respectively, may have a circle-like structure. The circle-like structure of the nucleic acid including the first target base sequence and the second target base sequence which are connected to the first determinant 111 and the second determinant 121, respectively, may be formed by forming the complementary bonds between base sequences of the first tag 112 adjacent to the first determinant 111 and base sequences of the second tag 122 spaced apart from the second determinant 121.

The "circle-like structure" used herein may be formed in such a manner that at least a partial region of a loop structure formed to have an arbitrary curvature is formed in double strands, and does not form an intact round shape due to the opening of at least a partial region of the loop structure.

According to an exemplary embodiment of the present application, depending on the complementary bonds between the first tag 112 and the second tag 122, whether a nucleic acid connected with the first determinant 111 and the second determinant 121 forms a circle-like structure may be determined. Depending on the complementary bonds between the first tag 112 and the second tag 122, whether the first label 113 and the second label 123 are linked may be determined. Depending on whether a nucleic acid connected with the first determinant 111 and the second determinant 121 has a circle-like structure, whether the first label 113 and the second label 123 performs a linked action may vary.

Referring to FIG. 24, the first determinant 111 may bind to a nucleic acid including a first target base sequence. The second determinant 121 may bind to a nucleic acid including a second target base sequence. The first determinant 111 and the second determinant 121 may bind to the nucleic acid including the first target base sequence and the second target base sequence.

The first tag 112 may complementarily bind to the second tag 122. The first tag 112 and the second tag 122 may have base sequences which allow complementary bonds between base sequences of the first tag 112 which are adjacent to the first determinant 111 and base sequences of the second tag 122 which are adjacent to the second determinant 121 to be formed. The first tag 112 and the second tag 122 may have base sequences which allow complementary bonds between base sequences of the first tag 112 which are adjacent to the first linker 114 and base sequences of the second tag 122 which are adjacent to the second linker 124 to be formed. In one example, the first tag 112 and the second tag 122 may have base sequences which can bind in the form shown in FIG. 12(b).

According to an exemplary embodiment of the present application, a nucleic acid including the first target base sequence and the second target base sequence may form a hairpin-like structure. The nucleic acid including the first target base sequence and the second target base sequence may complementarily bind to the first determinant 111 and the second determinant 121, respectively. When the first tag 112 and the second tag 122 complementarily bind to each other, the nucleic acids including the first target base sequence and the second target base sequence, which are connected with the first determinant 111 and the second determinant 121, respectively, may form a circle-like structure. When the first tag 112 and the second tag 122 complementarily bind to each other in a form in which base sequences of the first tag 112 adjacent to the first determinant 111 and base sequences of the second tag 122 adjacent to the second determinant 121 form complementary bonds, the nucleic acids including the first target base sequence and the second target base sequence, which are connected with the first determinant 111 and the second determinant 121, respectively, may form a hairpin-like structure.

The term "hairpin-like structure" used herein may mean that a loop structure and a stem structure linked to the loop structure are formed. Herein, at least a partial region of the loop structure formed to have an arbitrary curvature has double strands, and the stem structure is formed in a way that nucleic acids extended from end of each single strand included in the double strands are linked to each other.

In the nucleic acid complex pair 10 according to an exemplary embodiment of the present application, the first determinant 111 and the second determinant 121 may specifically bind to a related material.

In one example, the nucleic acid complex pair 10 may specifically bind to a nucleic acid (i.e., related material) including a first target base sequence complementarily binding to the first determinant 111 and a second target base sequence complementarily binding to the second determinant 121.

In another example, according to another exemplary embodiment of the present application, a first target nucleic acid including a first target base sequence to which the first determinant 111 specifically binds and a second target nucleic acid including a second target base sequence to which the second determinant 121 specifically binds may be associated afterward. The first determinant 111 and the second determinant 121 may be associated afterward in the form of which a double-stranded nucleic acid construct including the first determinant 111 and the second determinant 121 is formed.

Figure 25:
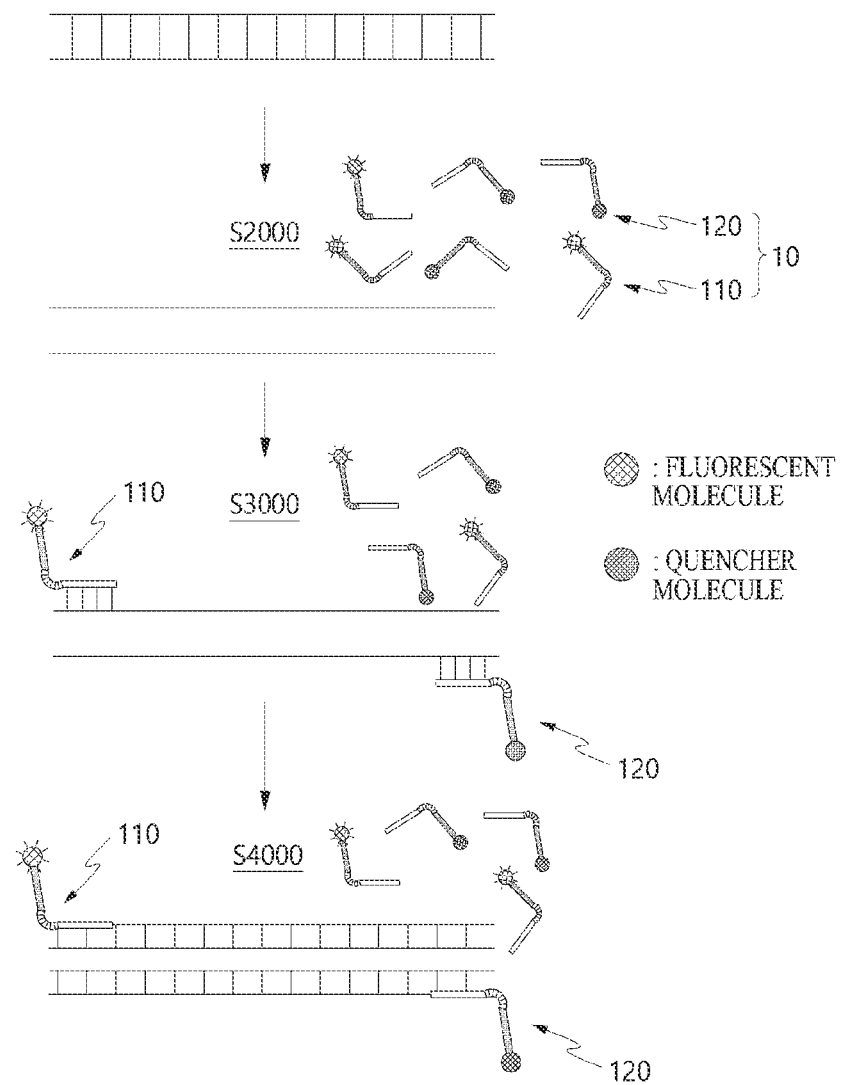
FIGS. 25 and 26 are diagrams illustrating the operations of a nucleic acid complex pair 10 that includes a first nucleic acid complex 110 and a second nucleic acid complex 120 as shown in FIG. 22 which can be forming a construct according to an exemplary embodiment of the present application.
Figure 26:
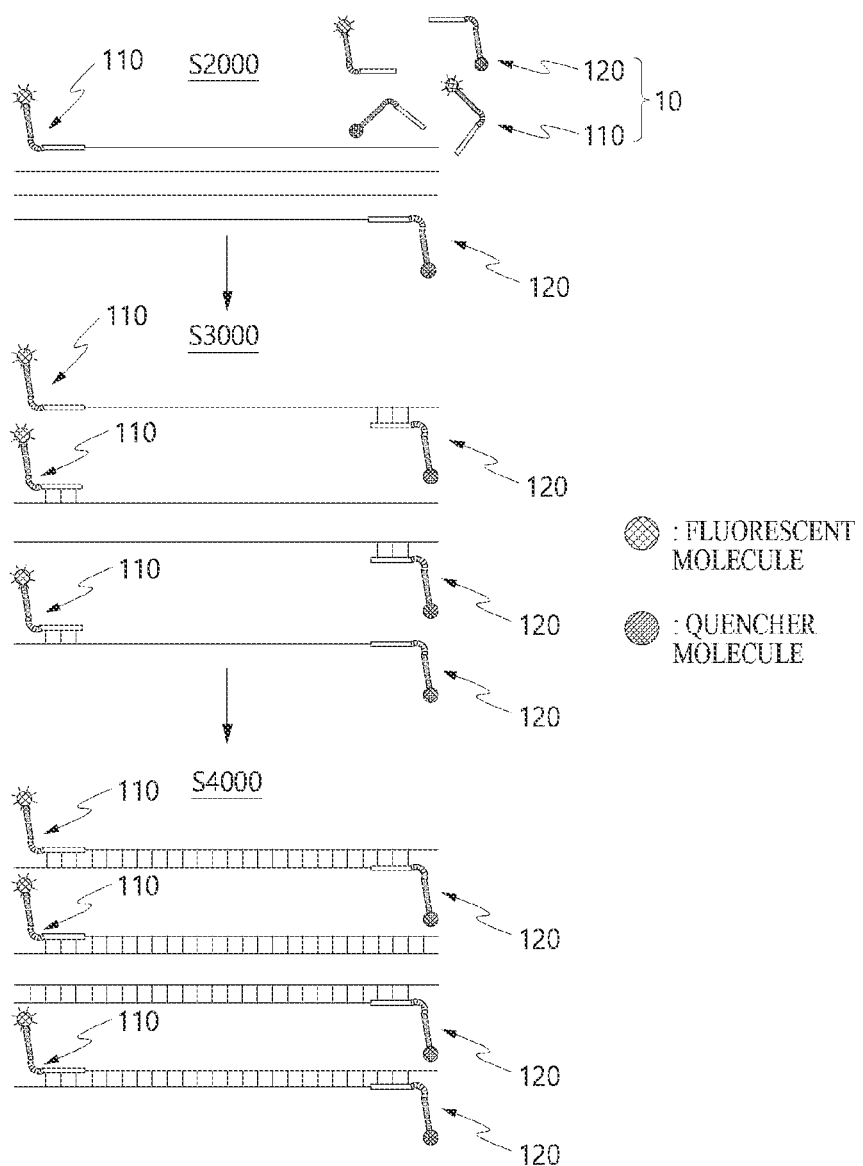

FIGS. 25 and 26 are diagrams illustrating a process of forming a construct including a first determinant 111 and a second determinant 121 according to an exemplary embodiment of the present application.

Referring to FIG. 25, a nucleic acid complex pair 10 and various samples may be provided to a unit cell (UC) in which PCR proceeds. In one example, double-stranded DNA including a first target base sequence and a second target base sequence may be present in the unit cell (UC). Double-stranded DNA may be provided in the unit cell (UC), wherein, in the double-stranded DNA, a first target base sequence is included in a first strand, a second target base sequence is included in a second strand, and the first and second strands are complementarily connected to each other.

In the thermal denaturation step (S2000), the double-stranded DNA present in the unit cell (UC) may be denatured into single-stranded DNAs by adjusting a temperature of the unit cell (UC). In the thermal denaturation step (S2000), the complementary bonds between the first strand including the first target base sequence and the second strand including the second target base sequence may be dissociated.

In an annealing step (S3000), the first determinant 111 of the first nucleic acid complex 110 may complementarily bind to the first strand. In the annealing step (S3000), the second determinant 121 of the second nucleic acid complex 120 may complementarily bind to the second strand.

In the annealing step (S3000), the first label 113 connected to the first determinant 111 binding to the first strand and the second label 123 connected to the second determinant 121 binding to the second strand may not perform a linked action. The first label 113 and the second label 123 are spaced relatively far from each other, and thus may not perform a linked action between each other. The first label 113 and the second label 123 may be spaced apart from each other farther than an effective linkage distance (LD), and thus may not perform a linked action between each other. In a specific example, when the first label 113 is a fluorescent molecule and the second label 123 is a quencher molecule, a fluorescence may be emitted due to the first label 113.

In the polymerization step (S4000), an amplification product may be produced for at least a part of the first strand including the first target base sequence to which the first determinant 111 binds, using the first determinant 111 as a starting point. In the polymerization step (S4000), an amplification product may be produced for at least a part of the second strand including the second target base sequence to which the second determinant 121 binds, using the second determinant 121 as a starting point.

One cycle is set to include a thermal denaturation step (S2000), an annealing step (S3000) and a polymerization step (S4000), and at least one or more cycles of PCR for a unit cell (UC) may be performed.

Referring to FIG. 26, in the thermal denaturation step (S2000) after the first cycle of PCR, the double-stranded DNA present in the unit cell (UC) may be separated into single-stranded DNAs by adjusting a temperature of the unit cell (UC).

In the thermal denaturation step (S2000), a single-stranded nucleic acid including an amplification product for the first strand including the first target base sequence and the first determinant 111 may be produced. The single-stranded nucleic acid including the amplification product for the first strand and the first determinant 111 may include a second target base sequence.

In the thermal denaturation step (S2000), a single-stranded nucleic acid including the amplification product for the second strand including the second target base sequence and the second determinant 121 may be produced. The single-stranded nucleic acid including the amplification product for the second strand and the second determinant 121 may include a first target base sequence.

In the annealing step (S3000), the first determinant 111 may complementarily bind to the single-stranded nucleic acid including the amplification product for the second strand including the second target base sequence and the second determinant 121. In the annealing step (S3000), the second determinant 121 may complementarily bind to the single-stranded nucleic acid including the amplification product for the first strand including the first target base sequence and the first determinant 111.

In the annealing step (S3000), as in the first cycle of PCR, the first determinant 111 may complementarily bind to the first strand including the first target base sequence. In addition, in the annealing step (S3000), as in the first cycle of PCR, the second determinant 121 may complementarily bind to the second strand including the second target base sequence.

In the annealing step (S3000), the first label 113 connected to the first determinant 111 binding to the first strand and the second label 123 connected to the second determinant 121 binding to the second strand may not perform a linked action. The first label 113 and the second label 123 are spaced a relatively large distance apart from each other, and thus may not perform a linked action. The first label 113 and the second label 123 may be spaced from each other farther than an effective linkage distance (LD), and thus may perform a linked action. In a specific example, when the first label 113 is a fluorescent molecule, and the second label 123 is a quencher molecule, a fluorescence may be emitted due to the first label 113.

In the polymerization step (S4000), an amplification product for a single-stranded nucleic acid including an amplification product for the second strand including the second target base sequence and the second determinant 121, to which the first determinant 111 binds, may be produced, using the first determinant 111 as a starting point. In the polymerization step (S4000), when the amplification product of the single-stranded nucleic acid including the amplification product for the second strand and the second determinant 121 is produced, the second linker 124 may prevent an amplification product for the second tag 122 from being produced.

In the polymerization step (S4000), an amplification product for a single-stranded nucleic acid including the amplification product for a first strand of a first target base sequence and a first determinant 111, to which the second determinant 121 binds, may be produced, using the second determinant 121 as a starting point. In the polymerization step (S4000), when the amplification product of the single-stranded nucleic acid including the amplification product for the first strand and the first determinant 111 is produced, the first linker 114 may prevent an amplification product for the first tag 112 from being produced.

In the polymerization step (S4000), as in the first cycle of PCR, an amplification product for at least a part of the first strand including the first target base sequence to which the first determinant 111 binds may be produced, using the first determinant 111 as a starting point. In addition, in the polymerization step (S4000), as in the first cycle of PCR, an amplification product for at least a part of the second strand including the second target base sequence to which the second determinant 121 binds may be produced, using the second determinant 121 as a starting point.

When at least two or more cycles of PCR is performed, a double-stranded nucleic acid construct, which includes a first target base sequence and a second target base sequence in a unit cell (UC) and further includes a first nucleic acid complex 110 and a second nucleic acid complex 120, may be produced. In the double-stranded nucleic acid construct including a first target base sequence and a second target base sequence and including a first nucleic acid complex 110 and a second nucleic acid complex 120, the first tag 112 and the second tag 122 may be maintained in a single-stranded form.

According to an exemplary embodiment of the present application, the first tag 112 and the second tag 122 maintained in a single-stranded form still remain in a single strand after PCR is completed, whereby complementary bonds between the first tag 112 and the second tag 122 can be formed. As a result, after the completion of PCR, according to whether there is a complementary bond between the first tag 112 and the second tag 122, a first label 113 and a second label 123 are detected, whereby the presence of a target nucleic acid can be detected. A specific embodiment of the nucleic acid complex pair 10 will be more specifically described in 1.3 Application of nucleic acid complex pair for target detection.

Figure 27:
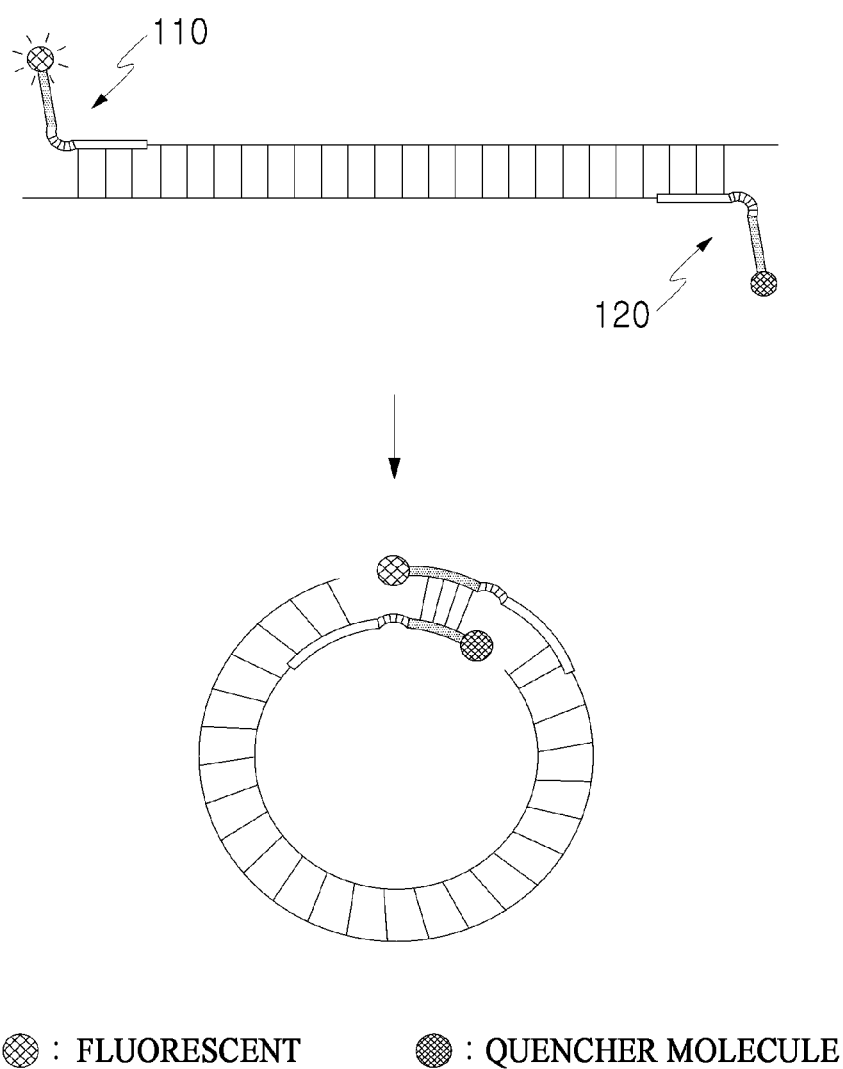
FIGS. 27 and 28 are diagrams illustrating the formation of a secondary structure of an amplicon from PCR steps including a first nucleic acid complex 110 and a second nucleic acid complex 120 according to an exemplary embodiment of the present application.
Figure 28:
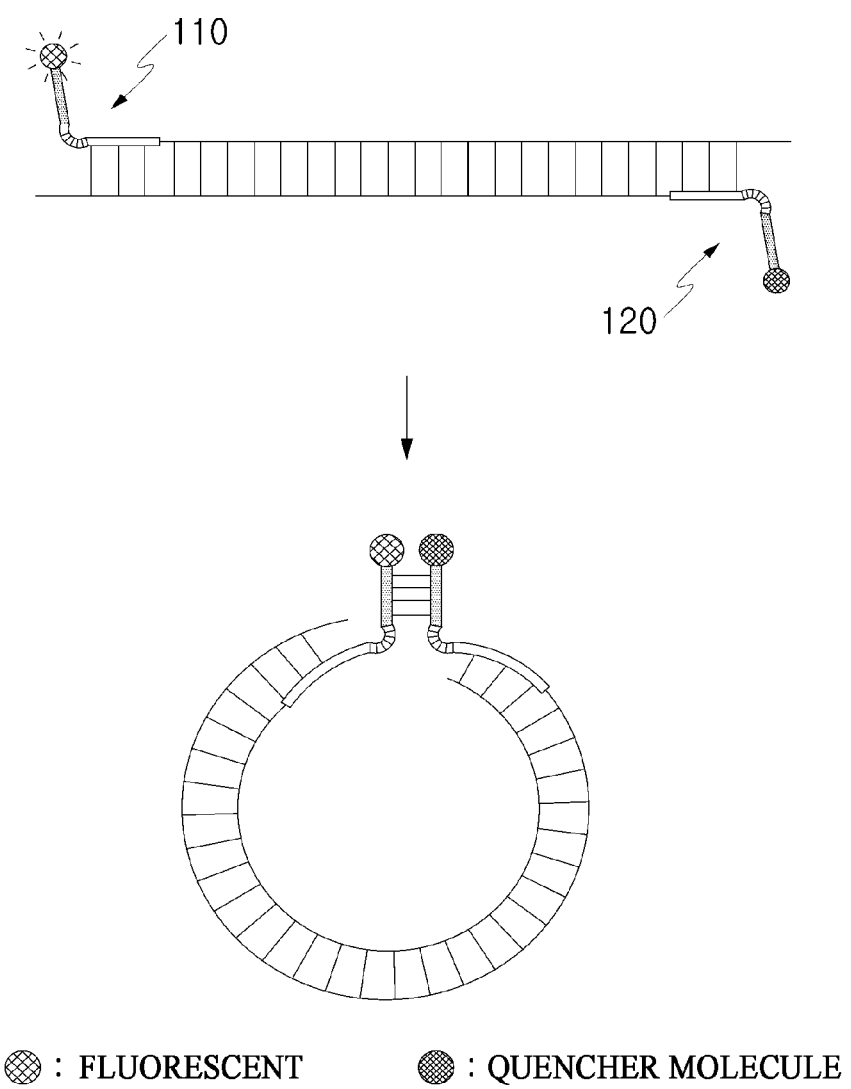

FIGS. 27 and 28 are diagrams illustrating the formation of a secondary structure of a construct including a first determinant 1 and a second determinant 121 according to an exemplary embodiment of the present application.

Referring to FIG. 27, a structure including a first nucleic acid complex 110, a second nucleic acid complex 120, a first target base sequence and a second target base sequence may form a secondary structure. In one example, a structure including a first nucleic acid complex 110, a second nucleic acid complex 120, a first target base sequence and a second target base sequence, which is produced by PCR, may form a secondary structure.

The first tag 112 may complementarily bind to the second tag 122. The first tag 112 and the second tag 122, which are maintained in a single-stranded form, may complementarily bind to each other. The first tag 112 and the second tag 122, which are maintained in a single-stranded nucleic acid, may complementarily bind to each other.

The first tag 112 and the second tag 122 may have base sequences which allow complementary bonds between base sequences of the first tag 112 which are adjacent to the first determinant 111 and base sequences of the second tag 122 which are spaced apart from the second determinant 121 to be formed. The first tag 112 and the second tag 122 may have base sequences which allow complementary bonds between base sequences of the first tag 112 which are adjacent to the first linker 114 and base sequences of the second tag 122 which are spaced apart from second linker 124 to be formed. In one example, the first tag 112 and the second tag 122 may have base sequences binding to each other in the form shown in FIG. 12(a).

According to an exemplary embodiment of the present application, although a nucleic acid construct including a first determinant 111, a second determinant 121, a first target base sequence and a second target base sequence has a double-stranded form, the construct including the first determinant 111, the second determinant 121, the first target base sequence and the second target base sequence may form a circle-like structure. The first tag 112 exposed at the 5' end of the first determinant 111 and the second tag 122 exposed at the 5' end of the second determinant 121 may complementarily bind to each other. The nucleic acid construct including the first determinant 111, the second determinant 121, the first target base sequence and the second target base sequence may have a circle-like structure formed by complementary binding between the first tag 112 and the second tag 122.

Referring to FIG. 28, a construct including a first nucleic acid complex 110, a second nucleic acid complex 120, a first target base sequence and a second target base sequence may form a secondary structure. In one example, the construct including the first nucleic acid complex 110, the second nucleic acid complex 120, the first target base sequence and the second target base sequence, produced by PCR, may form a secondary structure.

The first tag 112 may complementarily bind to the second tag 122. The first tag 112 and the second tag 122, which are maintained in a single-stranded form, may complementarily bind to each other. The first tag 112 and the second tag 122, which are maintained in a single-stranded nucleic acid, may complementarily bind to each other.

The first tag 112 and the second tag 122 may have base sequences which allow complementary bonds between base sequences of the first tag 112 which are adjacent to the first determinant 111 and base sequences of the second tan 122 which are adjacent to the second determinant 121 to be formed. The first tag 112 and the second tag 122 may have base sequences which allow complementary bonds between base sequences of the first tag 112 which are adjacent to the first linker 114 and base sequences which are adjacent to the second linker 124 to be formed. In one example, the first tag 112 and the second tag 122 may have base sequences that can bind to each other in the form shown in FIG. 12(*b*).

According to an exemplary embodiment of the present application, even if a nucleic acid construct including a first determinant 111, a second determinant 121, a first target base sequence and a second target base sequence may have a double-stranded form, the construct including the first determinant 111, the second determinant 121, the first target base sequence and the second target base sequence may form a hairpin-like structure. The first tag 112 exposed at the 5' end of the first determinant 111 and the second tag 122 exposed at the 5' end of the second determinant 121 may complementarily bind to each other. The nucleic acid construct including the first determinant 111, the second determinant 121, the first target base sequence and the second target base sequence may have a hairpin-like structure formed by complementarily binding the first tag 112 and the second tag 122.

1.2.2 Experimental Example #1 Related to Formation of Secondary Structure

Figure 29:
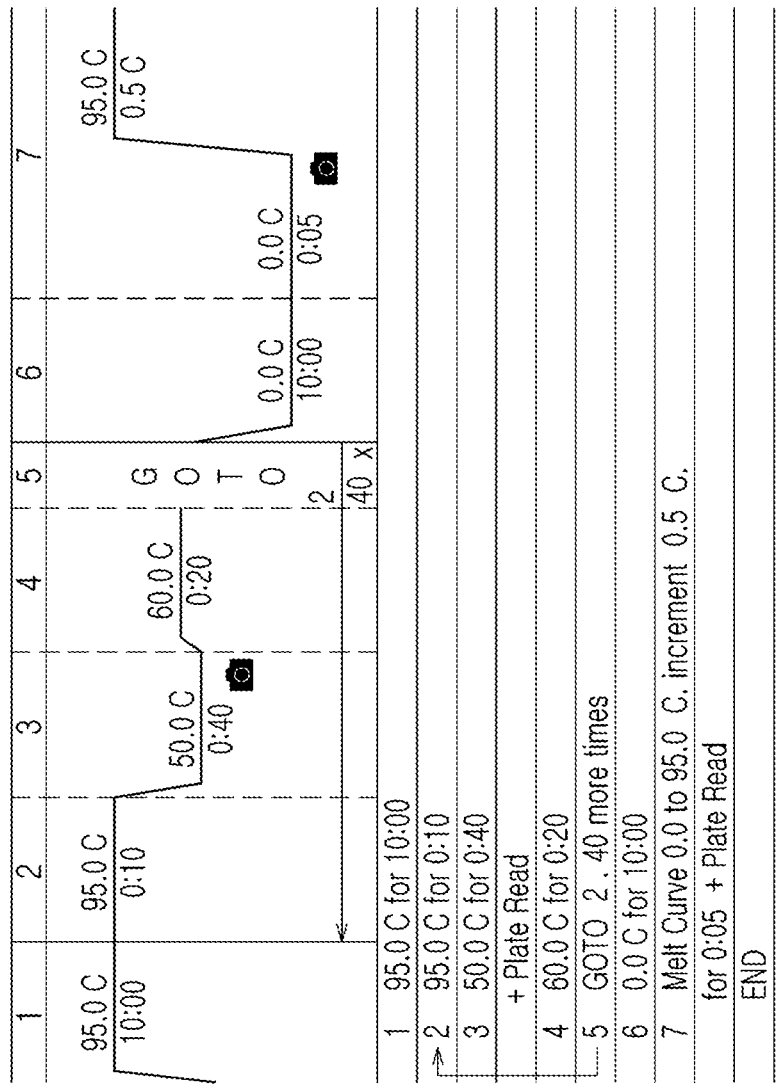
FIGS. 29 and 30 are diagrams illustrating the formation of a secondary structure of a nucleic acid construct including a nucleic acid complex pair according to an exemplary embodiment of the present application.
Figure 30:
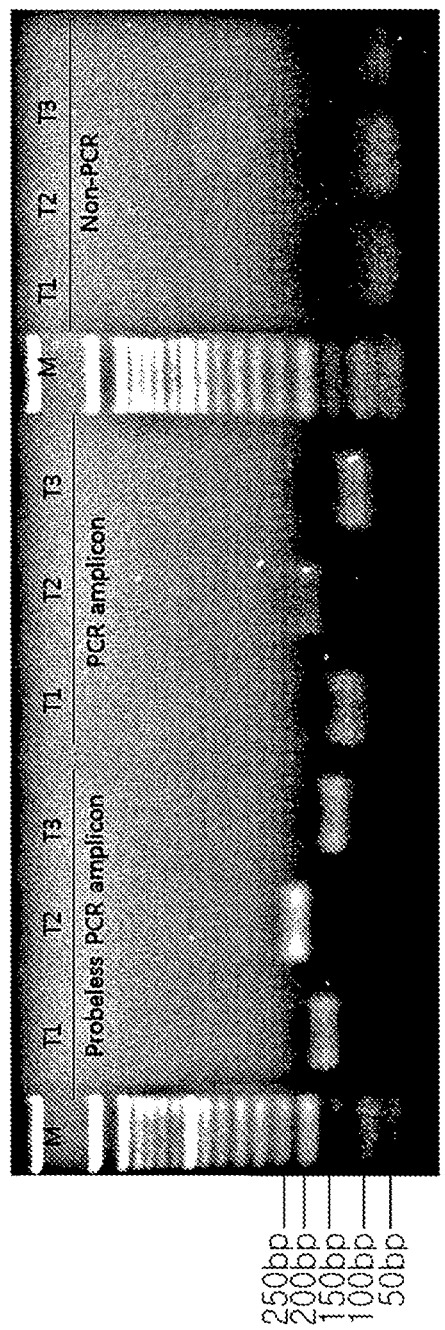

FIGS. 29 and 30 are diagrams illustrating the formation of a secondary structure of a nucleic acid construct including a nucleic acid complex pair 10 according to an exemplary embodiment of the present application.

During the progression of this experiment, Tris-HCl (pH 9.0), a salt (KCl), MaCl$_2$, a dNTP mixture, a protein stabilizer, a PCR enhancer (macromolecules), and fast hot-start Taq DNA polymerase were introduced into a tube (or well) of a PCT plate.

A first nucleic acid complex pair 10 was introduced into the first tube of the PCR plate.

The first nucleic acid complex pair 10 consisted of a first nucleic acid complex 110 and a second nucleic acid complex 120.

The first nucleic acid complex 110 was formed by sequentially connecting a first label 113, a first tag 112, a first linker 114 and a first determinant 111, wherein the first label 113 was FAM, the first tag 112 was AAAAAAAA (SEQ ID NO: 1), the first linker 114 was an 18-atom hexa-ethyleneglycol spacer (Spacer 18), and the first determinant 111 was TACGCCTGCTACTTTCACG (SEQ ID NO: 2).

The second nucleic acid complex 120 was formed by sequentially connecting a second label 123, a second tag 122, a second linker 124 and a second determinant 121, wherein the second label 123 was a quencher molecule (Iowa Black@ FQ (Iowa Black@ Quenchers)), the second tag 122 was TTTTTTTT (SEQ ID NO: 3), the second linker 124 was Spacer 18, and the second determinant 121 was ATATTTAAGGGCATAATTTCCG (SEQ ID NO: 4).

A second nucleic acid complex pair 10 was introduced into a second tube of the PCR plate. The second nucleic acid complex pair 10 consisted of a third nucleic acid complex 1 and a fourth nucleic acid complex 1.

The third nucleic acid complex 1 was formed by sequentially connecting a third label 300, a third tag 200, a third linker 400 and a third determinant 100, wherein the third label 300 was FAM, the third tag 200 was AAAAAAAAAA (SEQ ID NO: 5), the third linker 400 was Spacer 18, and the third determinant 100 was AGGTAAACGCTCCTCTGAA (SEQ ID NO: 6).

The fourth nucleic acid complex 1 was formed by sequentially connecting a fourth label 300, a fourth tag 200, a fourth linker 400 and a fourth determinant 100, wherein the fourth label 300 was a quencher molecule (Iowa Black@ FQ (Iowa Black@ Quenchers)), the fourth tag 200 was TTTTTTTTT (SEQ ID NO: 7), the fourth linker 400 was Spacer 18, and the fourth determinant 100 was GCGAGTTACGAAGACAAAA (SEQ ID NO: 8).

A third nucleic acid complex pair 10 was introduced into a third tube of the PCR plate. The third nucleic acid complex pair 10 consisted of a fifth nucleic acid complex 1 and a sixth nucleic acid complex 1.

The fifth nucleic acid complex 1 was formed by sequentially connecting a fifth label 300, a fifth tag 200, a fifth linker 400 and a fifth determinant 100, wherein the fifth label 300 was FAM, the fifth tag 200 was AACCTTGGGA (SEQ ID NO: 9), the fifth linker 400 was Spacer 18, and the fifth determinant 100 was AGCTCCTATTGCCAACGTA (SEQ ID NO: 10).

The sixth nucleic acid complex 1 was formed by sequentially connecting a sixth label 300, a sixth tag 200, a sixth linker 400 and a sixth determinant 100, wherein the sixth label 300 was a quencher molecule (Iowa Black@ FQ (Iowa Black@ Quenchers)), the sixth tag 200 was TCCCAAGGTT (SEQ ID NO: 11), the sixth linker 400 was Spacer 18, and the sixth determinant 100 was AATCTTTGTGTGGAGCATC (SEQ ID NO: 12).

A PCR reaction was performed on a solution in tubes by adjusting the temperature of the tubes into which the nucleic acid complex pair 10 and other enzymes were introduced. As shown in FIG. 29, the temperature of the tubes was maintained at 95° C. for 10 minutes, and a course of a thermal denaturation step (S2000; 95° C., 10 sec), a annealing step (S3000; 50° C., 40 sec) and a polymerization step (S4000; 60° C., 20 sec) was set as one cycle, and repeatedly performed for 40 cycles. In this experiment, Bio-Rad CFX96 (Permit Number 10-205) was used.

Afterward, the first tube, the second tube and the third tube were stabilized in a refrigerator for a predetermined time or more, and then an electrophoresis experiment was performed on the solutions in the first, second and third tubes.

Referring to FIG. 30, the result for the first tube corresponds to the second column (i.e., Probeless PCR amplicon T1). It was confirmed that the nucleic acid construct including a first nucleic acid complex pair 10 (i.e., the first nucleic acid complex 110, the second nucleic acid complex 120, an amplification product for at least a part of a first target nucleic acid including a first target base sequence, and an amplification product for at least a part of a second target nucleic acid including a second target base sequence) in the first tube has a mass of 180 bp.

As a control, an experiment using a fourth tube, which includes the same enzymes as the first tube, and includes a forward primer (TACGCCTGCTACTTTCACG (SEQ ID NO: 2)) and a reverse primer (ATATTTAAGGGCATAATTTCCG (SEQ ID NO: 4)) instead of the first nucleic acid complex 110 and the second nucleic acid complex 120, was performed, and the result corresponds to the fifth column (i.e., PCR amplicon T1). It was confirmed that the amplification product including the forward primer and the reverse primer (i.e., an amplification product for at least a part of a nucleic acid including a forward primer, a reverse primer, an amplification product for at least a part of a nucleic acid including a sequence complementary to the forward primer, and a sequence complementary to the reverse primer) has a mass of 143 bp.

Figure 31:
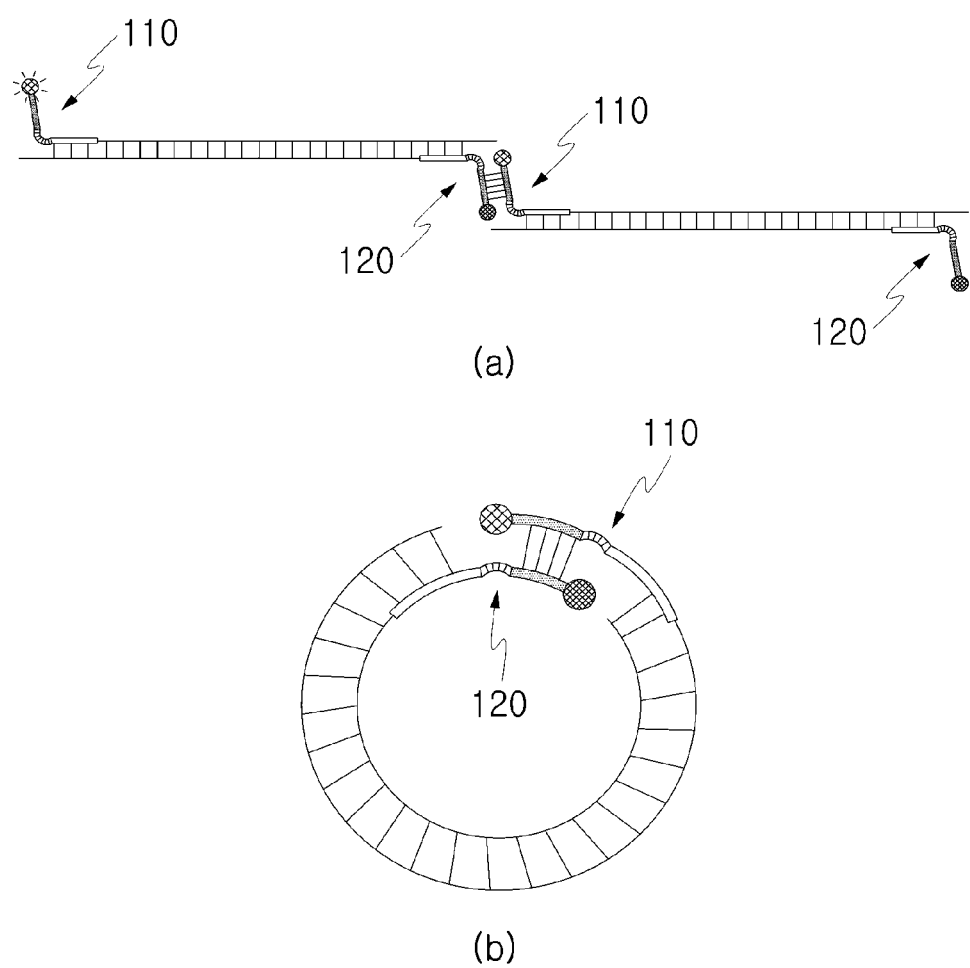
FIG. 31 is a diagram illustrating the formation of a secondary structure of amplicon from PCR steps including a first nucleic acid complex 110 and a second nucleic acid complex 120 according to an exemplary embodiment of the present application.

FIG. 31 is a diagram illustrating the formation of a secondary structure of a nucleic acid construct according to an exemplary embodiment of the present application.

Specifically, as shown in FIG. 31(a), provided that a first tag 112 of a nucleic acid complex pair 10 complementarily binds to a second tag 122 of another nucleic acid complex pair 10 in a unit cell (UC), a result obtained from an electrophoresis gel has to show a mass of 143*2=286 bp according to masses of at least two amplification products.

However, the result for the first tube shown in FIG. 30 shows a mass of 180 bp, and in light of the fact that the mass of the first tag 112 and the second tag 122 is, 16 bp, there is a difference in mass of approximately 180-143-16=21 bp. However, in consideration of the masses of a fluorescent molecule, a quencher molecule and a linker 400, as shown in FIG. 32(b), it is reasonable to consider that a secondary structure is formed.

From this, it can be confirmed that the nucleic acid construct including the nucleic acid complex pair 10 forms a secondary structure.

As such, the result for the second tube was 230 bp, shown in the third column (i.e., Probeless PCR amplicon T2), and the result for the fifth tube including the same enzymes as that of the second tube and further including a forward primer (AGGTAAACGCTCCTCTGAA(SEQ ID NO: 6)) and a reverse primer (GCGAGTTACGAAGACAAAA (SEQ ID NO: 8)) instead of the first nucleic acid complex 110 and the second nucleic acid complex 120 was 191 bp, shown in the sixth column (i.e., PCR amplicon T2).

In addition, the result for the third tube was 150 bp, shown in the fourth column (i.e., Probeless PCR amplicon T3), and the result for the sixth tube including the same enzymes as the third tube and further including a forward primer (AGCTCCTATTGCCAACGTA (SEQ ID NO: 10)) and a reverse primer (AATCTTTGTGTGGAGCATC(SEQ ID NO: 12)), instead of the first nucleic acid complex 110 and the second nucleic acid complex 120, was 113 bp, shown in the seventh column (i.e., PCR amplicon T3).

As a result, the mass of the nucleic acid construct including the nucleic acid complex pair 10 does not exceed twice the mass of a nucleic acid construct not including the nucleic acid complex pair 10, confirming that a first tag 112 of the nucleic acid construct including the nucleic acid complex pair 10 did not complementarily bind to a second tag 122 of a nucleic acid construct including another nucleic acid complex pair 10, and thus a secondary structure was formed by complementarily binding between the first tag 112 and the second tag 122 of the nucleic acid construct including the nucleic acid complex pair 10.

So far, the formation of a secondary structure of the nucleic acid complex pair 10 related nucleic acid and the shape of the secondary structure thereby have been described in detail. However, the nucleic acid complex 1 disclosed in the present application and related operations are briefly illustrated and described in detail so that one of ordinary skill in the art can easily understand the specification, and in interpreting the scope of the specification, it should not be construed as limited to the drawings or specific description.

Hereinafter, according to detection signals of an optical device which can vary due to the formation or dissociation of a secondary structure, an example of application for confirming whether there is a target nucleic acid to be detected in a unit cell (UC) will be described in detail.

1.3 Application of Nucleic Acid Complex Pair 10 for Target Detection 1.3.1 Configuration of Nucleic Acid Complex Pair 10

Figure 32:
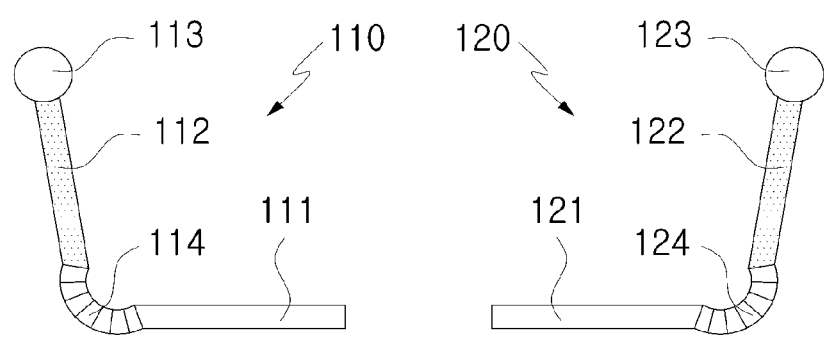
FIG. 32 is a diagram illustrating a nucleic acid complex pair 10 that includes a first nucleic acid complex 110 including a first determinant 111, a first tag 112, a first label 113 and a first linker 114 and a second nucleic acid complex 120 including a second determinant 121, a second tag 122, a second label 123 and a second linker 124 according to an exemplary embodiment of the present application.

FIG. 32 is a diagram illustrating the nucleic acid complex pair 10 according to an exemplary embodiment of the present application.

The nucleic acid complex pair 10 according to an exemplary embodiment of the present application may include a first nucleic acid complex 110 and a second nucleic acid complex 120. The first nucleic acid complex 110 may include a first determinant 111, a first tag 112, a first label 113 and a first linker 114. The second nucleic acid complex 120 may include a second determinant 121, a second tag 122, a second label 123 and a second linker 124.

The first determinant 111 may be a forward primer or a reverse primer. When the first determinant 111 is a forward primer, the second determinant 121 may be a reverse primer. When the first determinant 111 is a reverse primer, the second determinant 121 may be a forward primer.

In a specific example, the first determinant 111 may complementarily bind to a first target base sequence related to a specific disease, and the second determinant 121 may complementarily bind to a second target base sequence related to the same disease.

The first tag 112 may complementarily bind to the second tag 122. In one example, the second tag 122 may include a base sequence complementarily binding to the first tag 112. In another example, the second tag 122 may include a compound complementarily binding to the first tag 112.

The first linker 114 may prevent an amplification product for the first tag 112 from being produced. In a specific example, after an amplification product for at least a partial region of the first target nucleic acid including the first target base sequence is produced by complementarily binding between the first determinant 111 and the first target base sequence, the amplification product for at least a partial region of the first target nucleic acid is bonded with the second determinant 121 to initiate amplification for a single-stranded nucleic acid including the first determinant 111, and then the first linker 114 may prevent an amplification product for the first tag 112 from being produced.

The second linker 124 may prevent an amplification product for the second tag 122 from being produced. In a specific example, after an amplification product for at least a partial region of a second target nucleic acid including the second target base sequence is produced by complementarily binding between the second determinant 121 and a second target base sequence, the amplification product for at least a partial region of the second target nucleic acid binds to the first determinant 111 to initiate amplification for a single-stranded nucleic acid including the second determinant 121, and then the second linker 124 may prevent an amplification product for the second tag 122 from being produced.

In a specific example, the first linker 114 and the second linker 124 may be PCR blockers.

The first label 113 may be linked with the second label 123. When the detection value of an optical device for a unit cell (UC) including the first label 113 and the second label 123 is obtained, the detection value obtained when the first label 113 and the second label 123 are linked may differ from the detection value obtained when the first label 113 and the second label 123 are not linked. In one example, the first label 113 may be a fluorescent molecule, and the second label 123 may be a quencher molecule, and when the linked action is performed, light emitted from the first label 113 may be absorbed by the second label 123, and when the linked action is not performed, light emitted from the first label 113 may be detected using an optical device.

1.3.2 Operation of Nucleic Acid Complex Pair 10

The nucleic acid complex pair 10 according to an exemplary embodiment of the present application may be used as a primer in PCR.

According to an exemplary embodiment of the present application, the linkage in the nucleic acid complex pair 10 may be confirmed by detecting a signal of the unit cell (UC) including the nucleic acid complex pair 10, and the presence of a target nucleic acid in the unit cell (UC) may be detected by confirming the linkage of the nucleic acid complex pair 10.

Specifically, when a nucleic acid including a first target base sequence to which a first determinant 111 complementarily binds and a second target base sequence to which a second determinant 121 complementarily binds is present in a unit cell (UC), a detection value of an optical device for the unit cell (UC) may be changed at a specific temperature.

For example, at a temperature at which the binding between the first tag 112 and the second tag 122 is dissociated, according to a change in linkage between the first label 113 and the second label 123, it can be shown that a detection value for the unit cell (UC) obtained by an optical device may vary.

As a result, according to whether a detection value obtained by an optical device is changed at a specific temperature, it can be confirmed whether a target nucleic acid to be detected is present in the unit cell (UC).

Hereinafter, a detailed operation for confirming whether a target nucleic acid is present in the unit cell (UC) will be described.

Figure 33:
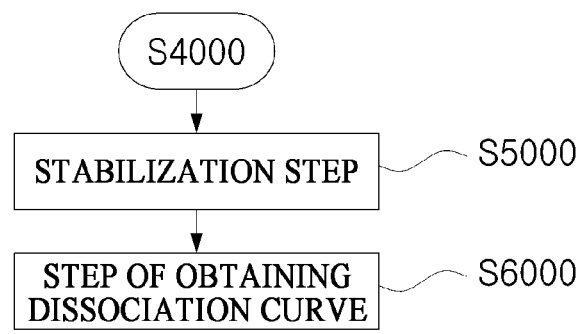
FIG. 33 is a diagram illustrating a detection step after PCR according to an exemplary embodiment of the present application.

FIG. 33 is a diagram illustrating a detection step after PCR according to an exemplary embodiment of the present application.

According to an exemplary embodiment of the present application, a stabilization step (S5000) for the PCR-completed unit cell (UC) may be performed. The stabilization step (S5000) may be performed in such a manner that a temperature of the unit cell (UC) is lowered to a predetermined temperature or less. The stabilization step (S5000) may be performed in such a manner that the temperature of a solution in the unit cell (UC) is lowered to at least 40° C. or less, and maintained for a predetermined time.

The temperature adjusted in the stabilization step (S5000) may be a temperature that induces binding between the first tag 112 and the second tag 122. Preferably, in the stabilization step (S5000), the temperature of the unit cell (UC) is not maintained over 20° C. Preferably, in the stabilization step (S5000), the temperature of the unit cell (UC) is not maintained over 15° C. Preferably, the temperature of the unit cell (UC) in the stabilization step (S5000) is not maintained over 10° C. Preferably, the temperature of the unit cell (UC) in the stabilization step (S5000) is not maintained over 5° C.

According to the stabilization step (S5000), complementary bonds between the first tag 112 and the second tag 122 of the nucleic acid complex pair 10 may be formed. As described above, due to the binding between the first tag 112 and the second tag 122, a nucleic acid including the first determinant 111 and the second determinant 121 may form a secondary structure.

Following the stabilization step (S5000), a step of obtaining a dissociation curve (S6000) may be performed. The step of obtaining a dissociation curve (S6000) may be performed for the unit cell which has undergone the stabilization step (S5000).

Here, the "dissociation curve" means a graph of a fluorescence value against a temperature of the unit cell (UC) within a temperature range including a temperature which dissociates the first tag 112 and the second tag 122.

In the step of obtaining a dissociation curve (S6000), as the temperature of a solution included in the unit cell (UC) increases, a fluorescence value of the solution included in the unit cell (UC) may be detected. In the step of obtaining a dissociation curve (S6000), a fluorescence value of the solution included in the unit cell (UC) may be detected as the temperature of the solution included in the unit cell (UC) increases at a constant rate.

Alternatively, in the step of obtaining a dissociation curve (S6000), as the temperature of the solution included in the unit cell (UC) decreases, a fluorescence value of the solution included in the unit cell (UC) may be detected. In the step of obtaining a dissociation curve (S6000), a fluorescence value of the solution included in the unit cell (UC) may be detected as the temperature of the solution included in the unit cell (UC) decreases at a constant rate.

In the step of obtaining a dissociation curve (S6000), fluorescence values in multiple wavelength bands of the solution included in the unit cell (UC) may be detected. In the step of obtaining a dissociation curve (S6000), some of the fluorescence values in multiple wavelength bands of the solution included in the unit cell (UC) may be detected. In the step of obtaining a dissociation curve (S6000), fluorescence values for previously-set some wavelength bands (or some wavelength band groups) among the fluorescence values in multiple wavelength bands may be detected from the solution included in the unit cell (UC).

Figure 34:
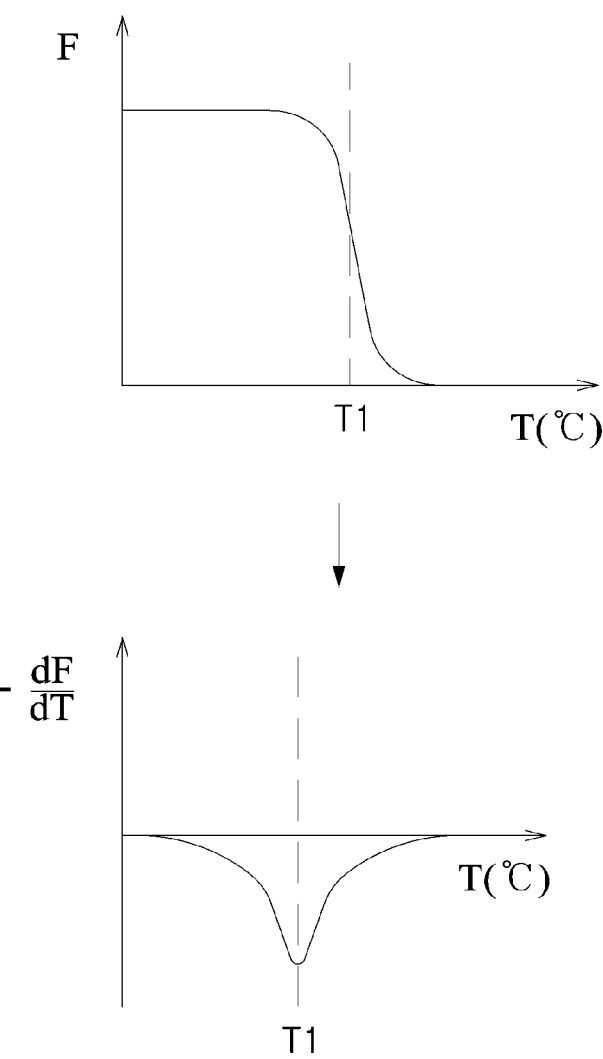
FIGS. 34 and 35 are diagrams illustrating the dissociation curve detection step (S6000) according to an exemplary embodiment of the present application. F, fluorescence; T, temperature; dF/dT, the rate of change in fluorescence with respect to temperature; T, dissociation peak value.

In the nucleic acid complex pair 10 according to an exemplary embodiment of the present application, when it is realized that light emitted from a first label 113 is extinguished by a second label 123 due to the linked action between the first label 113 and the second label 123, a dissociation curve obtained in the step of obtaining a dissociation curve (S6000) may be a graph showing that a fluorescence value decreases with an increase in temperature (see FIG. 34(*a*)). Specifically, when the first tag 112 and the second tag 122 complementarily bind to each other in the stabilization step (S5000), light emitted from the first label 113 may be extinguished due to the second label 123. As the temperature of the unit cell (UC) increases, when the complementary bond between the first tag 112 and the second tag 122 is dissociated, light emitted from the first label 113 may not be extinguished due to the second label 123, and light from the first label 113 is emitted.

According to an exemplary embodiment of the present application, a differential graph may be obtained from a fluorescence graph according to a detected temperature. In other words, the fluorescence graph according to a temperature according to the detected step of obtaining a dissociation curve (S6000) may be transformed into a graph of relationship between temperature and the rate of change in fluorescence with respect to temperature. The fluorescence graph according to temperature shown in FIG. 34(*a*) may be shown as a graph of relationship between temperature and the rate of change in fluorescence with respect to temperature as shown in FIG. 34(*b*).

According to the graph of relationship between temperature and the rate of change in fluorescence with respect to temperature, a dissociation peak value may be obtained. The "dissociation peak value" used herein may mean a temperature at which the complementary bond between the first tag 112 and the second tag 122 of the nucleic acid complex pair 10 is dissociated. Alternatively, the "dissociation peak value" used herein may mean a temperature at the point where the change in fluorescence value is greatest or smallest based on a fluorescence value obtained in the step of obtaining a dissociation curve (S6000). Alternatively, the "dissociation peak value" used herein may mean a temperature corresponding to the maximum point or a temperature corresponding to the minimum point on a graph showing a relationship between temperature and a negative change in fluorescence value with respect to temperature obtained based on the dissociation curve (see FIGS. 34(b) and 35(b)). Alternatively, the "dissociation peak value" may mean, when a fluorescence is changed more than a reference amount in a specific temperature range based on the dissociation curve, a temperature of the point at which fluorescence is reduced by a fluorescence amount corresponding to ½ of the changed fluorescence amount. Alternatively, the "dissociation peak value" used herein may mean a temperature at which the fluorescence value for one type of the nucleic acid complex pair 10 decreases below a predetermined ratio.

In one example, referring to FIG. 34(b), T1 is a temperature corresponding to the minimum point in a graph showing a relationship between temperature and a negative change in fluorescence value with respect to temperature, obtained based on the dissociation curve, and therefore, T1 may be a dissociation peak value.

Figure 35:
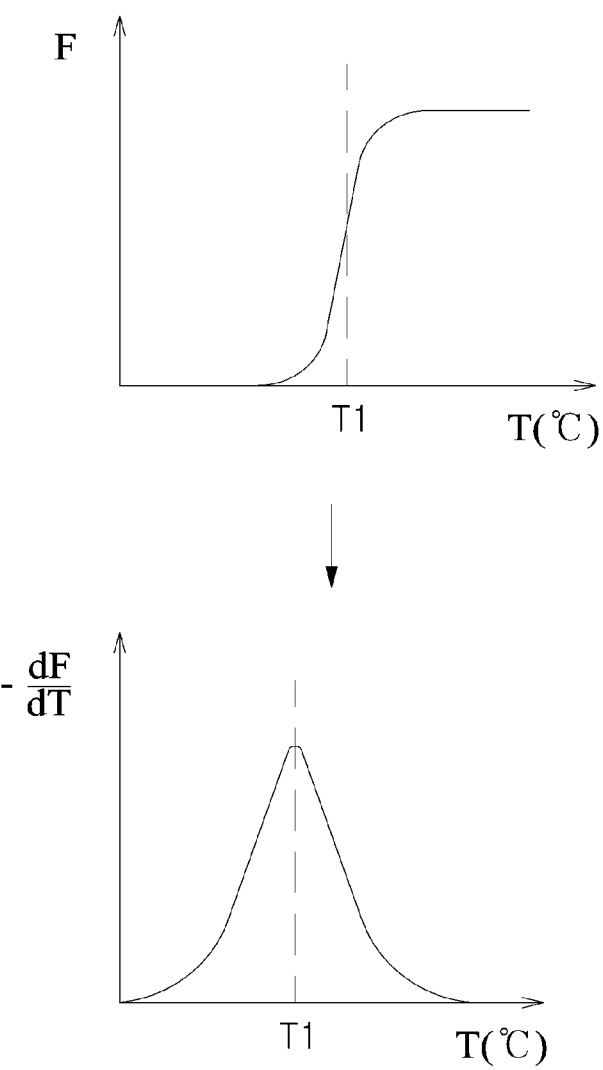

In the nucleic acid complex pair 10 according to an exemplary embodiment of the present application, when light emitted from a first label 113 is converted into detectable light by a second label 123 due to a linked action between the first label 113 and the second label 123, a dissociation curve obtained in the step of obtaining a dissociation curve (S6000) may be a graph in which a fluorescence value increases according to an increase in temperature (see FIG. 35(a)). Specifically, when the first tag 112 and the second tag 122 complementarily bind to each other in the stabilization step (S5000), light from the first label 113 may be converted into detectable light t by the second label 123. When the complementary bond between the first tag 112 and the second tag 122 is dissociated as the temperature of the unit cell (UC) increases, light from the first label 113 may not be converted by the second label 123, and thus an optical device cannot detect the light from the first label 113, determining as light-extinguished state.

In one example, referring to FIG. 35(b), T1 is a temperature corresponding to the maximum point in a graph showing a relationship between temperature and a negative change in fluorescence value with respect to temperature, obtained based on the dissociation curve, and thus T1 may be a dissociation peak value.

In confirming whether there is a target nucleic acid in the unit cell (UC) using the nucleic acid complex pair 10 according to an exemplary embodiment of the present application, when the negative change in fluorescence value with respect to temperature/temperature exceeds the reference value at a specific temperature, based on the information obtained in the step of obtaining a dissociation curve (S6000), it can be confirmed that a target nucleic acid related to a dissociation peak value is present in the unit cell (UC).

1.3.3 Experimental Example #2 Related to Application of Nucleic Acid Complex Pair 10 for Target Detection In confirming whether there is a target nucleic acid in the unit cell (UC) using the nucleic acid complex pair 10 according to an exemplary embodiment of the present application, it is possible to confirm the concentration of a target nucleic acid.

Figure 36:
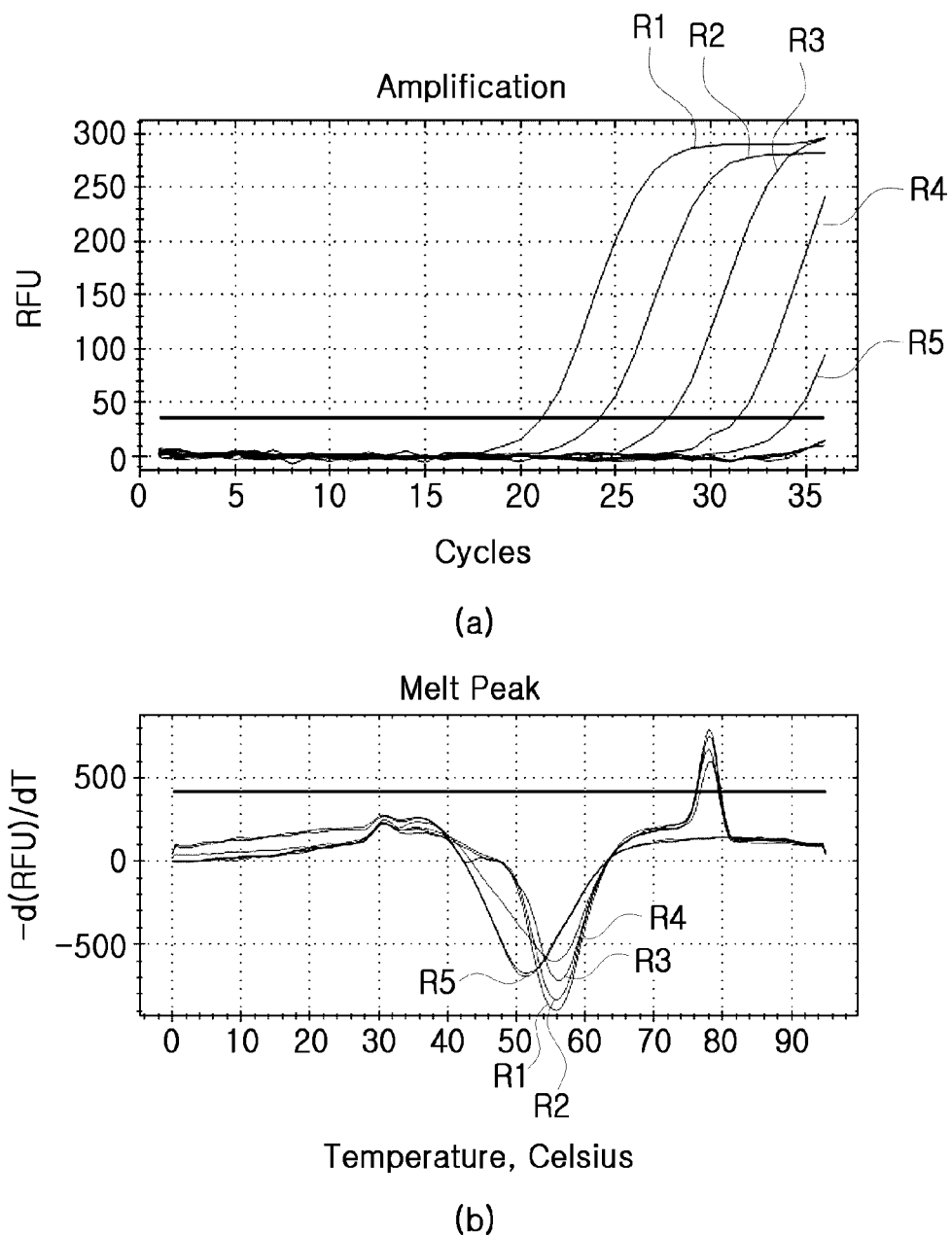
FIG. 36 is a set of graphs illustrating a confirmation of the concentration of a target nucleic acid present in a unit cell (UC) according to an exemplary embodiment of the present application. R1-R5 represent the dissociation curve corresponding to $10^5$, $10^4$, $10^3$, $10^2$, and 10 copies of targets, respectively. RFU, relative fluorescence unit; d(RFU)/dT, the rate of change in RFU with respect to temperature.

FIG. 36 is a diagram illustrating the confirmation of the concentration of a target nucleic acid present in a unit cell (UC) according to an exemplary embodiment of the present application.

During the progression of this experiment, Tris-HCl (pH 9.0), a salt (KCl), $MaCl_2$, a dNTP mixture, a protein stabilizer, a PCR enhancer (macromolecules), and fast hot-start Taq DNA polymerase were introduced into a tube (or well) of a PCT plate.

A first nucleic acid complex pair 10 was introduced into first to fifth tubes of the PCR plate. The first nucleic acid complex pair 10 consisted of a first nucleic acid complex 110 and a second nucleic acid complex 120. Specifically, as much as 1.5 pmol/Rxn of each of the first nucleic acid complex 110 and the second nucleic acid complex 120 may be introduced.

The first nucleic acid complex 110 was formed by sequentially connecting a first label 113, a first tag 112, a first linker 114 and a first determinant 111, wherein the first label 113 was a quencher molecule (Iowa Black@ FQ (Iowa Black@ Quenchers)), the first tag 112 was ACCGCGCGGG (SEQ ID NO: 13), the first linker 114 was Spacer 18, and the first determinant 111 was TGGAGATACACCTACATTG (SEQ ID NO: 14).

The second nucleic acid complex 120 was formed by sequentially connecting a second label 123, a second tag 122, a second linker 124 and a second determinant 121, wherein the second label 123 was FAM, the second tag 122 was CCCGCGCGGT (SEQ ID NO: 15), the second linker 124 was Spacer 18, and the second determinant 121 was GCTGGACCATCTATTTCATC (SEQ ID NO: 16).

A PCR reaction was performed on a solution in a tube by adjusting the temperature of the tube into which the nucleic acid complex pair 10 and other enzymes were introduced. As shown in FIG. 29, the temperature of the tube was maintained at 95° C. for 10 minutes, and then a process including a thermal denaturation step (S2000; 95° C., 10 sec), an annealing step (S3000; 50° C., 40 sec) and a polymerization step (S4000; 60° C., 20 sec) was repeated for 40 cycles. In this experiment, Bio-Rad CFX96 (Permit Number 10-205) was used.

Afterward, a dissociation curve for the first tube was detected, and then as shown in FIG. 36, a graph of a relationship between temperature and fluorescence with respect to temperature was obtained.

When there were $10^5$ copies of targets (HPV16) corresponding to the first determinant 111 and the second determinant 121 (R1), the smallest minimum value of fluorescence with respect to temperature/temperature was detected.

When there were $10^4$ copies of targets (HPV16) corresponding to the first determinant 111 and the second determinant 121 (R2), the minimum value of fluorescence with respect to temperature/temperature, which was relatively larger than that of R1, was detected.

When there were $10^3$ copies of targets (HPV16) corresponding to the first determinant 111 and the second determinant 121 (R3), the minimum value of fluorescence with respect to temperature/temperature, which was relatively larger than that of R2, was detected.

When there were $10^2$ copies of targets (HPV16) corresponding to the first determinant 111 and the second determinant 121 (R4), the minimum value of fluorescence with respect to temperature/temperature, which was relatively larger than that of R3, was detected.

When there were 10 copies of targets (HPV16) corresponding to the first determinant 111 and the second determinant 121 (R5), a graph having the minimum value at a temperature different from the temperatures at which R1 to R4 have the minimum values was obtained, and in this case, it is unclear whether the data was the minimum value due to the nucleic acid complex pair 10, and thus the data was not used in analysis.

As a result, in the graph of the negative rate of change in fluorescence value with respect to temperature/temperature, it can be confirmed whether there is a target nucleic acid in a unit cell (UC) based on whether a dissociation peak value is detected at a specific temperature, and it was confirmed that the concentration of the target nucleic acid can be estimated by specifically confirming the minimum or maximum value of the dissociation peak in the graph of the negative rate of change in fluorescence value with respect to temperature/temperature.

1.3.4 Application of Nucleic Acid Complex Pair 10 According to Fifth Exemplary Embodiment As the number of base sequences involved in the complementary sequence between the first tag 112 and the second tag 122 increases, the complementary bond between the first tag 112 and the second tag 122 may be dissociated at a high temperature. However, when the number of base sequences involved in the complementary sequence between the first tag 112 and the second tag 122 is higher than the reference value, the first tag 112 or the second tag 122 may form a hairpin structure by itself.

When such a phenomenon occurs, the formation of complementary bonds between the first tag 112 and the second tag 122 may be inhibited in the stabilization step (S5000). In other words, the first tag 112 may form a hairpin structure by itself, and thus the second tag 122 may not bind to the first tag 112.

In the nucleic acid complex 1 according to the fifth exemplary embodiment of the present application, when a first tag 112 and a second tag 122 are designed, if cytosine (C) is included in the first tag 112, the first tag 112 may be designed not to include guanine (G). In addition, if guanine (G) is included in the second tag 122, the second tag 122 may be designed not to include cytosine (C).

In the nucleic acid complex 1 according to the fifth exemplary embodiment of the present application, as needed, when a first tag 112 and a second tag 122 are designed, if adenine (A) is included in the first tag 112, the first tag 112 may be designed not to include thymine (T). In addition, if thymine (T) is included in the second tag 122, the second tag 122 may be designed not to include adenine (A).

In the nucleic acid complex pair 10 according to an exemplary embodiment of the present application, since the binding involved in a dissociation peak value is the binding between the first tag 112 and the second tag 122, depending on a target to be detected, there is less of a need to change the base sequences of the first tag 112 and the second tag 122 (i.e., the base sequences involved in a dissociation peak value).

As a result, the nucleic acid complex pair 10 according to an exemplary embodiment of the present application may be easily designed according to the base sequences of the first tag 112 and the second tag 122 involved in a dissociation peak value, and the nucleic acid complex pair 10 according to the fifth exemplary embodiment may also be used.

1.4 Improved Example for Application of Nucleic Acid Complex Pair 10 for Target Detection 1.4.1 Configuration of Competitive Construct (2)

Figure 37:
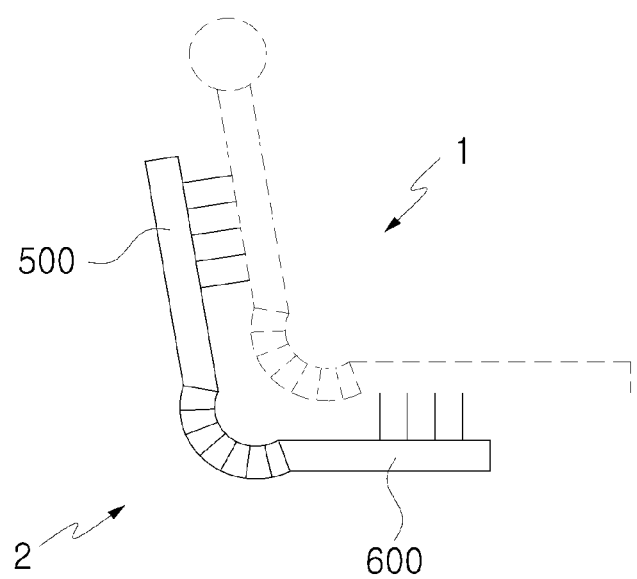
FIG. 37 is a diagram illustrating a competitive construct 2 that includes a tag competitive region 500 and a primer competitive region 600 according to an exemplary embodiment of the present application.

FIG. 37 is a diagram illustrating a competitive construct 2 according to an exemplary embodiment of the present application.

According to an exemplary embodiment of the present application, in PCR using a nucleic acid complex pair 10, a competitive construct 2 may be further used. In other words, the competitive construct 2 may be provided to a unit cell (UC) including a nucleic acid complex pair 10, and PCR for the unit cell (UC) may be performed.

The competitive construct 2 may include a tag competitive region 500 and a primer competitive region 600.

The tag competitive region 500 may include a unit molecule of a nucleic acid. The tag competitive region 500 may consist of a unit molecule of a nucleic acid. The tag competitive region 500 may consist of a polymer of a unit molecule of a nucleic acid.

The tag competitive region 500 may include a unit molecule of a nucleic acid analog. The tag competitive region 500 may consist of a unit molecule of a nucleic acid analog. The tag competitive region 500 may consist of a polymer of a unit molecule of a nucleic acid analog.

The tag competitive region 500 may include a unit molecule of a nucleic acid and a unit molecule of a nucleic acid analog. The tag competitive region 500 may consist of a unit molecule of a nucleic acid and a unit molecule of a nucleic acid analog. The tag competitive region 500 may consist of a polymer of a unit molecule of a nucleic acid analog and a unit molecule of a nucleic acid. The tag competitive region 500 may consist of a polymer of a unit molecule of a nucleic acid and a unit molecule of a nucleic acid analog. The tag competitive region 500 may consist of a polymer of a unit molecule of a nucleic acid and a polymer of a unit molecule of a nucleic acid analog.

The tag competitive region 500 may have a sequence complementary to the base sequence of the tag 200 of the nucleic acid complex 1. The tag competitive region 500 may include a sequence complementary to at least a part of the base sequence of the tag 200 of the nucleic acid complex 1. Preferably, the tag competitive region 500 includes a sequence complementary to 90% of the base sequence of the tag 200. Preferably, the tag competitive region 500 includes a sequence complementary to 85% of the base sequence of the tag 200. Preferably, the tag competitive region 500 includes a sequence complementary to 80% of the base sequence of the tag 200. The tag competitive region 500 may include a sequence complementary to 75% of the base sequence of the tag 200.

According to an exemplary embodiment of the present application, the tag competitive region 500 may be designed to have a relatively longer base sequence complementarily binding to the base sequence of the tag 200 as the wavelength of the label 300 increases.

The primer competitive region 600 may include a unit molecule of a nucleic acid. The primer competitive region 600 may consist of a unit molecule of a nucleic acid. The primer competitive region 600 may consist of a polymer of a unit molecule of a nucleic acid.

The primer competitive region 600 may include a unit molecule of a nucleic acid analog. The primer competitive region 600 may consist of a unit molecule of a nucleic acid analog. The primer competitive region 600 may consist of a polymer of a unit molecule of a nucleic acid analog.

The primer competitive region 600 may include a unit molecule of a nucleic acid and a unit molecule of a nucleic acid analog. The primer competitive region 600 may consist of a unit molecule of a nucleic acid and a unit molecule of a nucleic acid analog. The primer competitive region 600 may consist of a polymer of a unit molecule of a nucleic acid analog and a unit molecule of a nucleic acid. The primer competitive region 600 may consist of a polymer of a unit molecule of a nucleic acid and a unit molecule of a nucleic acid analog. The primer competitive region 600 may consist of a polymer of a unit molecule of a nucleic acid and a polymer of a unit molecule of a nucleic acid analog.

The primer competitive region 600 may include a sequence complementary to the base sequence of the determinant 100 of the nucleic acid complex 1. The primer competitive region 600 may include a sequence complementary to at least a part of the base sequence of the determinant 100 of the nucleic acid complex 1. Preferably, the primer competitive region 600 has a sequence corresponding to an annealing temperature ranging from 10 to 35° C., and the sequence of the primer competitive region 600 may be a sequence complementary to the primer. Preferably, the primer competitive region 600 has a sequence corresponding to an annealing temperature ranging from 20 to 30° C., and the sequence of the primer competitive region 600 may be a sequence complementary to the primer.

According to an exemplary embodiment of the present application, the primer competitive region 600 may be designed to have a relatively longer base sequence complementarily binding to the base sequence of the determinant 200 as the wavelength of the label 300 increases.

The competitive construct 2 may be embodied with respect to the nucleic acid complex 1. The competitive construct 2 may have a sequence complementary to at least a part of the base sequence of the determinant 100 of the nucleic acid complex 1, and have a sequence complementary to at least a part of the base sequence of the tag 200 of the nucleic acid complex 1.

The competitive construct 2 may be embodied with respect to the nucleic acid complex pair 10. For the nucleic acid complex pair 10 including the first nucleic acid complex 110 and the second nucleic acid complex 120, a competitive construct 2 for the first nucleic acid complex 110 may be provided, but a competitive construct 2 for the second nucleic acid complex 120 may not be provided. Alternatively, for the nucleic acid complex pair 10 including the first nucleic acid complex 110 and the second nucleic acid complex 120, a competitive construct 2 for the second nucleic acid complex 120 may be provided, but a competitive construct 2 for the first nucleic acid complex 110 may not be provided. Alternatively, for the nucleic acid complex pair 10 including the first nucleic acid complex 110 and the second nucleic acid complex 120, a first competitive construct 2 for the first nucleic acid complex 110 may be provided, and a second competitive construct 2 for the second nucleic acid complex 120 may be provided.

In the nucleic acid complex pair 10 according to an exemplary embodiment of the present application, the complementary binding force between the first tag 112 and the first tag competitive region 500 may be smaller than that between the first tag 112 and the second tag 122. In the nucleic acid complex pair 10 according to an exemplary embodiment of the present application, the number of base sequences formed by complementary binding between the first tag 112 and the first tag competitive region 500 may be smaller than that between the first tag 112 and the second tag 122. In the nucleic acid complex pair 10 according to an exemplary embodiment of the present application, the number of C-G to the number of A-T in the base sequence formed by complementary binding between the first tag 112 and the second tag 122 may be smaller than that in the base sequence formed by complementary binding between the first tag 112 and the first tag competitive region 500.

This may be for preventing the active bonds between the first tag 112 and the first tag competitive region 500 from inhibiting the binding between the first tag 112 and the second tag 122.

In the nucleic acid complex pair 10 according to an exemplary embodiment of the present application, the complementary binding force between the second tag 122 and the second tag competitive region 500 may be smaller than that between the first tag 112 and the second tag 122. In the nucleic acid complex pair 10 according to an exemplary embodiment of the present application, the number of base sequences formed by complementary binding between the second tag 122 and the second tag competitive region 500 may be smaller than that between the first tag 112 and the second tag 122. In the nucleic acid complex pair 10 according to an exemplary embodiment of the present application, the number of C-G to the number of A-T in the base sequence formed by complementary binding between the first tag 112 and the second tag 122 may be smaller than that in the base sequence formed by complementary binding between the first tag 112 and the first tag competitive region 500.

This may be for preventing the active bonds between the second tag 122 and the second tag competitive region 500 from inhibiting the binding between the first tag 112 and the second tag 122.

In the nucleic acid complex pair 10 according to an exemplary embodiment of the present application, the complementary binding force between the first determinant 111 and the first primer competitive region 600 may be smaller than that between the first determinant 111 and the first target base sequence. In the nucleic acid complex pair 10 according to an exemplary embodiment of the present application, the number of base sequences formed by complementary binding between the first determinant 111 and the first primer competitive region 600 may be smaller than that between the first determinant 111 and the first target base sequence. In the nucleic acid complex pair 10 according to an exemplary embodiment of the present application, the number of C-G to the number of A-T in the base sequence formed by complementary binding between the first determinant 111 and the first target base sequence may be smaller than that in the base sequence formed by complementary binding between the first determinant 111 and the primer competitive region 600.

This may be for preventing the active bonds between the first determinant 111 and the first primer competitive region 600 from inhibiting the binding between the first determinant 111 and the first target base sequence.

In the nucleic acid complex pair 10 according to an exemplary embodiment of the present application, the complementary binding force between the second determinant 121 and the second primer competitive region 600 may be smaller than that between the second determinant 121 and the second target base sequence. In the nucleic acid complex pair 10 according to an exemplary embodiment of the present application, the number of base sequences formed by complementary binding between the second determinant 121 and the second primer competitive region 600 may be smaller than that between the second determinant 121 and the second target base sequence. In the nucleic acid complex pair 10 according to an exemplary embodiment of the present application, the number of C-G to the number of A-T in the base sequence formed by complementary binding between the second determinant 121 and the second target base sequence may be smaller than that in the base sequence formed by complementary binding between the second determinant 121 and the primer competitive region 600.

This may be for preventing the active bonds between the second determinant 121 and the second primer competitive region 600 from inhibiting the binding between the second determinant 121 and the second target base sequence.

According to an exemplary embodiment of the present application, the competitive construct 2 may be embodied in the form in which a PCR blocker is placed between the tag competitive region 500 and the primer competitive region 600. In addition, according to an exemplary embodiment of the present application, the competitive construct 2 may be embodied in the form in which the tag competitive region 500, the PCR blocker, the primer competitive region 600 and 3' phosphorylation are connected.

1.4.2 Operation of Competitive Construct 2

Figure 38:
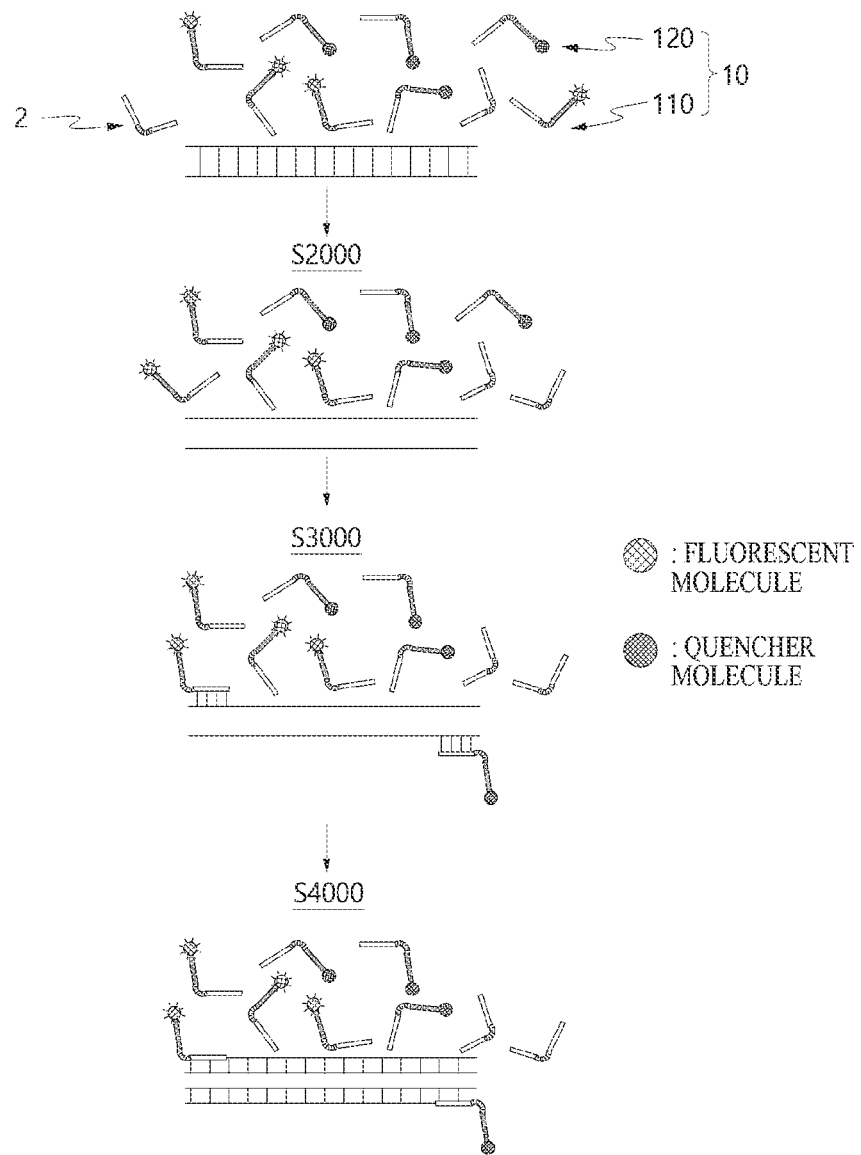
FIGS. 38 and 39 are diagrams illustrating the operations of a competitive construct 2 and a nucleic acid complex pair 10 that includes a first nucleic acid complex 110 and a second nucleic acid complex 120 as shown in FIG. 32 according to an exemplary embodiment of the present application.
Figure 39:
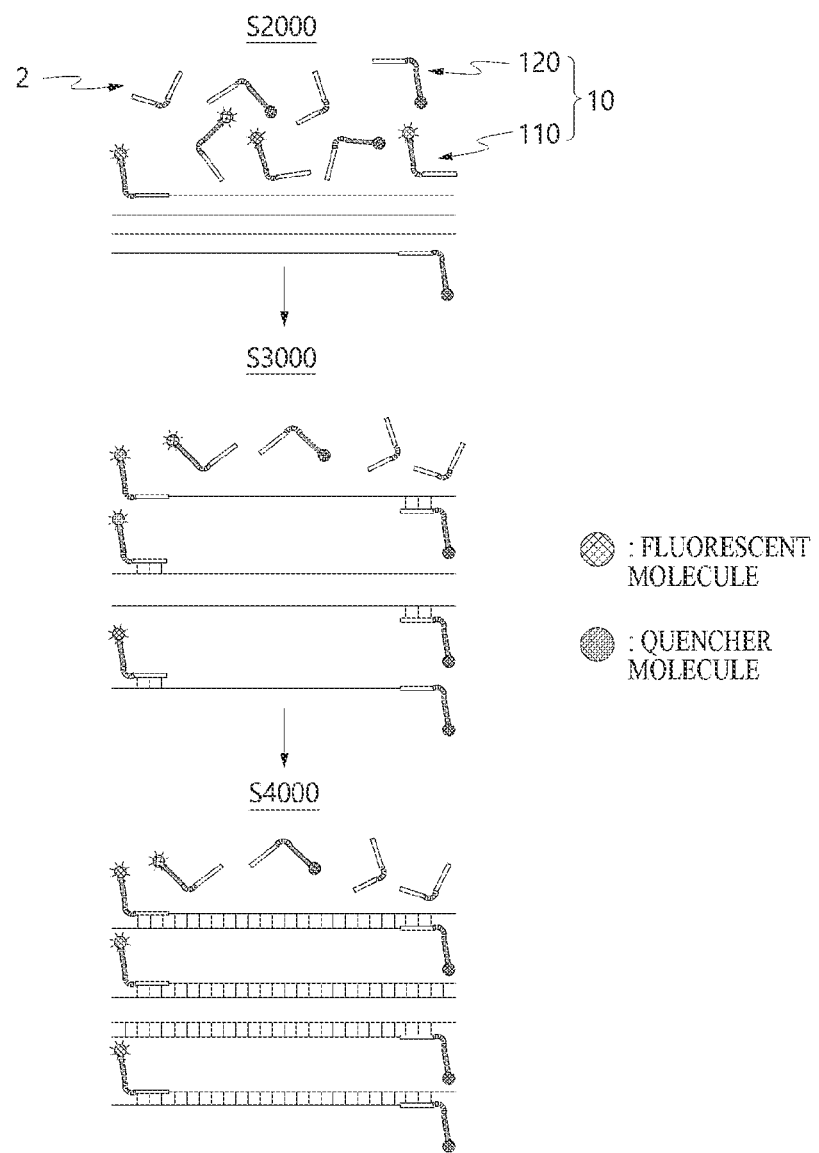
Figure 40:
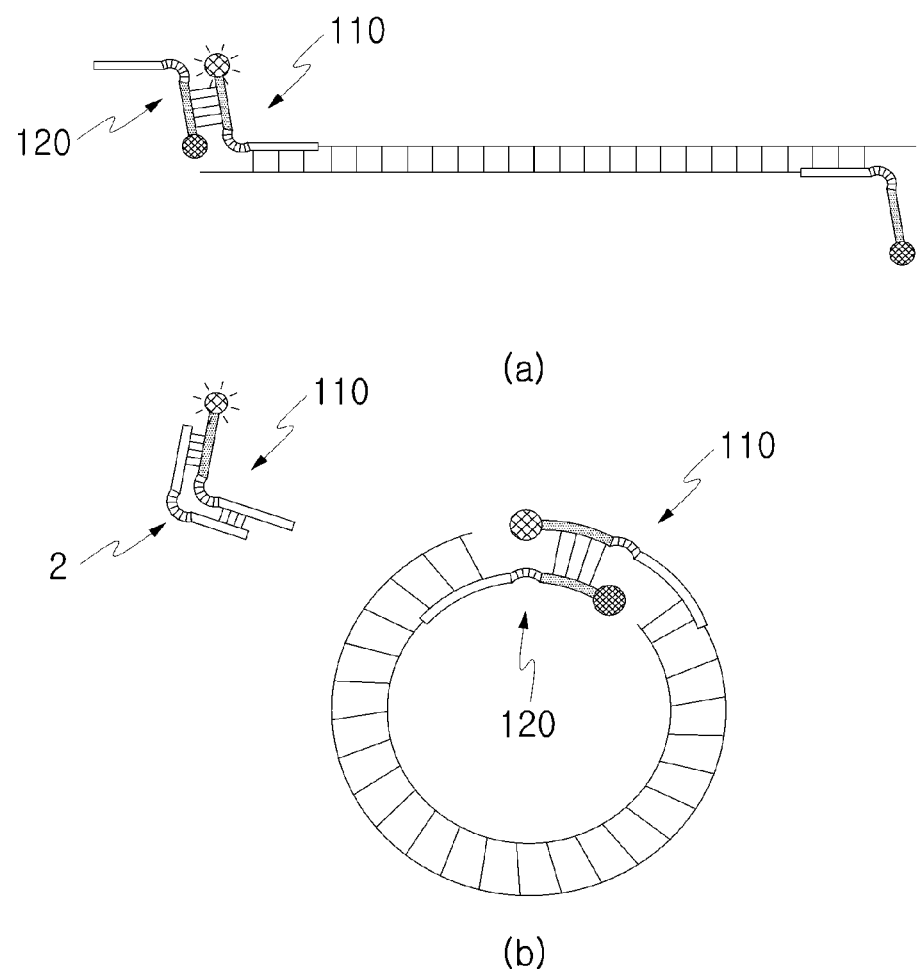
FIG. 40 is a diagram illustrating the operations of a competitive construct 2, a first nucleic acid complex 110 and a second nucleic acid complex 120 as shown in FIG. 32 according to an exemplary embodiment of the present application.

FIGS. 38 to 40 are diagrams illustrating the operations of the competitive construct 2 according to an exemplary embodiment of the present application.

Hereinafter, for convenience of description, the descriptions will be provided under the assumption that there are four first nucleic acid complexes 110, four second nucleic acid complexes 120, competitive constructs 2 for two first nucleic acid complexes 110, a first strand including a first target base sequence and a second strand including a second target base sequence in a unit cell (UC) subjected to PCR.

However, FIGS. 38 to 40 and the descriptions are merely drawings and descriptions for helping the understanding the present invention and provided under the assumption of there are four first nucleic acid complexes 110, four second nucleic acid complexes 120, competitive constructs 2 for two first nucleic acid complexes 110, a first strand including a first target base sequence and a second strand including a second target base sequence in a unit cell (UC), which does not mean that PCR is performed by actually providing four first nucleic acid complexes 110, four second nucleic acid complexes 120, competitive constructs 2 for two first nucleic acid complexes 110, a first strand including a first target base sequence and a second strand including a second target base sequence in the unit cell (UC).

Referring to FIG. 38, in the unit cell (U) subjected to PCR, four first nucleic acid complexes 110, four second nucleic acid complexes 120, competitive constructs 2 for two first nucleic acid complexes 110, a first strand including a first target base sequence and a second strand including a second target base sequence may be present.

In one example, in the unit cell (UC), double-stranded DNA in which the first strand and the second strand complementarily bind to each other may be present.

In the thermal denaturation step (S2000), the double-stranded DNA present in the unit cell (UC) may be transformed into single-stranded DNAs by adjusting the temperature of the unit cell (UC). In the thermal denaturation step (S2000), the complementary bond between the first strand including the first target base sequence and the second strand including the second target base sequence may be dissociated.

In the annealing step (S3000), the first determinant 111 of the first nucleic acid complex 110 may complementarily bind to the first strand. The first determinant 111 may complementarily bind to the first target base sequence of the first strand. In the annealing step (S3000), the second determinant 121 of the second nucleic acid complex 120 may complementarily bind to the second strand. The second determinant 121 may complementarily bind to the second target base sequence of the second strand.

In the annealing step (S3000), three first nucleic acid complexes 110, three second nucleic acid complexes 120 and competitive constructs 2 for two first nucleic acid complexes 110, which do not participate in a reaction, may flow in the unit cell (UC).

In the polymerization step (S4000), an amplification product for at least a part of the first strand including the first target base sequence to which the first determinant 111 binds may be produced, using the first determinant 111 as a starting point. In the polymerization step (S4000), an amplification product for at least a part of the second strand including the second target base sequence to which the second determinant 121 binds may be produced, using the second determinant 121 as a starting point.

In the polymerization step (S4000), three first nucleic acid complexes 110, three second nucleic acid complexes 120 and competitive constructs 2 for two first nucleic acid complexes 110, which do not participate in a reaction, may flow in the unit cell (UC).

According to an exemplary embodiment of the present application, at least one cycle of PCR may be performed on the unit cell (UC), each cycle consisting of a thermal denaturation step (S2000), an annealing step (S3000) and a polymerization step (S4000).

Referring to FIG. 39, in the thermal denaturation step (S2000) after the first cycle, the double-stranded DNA present in the unit cell (UC) may be separated into single-stranded DNAs by adjusting the temperature of the unit cell (UC).

In the thermal denaturation step (S2000), a single-stranded nucleic acid including an amplification product for the first strand including the first target base sequence and the first determinant 111 may be produced. The single-stranded nucleic acid including the amplification product for the first strand and the first determinant 111 may include a second target base sequence.

In the thermal denaturation step (S2000), double-stranded DNA present in the unit cell (UC) may be separated into a single-stranded nucleic acid including an amplification product for the second strand and the second determinant 121. The single-stranded nucleic acid including an amplification product for the second strand and the second determinant 121 may include a first target base sequence.

In the thermal denaturation step (S2000), three first nucleic acid complexes 110, three second nucleic acid complexes 120 and competitive constructs 2 for two first nucleic acid complexes 110, which do not participate in a reaction, may flow in the unit cell (UC).

In the annealing step (S3000), the first determinant 111 may complementarily bind to the single-stranded nucleic acid including an amplification product for the second strand and the second determinant 121. In the annealing step (S3000), the second determinant 121 may complementarily bind to the single-stranded nucleic acid including amplification product for the first strand and the first determinant 111.

In the annealing step (S3000), as in the first cycle of PCR, the first determinant 111 may complementarily bind to the first strand including a first target base sequence. In addition, in the annealing step (S3000), as in the first cycle of PCR, the second determinant 121 may complementarily bind to the second strand including a second target base sequence.

In the annealing step (S3000), one first nucleic acid complex 110, one second nucleic acid complex 120 and competitive constructs 2 for two first nucleic acid complexes 110, which do not participate in a reaction, may flow in a unit cell (UC).

In the polymerization step (S4000), using the first determinant 111 as a starting point, an amplification product for a single-stranded nucleic acid including an amplification product for the second strand and the second determinant 121, to which the first determinant 111 binds, may be produced. In the polymerization step (S4000), using the second determinant 121 as a starting point, an amplification product for a single-stranded nucleic acid including an amplification product for the first strand and the first determinant 111, to which the second determinant 121 binds, may be produced.

In the polymerization step (S4000), as in the first cycle of PCR, using the first determinant 111 as a starting point, an amplification product for at least a part of the first strand including the first target base sequence, to which the first determinant 111 binds, may be produced. In addition, in the polymerization step (S4000), as in the first cycle of PCR, using the second determinant 121 as a starting point, an amplification product for at least a part of the second strand including the second target base sequence to which the second determinant 121 binds may be produced.

In the polymerization step (S4000), one first nucleic acid complex 110, one second nucleic acid complex 120 and competitive constructs 2 for two first nucleic acid complexes 110, which do not participate in a reaction, may flow in a unit cell (UC).

When at least two cycles of PCR are done, a double-stranded nucleic acid construct including the first target base sequence and the second target base sequence, and further including the first nucleic acid complex 110 and the second nucleic acid complex 120 may be produced in a unit cell (UC). In the double-stranded nucleic acid construct including the first target base sequence and the second target base sequence, and further including the first nucleic acid complex 110 and the second nucleic acid complex 120, the first tag 112 and the second tag 122 may be maintained in a single-stranded form.

According to an exemplary embodiment of the present application, the first tag 112 and the second tag 122, which are maintained in a single-stranded form, still remain as a single strand after the PCR is completed, and thus complementary bonds between the first tag 112 and the second tag 122 may be formed. As a result, depending on whether there is a complementary bond between the first tag 112 and the second tag 122 after the PCR is completed, whether the first label 113 and the second label 123 are linked is checked so as to confirm the presence of a target nucleic acid.

However, when the second tag 122 of one second nucleic acid complex 120, which is flowing, in the polymerization step (S4000) complementarily binds to the first tag 112 of the double-stranded nucleic acid construct including the first target base sequence and the second target base sequence, and further including the first nucleic acid complex 110 and the second nucleic acid complex 120 (see FIG. 40(a)), there may be a problem of acquiring incorrect data on the presence of a target nucleic acid (i.e., target DNA to be detected) and the concentration of the target nucleic acid.

In addition, in the first nucleic acid complex 110 and the second nucleic acid complex 120 flowing in a unit cell (UC), even if an amplification product is not formed by PCR, a signal may be generated due to the linkage between the first label 113 and the second label 123, by forming complementary bonds between the first tag 112 and the second tag 122. In other words, despite the absence of a target nucleic acid in a unit cell (UC), there may be the problem of acquiring incorrect data due to detection of a signal caused by the linkage between the first label 113 and the second label 123.

To improve such a problem, PCR may be performed further using the competitive construct 2. According to the PCR process according to FIGS. 38 and 39, the competitive construct 2 flowing after the PCR is completed may complementarily bind to the first nucleic acid complex 110 not participating in the reaction (see FIG. 40(b)). In other words, as the competitive construct 2 flowing after the PCR is completed reacts with the first nucleic acid complex 110 not participating in the reaction, the problem of acquiring incorrect data on the presence of a target nucleic acid and the concentration of the target nucleic acid generated by the reaction of the first nucleic acid complex 110 and the second nucleic acid complex 120, which are flowing but do not participate in the reaction, can be prevented.

1.4.3 Experimental Example #3 Related to Operation of Competitive Construct 2

According to an exemplary embodiment of the present application, when the presence of a target nucleic acid in a unit cell (UC) is confirmed using a nucleic acid complex pair 10 and a competitive construct 2, the accuracy of the detection of the presence of the target nucleic acid may be improved.

Figure 41:
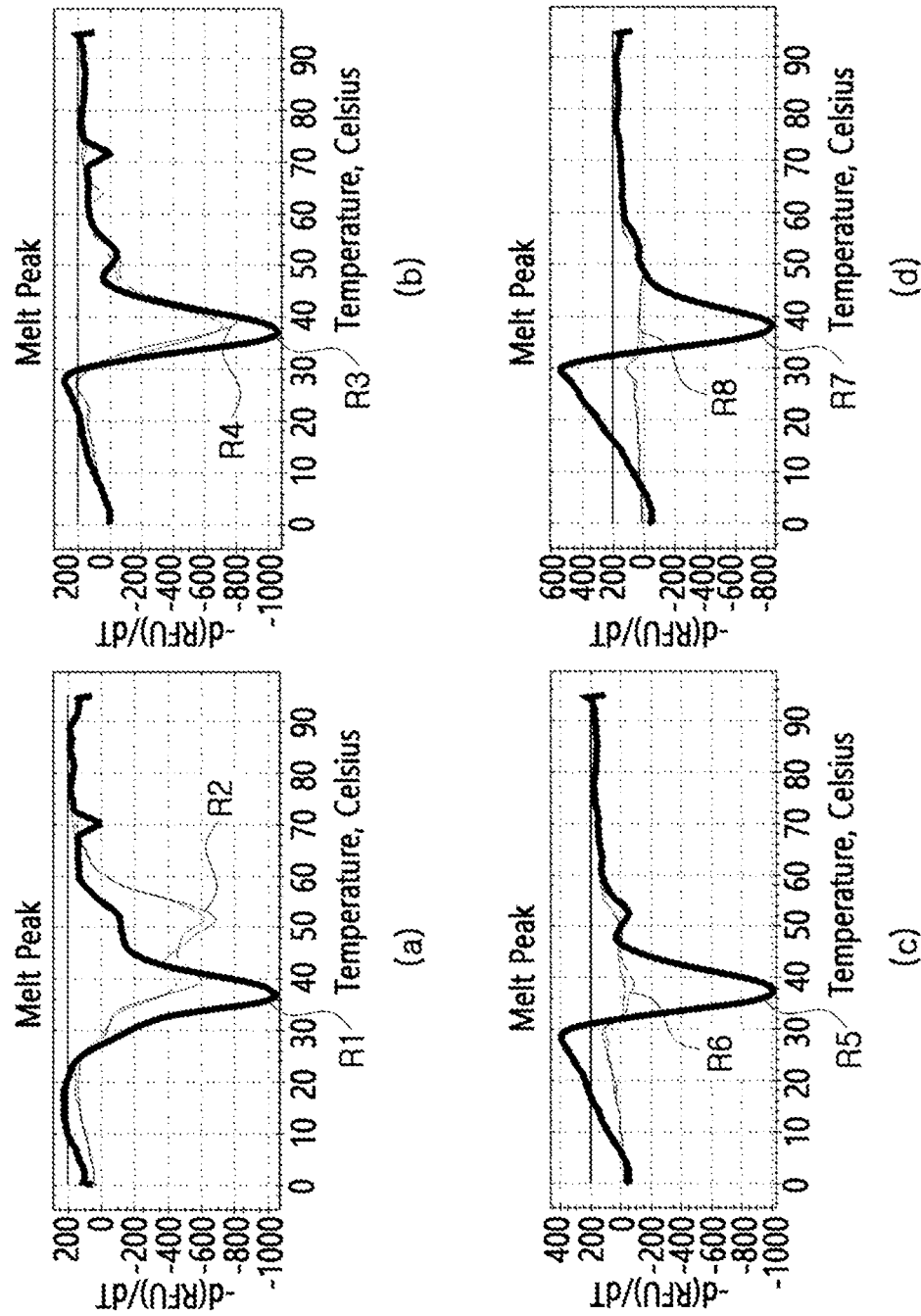
FIG. 41 is a diagram illustrating a PCR result using a nucleic acid complex pair 10 and a competitive construct 2 according to an exemplary embodiment of the present application. R1-R8 represent the dissociation curve corresponding to different PCR reaction conditions as described herein. RFU, relative fluorescence unit; d(RFU)/dT, the rate of change in RFU with respect to temperature.

FIG. 41 is a diagram illustrating the PCR result using a nucleic acid complex pair 10 and a competitive construct 2 according to an exemplary embodiment of the present application.

During the progression of this experiment, Tris-HCl (pH 9.0), a salt (KCl), $MaCl_2$, a dNTP mixture, a protein stabilizer, a PCR enhancer (macromolecules), and fast hot-start Taq DNA polymerase were introduced into a tube (or well) of a PCT plate.

A nucleic acid complex pair 10 was introduced into first to fourth tubes of the PCR plate. The nucleic acid complex pair 10 consisted of a first nucleic acid complex 110 and a second nucleic acid complex 120.

The first nucleic acid complex 110 was formed by sequentially connecting a first label 113, a first tag 112, a first linker 114 and a first determinant 111, wherein the first label 113 was FAM, the first tag 112 was AACCTTGGGA (SEQ ID NO: 9), the first linker 114 was Spacer 18, and the first determinant 111 was AGCTCCTATTGCCAACGTA (SEQ ID NO: 10).

The second nucleic acid complex 120 was formed by sequentially connecting a second label 123, a second tag 122, a second linker 124 and a second determinant 121, wherein the second label 123 was a quencher molecule (Iowa Black@ FQ (Iowa Black@ Quenchers)), the second tag 122 was TCCCAAGGTT (SEQ ID NO: 0.1), the second linker 124 was Spacer 18, and the second determinant 121 was GCGAGTTACGAAGACAAAA (SEQ ID NO: 8). 1.5 pmol/Rxn of each of the first nucleic acid complex 110 and the second nucleic acid complex 120 were introduced into the first to fourth tubes.

A competitive construct 2 was not provided to the first tube of the PCR plate, and a competitive construct 2 for the second nucleic acid complex 120 was provided to each of the second to fourth tubes of the PCR plate.

1.5 pmol/Rxn of the competitive construct 2 was introduced into the second tube. 3 pmol/Rxn of the competitive construct 2 was introduced into the third tube. 12 pmol/Rxn of the competitive construct 2 was introduced into the second tube.

The concentration of the competitive construct 2 for the second nucleic acid complex 120 introduced into the second tube was approximately one-fold that of the first nucleic acid complex 110. The concentration of the competitive construct 2 for the second nucleic acid complex 120 introduced into the second tube was approximately one-fold that of the second nucleic acid complex 120. The concentration of the competitive construct 2 for the second nucleic acid complex 120 introduced into the third tube was approximately two-fold that of the first nucleic acid complex 110. The concentration of the competitive construct 2 for the second nucleic acid complex 120 introduced into the third tube was approximately two-fold that of the second nucleic acid complex 120. The concentration of the competitive construct 2 for the second nucleic acid complex 120 introduced into the fourth tube was approximately eight-fold that of the first nucleic acid complex 110. The concentration of the competitive construct 2 for the second nucleic acid complex 120 introduced into the fourth tube was approximately eight-fold that of the second nucleic acid complex 120.

The competitive construct 2 for the second nucleic acid complex 120 was formed by sequentially connecting a primer competitive region 600, a PCR blocker and a tag competitive region 500, wherein the tag competitive region 500 was AAAAAAAACCTT (SEQ ID NO: 17), the PCR blocker was Spacer 18, and the primer competitive region 600 was CCACACAAAGATT (SEQ ID NO: 18).

A PCR reaction was performed on the solution in tubes by adjusting the temperature of the first to fourth tubes into which the nucleic acid complex pair 10 and other enzymes were introduced. As shown in FIG. 29, the temperature of the tubes was maintained at 95° C. for 10 minutes, and a course of a thermal denaturation step (S2000; 95° C., 10 sec), a annealing step (S3000; 50° C., 40 sec), and a polymerization step (S4000; 60° C., 20 sec) was set as one cycle, and repeatedly performed for 50 cycles. In this experiment, Bio-Rad CFX96 (Permit Number 10-205) was used.

As a result of the experiment, when there are a first target base sequence corresponding to the first determinant 111 and a second target base sequence corresponding to the second determinant 121 in the first tube to which the competitive construct 2 was not provided, the presence of a target nucleic acid was able to be detected (R1) by detecting a dissociation peak value at approximately 38° C.

However, even if the first target base sequence corresponding to the first determinant 111 and the second target base sequence corresponding to the second determinant 121 are not present in the first tube to which the competitive construct 2 is not provided, a peak value of approximately −600 [−d/(RFU/dT)] was detected (R2) at approximately 40° C., showing a phenomenon in which detection accuracy is degraded depending on the presence of the first target base sequence corresponding to the first determinant 111 and the second target base sequence corresponding to the second determinant 121.

When there are the first target base sequence corresponding to the first determinant 111 and the second target base sequence corresponding to the second determinant 121 in the second tube to which the competitive construct 2 is provided one-fold the first nucleic acid complex 110 (or the second nucleic acid complex 120), the presence of a target nucleic acid was able to be detected (R3) by detection of a dissociation peak value at approximately 38° C.

However, when there are no first target base sequence corresponding to the first determinant 111 and second target base sequence corresponding to the second determinant 121 in the second determinant 121 in the second tube to which the competitive construct 2 is provided one-fold the first nucleic acid complex 110 (or the second nucleic acid complex 120), a peak value of approximately −800[−d/(RFU/dT)] was detected (R4) at approximately 40° C., showing a phenomenon in which the detection accuracy is degraded depending on the presence of the first target base sequence corresponding to the first determinant 111 and the second target base sequence corresponding to the second determinant 121.

When there are the first target base sequence corresponding to the first determinant 111 and the second target base sequence corresponding to the second determinant 121 in the third tube to which the competitive construct 2 is provided two-fold the first nucleic acid complex 110 (or the second nucleic acid complex 120), target detection (R5) was possible by detecting a dissociation peak value at approximately 38° C.

In addition, where there are no first target base sequence corresponding to the first determinant 111 and second target base sequence corresponding to the second determinant 121 in the third tube to which the competitive construct 2 is provided two-fold the first nucleic acid complex 110 (or the second nucleic acid complex 120), no peak value exceeding −200 [−d/(RFU/dT)] was detected (R6) at approximately 38° C.

When there are the first target base sequence corresponding to the first determinant 111 and the second target base sequence corresponding to the second determinant 121 in the fourth tube to which the competitive construct 2 is provided eight-fold the first nucleic acid complex 110 (or the second nucleic acid complex 120), target detection (R7) was possible by detecting a dissociation peak value at approximately 38° C.

In addition, where there are no first target base sequence corresponding to the first determinant 111 and second target base sequence corresponding to the second determinant 121 in the fourth tube to which the competitive construct 2 is provided eight-fold the first nucleic acid complex 110 (or the second nucleic acid complex 120), no peak value exceeding −200 [−d/(RFU/dT)] was detected (R8) at approximately 38° C.

Therefore, when the competitive construct 2 is provided in a certain ratio (e.g., 1:2) with respect to the first nucleic acid complex 110 (or the second nucleic acid complex 120) to detect the presence of a target nucleic acid using the nucleic acid complex pair 10, it was confirmed that the detection accuracy depending on the presence of the first target base sequence corresponding to the first determinant 111 and the second target base sequence corresponding to the second determinant 121 was improved.

2. Application #2 of Nucleic Acid Complex Pair 10—Multiplex PCR

According to an exemplary embodiment of the present application, the presence of a target nucleic acid may be confirmed by confirming the linkage between a first label 113 and a second label 123 based on the binding between a first tag 112 and a second tag 122 of a nucleic acid complex pair 10.

According to another exemplary embodiment of the present application, by varying a temperature at which the binding between one tag 200 (i.e., first tag 112) and the other tag 200 (i.e., second tag 122) of multiple types of nucleic acid complex pairs 10 is dissociated, a specific temperature at which there is a change in the linkage between the first label 113 and the second label 123 may be checked, thereby confirming the presence of multiple types of target nucleic acids in a unit cell (UC).

Specifically, taking advantage of the characteristic in which a bond retention force for retaining the binding between the first tag 112 and the second tag 122 of the nucleic acid complex pair 10 according to an exemplary embodiment of the present application may vary according to the components and structure of the nucleic acid complex 1, multiple types of the nucleic acid complex pairs 10 to which the same label is attached can be labeled separately.

2.1 Bond Retention Force 2.1.1 Definition of Bond Retention Force

A nucleic acid construct including a first determinant 111 and a second determinant 121 according to an exemplary embodiment of the present application may form a secondary structure according to bonds between the first tag 112 and the second tag 122. This has been described in detail in 1.2 Formation of secondary structure above, and duplicated descriptions will be omitted.

Here, compared to the minimum external force to be applied to simply dissociate the complementary bond between the first tag 112 and the second tag 122, in the nucleic acid construct including the first determinant 111 and the second determinant 121, the minimum external force to be applied to dissociate the binding between the first tag 112 and the second tag 122 when a secondary structure is formed by complementary bonds between the first tag 112 and the second tag 122 may be higher.

In other words, compared to complementary bonds simply formed between the first tag 112 and the second tag 122, in the nucleic acid construct including the first determinant 111 and the second determinant 121, a binding force between the first tag 112 and the second tag 122 when a second structure is formed by the complementary bond between the first tag 112 and the second tag 122 may be higher.

In the specification, in the nucleic acid construct including the first determinant 111 and the second determinant 121, when a secondary structure of the nucleic acid construct is formed by the complementary bond between the first tag 112 and the second tag 122, the minimum external force applied to dissociate the binding between the first tag 112 and the second tag 122 of the nucleic acid complex pair 10 is called "bond retention force."

Some factors related to the nucleic acid complex pair 10, which affect the bond retention force, will be described in detail below.

2.1.2 Factors Affecting Bond Retention Force 2.1.2.1 Types of Unit Nucleic Acids of First Tag 112 and Second Tag 122

The bond retention force according to an exemplary embodiment of the present application may be associated with a type of unit molecule of a nucleic acid and/or a nucleic acid analog of the first tag 112 and the second tag 122. The bond retention force according to an exemplary embodiment of the present application may increase or decrease according to a binding force of the unit molecules of the nucleic acids constituting the first tag 112 and the second tag 122.

In one example, as the binding force of the unit molecule of the nucleic acid and/or nucleic acid analog of the first tag 112 increases, the bond retention force of the nucleic acid complex pair 10 may increase. In another example, as the binding force of the unit molecule of the nucleic acid and/or nucleic acid analog constituting the second tag 122 increases, the bond retention force of the nucleic acid complex pair 10 may increase.

In a specific example, when the unit molecule constituting the first tag 112 is PNA, compared to when the unit molecule constituting the first tag 112 is DNA, the bond retention force of the nucleic acid complex pair 10 may increase. In another specific example, when the unit molecule constituting the second tag 122 is LNA, compared to when the unit molecule constituting the second tag 122 is DNA, the bond retention force of the nucleic acid complex pair 10 may increase. In still another example, when the unit molecules constituting the first tag 112 and the second tag 122 are PNA, compared to when the unit molecule constituting the first tag 112 is PNA, and the unit molecule constituting the second tag 122 is DNA, a bond retention force may be higher.

2.1.2.2 Kinds of Bases in Base Sequences of First Tag 112 and Second Tag 122

The bond retention force according to an exemplary embodiment of the present application may be associated with the base sequences of the first tag 112 and the second tag 122. The bond retention force according to an exemplary embodiment of the present application may increase or decrease according to kinds of bases in the base sequences of the first tag 112 and the second tag 122.

In a specific example, the bond retention force according to an exemplary embodiment of the present application may increase or decrease according to kinds of bases in the base sequence included in the first tag 112 complementarily binding to the second tag 122.

In one example, the more cytosines (C) in a base sequence involved in binding with the second tag 122 of the base sequence constituting the first tag 112, the higher the bond retention force of the nucleic acid complex pair 10. In another example, the more guanines (G) in a base sequence involved in binding with the second tag 122 of the base sequence constituting the first tag 112, the higher the bond retention force of the nucleic acid complex pair 10. In still another example, assuming first tags 112 of the same length, the higher the cytosine (C)-guanine (G)/adenine (A)-thymine (T) ratio of the first tag 112, the higher the bond retention force of the nucleic acid complex pair 10.

In still another specific example, the bond retention force according to an exemplary embodiment of the present application may increase or decrease according to the kinds of bases in the base sequence included in the second tag 122 complementarily binding to the first tag 112.

In one example, the more cytosines (C) in the base sequence involved in binding with the first tag 112 of the base sequence constituting the second tag 122, the higher the bond retention force of the nucleic acid complex pair 10. In another example, the more guanines (G) in the base sequence involved in binding with the first tag 112 of the base sequence constituting the second tag 122, the higher the bond retention force of the nucleic acid complex pair 10. In still another example, assuming second tags 122 of the same length, the higher the cytosine (C)-guanine (G)/adenine (A)-thymine (T) ratio of the second tag 122, the higher the bond retention force of the nucleic acid complex pair 10.

2.1.2.3 Arrangement of Bases in Base Sequences of First Tag 112 and Second Tag 122

The bond retention force according to an exemplary embodiment of the present application may be associated with the base sequences of the first tag 112 and the second tag 122. The bond retention force according to an exemplary embodiment of the present application may increase or decrease according to the arrangement of bases in the base sequences of the first tag 112 and the second tag 122.

In a specific example, the bond retention force may increase or decrease according to the arrangement of bases in the base sequence of the first tag 112.

In one example, although the base sequence constituting the first tag 112 includes five cytosines (C) and five adenines (A), the bond retention force caused by the binding between a first tag 112 consisting of 5'-CCCCCAAAAA-3' (SEQ ID NO: 37) and a second tag 122 consisting of 5'-TTTGGGGG-3' (SEQ ID NO: 38) and the bond retention force caused by the binding between a first tag 112 consisting of 5'-CCAAAAACCC-3' (SEQ ID NO: 39) and a second tag 122 consisting of 5'-GGGTTTfTGG-3' (SEQ ID NO: 40) may be different from each other.

In another example, although the base sequence constituting the first tag 112 includes five guanines (G) and five adenines (A), depending on whether guanines (G) are located adjacent to a first label 113, or guanines (G) are located adjacent to a first linker 114, a bond retention force may vary.

In another specific example, a bond retention force may increase or decrease according to the arrangement of bases in the base sequence of the second tag 122.

In one example, even when the base sequence constituting the second tag 122 consists of five cytosines (C) and five adenines (A), the bond retention force caused by the binding between a second tag 122 consisting of 5'-CCCCCAAAAA-3' (SEQ ID NO: 37) and a first tag 112 consisting of 5'-TTTTTGGGGG-3' (SEQ ID NO: 38) may be different from that caused by the binding between a second tag 122 consisting of 5'-CCAAAAACCC-3' (SEQ ID NO: 39) and a first tag 112 consisting of 5'-GGGTTTTTGG-3' (SEQ ID NO: 40).

In another example, even when the base sequence consisting of the second tag 122 consists of five guanines (G) and five adenines (A), the bond retention force of the nucleic acid complex pair 10 may vary according to whether the guanines (G) are located adjacent to the second label 123 or located adjacent to the second linker 124.

2.1.2.4 Number of Bases Involved in Complementary Binding Between First Tag 112 and Second Tag 122

The bond retention force according to an exemplary embodiment of the present application may be associated with the number of bases involved in complementary binding between the first tag 112 and the second tag 122. The bond retention force according to an exemplary embodiment of the present application may increase or decrease according to the number of bases involved in complementary binding between the first tag 112 and the second tag 122.

In a specific example, as the number of bases involved in complementary binding between the first tag 112 and the second tag 122 increases, the bond retention force of the nucleic acid complex pair 10 may increase. The higher the number of bases of the first tag 112, which bind to the second tag 122, the higher the bond retention force of the nucleic acid complex pair 10. The higher the number of bases of the second tag 122 binding to the first tag 112, the higher the bond retention force of the nucleic acid complex pair 10.

2.1.2.5 Relative Base Sequences Between First Tag 112 and Second Tag 122

The bond retention force according to an exemplary embodiment of the present application may be associated with a relative base sequence between the first tag 112 and the second tag 122. According to a binding direction between the first tag 112 and the second tag 122, the bond retention force may increase or decrease.

The binding direction between the first tag 112 and the second tag 122 has been described in detail in 2.2 Tag 200 and 1.2 Formation of secondary structure, and duplicated descriptions will be omitted.

In a specific example, the bond retention force of a nucleic acid complex pair 10 in which base sequences of the first tag 112 adjacent to the first determinant 111 and base sequences of the second tag 122 spaced apart from the second determinant 121 form complementary bonds may be different from that of a nucleic acid complex pair 10 in which base sequences of the first tag 112 adjacent to the first determinant 111 and base sequences of the second tag 122 adjacent to the second determinant 121 form complementary bonds.

2.1.2.6 Number of Mismatched Base Sequences Between First Tag 112 and Second Tag 122

The bond retention force according to an exemplary embodiment of the present application may be associated with mismatched base sequences between the first tag 112 and the second tag 122. The bond retention force may increase or decrease according to the presence of mismatched base sequences between the first tag 112 and the second tag 122 and/or the number of mismatched base sequences.

In a specific example, when there is a mismatched base sequence between the first tag 112 and the second tag 122, the bond retention force may decrease. In one example, provided that the first tag 112 has a base sequence of 5'-AAACCCGG-3', when the second tag 122 has 5'-CCGGGTTT-3', compared to when the second tag 122 has 5'-CCGGTTTT-3', the bond retention force thereof may be higher.

2.1.2.7 Relative Position(s) of First Label 113 and/or Second Label 123

The bond retention force according to an exemplary embodiment of the present application may be associated with the position(s) of the first label 113 and/or the second label 123. According to the positional relationship between each component of a first nucleic acid complex 110 and the first label 113, the bond retention force may increase or decrease. According to the positional relationship between each component of a second nucleic acid complex 120 and the second label 123, the bond retention force may increase or decrease.

In a specific example, when the first nucleic acid complex 110 is formed by sequentially connecting a first label 113, a first tag 112, a first linker 114 and a first determinant 111, a second nucleic acid complex 120 formed by sequentially connecting a second tag 122, a second linker 124, a second label 123 and a second determinant 121 may have a higher bond retention force than that formed by sequentially connecting a second label 123, a second tag 122, a second linker 124 and a second determinant 121.

2.1.2.8 Kind(s) of First Label 113 and/or Second Label 123

The bond retention force according to an exemplary embodiment of the present application may be associated with the kind(s) of the first label 113 and/or the second label 123. According to the kind of the first label 113, the bond retention force may increase or decrease. According to the kind of the second label 123, the bond retention force may increase or decrease.

In a specific example, the bond retention force of the nucleic acid complex pair 10 in which the first label 113 is FAM may be different from that of the nucleic acid complex pair 10 in which the first label 113 is HEX The bond retention force of the nucleic acid complex pair 10 in which the second label 123 is FAM may be different from that of the nucleic acid complex pair 10 in which the second label 123 is HEX.

2.1.2.9 Kinds of Bases in Base Sequence of Amplification Product

The bond retention force according to an exemplary embodiment of the present application may be associated with an amplification product for a first strand including a first target base sequence and/or an amplification product of a second strand including a second target base sequence, which are (is) formed by complementary bonds between the first determinant 111 and/or the second determinant 121 and PCR. According to the kinds of bases in the base sequence included in the amplification product for the first strand including the first target base sequence, formed by complementary bonds between the first determinant 111 and/or the second determinant 121 and PCR, the bond retention force may increase or decrease. According to the kinds of bases in the base sequence included in the amplification product for the second strand including the second target base sequence, formed by complementary bonds between the first determinant 111 and/or the second determinant 121 and PCR, the bond retention force may increase or decrease.

In a specific example, the more the cytosine (C)-guanine (G) in the base sequence included in the amplification product for the first strand including the first target base sequence, the higher the bond retention force. The more the cytosine (C)-guanine (G) in the base sequence included in the amplification product for the second strand including the second target base sequence, the higher the bond retention force.

2.1.2.10 Length of Amplification Product

The bond retention force according to an exemplary embodiment of the present application may be associated with the amplification product for the first strand including the first target base sequence and/or the amplification product for the second strand including the second target base sequence, which are (is) formed by complementary bonds between the first determinant 111 and/or the second determinant 121 and PCR. According to the length of the amplification product for the first strand including the first target base sequence, formed by complementary bonds between the first determinant 111 and/or the second determinant 121 and PCR, the bond retention force may increase or decrease. According to the length of the amplification product for the second strand including the second target base sequence, formed by complementary bonds between the first determinant 111 and/or the second determinant 121 and PCR, the bond retention force may increase or decrease.

In one example, as the amplification product for the first strand including the first target base sequence varies, the bond retention force may increase or decrease. In another example, as the length of a nucleic acid strand including the first determinant 111 and the amplification product for the first strand including the first target base sequence varies, the bond retention force may increase or decrease. In still another example, as the length of the amplification product for the second strand including the second target base sequence varies, the bond retention force may increase or decrease. In another example, as the length of a nucleic acid strand including the second determinant 121 and the amplification product for the second strand including the second target base sequence varies, the bond retention force may increase or decrease.

2.1.2.11 Base Sequence(s) of First Determinant 111 and/or Second Determinant 121

The bond retention force according to an exemplary embodiment of the present application may be associated with the base sequence(s) of the first determinant 111 and/or the second determinant 121. The bond retention force may be associated with the first target base sequence and/or the second target base sequence. The bond retention force may be associated with a specific disease targeted by the first determinant 111 and/or a specific disease targeted by the second determinant 121. The bond retention force may be associated with a specific disease targeted by the first determinant 111 and the second determinant 121.

In one example, according to the kinds of bases in the base sequence of the first determinant 111, the bond retention force may increase or decrease. In another example, according to the arrangement of bases in the base sequence of the first determinant 111, the bond retention force may increase or decrease. In still another example, according to the length of the base sequence of the first determinant 111, the bond retention force may increase or decrease. In yet another example, according to the kinds of bases in the base sequence of the second determinant 121, the bond retention force may increase or decrease. In yet another example, according to the arrangement of bases in the base sequence of the second determinant 121, bond retention force may increase or decrease. In yet another example, according to the length of the base sequence of the second determinant 121, the bond retention force may increase or decrease.

2.2 Configuration of Nucleic Acid Complex Pair 10

According to an exemplary embodiment of the present application, at least a first nucleic acid complex pair 10 and a second nucleic acid complex pair 10 may be used.

The first nucleic acid complex pair 10 may include a first nucleic acid complex 110 and a second nucleic acid complex 120. The first nucleic acid complex 110 may include a first determinant 111, a first linker 114, a first tag 112 and a first label 113. The first nucleic acid complex 110 may be formed by sequentially connecting a first determinant 111, a first linker 114, a first tag 112 and a first label 113. The second nucleic acid complex 120 may include a second determinant 121, a second linker 124, a second tag 122 and a second label 123. The second nucleic acid complex 120 may be formed by sequentially connecting a second determinant 121, a second linker 124, a second tag 122 and a second label 123.

The second nucleic acid complex pair 10 may include a third nucleic acid complex 1 and a fourth nucleic acid complex 1. The third nucleic acid complex 1 may include a third determinant 100, a third linker 400, a third tag 200 and a third label 300. The third nucleic acid complex 1 may be formed by sequentially connecting a third determinant 100, a third linker 400, a third tag 200 and a third label 300. The fourth nucleic acid complex 1 may include a fourth determinant 100, a fourth linker 400, a fourth tag 200 and a fourth label 300. The fourth nucleic acid complex 1 may be formed by sequentially connecting a fourth determinant 100, a fourth linker 400, a fourth tag 200 and a fourth label 300.

The first determinant 111 and the second determinant 121 may be primers. When the first determinant 111 is a forward primer, the second determinant 121 may be a reverse primer. When the first determinant 111 is a reverse primer, the second determinant 121 may be a forward primer.

In a specific example, the first determinant 111 may be a primer for amplifying a first strand including a first target base sequence related to a first disease, and the second determinant 121 may be a primer for amplifying a second strand including a second target base sequence related to the first disease.

The third determinant 100 and the fourth determinant 100 may be primers. When the third determinant 100 is a forward primer, the fourth determinant 100 may be a reverse primer. When the third determinant 100 is a reverse primer, the fourth determinant 100 may be a forward primer.

In a specific example, the third determinant 100 may be a primer for amplifying a third strand including a third target base sequence related to a second disease, and the fourth determinant 100 may be a primer for amplifying a fourth strand including a fourth target base sequence related to a second disease.

According to an exemplary embodiment of the present application, the first determinant 111, the second determinant 121, the third determinant 100 and the fourth determinant 100 may have similar annealing temperatures. In other words, in the design of the primers, the annealing temperature (Tm) at which the above-mentioned components bind to the target base sequence may be calculated using a program. Since the first determinant 111, the second determinant 121, the third determinant 100 and the fourth determinant 100 bind to respective target base sequences in a step of annealing a unit cell (UC)(S3000), the annealing temperatures of the first determinant 100, the second determinant 121, the third determinant 100 and the fourth determinant 100 may be designed to be similar to each other.

The first tag 112 and the second tag 122 may complementarily bind to each other. The third tag 200 and the fourth tag 200 may complementarily bind to each other. The bond retention force of the first nucleic acid complex pair 10 may be different from that of the second nucleic acid complex pair 10. In a specific example, the base sequence involved in complementary binding between the first tag 112 and the second tag 122 may consist of four C-G and three A-T. The base sequence involved in complementary binding between the third tag 200 and the fourth tag 200 may consist of five C-G and five A-T. The bond retention force between the first tag 112 and the second tag 122 may be smaller than that between the third tag 200 and the fourth tag 200.

The first label 113 may include a first signal-generating material. The third label 300 may include the same signal-detection material which is detected with the same signal as that of the first label 113.

The "same signal-detection material" used herein may include materials of the same type. In one example, when a first signal material included in the first nucleic acid complex pair 10 is JOE, and a second signal material included in the second nucleic acid complex pair 10 may be JOE.

Here, the "same signal-detection material" may include multiple types of different materials detected with the same signal (e.g., a signal included in a wavelength band range corresponding to a predetermined wavelength band) based on the specifications of a device. In one example, when a first signal material included in the first nucleic acid complex pair 10 is TET with an emission wavelength of 548 lambda, signal materials, JOE and TET, may be detected with light in the same wavelength range according to the specifications of a device, and here, JOE and TET may be the same signal-detection materials.

The second label 123 may include a first signal conversion material which converts a first signal of the first label 113. The fourth label 300 may include a second signal conversion material which converts a signal of the third label 300 detected with the same signal as the first signal of the first label 113. When the first label 113 and the third label 300 are formed of the same material, the second label 123 and the fourth label 300 may be the same materials. When the first label 113 and the third label 300 are the same materials, the second label 123 and the fourth label 300 may be different materials.

The first label 113 and the second label 123 may perform a linked action. Based on whether the first tag 112 and the second tag 122 are bound, the first label 113 and the second label 123 may perform a linked action. The third label 300 and the fourth label 300 may perform a linked action. Based on whether the third tag 200 and the fourth tag 200 are bound, the third label 300 and the fourth label 300 may perform a linked action.

The bond retention force between the first tag 112 and the second tag 122 may be different from that between the third tag 200 and the fourth tag 200.

According to an exemplary embodiment of the present application, when an optical signal is measured by increasing a temperature of a unit cell (UC) including a first nucleic acid complex pair 10 and a second nucleic acid complex pair 10, a point of time at which the linkage between the first label 113 and the second label 123 is dissociated and a point of time at which the linkage between the third label 300 and the fourth label 300 is dissociated may be detected separately. When an optical signal is measured by increasing a temperature of a unit cell (UC) including a first nucleic acid complex pair 10 and a second nucleic acid complex pair 10, a temperature at which the linkage between the first label 113 and the second label 123 is dissociated and a temperature at which the linkage between the third label 300 and the fourth label 300 is dissociated may be different from each other.

According to an exemplary embodiment of the present application, when an optical signal emitted from a unit cell (UC) including a first nucleic acid complex pair 10 and a second nucleic acid complex pair 10 is measured by decreasing a temperature, a point of time at which the linkage between the first label 113 and the second label 123 is dissociated and a point of time at which the linkage between the third label 300 and the fourth label 300 is dissociated may be detected separately. When an optical signal emitted from a unit cell (UC) including a first nucleic acid complex pair 10 and a second nucleic acid complex pair 10 is measured by decreasing a temperature, a temperature at which the linkage between the first label 113 and the second label 123 is dissociated and a temperature at which the linkage between the third label 300 and the fourth label 300 is dissociated may be different from each other.

The first linker 114, the second linker 124, the third linker 400 and the fourth linker 400 may be a PCR blocker. The first linker 114 may prevent an amplification product for the first tag 112 from being produced. The second linker 124 may prevent an amplification product for the second tag 122 from being produced. The third linker 400 may prevent an amplification product for the third tag 200 from being produced. The fourth linker 400 may prevent an amplification product for the fourth tag 200 from being produced.

According to an exemplary embodiment of the present application, using multiple types of nucleic acid complex pairs 10, multiple types of target nucleic acids may be detected in one unit cell (UC).

According to an exemplary embodiment of the present application, using multiple types of nucleic acid complex pairs 10, one target nucleic acid may be detected per fluorescent channel in one unit cell (UC), and multiple types of target nucleic acids may be detected in one unit cell (UC) using a plurality of fluorescent channels.

According to an exemplary embodiment of the present application, since the bond retention forces between multiple types of nucleic acid complex pairs 10 and multiple types of nucleic acid complexes 1 are different, multiple types of target nucleic acids may be detected per one fluorescent channel.

Multiple kinds of nucleic acid complex pairs 10 used to detect multiple types of target nucleic acids per fluorescent channel may be designed to have bond retention forces that do not overlap, in consideration of the various factors described above in 2.1 Bond retention force. Multiple kinds of nucleic acid complex pairs 10 used to detect multiple types of target nucleic acids per fluorescent channel may be designed to have dissociation peak values, which do not overlap, in consideration of the various factors described above in 2.1 Bond retention force.

In one example, by changing the positional relationship between a fluorescent material included in a nucleic acid complex pair 10 (i.e., first label 113) and each component of the nucleic acid complex pair 10, the first nucleic acid complex pair 10 and the second nucleic acid complex pair 10 may be designed such that a dissociation peak value of the first nucleic acid complex pair 10 and a dissociation peak value of the second nucleic acid complex pair 10 are different, even when the first tag 112 and the third tag 200 have the same base sequence, and the second tag 122 and the fourth tag 200 have the same base sequence.

The multiple types of nucleic acid complexes 1 used to detect multiple types of target nucleic acids in one fluorescent channel may have at least one different determinant 100 sequence. In other words, the base sequence of the first determinant 111 may be different from that of the third determinant 100. Alternatively, the base sequence of the second determinant 121 may be different from that of the fourth determinant 100. Alternatively, the base sequence of the first determinant 111 may be different from that of the third determinant 100, and the base sequence of the second determinant 121 may be different from that of the fourth determinant 100.

To detect multiple types of target nucleic acids in one fluorescent channel in one unit cell, each of the plurality of dissociation peak values may be assigned to the nucleic acid complex pairs 10 corresponding to different target base sequences. For example, when the dissociation peak value corresponding to the first nucleic acid complex pair 10 is 40 C, the dissociation peak value corresponding to the second nucleic acid complex pair 10 may be designed to be 55 C.

2.3 Operation of Nucleic Acid Complex Pair 10

According to an exemplary embodiment of the present application, PCR may be performed to detect multiple types of target nucleic acids. According to an exemplary embodiment of the present application, PCR may be performed to detect multiple types of target nucleic acids per fluorescent channel.

Except that a target nucleic acid reacted with the first nucleic acid complex pair 10 and a target nucleic acid reacted with the second nucleic acid complex pair 10 may be different from each other, a thermal denaturation step (S2000), an annealing step (S3000) and a polymerization step (S4000) in PCR have been described above in 1.3.2 Operation of nucleic acid complex pair 10, and thus detailed descriptions will be omitted.

A stabilization step (S5000) may be performed on a unit cell (UC) including the PCR-completed multiple types of nucleic acid complex pairs 10. In the stabilization step (S5000), complementary binding between the first tag 112 and the second tag 122 and complementary binding between the third tag 200 and the fourth tag 200 may be induced.

As the stabilization step (S5000) progresses, a step of obtaining a dissociation curve (S6000) may be performed. In other words, a fluorescence value may be detected according to the temperature of the unit cell (UC). A graph of between a temperature and the negative rate of change in fluorescence with respect to temperature may be obtained by analyzing a fluorescence value according to the detected temperature, and a dissociation peak value may be confirmed.

More specifically, when PCR is performed using a first nucleic acid complex pair 10 designed to have a dissociation peak value at a first temperature and a second nucleic acid complex pair 10 designed to have a dissociation peak value at a second temperature, based on whether a dissociation peak value is confirmed at the first temperature, the presence of a first target base sequence (i.e., a sequence complementary to at least a part of the first determinant 111) and a second target base sequence (i.e., a sequence complementary to at least a part of the second determinant 121) of the first nucleic acid complex pair 10 may be confirmed, and based on whether a dissociation peak value is confirmed at the second temperature, the presence of a third target base sequence (i.e., a sequence complementary to at least a part of the third determinant 100) and a fourth target base sequence (i.e., a sequence complementary to at least a part of the fourth determinant 100) of the second nucleic acid complex pair 10 may be confirmed.

FIG. 42 shows a graph of fluorescence vs. temperature and a graph of the negative rate of change in fluorescence with respect to temperature/temperature in one fluorescent channel according to an exemplary embodiment of the present application.

The first label 113 and the third label 300 are signal-generating materials detected with the same signal, the second label 123 may be a signal conversion material absorbing light emitted from the first label 113, and the fourth label 300 may be a signal conversion material absorbing light emitted from the third label 300.

When there are a target nucleic acid related to the first nucleic acid complex pair 10 and a target nucleic acid related to the second nucleic acid complex pair 10 in a unit cell (UC), on the graph of fluorescence with respect to temperature, fluorescence values detected from the unit cell (UC) at the temperatures corresponding to a dissociation peak value (T1) related to the first nucleic acid complex pair 10 and a dissociation peak value (T2) related to the second nucleic acid complex pair 10 may increase (see FIG. 42(a)).

In other words, when there are a target nucleic acid related to the first nucleic acid complex pair 10 and a target nucleic acid related to the second nucleic acid complex pair 10 in a unit cell (UC), a nucleic acid construct including the first nucleic acid complex pair 10 may have a secondary structure formed by bonds between the first tag 112 and the second tag 122, and the second nucleic acid complex pair 10 may have a secondary structure formed by bonds between the third tag 200 and the fourth tag 200.

When a fluorescence value generated from a unit cell (UC) is detected by increasing a temperature, light of the first label 113, which has been absorbed by the second label 123, may be emitted due to dissociation of the binding between the first tag 112 and the second tag 122. As a result, on the graph of fluorescence with respect to a temperature, at a temperature corresponding to a dissociation peak value (T1) related to the first nucleic acid complex pair 10, a fluorescence level detected from the unit cell (UC) may increase.

In addition, when a fluorescence value generated from a unit cell (UC) is detected by increasing a temperature, light of the third label 300, which has been absorbed by the fourth label 300, may be emitted due to dissociation of the binding between the third tag 200 and the fourth tag 200. As a result, on the graph of fluorescence with respect to a temperature, a fluorescence value detected from the unit cell (UC) at a temperature corresponding to a dissociation peak value (T2) related to the second nucleic acid complex pair 10 may increase.

According to an exemplary embodiment of the present application, the temperature-fluorescence graph may be converted into a graph of the negative rate of change in fluorescence with respect to temperature/temperature.

When there are a target nucleic acid related to the first nucleic acid complex pair 10 and a target nucleic acid related to the second nucleic acid complex pair 10 in a unit cell (UC), on the graph of the negative rate of change in fluorescence with respect to temperature/temperature, at a temperature corresponding to the dissociation peak value (T1) related to the first nucleic acid complex pair 10 and a temperature corresponding to the dissociation peak value (T2) related to the second nucleic acid complex pair 10, the maximum point or the minimum point may be confirmed.

On the graph of the negative rate of change in fluorescence with respect to temperature/temperature, when the minimum points are confirmed at the temperature corresponding to the dissociation peak value (T) related to the first nucleic acid complex pair 10 and the temperature corresponding to the dissociation peak value (T2) related to the second nucleic acid complex pair 10, the presence of a target nucleic acid related to the first nucleic acid complex pair 10 and a target nucleic acid related to the second nucleic acid complex pair 10 may be confirmed.

The first label 113 and the third label 300 may be signal-generating materials detected with the same signal, the second label 123 may be a signal conversion material absorbing light emitted from the first label 113, and the fourth label 300 may be a signal conversion material absorbing light emitted from the third label 300. When there are a target nucleic acid related to the first nucleic acid complex pair 10 and a target nucleic acid related to the second nucleic acid complex pair 10 in a unit cell (UC), on the graph of the negative rate of change in fluorescence with respect to temperature/temperature, at the temperature corresponding to a first temperature (i.e., a dissociation peak value related to the first nucleic acid complex pair 10) and the temperature corresponding to a second temperature (i.e., a dissociation peak value related to the second nucleic acid complex pair 10) may be confirmed (see FIG. 42(*b*)).

At least the temperature difference between the first and second temperatures can be designed based on a distinguishable range using a device. In one example, preferably, multiple types of nucleic acid complex pairs 10 are designed such that a temperature difference between the first temperature and the second temperature is in the range of 1 to 10 C.

According to an exemplary embodiment of the present application, based on the detection of a dissociation peak value related to the nucleic acid complex pair 10, whether there is a target nucleic acid related to the nucleic acid complex pair 10 in a unit cell (UC) may be confirmed.

A dissociation peak value may be adjusted based on a bond retention force between the first tag 112 and the second tag 122 of the nucleic acid complex pair 10. Accordingly, compared to another probe for confirming whether there is a target nucleic acid based on the change in fluorescence value due to dissociation of a region binding to the target nucleic acid, the presence of a target nucleic acid is confirmed using the nucleic acid complex pair 10 according to an exemplary embodiment of the present application, based on a bond retention force of a region not binding to the target nucleic acid (i.e., the first tag 112 and the second tag 122), achieving an advantage of a simpler and more flexible design of the first tag 112, the second tag 122 and a dissociation peak value based on the first and second tags 112 and 122.

In addition, in the confirmation whether there is a target nucleic acid using the nucleic acid complex pair 10 according to an exemplary embodiment of the present application, it is less necessary to provide a binding position of another probe, so that the target nucleic acid can be detected even by symmetric PCR, achieving an advantage of higher detection sensitivity.

A PCR kit, which includes the nucleic acid complex pair 10 disclosed in the present application may include two or more kinds of nucleic acid complex pairs 10. The PCR kit may include at least two or more kinds of nucleic acid complex pairs 10. The PCR kit may further include at least one of enzymes involved in polymerization, base fragments, coenzymes involved in PCR, and buffers used to provide optimal pH and/or salt concentrations for PCR.

The PCR kit may be realized in a form in which a composition including at least one material (e.g., a container containing a composition including one type of nucleic acid complex pair 10) is put in one container, and multiple containers (e.g., a container containing a composition including one type of nucleic acid complex pair 10 and a container containing a composition including another type of nucleic acid complex pair 10) are put in one package for sale. The PCR kit may be embodied in a form in which a composition including at least one material is contained in one container. The PCR kit may be embodied in the form in which at least one material is dried and put in a container.

The PCR kit may include X types or less of nucleic acid complex pairs 10. The value X may be dependent on a minimum dissociation peak value difference ($\Delta T$) to distinguish multiple dissociation peak values according to dissociation of the complementary bond between one tag 200 (i.e., first tag 112) and another tag 200 (i.e., second tag 122) of multiple types of nucleic acid complex pairs 10 and a temperature range for detecting a signal depending on a device. The value X may be dependent on the number of groups in wavelength ranges that can be distinguished by a device. The value X may be dependent on the type of signal material included in the multiple types of nucleic acid complex pairs 10.

For example, when the minimum temperature at which a signal may be detected is 10° C., the maximum temperature is 70° C., and the $\Delta T$ is 5° C., the number of kinds of target nucleic acids, which can be detected separately by one fluorescent channel is (70-10)/5=12, and the number of groups in wavelength ranges which can be distinguished by a device is five, the X value may be 12*5=60.

Therefore, when a composition for PCR including multiple types of nucleic acid complex pairs 10 according to an exemplary embodiment of the present application, it is possible to confirm whether there are 60 different kinds of target nucleic acids in one tube. When a composition for PCR including 60 kinds of nucleic acid complex pairs 10 according to an exemplary embodiment of the present application, it is possible to confirm whether there are 60 different kinds of target nucleic acids in one tube using five fluorescent channels.

When the first label 113 and the second label 123 according to an exemplary embodiment of the present application are linked, the second label 123 may be designed to quench light emitted from the first label 113 (hereinafter, signal quencher type). Alternatively, when the first label 113 and the second label 123 according to an exemplary embodiment of the present application are linked, the second label 123 may be designed to convert light emitted from the first label 113 and to be detected by a device (hereinafter, signal emission type).

When the multiple types of nucleic acid complex pairs 10 are used in PCR, at least a first nucleic acid complex pair 10 and a second nucleic acid complex pair 10 may be designed to be the same type (for example, the first nucleic acid complex pair 10 and the second nucleic acid complex pair 10 are designed as the signal quencher type), or different types (for example, the first nucleic acid complex pair 10 is designed as the signal emission type and the second nucleic acid complex pair 10 is designed as the signal quencher type).

When the PCR kit includes X types or less of nucleic acid complex pairs 10, the kit may consist of X/2 kinds of nucleic acid complex pairs 10 designed as a signal quencher type and X/2 kinds of nucleic acid complex pairs 10 designed as a signal emission type. In this case, the number of kinds of target nucleic acids that can be detected in one tube may increase.

When some of the multiple types of nucleic acid complex pairs are designed as a signal quencher type and the other multiple types of nucleic acid complex pairs are designed as a signal emission type, under the same conditions (e.g., the minimum temperature for signal measurement is 10° C., the maximum temperature is 70° C., ΔT is 5° C., and the number of groups in wavelength bands that can be detected by a device is 5), an X value related to the number of kinds of detectable target nucleic acids may be doubled to 60*2=120.

2.4 Experimental Example #4 Related to Application of Nucleic Acid Complex Pair 10

According to an exemplary embodiment of the present application, the presence of multiple types of target nucleic acids in a unit cell (UC) may be confirmed using the multiple types of nucleic acid complex pairs 10.

Figure 43:
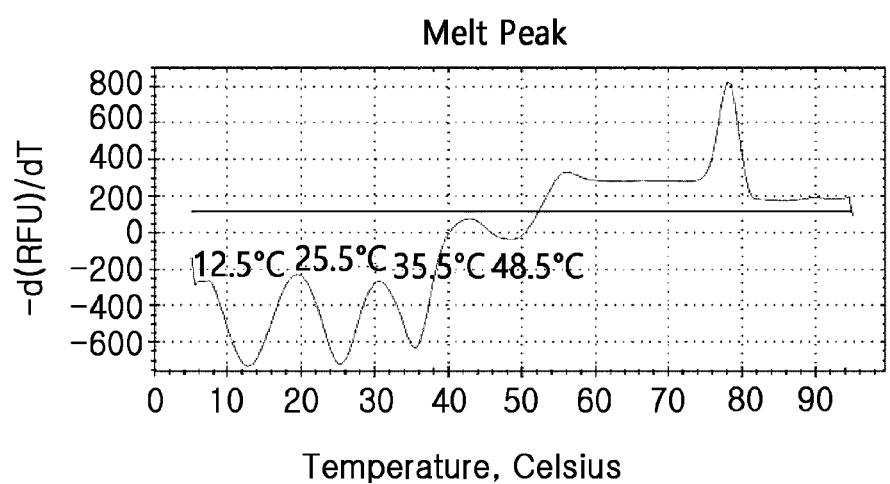
FIG. 43 is a graph illustrating a result according to an experiment for confirming at least four kinds of target nucleic acids present in a unit cell (UC) according to an exemplary embodiment of the present application. RFU, relative fluorescence unit; d(RFU)/dT, the rate of change in RFU with respect to temperature.

FIG. 43 is a diagram illustrating the result according to an experiment for confirming at least four kinds of target nucleic acids present in a unit cell (UC) according to an exemplary embodiment of the present application.

In the progression of this experiment, Tris-HCl (pH 9.0), a salt (KCl), MaCl$_2$, a dNTP mixture, a protein stabilizer, a PCR enhancer (macromolecules), and fast hot-start Taq DNA polymerase were introduced into a tube (or well) of a PCT plate.

A first nucleic acid complex pair 10 to a fourth nucleic acid complex pair 10 were introduced into a first tube of the PCR plate.

The first nucleic acid complex pair 10 consisted of a first nucleic acid complex 110 and a second nucleic acid complex 120. The second nucleic acid complex pair 10 consisted of a third nucleic acid complex 110 and a fourth nucleic acid complex 120. The third nucleic acid complex pair 10 consisted of a fifth nucleic acid complex 110 and a sixth nucleic acid complex 120. The fourth nucleic acid complex pair 10 consisted of a seventh nucleic acid complex 110 and an eighth nucleic acid complex 120.

1 pmol/Rxn of the first nucleic acid complex 110 was introduced. 1 pmol/Rxn of the second nucleic acid complex 120 was introduced. 1 pmol/Rxn of the third nucleic acid complex 110 was introduced. 1 pmol/Rxn of the fourth nucleic acid complex 120 was introduced. 1 pmol/Rxn of the fifth nucleic acid complex 110 was introduced. 1 pmol/Rxn of the sixth nucleic acid complex 120 was introduced. 1 pmol/Rxn of the seventh nucleic acid complex 110 was introduced. 1 pmol/Rxn of the eighth nucleic acid complex 120 was introduced.

The first nucleic acid complex 110 was formed by sequentially connecting a first label 113, a first tag 112, a first linker 114 and a first determinant 111, wherein the first label 113 was a quencher molecule (Iowa Black@ FQ (Iowa Black@ Quenchers)), the first tag 112 was CCCGCGCG (SEQ ID NO: 19), the first linker 114 was Spacer 18, and the first determinant 111 was TGGAGATACACCTACATTG (SEQ ID NO: 14).

The second nucleic acid complex 120 was formed by sequentially connecting a second label 123, a second tag 122, a second linker 124 and a second determinant 121, wherein the second label 123 was FAM the second tag 122 was CGCGCGGG (SEQ ID NO: 20), the second linker 124 was Spacer 18, and the second determinant 121 was GCTGGACCATCTATTTCATC (SEQ ID NO: 16).

The third nucleic acid complex 110 was formed by sequentially connecting a third label 113, a third tag 112, a third linker 114 and a third determinant 111, wherein the third label 113 was a quencher molecule (Iowa Black@ FQ (Iowa Black@ Quenchers)), the third tag 112 was AAAAAAAA (SEQ ID NO: 1), the third linker 114 was Spacer 18, and the third determinant 111 was TACGCCTGCTACTTTCACG (SEQ ID NO: 2).

The fourth nucleic acid complex 120 was formed by sequentially connecting a fourth label 123, a fourth tag 122, a fourth linker 124 and a fourth determinant 121, wherein the fourth label 123 was FAM, the fourth tag 122 was TTTTTTTT (SEQ ID NO: 3), the fourth linker 124 was Spacer 18, and the fourth determinant 121 was ATATTTAAGGGCATAATTTCCG (SEQ ID NO: 4).

The fifth nucleic acid complex 110 was formed by sequentially connecting a fifth label 113, a fifth tag 112, a fifth linker 114 and a fifth determinant 111, wherein the fifth label 113 was a quencher molecule (Iowa Black@ FQ (Iowa Black® Quenchers)), the fifth tag 112 was AAAAAAAAAA (SEQ ID NO: 5), the fifth linker 114 was Spacer 18, and the fifth determinant 111 was AGGTAAACGCTCCTCTGAA (SEQ ID NO: 6).

The sixth nucleic acid complex 120 was formed by sequentially connecting a sixth label 123, a sixth tag 122, a sixth linker 124 and a sixth determinant 121, wherein the sixth label 123 was FAM, the sixth tag 122 was TTTTTTTTTT (SEQ ID NO: 7), the sixth linker 124 was Spacer 18, and the sixth determinant 121 was GCGAGTTACGAAGACAAAA (SEQ ID NO: 8).

The seventh nucleic acid complex 110 was formed by sequentially connecting a seventh label 113, a seventh tag 112, a seventh linker 114 and a seventh determinant 111, wherein the seventh label 113 was a quencher molecule (Iowa Black@ FQ (Iowa Black Quenchers)), the seventh tag 112 was AACCTTGGGA (SEQ ID NO: 9), the seventh linker 114 was Spacer 18, and the seventh determinant 111 was AGCTCCTATTGCCAACGTA (SEQ ID NO: 10).

The eighth nucleic acid complex 120 was formed by sequentially connecting an eighth label 123, an eighth tag 122, an eighth linker 124 and an eighth determinant 121, wherein the eighth label 123 was FAM, the eighth tag 122 was TCCCAAGGTT (SEQ ID NO: 11), the eighth linker 124 was Spacer 18, and the eighth determinant 121 was AATCTTTGTGTGGAGCATC (SEQ ID NO: 12).

A competitive construct 2 for the first nucleic acid complex 110, a competitive construct 2 for the fourth nucleic acid complex 120, a competitive construct 2 for the sixth nucleic acid complex 120, and a competitive construct 2 for the eighth nucleic acid complex 120 were provided to a first tube of the PCR plate.

2 pmol/Rxn of the competitive construct 2 for the first nucleic acid complex 110 was introduced. 8 pmol/Rxn of the competitive construct 2 for the fourth nucleic acid complex 120 was introduced. 2 pmol/Rxn of the competitive construct 2 for the sixth nucleic acid complex 120 was introduced. 8 pmol/Rxn of the competitive construct 2 for the eighth nucleic acid complex 120 was introduced.

The competitive construct 2 for the first nucleic acid complex 110 was formed by sequentially connecting a primer competitor 600, a PCR blocker and a tag competitor 500, wherein the tag competitor 500 was CGCGCG (SEQ ID NO: 21), the PCR blocker was Spacer 18, and the primer competitor 600 was GGTGTATCTCCA (SEQ ID NO: 22).

The competitive construct 2 for the fourth nucleic acid complex 120 was formed by sequentially connecting a primer competitor 600, a PCR blocker and a tag competitor 500, wherein the tag competitor 500 was AAAAAA (SEQ ID NO: 23), the PCR blocker was Spacer 18, and the primer competitor 600 was TATGCCCTTAAATAT (SEQ ID NO: 24).

The competitive construct 2 for the sixth nucleic acid complex 120 was formed by sequentially connecting a primer competitor 600, a PCR blocker and a tag competitor 500, wherein the tag competitor 500 was AAAAAAAA (SEQ ID NO: 1), the PCR blocker was Spacer 18, and the primer competitor 600 was GTAACTCGC (SEQ ID NO: 25).

The competitive construct 2 for the eighth nucleic acid complex 120 was formed by sequentially connecting a primer competitor 600, a PCR blocker and a tag competitor 500, wherein the tag competitor 500 was AACCTTGG (SEQ ID NO: 26), the PCR blocker was Spacer 18, and the primer competitor 600 was CCACACAAAGATT (SEQ ID NO: 18).

A PCR reaction was performed on a solution in a tube by adjusting the temperature of the tube into which each of the multiple types of nucleic acid complex pairs 10, the competitive construct 2 and other enzymes were introduced. As shown in FIG. 29, the temperature of the tube was maintained at 95° C. for 10 minutes, and a sequence of a thermal denaturation step (S2000)(95° C., 10 sec), an annealing step (S3000)(50° C., 40 sec) and a polymerization step (S4000) (60° C., 20 sec) was set as one cycle, and repeatedly performed for 40 cycles. In this experiment, Bio-Rad CFX96 (Permit Number 10-205) was used.

Afterward, a dissociation curve for the first tube was obtained, and as shown in FIG. 43, a graph of the negative rate of change in fluorescence with respect to temperature/temperature was then obtained.

In the graph of the negative rate of change in fluorescence with respect to temperature/temperature, the minimum dissociation peak value of the second nucleic acid complex pair 10 was confirmed at 12.5° C. In the graph of the negative rate of change in fluorescence with respect to temperature/temperature, the minimum dissociation peak values of the third tag 200 and the fourth tag 200 were confirmed at 12.5° C. Therefore, it can be confirmed that there was a target nucleic acid related to the second nucleic acid complex pair 10 in a unit cell (UC).

In the graph of the negative rate of change in fluorescence with respect to temperature/temperature, the minimum dissociation peak value of the third nucleic acid complex pair 10 was confirmed at 25.5° C. In the graph of the negative rate of change in fluorescence with respect to temperature/temperature, the minimum dissociation peak values of the fifth tag 200 and the sixth tag 200 were confirmed at 25.5° C. Therefore, it can be confirmed that there was a target nucleic acid related to the third nucleic acid complex pair 10 in a unit cell (UC).

In the graph of the negative rate of change in fluorescence with respect to temperature/temperature, the minimum dissociation peak value of the fourth nucleic acid complex pair 10 was confirmed at 35.5° C. In the graph of the negative rate of change in fluorescence with respect to temperature/temperature, the minimum values of the seventh tag 200 and the eighth tag 200 were confirmed at 35.5° C. Therefore, it was confirmed that there was a target nucleic acid related to the fourth nucleic acid complex pair 10 in a unit cell (UC).

In the graph of the negative rate of change in fluorescence with respect to temperature/temperature, the minimum dissociation peak value of the first nucleic acid complex pair 10 was confirmed at 48.5° C. In the graph of the negative rate of change in fluorescence with respect to temperature/temperature, the minimum dissociation peak values of the first tag 112 and the second tag 122 were confirmed at 48.5° C. Therefore, it was confirmed that there was a target nucleic acid related to the first nucleic acid complex pair 10 in a unit cell (UC).

As a result, according to an exemplary embodiment of the present application, a graph of the negative rate of change in fluorescence with respect to temperature/temperature was obtained to confirm the detection of a dissociation peak value at a specific temperature, and thus it can be confirmed whether there was a target nucleic acid in a unit cell (UC).

2.5 Application of Nucleic Acid Complex Pair 10 According to Seventh Exemplary Embodiment FIGS. 44 and 45 are diagrams illustrating the usage of a nucleic acid complex pair 10 according to a seventh exemplary embodiment of the present application.

Referring to FIG. 44, the nucleic acid complex pair 10 may include a first nucleic acid complex 110 and a second nucleic acid complex 120.

The first nucleic acid complex 110 may include at least a first determinant 111, a first tag 112 and a first label 113. In one example, the first nucleic acid complex 110 may include a first determinant 111, a first tag 112, a first label 113 and a first linker 114.

The second nucleic acid complex 120 may include at least a second determinant 121, a second tag 122 and a second label 123. In one example, the second nucleic acid complex 120 may include a second determinant 121, a second tag 122, a second label 123 and a second linker 124.

According to an exemplary embodiment of the present application, the first tag 112 and the second tag 122 may complementarily bind to each other. The first tag 112 and the second tag 122 may include regions complementarily binding to each other.

According to an exemplary embodiment of the present application, physical lengths of the first tag 112 and the second tag 122 may be the same. For example, the base sequence of the first tag 112 may include only base sequences complementarily binding to the second tag 122. The base sequence of the second tag 122 may include only base sequences complementarily binding to the first tag 112. In a specific example, when the first tag 112 is configured to have a base sequence of AAAAAAAA (SEQ ID NO: 1), the second tag 122 may be configured to have a base sequence of TTTTTTTT (SEQ ID NO: 3).

According to another exemplary embodiment of the present application, the physical lengths of the first tag 112 and the second tag 122 may be different from each other.

For example, the first tag 112 may include a region complementarily binding to the second tag 122, and a region not complementarily binding to the second tag 122. The base sequence of the second tag 122 may include only base sequences complementarily binding to the first tag 112. In a specific example, when the first tag 112 is configured to have abase sequence of AAAAAAAA (SEQ ID NO: 1), the second tag 122 may be configured to have a base sequence of 5'-TTTTTT-3'.

For example, the first tag 112 may include a region complementarily binding to the second tag 122, and a region not complementarily binding to the second tag 122. The second tag 122 may include a region complementarily binding to the first tag 112, and a region not complementarily binding to the first tag 112. The first tag 112 may have a physical length different from that of the second tag 122. In a specific example, when the first tag 112 is configured to have a base sequence of AAAAAAAA (SEQ ID NO: 1), the second tag 122 may be configured to have a base sequence of 5'-TTTTTTG-3'.

To detect a target nucleic acid using the multiple types of nucleic acid complex pairs 10 according to an exemplary embodiment of the present application, at least the first nucleic acid complex pair 10 and the second nucleic acid complex pair 10 may be used.

In a specific example, the first nucleic acid complex pair 10 may include a first nucleic acid complex 110 and a second nucleic acid complex 120. The second nucleic acid complex pair 10 may include a third nucleic acid complex 110 and a fourth nucleic acid complex 120.

The base sequences of the first tag 112 and the third tag 112 of the multiple types of nucleic acid complex pairs 10 according to the exemplary embodiment may be the same.

In the multiple types of nucleic acid complex pairs 10 according to an exemplary embodiment of the present application, even when the first tag 112 and the third tag 112 have the same base sequence, a bond retention force caused by the complementary bond between the base sequence of the first tag 112 and the base sequence of the second tag 122 may be different from that caused by the complementary bond between the base sequence of the third tag 121 and the fourth tag 122.

In one example, even when the first tag 112 and the third tag 112 have the same base sequence, the length of the base sequence of the second tag 122 complementarily binding to the base sequence of the first tag 112 may be shorter than that of the base sequence of the fourth tag 122 complementarily binding to the base sequence of the third tag 112 (see FIGS. 44(a), (b)).

When the length of the base sequence of the second tag 122 complementarily binding to the base sequence of the first tag 112 is shorter than that of the base sequence of the fourth tag 122 complementarily binding to the base sequence of the third tag 112, a bond retention force caused by the complementary bond between the base sequence of the first tag 112 and the base sequence of the second tag 122 may be smaller than that caused by the complementary bond between the base sequence of the third tag 112 and the base sequence of the fourth tag 122.

In another example, even when the first tag 112 and the third tag 112 have the same base sequence, a location of the complementary binding of the second tag 122 to the first tag 112 may be different from that of the complementary binding of the fourth tag 122 to the third tag 112.

In a specific example, the location of the complementary binding of the second tag 112 to the first tag 112 may partially overlap that of the complementary binding of the fourth tag 122 to the third tag 112, and a part may not overlap. In another specific example, the location of the complementary binding of the second tag 122 to the first tag 112 may not overlap that of the complementary binding of the fourth tag 122 to the third tag 112.

According to the configuration of the base sequence at the location of the complementary binding of the second tag 122 to the first tag 112 and the configuration of the complementary binding of the fourth tag 122 to the third tag 112, a bond retention force caused by the complementary bond between the base sequence of the first tag 112 and the base sequence of the second tag 122 may be different from that caused by the complementary bond between the base sequence of the third tag 112 and the base sequence of the fourth tag 122.

The detailed description of a method of binding the first tag 112 (or the third tag 112) and the second tag 122 (or the fourth tag 122) (e. g, the detailed description of the operation of the nucleic acid complex pair 10 and the location of the complementary binding of the second tag 122 to the first tag 112 when the first tag 112 and the second tag 122 have different lengths) has been provided in 2.2 Tag 200, and thus duplicated description will be omitted.

In addition, changes in bond retention force according to the kind, number and material characteristics of the base sequence involved in complementary binding between the first tag 112 (or the third tag 112) and the second tag 122 (or the fourth tag 122) have been described in detail in 2.1 Bond retention force, and thus duplicated description will be omitted.

As described above, even when the first tag 112 and the third tag 112 are the same, the bond retention force between the first tag 112 and the second tag 122 and the bond retention force between the third tag 112 and the fourth tag 122 may be different from each other.

In a specific example, even when the first tag 112 and the third tag 112 are the same, and the length of the second tag 122 binding to the first tag 112 is designed to be different from that of the fourth tag 122 binding to the third tag 112, the bond retention force between the first tag 112 and the second tag 122 and the bond retention force between the third tag 112 and the fourth tag 122 may be different from each other.

Even when the first tag 112 and the third tag 112 are the same, and the length of the second tag 122 binding to the first tag 112 and the length of the fourth tag 122 binding to the third tag 112 are different from each other, a secondary structure of a nucleic acid construct including the first nucleic acid complex 110 and the second nucleic acid complex 120 may be formed by the complementary bond between the first tag 112 and the second tag 122 (see FIG. 45(a)).

Even when the first tag 112 and the third tag 112 are the same, and the length of the second tag 122 binding to the first tag 112 and the length of the fourth tag 122 binding to the third tag 112 are different from each other, a secondary structure of a nucleic acid construct including the third nucleic acid complex 110 and the fourth nucleic acid complex 120 may be formed by the complementary bond between the third tag 112 and the fourth tag 122 (see FIG. 45(b)).

Even when the first tag 112 and the third tag 112 are the same, and the length of the second tag 122 binding to the first tag 112 and the length of the fourth tag 122 binding to the third tag 112 are different from each other, based on the fact that the bond retention force of the first nucleic acid complex pair 10 and the bond retention force of the second nucleic acid complex pair 10 are different from each other, through detection of a fluorescence value according to a temperature (and analysis of a graph of the negative rate of change in fluorescence with respect to temperature/temperature), the presence of the first target base sequence and the second target base sequence may be confirmed, and the presence of the third target base sequence and the fourth target base sequence may be confirmed.

As such, in an exemplary embodiment for detecting multiple types of target nucleic acids using multiple types of nucleic acid complex pairs 10 in one unit cell (UC), multiple types of target nucleic acids can be detected in one unit cell (UC) by constructing the second tag 122 complementarily binding to the first tag 112 and the fourth tag 122 complementarily binding to the third tag 112 to have different base sequences even when the first tag 112 and the third tag 112 are constructed to have the same base sequence.

Here, the first determinant 111 of the first nucleic acid complex 110 and the third determinant 111 of the third nucleic acid complex 110 may include different base sequences. Specifically, the first determinant 111 may complementarily bind to a first target base sequence related to a first disease, and the third determinant 111 may complementarily bind to a first target base sequence related to a second disease.

Alternatively, the first determinant 111 of the first nucleic acid complex 110 and the third determinant 111 of the third nucleic acid complex 110 may be constructed to have the same base sequence. Specifically, a first target base sequence corresponding to the first determinant 111 and a third target base sequence corresponding to the third determinant 111 may be the same. The first target base sequence and the third target base sequence may be base sequences corresponding to at least a partial region of a non-disease-specific conserved region. Here, the second determinant 121 may complementarily bind to a second target base sequence related to the first disease, and the fourth determinant 121 may complementarily bind to a fourth target base sequence related to the second disease.

2.6 Application of Nucleic Acid Complex Pair 10 According to Eighth Exemplary Embodiment 2.6.1. Detection of Target Nucleic Acid Using Nucleic Acid Complex Pair 10 and Probe Complex 600

When a nucleic acid complex pair 10 according to an exemplary embodiment of the present application was subjected to PCR to confirm whether there is a target nucleic acid in a unit cell (UC), the nucleic acid complex pair 10 binds to a first target base sequence and/or a second target base sequence of the target nucleic acid.

Therefore, there may be a probe complex 600-binding region (PR) in the remaining region except a first target base sequence and/or a second target base sequence among regions in which a PCR amplification product is produced (e.g., the first strand including a first target base sequence, a strand having the same base sequence as the first strand including the first target base sequence produced by amplification, the second strand including a second target base sequence, and a strand having the same base sequence as the first strand including the second target base sequence produced by amplification).

In other words, as the probe complex 600 binds to at least one region of the remaining region except the first target base sequence and/or the second target base sequence, the presence of a target nucleic acid related to the probe complex 600 may be detected.

As a result, both methods of detecting a target nucleic acid according to a first labeling method (i.e., a method of detecting a target nucleic acid using a nucleic acid complex pair 10) and a second labeling method (i.e., a method of detecting a target nucleic acid using a probe complex 600) may progress in one unit cell (UC).

In a specific example, the second labeling method may be a Taqman method, a molecular beacon method, a TOCE method, a PNA probe method, a scorpion method or a combination thereof. This is merely described with reference to specific examples, and a method that can be used as the second labeling method is not limited to the above-described examples.

According to the labeling methods disclosed herein, compared to a conventional method, almost 2 to 20-fold larger kinds of target nucleic acids may be confirmed through one unit cell (UC) (i.e., PCR tube).

To perform detection of a target nucleic acid in a sample using the first labeling method and the second labeling method, a process of designing to avoid overlapping of a dissociation peak value related to the first labeling method and a dissociation peak value related to the second labeling method may be required. The "dissociation peak value" used herein may mean a temperature value corresponding to the maximum point or the minimum point in a graph illustrating the negative rate of change for fluorescence with respect to a temperature based on a dissociation curve.

According to an exemplary embodiment of the present application, when there are total of four detectable dissociation peak values, for example, T1, T2, T3 and T4, of an optical device for a provided unit cell (UC), the nucleic acid complex pair 10 and the probe complex 600 may be designed in the form in which the dissociation peak value included at a first temperature window is assigned to the first labeling method, and the dissociation peak value included at a second temperature window is assigned to the second labeling method. In one example, T1 and T2 may be assigned as dissociation peak values related to the first labeling method, and T3 and T4 may be assigned as dissociation peak values related to the second labeling method.

Alternatively, according to another exemplary embodiment of the present application, when there are a total of four detectable dissociation peak values, for example, T1, T2, T3 and T4, of an optical device for the provided unit cell (UC), the nucleic acid complex pair 10 and the probe complex 600 may be designed in the form in which the dissociation peak values corresponding to some temperatures are assigned to the first labeling method, and the dissociation peak values corresponding to the temperatures that are not assigned to the first labeling method are assigned to the second labeling method. In one example, T1 and T3 may be assigned as dissociation peak values related to the first labeling method, and T2 and T4 may be assigned as dissociation peak values related to the second labeling method.

In a more specific example, when the minimum temperature at which a signal can be detected from a unit cell (UC) by an optical device is 35° C., the maximum temperature is 60° C., and $\Delta T$ is 5° C., six maximum dissociation peak values, for example, 35, 40, 45, 50, 55 and 60° C. can be detected for one fluorescent channel.

In one example, the multiple types of nucleic acid complex pairs 10 may be designed such that 35, 40 and 45° C. are assigned as the dissociation peak values corresponding to the first labeling method, and the probe complex 600 may be designed such that 50, 55 and 60° C. are assigned as the dissociation peak values corresponding to the second labeling method. When binding of the probe complex 600 to the probe-binding region (PR) needs to be performed in PCR using the nucleic acid complex pairs 10 and probe complex 600, which are designed in such forms, an advantage in which, in consideration of an annealing temperature in PCR, relatively high temperatures, such as 50, 55 and 60° C. may be assigned as the dissociation peak values related to the probe complex 600, and 35, 40 and 45° C. may be assigned as the dissociation peak values related to the nucleic acid complex pairs 10 is achieved.

In another example, the nucleic acid complex pairs 10 may be designed to assign 35, 45 and 55° C. as the dissociation peak values corresponding to the first labeling method, and the probe complex 600 may be designed to assign 40, 50 and 60° C. as the dissociation peak values corresponding to the second labeling method. When it is difficult to design multiple types of nucleic acid complex pairs 10 and multiple types of probe complexes 600 so as to have a 5° C. difference in dissociation peak value, using the nucleic acid complex pairs 10 and the probe complex 600 which have been designed in such a form, an advantage that a relatively wide temperature range can be utilized may be obtained by using multiple types of nucleic acid complex pairs 10 and multiple types of probe complexes 600 having a 10° C. difference in dissociation peak value.

Figure 46:
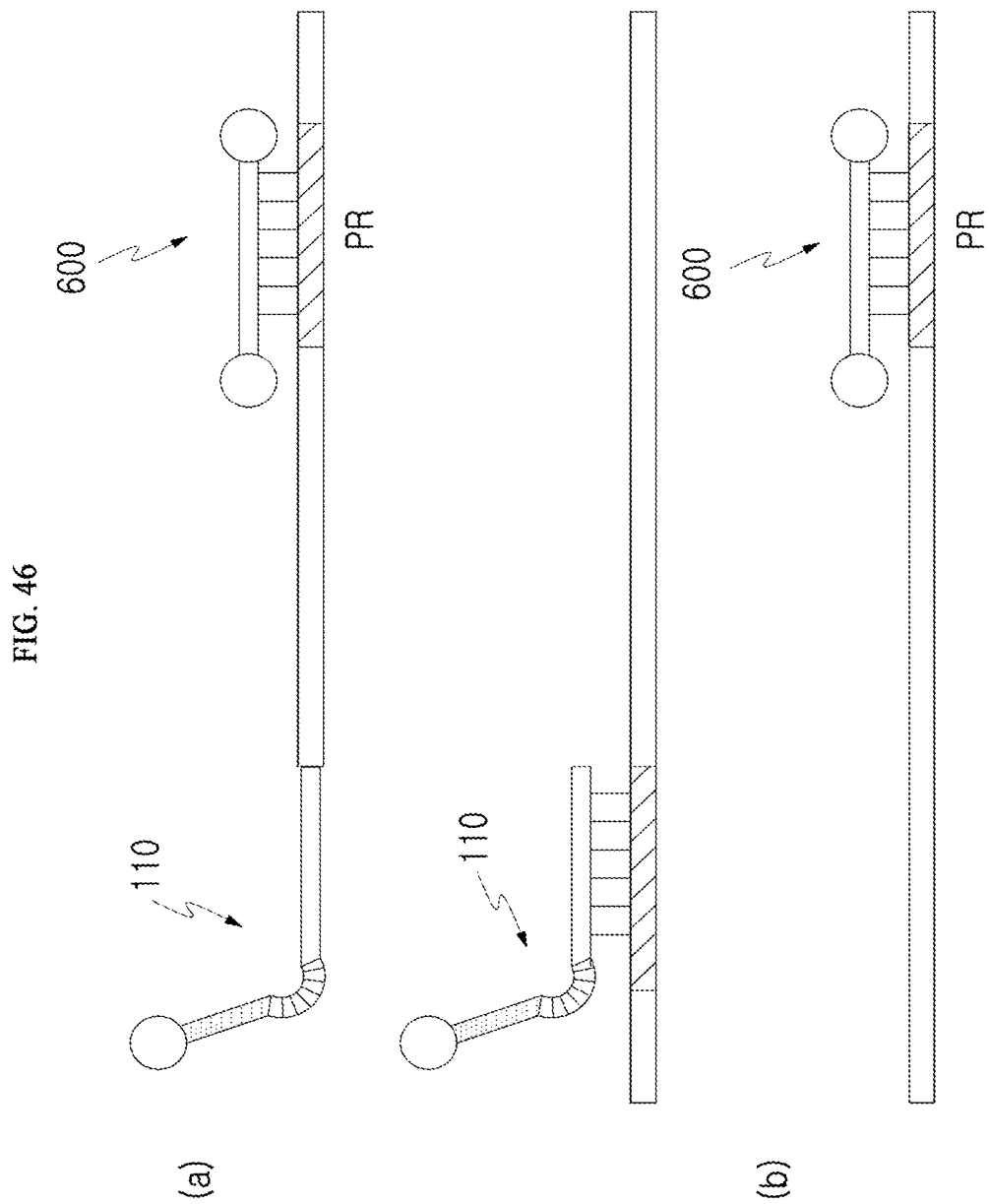
FIG. 46 is a diagram illustrating a target detection using a nucleic acid complex pair 10 and a probe complex 600 according to an exemplary embodiment of the present application.

FIG. 46 is a diagram illustrating the detection of a target nucleic acid using a nucleic acid complex pair 10 and a probe complex 600 according to an exemplary embodiment of the present application.

According to an exemplary embodiment of the present application, when a nucleic acid complex pair 10 is used as a primer related to production of an amplification product including a probe-binding region (PR) to which a probe complex 600 binds (see FIG. 46(*a*)), the number of kinds of target nucleic acids that can be detected using a nucleic acid complex pair 10 and a probe complex 600 may be the number (N1) of kinds of target nucleic acids that can be detected using the probe complex 600*the number (N2) of kinds of target nucleic acids that can be detected using the nucleic acid complex pair 10.

In a specific example, in the case in which the temperatures of the dissociation peak values assigned to the first labeling method are 40, 45 or 50° C., the temperatures of the dissociation peak values assigned to the second labeling method are 55, 60 and 65° C., and a total of five fluorescent wavelength bands (or fluorescent materials) can be detected, when a nucleic acid complex pair 10 is used as a primer related to production of an amplification product including a probe-binding region (PR) to which the probe complex 600 binds, the number of kinds of target nucleic acids that can be detected using a nucleic acid complex pair 10 and a probe complex 600 may be 3*5*3*5=225.

TABLE 1

| Target | 1번표지 | | | | | 2번표지 | | | | |
| --- | --- | --- | --- | --- | --- | --- | --- | --- | --- | --- |
| ID | FAM | HEX | ROX | Cy5 | 705 | FAM | HEX | ROX | Cy5 | 705 |
| 1 | 40 | | | | | 55 | | | | |
| 2 | | 40 | | | | | 55 | | | |
| 3 | | | 40 | | | | | 55 | | |
| 4 | | | | 40 | | | | | 55 | |
| 5 | | | | | 40 | | | | | 55 |
| 6 | 40 | | | | | | 55 | | | |
| 7 | | 40 | | | | | | 55 | | |
| 8 | | | 40 | | | | | | 55 | |
| 9 | | | | 40 | | | | | | 55 |
| 10 | | | | | 40 | 55 | | | | |
| 11 | 40 | | | | | | | 55 | | |
| 12 | | 40 | | | | | | | 55 | |
| 13 | | | 40 | | | | | | | 55 |
| 14 | | | | 40 | | 55 | | | | |
| 15 | | | | | 40 | | 55 | | | |
| 16 | 40 | | | | | | | | 55 | |
| 17 | | 40 | | | | | | | | 55 |
| 18 | | | 40 | | | 55 | | | | |
| 19 | | | | 40 | | | 55 | | | |
| 20 | | | | | 40 | | | 55 | | |
| 21 | 40 | | | | | | | | | 55 |
| 22 | | 40 | | | | 55 | | | | |
| 23 | | | 40 | | | | 55 | | | |
| 24 | | | | 40 | | | | 55 | | |
| 25 | | | | | 40 | | | | 55 | |
| 26 | 40 | | | | | | 60 | | | |
| 27 | | 40 | | | | | 60 | | | |
| 28 | | | 40 | | | | | 60 | | |
| 29 | | | | 40 | | | | | 60 | |
| 30 | | | | | 40 | | | | | 60 |
| 31 | 40 | | | | | | 60 | | | |
| 32 | | 40 | | | | | | 60 | | |
| 33 | | | 40 | | | | | | 60 | |
| 34 | | | | 40 | | | | | | 60 |
| 35 | | | | | 40 | 60 | | | | |
| 36 | 40 | | | | | | | 60 | | |
| 37 | | 40 | | | | | | | 60 | |
| 38 | | | 40 | | | | | | | 60 |
| 39 | | | | 40 | | 60 | | | | |
| 40 | | | | | 40 | | 60 | | | |
| 41 | 40 | | | | | | | | 60 | |
| 42 | | 40 | | | | | | | | 60 |
| 43 | | | 40 | | | 60 | | | | |
| 44 | | | | 40 | | | 60 | | | |
| 45 | | | | | 40 | | | 60 | | |
| 46 | 40 | | | | | | | | | 60 |
| 47 | | 40 | | | | 60 | | | | |
| 48 | | | 40 | | | | 60 | | | |
| 49 | | | | 40 | | | | 60 | | |
| 50 | | | | | 40 | | | | 60 | |
| 51 | 40 | | | | | | 65 | | | |
| 52 | | 40 | | | | | | 65 | | |
| 53 | | | 40 | | | | | | 65 | |
| 54 | | | | 40 | | | | | | 65 |
| 55 | | | | | 40 | | | | | 65 |

TABLE 1-continued

| Target ID | 1번표지 | | | | | 2번표지 | | | | |
|---|---|---|---|---|---|---|---|---|---|---|
| | FAM | HEX | ROX | Cy5 | 705 | FAM | HEX | ROX | Cy5 | 705 |
| 56 | 40 | | | | | | 65 | | | |
| 57 | | 40 | | | | | | 65 | | |
| 58 | | | 40 | | | | | | 65 | |
| 59 | | | | 40 | | | | | | 65 |
| 60 | | | | | 40 | 65 | | | | |
| 61 | 40 | | | | | | | 65 | | |
| 62 | | 40 | | | | | | | 65 | |
| 63 | | | 40 | | | | | | | 65 |
| 64 | | | | 40 | | 65 | | | | |
| 65 | | | | | 40 | | 65 | | | |
| 66 | 40 | | | | | | | | 65 | |
| 67 | | 40 | | | | | | | | 65 |
| 68 | | | 40 | | | 65 | | | | |
| 69 | | | | 40 | | | 65 | | | |
| 70 | | | | | 40 | | | 65 | | |
| 71 | 40 | | | | | | | | | 65 |
| 72 | | 40 | | | | 65 | | | | |
| 73 | | | 40 | | | | 65 | | | |
| 74 | | | | 40 | | | | 65 | | |
| 75 | | | | | 40 | | | | 65 | |
| 76 | 45 | | | | | 55 | | | | |
| 77 | | 45 | | | | | 55 | | | |
| 78 | | | 45 | | | | | 55 | | |
| 79 | | | | 45 | | | | | 55 | |
| 80 | | | | | 45 | | | | | 55 |
| 81 | 45 | | | | | | 55 | | | |
| 82 | | 45 | | | | | | 55 | | |
| 83 | | | 45 | | | | | | 55 | |
| 84 | | | | 45 | | | | | | 55 |
| 85 | | | | | 45 | 55 | | | | |
| 86 | 45 | | | | | | | 55 | | |
| 87 | | 45 | | | | | | | 55 | |
| 88 | | | 45 | | | | | | | 55 |
| 89 | | | | 45 | | 55 | | | | |
| 90 | | | | | 45 | | 55 | | | |
| 91 | 45 | | | | | | | | 55 | |
| 92 | | 45 | | | | | | | | 55 |
| 93 | | | 45 | | | 55 | | | | |
| 94 | | | | 45 | | | 55 | | | |
| 95 | | | | | 45 | | | 55 | | |
| 96 | 45 | | | | | | | | | 55 |
| 97 | | 45 | | | | 55 | | | | |
| 98 | | | 45 | | | | 55 | | | |
| 99 | | | | 45 | | | | 55 | | |
| 100 | | | | | 45 | | | | 55 | |
| 101 | 45 | | | | | 60 | | | | |
| 102 | | 45 | | | | | 60 | | | |
| 103 | | | 45 | | | | | 60 | | |
| 104 | | | | 45 | | | | | 60 | |
| 105 | | | | | 45 | | | | | 60 |
| 106 | 45 | | | | | | 60 | | | |
| 107 | | 45 | | | | | | 60 | | |
| 108 | | | 45 | | | | | | 60 | |
| 109 | | | | 45 | | | | | | 60 |
| 110 | | | | | 45 | 60 | | | | |
| 111 | 45 | | | | | | | 60 | | |
| 112 | | 45 | | | | | | | 60 | |
| 113 | | | 45 | | | | | | | 60 |
| 114 | | | | 45 | | 60 | | | | |
| 115 | | | | | 45 | | 60 | | | |
| 116 | 45 | | | | | | | | 60 | |
| 117 | | 45 | | | | | | | | 60 |
| 118 | | | 45 | | | 60 | | | | |
| 119 | | | | 45 | | | 60 | | | |
| 120 | | | | | 45 | | | 60 | | |
| 121 | 45 | | | | | | | | | 60 |
| 122 | | 45 | | | | 60 | | | | |
| 123 | | | 45 | | | | 60 | | | |
| 124 | | | | 45 | | | | 60 | | |
| 125 | | | | | 45 | | | | 60 | |
| 126 | 45 | | | | | 65 | | | | |
| 127 | | 45 | | | | | 65 | | | |
| 128 | | | 45 | | | | | 65 | | |
| 129 | | | | 45 | | | | | 65 | |
| 130 | | | | | 45 | | | | | 65 |
| 131 | 45 | | | | | | 65 | | | |

TABLE 1-continued

| Target ID | 1번표지 | | | | | 2번표지 | | | | |
|---|---|---|---|---|---|---|---|---|---|---|
| | FAM | HEX | ROX | Cy5 | 705 | FAM | HEX | ROX | Cy5 | 705 |
| 132 | | 45 | | | | | | 65 | | |
| 133 | | | 45 | | | | | | 65 | |
| 134 | | | | 45 | | | | | | 65 |
| 135 | | | | | 45 | 65 | | | | |
| 136 | 45 | | | | | | | 65 | | |
| 137 | | 45 | | | | | | | 65 | |
| 138 | | | 45 | | | | | | | 65 |
| 139 | | | | 45 | | 65 | | | | |
| 140 | | | | | 45 | | 65 | | | |
| 141 | 45 | | | | | | | | 65 | |
| 142 | | 45 | | | | | | | | 65 |
| 143 | | | 45 | | | 65 | | | | |
| 144 | | | | 45 | | | 65 | | | |
| 145 | | | | | 45 | | | 65 | | |
| 146 | 45 | | | | | | | | | 65 |
| 147 | | 45 | | | | 65 | | | | |
| 148 | | | 45 | | | | 65 | | | |
| 149 | | | | 45 | | | | 65 | | |
| 150 | | | | | 45 | | | | 65 | |
| 151 | 50 | | | | | 55 | | | | |
| 152 | | 50 | | | | | 55 | | | |
| 153 | | | 50 | | | | | 55 | | |
| 154 | | | | 50 | | | | | 55 | |
| 155 | | | | | 50 | | | | | 55 |
| 156 | 50 | | | | | | 55 | | | |
| 157 | | 50 | | | | | | 55 | | |
| 158 | | | 50 | | | | | | 55 | |
| 159 | | | | 50 | | | | | | 55 |
| 160 | | | | | 50 | 55 | | | | |
| 161 | 50 | | | | | | | 55 | | |
| 162 | | 50 | | | | | | | 55 | |
| 163 | | | 50 | | | | | | | 55 |
| 164 | | | | 50 | | 55 | | | | |
| 165 | | | | | 50 | | 55 | | | |
| 166 | 50 | | | | | | | | 55 | |
| 167 | | 50 | | | | | | | | 55 |
| 168 | | | 50 | | | 55 | | | | |
| 169 | | | | 50 | | | 55 | | | |
| 170 | | | | | 50 | | | 55 | | |
| 171 | 50 | | | | | | | | | 55 |
| 172 | | 50 | | | | 55 | | | | |
| 173 | | | 50 | | | | 55 | | | |
| 174 | | | | 50 | | | | 55 | | |
| 175 | | | | | 50 | | | | 55 | |
| 176 | 50 | | | | | 60 | | | | |
| 177 | | 50 | | | | | 60 | | | |
| 178 | | | 50 | | | | | 60 | | |
| 179 | | | | 50 | | | | | 60 | |
| 180 | | | | | 50 | | | | | 60 |
| 181 | 50 | | | | | | 60 | | | |
| 182 | | 50 | | | | | | 60 | | |
| 183 | | | 50 | | | | | | 60 | |
| 184 | | | | 50 | | | | | | 60 |
| 185 | | | | | 50 | 60 | | | | |
| 186 | 50 | | | | | | | 60 | | |
| 187 | | 50 | | | | | | | 60 | |
| 188 | | | 50 | | | | | | | 60 |
| 189 | | | | 50 | | 60 | | | | |
| 190 | | | | | 50 | | 60 | | | |
| 191 | 50 | | | | | | | | 60 | |
| 192 | | 50 | | | | | | | | 60 |
| 193 | | | 50 | | | 60 | | | | |
| 194 | | | | 50 | | | 60 | | | |
| 195 | | | | | 50 | | | 60 | | |
| 196 | 50 | | | | | | | | | 60 |
| 197 | | 50 | | | | 60 | | | | |
| 198 | | | 50 | | | | 60 | | | |
| 199 | | | | 50 | | | | 60 | | |
| 200 | | | | | 50 | | | | 60 | |
| 201 | 50 | | | | | 65 | | | | |
| 202 | | 50 | | | | | 65 | | | |
| 203 | | | 50 | | | | | 65 | | |
| 204 | | | | 50 | | | | | 65 | |
| 205 | | | | | 50 | | | | | 65 |
| 206 | 50 | | | | | | 65 | | | |
| 207 | | 50 | | | | | | 65 | | |

TABLE 1-continued

| Target | 1번표지 | | | | | 2번표지 | | | | |
|---|---|---|---|---|---|---|---|---|---|---|
| ID | FAM | HEX | ROX | Cy5 | 705 | FAM | HEX | ROX | Cy5 | 705 |
| 208 |  |  | 50 |  |  |  |  |  | 65 |  |
| 209 |  |  |  | 50 |  |  |  |  |  | 65 |
| 210 |  |  |  |  | 50 | 65 |  |  |  |  |
| 211 | 50 |  |  |  |  |  |  |  | 65 |  |
| 212 |  | 50 |  |  |  |  |  |  | 65 |  |
| 213 |  |  | 50 |  |  |  |  |  |  | 65 |
| 214 |  |  |  | 50 |  | 65 |  |  |  |  |
| 215 |  |  |  |  | 50 |  | 65 |  |  |  |
| 216 | 50 |  |  |  |  |  |  |  | 65 |  |
| 217 |  | 50 |  |  |  |  |  |  |  | 65 |
| 218 |  |  | 50 |  |  | 65 |  |  |  |  |
| 219 |  |  |  | 50 |  |  | 65 |  |  |  |
| 220 |  |  |  |  | 50 |  |  | 65 |  |  |
| 221 | 50 |  |  |  |  |  |  |  |  | 65 |
| 222 |  | 50 |  |  |  | 65 |  |  |  |  |
| 223 |  |  | 50 |  |  |  | 65 |  |  |  |
| 224 |  |  |  | 50 |  |  |  | 65 |  |  |
| 225 |  |  |  |  | 50 |  |  |  | 65 |  |

According to another exemplary embodiment of the present application, when a primer related to production of an amplification product including a probe-binding region (PR) to which the probe complex 600 binds is not a nucleic acid complex pair 10 (see FIG. 46(b)), the number of kinds of target nucleic acids that can be detected using the nucleic acid complex pair 10 and the probe complex 600 may be the number (N1) of kinds of target nucleic acids that can be detected using the probe complex 600+the number (N2) of kinds of target nucleic acids that can be detected using the nucleic acid complex pair 10.

In a more specific example, when the temperatures of the dissociation peak values assigned to the first labeling method are 40, 45 or 50° C., the temperatures of the dissociation peak values assigned to the second labeling method are 55, 60 and 65° C., and a total of five fluorescent wavelength bands (or fluorescent materials) can be detected, although a primer related to production of an amplification product including a probe-binding region (PR) to which the probe complex 600 binds is not a nucleic acid complex pair 10, a total of 3*5+3*5=30 target nucleic acids can be detected using the nucleic acid complex pair 10 and the probe complex 600.

TABLE 2

| Target | 1번표지 | | | | | 2 | | | | |
|---|---|---|---|---|---|---|---|---|---|---|
| ID | FAM | HEX | ROX | Cy5 | 705 | FAM | HEX | ROX | Cy5 | 705 |
| 1 | 40 |  |  |  |  |  |  |  |  |  |
| 2 |  | 40 |  |  |  |  |  |  |  |  |
| 3 |  |  | 40 |  |  |  |  |  |  |  |
| 4 |  |  |  | 40 |  |  |  |  |  |  |
| 5 |  |  |  |  | 40 |  |  |  |  |  |
| 6 | 45 |  |  |  |  |  |  |  |  |  |
| 7 |  | 45 |  |  |  |  |  |  |  |  |
| 8 |  |  | 45 |  |  |  |  |  |  |  |
| 9 |  |  |  | 45 |  |  |  |  |  |  |
| 10 |  |  |  |  | 45 |  |  |  |  |  |
| 11 | 50 |  |  |  |  |  |  |  |  |  |
| 12 |  | 50 |  |  |  |  |  |  |  |  |
| 13 |  |  | 50 |  |  |  |  |  |  |  |
| 14 |  |  |  | 50 |  |  |  |  |  |  |
| 15 |  |  |  |  | 50 |  |  |  |  |  |
| 16 |  |  |  |  |  | 55 |  |  |  |  |
| 17 |  |  |  |  |  |  | 55 |  |  |  |
| 18 |  |  |  |  |  |  |  | 55 |  |  |
| 19 |  |  |  |  |  |  |  |  | 55 |  |
| 20 |  |  |  |  |  |  |  |  |  | 55 |
| 21 |  |  |  |  |  | 60 |  |  |  |  |
| 22 |  |  |  |  |  |  | 60 |  |  |  |
| 23 |  |  |  |  |  |  |  | 60 |  |  |
| 24 |  |  |  |  |  |  |  |  | 60 |  |
| 25 |  |  |  |  |  |  |  |  |  | 60 |
| 26 |  |  |  |  |  | 65 |  |  |  |  |
| 27 |  |  |  |  |  |  | 65 |  |  |  |
| 28 |  |  |  |  |  |  |  | 65 |  |  |
| 29 |  |  |  |  |  |  |  |  | 65 |  |
| 30 |  |  |  |  |  |  |  |  |  | 65 |

So far, the designs and operations of the nucleic acid complex pair 10 and the probe complex 600 used in the unit cell (UC) to detect the presence of a target nucleic acid in a unit cell (UC) have been described above.

Hereinafter, methods of detecting a target nucleic acid using a probe complex 600 and a nucleic acid complex pair 10 according to some exemplary embodiments of the present application will be described in detail.

2.6.2 Probe Complex 610 According to First Exemplary Embodiment 2.6.2.1 Configuration of Probe Complex 610 According to First Exemplary Embodiment.

Figure 47:
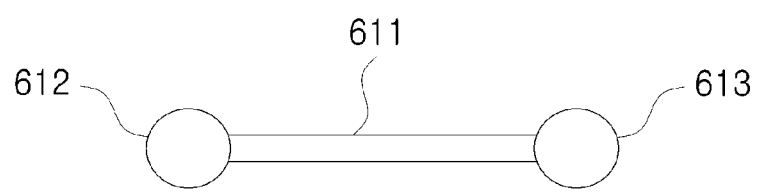
FIG. 47 is a diagram illustrating a probe complex 610 that includes a determinant 611, a first label 612 and a second label 613 according to an exemplary embodiment of the present application.

FIG. 47 is a diagram illustrating a probe complex 610 according to an exemplary embodiment of the present application.

The probe complex 610 according to an exemplary embodiment of the present application may at least include a determinant 611, a first label 612 and a second label 613.

The determinant 611 may include a unit molecule of a nucleic acid and/or a unit molecule of a nucleic acid analog. Examples of the unit molecule of a nucleic acid may be represented by Formulas 1 and 2 shown above. Examples of the unit molecule of a nucleic acid analog may be represented by Formulas 3 to 9 shown above.

The first label 612 may be an energy donor. The first label 612 may be a molecule emitting energy. An example of the energy donor may be FAM, JOE, TET, HEX, VIC, Oregon Green®, TAMRA, ROX, Cyanine-3, Cyanine-3.5, Cyanine-5, Cyanine-5.5, Aequorin or a cyan fluorescent protein (CFP).

The second label 613 may be an energy acceptor. The second label 613 may be a molecule accepting energy. An example of the energy acceptor may be a Black Hole quencher (BHQ), a green fluorescent protein (GFP) or a yellow fluorescent protein (YFP).

The determinant 611 may be connected to the first label 612 and the second label 613. The first label 612 may be connected to one side of the determinant 611, and the second label 613 may be connected to the other side of the determinant 611. The determinant 611 and the first label 612 may be directly connected to each other, or connected via a specific compound. The determinant 611 and the second label 613 may be directly connected, or connected via a specific compound.

The determinant 611 may include a region complementarily binding to a specific base sequence. The determinant 611 may include a region complementarily binding to at least a part of a target nucleic acid to be detected. The sentence "the determinant 611 includes a region complementarily binding to at least a part of a target nucleic acid" may mean that at least a partial region of the determinant 611 corresponds to at least one property of electrical, chemical and physical properties, and is linked to at least a part of the target nucleic acid to be detected.

The determinant 611 may complementarily bind to a probe-binding region (PR). The determinant 611 may specifically bind to a probe-binding region (PR). Here, the "probe-binding region (PR)" may mean a specific base sequence that can complementarily bind to the determinant 611.

According to an exemplary embodiment of the present application, a dissociation peak value may be determined based on a temperature at which the bond between the determinant 611 and the probe-binding region (PR) is dissociated. A binding force between the determinant 611 and the probe-binding region (PR) may be determined based on the kind, sequence and number of bases used in the bond between the determinant 611 and the probe-binding region (PR), and thus, a dissociation peak value may be determined based on the kind, sequence and number of bases used in the bond between the determinant 611 and the probe-binding region (PR).

The first label 612 and the second label 613 may include a region in which a linked action is performed. The first label 612 may include a region donating energy. The second label 613 may include a region accepting energy.

The linked action between the first label 612 and the second label 613 may depend on a distance between them. When the first label 612 and the second label 613 perform the linked action, compared to before the linked action between the first label 612 and the second label 613 is performed, an optical characteristic detected from a unit cell (UC) may be changed.

In a specific example, when the first label 612 and the second label 613 perform the linked action, light emitted from the first label 612 may be absorbed by the second label 613. In another specific example, when the first label 612 and the second label 613 perform the linked action, the wavelength band and intensity of light emitted from the first label 612 may be changed by the second label 613.

According to an exemplary embodiment of the present application, whether the linked action between the first label 612 and the second label 613 is performed or not may be determined based on the bond between the determinant 611 and the probe-binding region (PR).

Specifically, when the determinant 611 of the probe complex 610 does not form double strand which may be caused by the bonding between the determinant 611 of the probe complex 610 and the probe-binding region (PR), the first label 612 and the second label 613 may perform the linked action since they are adjacent to each other due to self-aggregation of the probe complex 610.

When the probe complex 610 is annealed to the probe-binding region (PR), the first label 612 and the second label 613 may be spaced at least the length of the determinant 611 apart from each other. As a result, the first label 612 and the second label 613 may not perform the linked action.

2.6.2.2 Operation of Probe Complex 610 According to First Exemplary Embodiment

The probe complex 610 according to the first exemplary embodiment of the present application may be used in PCR to detect a target nucleic acid.

Specifically, the probe complex 610 according to the first exemplary embodiment may be provided to a unit cell (UC). In addition to the probe complex 610, at least one of enzymes involved in polymerization (e.g., polymerase), base fragments (e.g., deoxynucleotide triphosphate (dNTP)), coenzymes involved in PCR (e.g., $MgCl_2$, $MgSO_4$), and buffers for providing optimum pH and/or salt concentrations in PCR may be further included in the unit cell (UC).

A thermal denaturation step (S2000), an annealing step (S3000) and a polymerization step (S4000) may be sequentially performed on the solution in the unit cell (UC) by adjusting the temperature of the unit cell (UC).

The PCR-completed unit cell (UC) may be subjected to a stabilization step (S5000) and a step of obtaining a dissociation curve (S6000). Based on the obtained dissociation curve, a graph of the negative rate of change in fluorescence with respect to temperature/temperature may be obtained. On the graph of between temperature and the negative rate of change in fluorescence with respect to temperature, a dissociation peak value may be confirmed.

The dissociation peak value may be related to a temperature at which the determinant 611 of the probe complex 610 is dissociated from the probe-binding region (PR). To an extreme degree, the dissociation peak value may correspond to a temperature at which the determinant 611 of the probe complex 610 is dissociated from a probe-binding region (PR).

In detection of multiple types of target nucleic acids using multiple types of probe complexes 610, the multiple types of probe complexes 610 may be designed to have different dissociation peak values by adjusting the base sequence of a probe-binding region (PR) targeted by the determinant 611 and the binding force between the determinant 611 and the probe-binding region (PR).

The kind of a target nucleic acid present in a sample may be identified by confirming the kind of a probe complex 610 corresponding to the dissociation peak value confirmed by analyzing the graph obtained in the step of obtaining a dissociation curve (S6000). The target nucleic acid may be a sequence corresponding to the probe-binding region (PR). The target nucleic acid may be a specific nucleic acid including the probe-binding region (PR).

In short, in the method of detecting the presence of a target nucleic acid using the probe complex 610, when a fluorescence value according to a temperature is detected for a unit cell (UC), a specific temperature at which a fluorescence value decreases or increases may be confirmed, and therefore, the presence of a target nucleic acid may be confirmed. In the method of detecting the presence of a target nucleic acid using the probe complex 610, based on a fluorescent value according to a temperature for the unit cell (UC), a graph of the negative rate of fluorescence according to temperature/temperature may be obtained, and the presence of a target nucleic acid may be confirmed based on the presence of a dissociation peak value.

The determinant 611 of the probe complex 610 according to a first exemplary embodiment of the present application may consist of a polymer of the unit molecule of PNA. Therefore, the determinant 611 of the probe complex 610 may not be decomposed by a DNA polymerase. This is because PNA has a different structure from DNA.

However, the determinant 611 of the probe complex 610 according to the first exemplary embodiment of the present application may consist of a polymer of the unit molecule of DNA. Therefore, the determinant 611 of the probe complex 610 may be decomposed by a DNA polymerase.

To this end, the probe complex 610 according to an exemplary embodiment of the present application may be in a state in which the DNA polymerase is bound with an enzyme for inhibiting the cleavage of the determinant 611 of the probe complex 610. Alternatively, in PCR using the probe complex 610 according to an exemplary embodiment of the present application, a DNA polymerase lacking an activity of a specific domain may be used. In a specific example, by performing PCR using a DNA polymerase lacking exonuclease activity, the cleavage of the determinant 611 of the probe complex 610 may be prevented.

2.6.2.3 Method of Detecting Target Nucleic Acid Using Probe Complex 610 and Nucleic Acid Complex Pair 10 According to First Exemplary Embodiment To detect a target nucleic acid using a probe complex 610 and a nucleic acid complex pair 10 according to an exemplary embodiment of the present application, a unit cell (UC) may be subjected to a thermal denaturation step (S2000), an annealing step (S3000), a polymerization step (S4000), a stabilization step (S5000) and a step of obtaining a dissociation curve (S6000). A sequence of the thermal denaturation step (S2000), the annealing step (S3000) and the polymerization step (S4000) is set as one cycle, and may be repeatedly performed for more than one cycle.

At least one kind of nucleic acid complex pair 10 and at least one kind of probe complex 610 may be provided to a unit cell (UC).

When multiple types of probe complexes 610 are provided to a unit cell (UC) according to an exemplary embodiment of the present application, the multiple types of probe complexes 610 may be designed to have different binding forces between a determinant 611 of each probe complex 610 and a probe-binding region (PR). In a specific example, when the multiple types of probe complexes 610 are provided to a unit cell (UC), the multiple types of probe complex 610 may be designed to have different temperatures at which the bond between a determinant 611 of each probe complex 610 and the probe-binding region (PR) is dissociated.

When the multiple types of nucleic acid complex pairs 10 are provided to a unit cell (UC) according to an exemplary embodiment of the present application, the multiple types of nucleic acid complex pairs 10 may be designed to have different bond dissociation forces between a first tag 112 and a second tag 122. In a specific example, when the multiple types of nucleic acid complex pairs 10 are provided to a unit cell (UC), the multiple types of nucleic acid complex pairs 10 may be designed to have different dissociation peak values based on the number of bases, the kinds of bases, and the kinds of unit nucleic acids according to complementary binding between the first tag 112 and the second tag 122.

Enzymes, base fragments, coenzymes, and/or buffers, which are used in PCR, may be further provided to the unit cell (UC). A PCR kit that can be provided to the unit cell (UC) may include the probe complex 610 according to the first exemplary embodiment, the nucleic acid complex pair 10, and at least one of enzymes, base fragments, coenzymes and buffers, which are used in PCR.

In one example, when there are a total of six dissociation peak values that can be detected by an optical device, the PCR kit may include three kinds of the probe complexes 610 according to the first exemplary embodiment, which correspond to three dissociation peak values, respectively, and three kinds of nucleic acid complex pairs 10, which correspond to three dissociation peak values, respectively.

The PCR kit may be embodied in the form in which a composition including at least one material (e.g., a container containing a composition including one kind of nucleic acid complex pair 10) is contained in one container, and multiple containers (e.g., a container containing a composition having one kind of nucleic acid complex pair 10 and a container containing a composition having a different kind of nucleic acid complex pair 10) are contained in one package. The PCR kit may be embodied in the form of a composition including at least one material, and sold in one container. The PCR kit may be embodied in the form in which at least one material is dried, and sold in one container.

Figure 48:
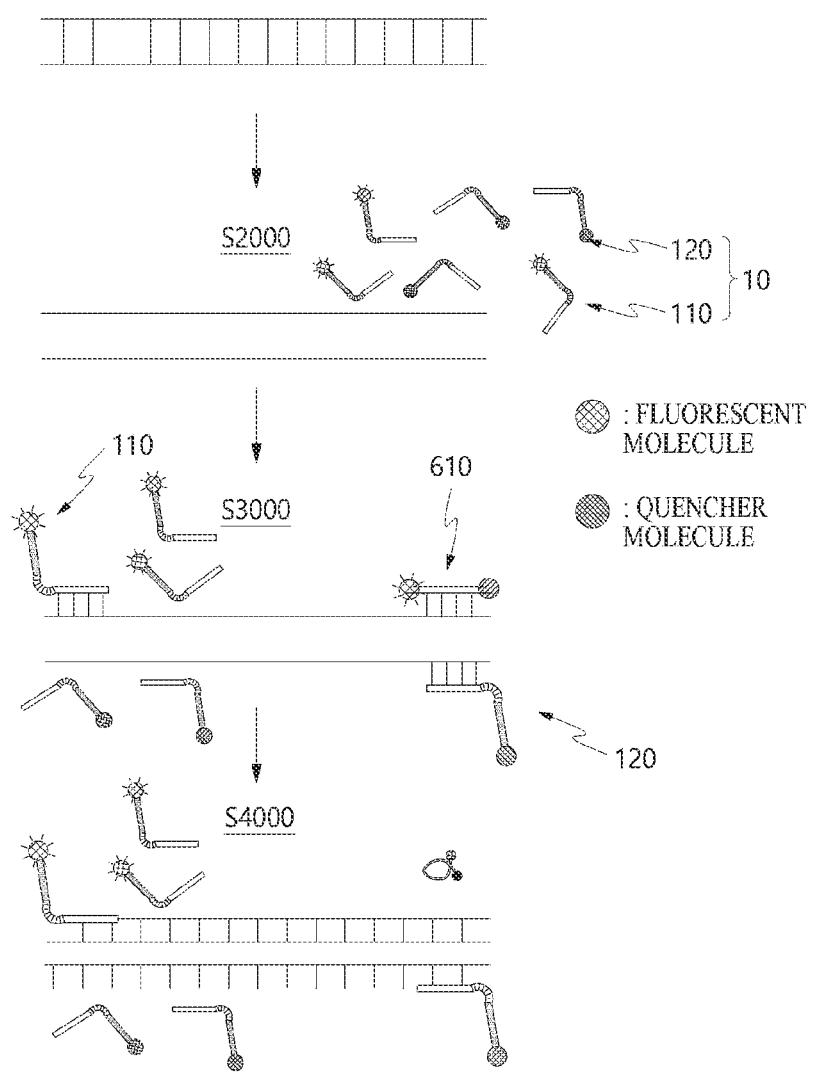
FIGS. 48 and 49 are diagrams illustrating PCR of a solution provided in a unit cell UC including a probe complex 610 as shown in FIG. 47 and a nucleic acid complex pair 10 that includes a first nucleic acid complex 110 and a second nucleic acid complex 120 as shown in FIG. 32 according to an exemplary embodiment of the present application.
Figure 49:
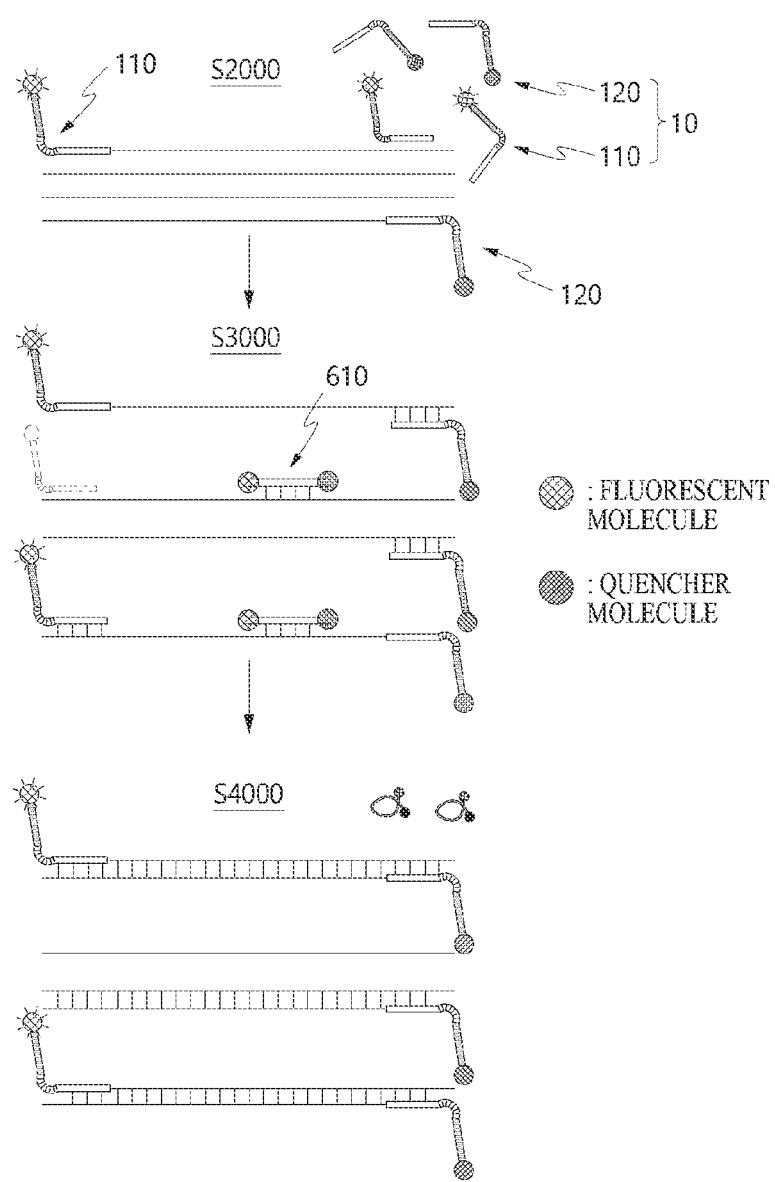

FIGS. 48 and 49 are diagrams illustrating PCR of a solution provided to a unit cell (UC) including a probe complex 610 and a nucleic acid complex pair 10 according to an exemplary embodiment of the present application.

According to an exemplary embodiment of the present application, PCR using the probe complex 610 and the nucleic acid complex pair 10 may be performed according to an asymmetric PCR method.

Hereinafter, the PCR according to an asymmetric method will be described. The PCR according to the asymmetric method may include a relatively large proportion of the first nucleic acid complex 110, compared to the second nucleic acid complex 120, in a unit cell (UC). Alternatively, in the PCR mixed solution according to an asymmetric method, compared to the first nucleic acid complex 110 in the unit cell (UC), a relatively large proportion of the second nucleic acid complex 120 may be included.

In the thermal denaturation step (S2000), double-stranded DNA may be separated into single-stranded DNA by adjusting the temperature of the unit cell (UC). In the thermal denaturation step (S2000), double-stranded DNA including a first target base sequence corresponding to the first determinant 111 of the first nucleic acid complex 110, a second target base sequence corresponding to the second determinant 121 of the second nucleic acid complex 120, and/or a probe-binding region (PR) may be separated into two single strands of DNA.

In the annealing step (S3000), the first nucleic acid complex 110, second nucleic acid complex 120 and/or probe complex 610 may bind to at least a partial region of DNA separated into single strands. Specifically, the first nucleic acid complex 110 may complementarily bind to the first target base sequence. The second nucleic acid complex 120 may complementarily bind to the second target base sequence. The probe complex 610 may complementarily bind to the probe-binding region (PR).

In the polymerization step (S4000), using the first determinant 111 as a starting point, an amplification product for the first strand including the first target base sequence to which the first determinant 111 binds may be produced. In the polymerization step (S4000), using the second determinant 121 as a starting point, an amplification product for the second strand including the second target base sequence to which the second determinant 121 binds may be produced.

According to an exemplary embodiment of the present application, when the first determinant 111 or the second determinant 121 is used as a primer related to the probe complex 610, in the polymerization step (S4000), the probe complex 610 binding to the probe-binding region (PR) may be separated from the probe-binding region (PR). In the polymerization step (S4000), the probe complex 610 binding to the probe-binding region (PR) may not be decomposed.

In a specific example, when the first determinant 111 or the second determinant 121 is used as a primer related to the probe complex 610, using the first determinant 111 or the second determinant 121 as a starting point, after the initiation of the amplification product for the first strand or second strand, the probe complex 610 may be separated from the probe-binding region (PR) at the time of production of an amplification product for a base sequence adjacent to the region to which the probe complex 610 binds.

According to an exemplary embodiment of the present application, even when the first determinant 111 or the second determinant 121 is not used as a primer related to the probe complex 610, the probe complex 610 binding to the probe-binding region (PR) may be separated from the probe-binding region (PR) at the time of production of an amplification product for a nucleic acid included in the probe-binding region (PR) in a region adjacent to the probe complex 610 according to the initiation of the primer related to the probe complex 610 in the polymerization step (S4000). In the polymerization step (S4000), the probe complex 610 binding to the probe-binding region (PR) may not be decomposed.

After one cycle of PCR, in the thermal denaturation step (S2000), the double-stranded DNA in the unit cell (UC) maybe separated into single-stranded DNA. Here, the double-stranded DNA including at least one nucleic acid complex 1 formed in the polymerization step (S4000) may also be separated into two single strands of DNA.

After one cycle of PCR, in the annealing step (S3000), the first nucleic acid complex 110 or the second nucleic acid complex 120 may bind to a first target base sequence and/or a second target base sequence of the single strand in the unit cell (UC). In some cases, the first nucleic acid complex 110 may bind to single-stranded DNA including the second nucleic acid complex 120. The second nucleic acid complex 120 may bind to single-stranded DNA including the first nucleic acid complex 110.

After one cycle of PCR, in the polymerization step (S4000), using the first determinant 111 as a starting point, an amplification product for a nucleic acid including the second determinant 121 may be produced. After one cycle of PCR in the polymerization step (S4000), using the second determinant 121 as a starting point, an amplification product for a nucleic acid including the first determinant 111 maybe produced.

According to an exemplary embodiment of the present application, when the first determinant 111 or the second determinant 121 is used as a primer related to the probe complex 610, in the polymerization step (S4000), the probe complex 610 binding to the probe-binding region (PR) may be separated from the probe-binding region (PR).

In a solution included in the unit cell (UC), which has been subjected to at least two cycles of PCR, a nucleic acid construct including the first nucleic acid complex 110 and the second nucleic acid complex 120, a nucleic acid construct including the first nucleic acid complex 110, a nucleic acid construct including the second nucleic acid complex 120, and a nucleic acid construct not including the first nucleic acid complex 110 and the second nucleic acid complex 120 may flow.

In addition, in a solution included in the unit cell (UC) which has been subjected to two cycles of PCR, before PCR, the concentration of the provided second nucleic acid complex 120 is different from that of the first nucleic acid complex 110 (asymmetric PCR method), the single-stranded DNA including the first nucleic acid complex 110 and/or the single-stranded DNA including the second nucleic acid complex 120 may remain in the unit cell (UC) after the reaction.

After PCR is completed, a stabilization step (S5000) may be performed. In the stabilization step (S5000), the probe complex 610 may bind to a strand including the probe-binding region (PR) of the remaining single-stranded DNA including the first nucleic acid complex 110 or the remaining single-stranded DNA including the second nucleic acid complex 120.

In addition, in the stabilization step (S5000), complementary bonds may be formed between the first tag 112 and the second tag 122 of the nucleic acid construct including the first nucleic acid complex 110 and the second nucleic acid complex 120.

After the stabilization step (S5000), a step of obtaining a dissociation curve (S6000) for the unit cell (UC) may be performed. Here, based on a graph of a fluorescence with respect to a temperature obtained from the unit cell (UC), a graph of the negative rate of change in fluorescence with respect to temperature/temperature may be obtained, confirming a dissociation peak value for the unit cell (UC).

Figure 50:
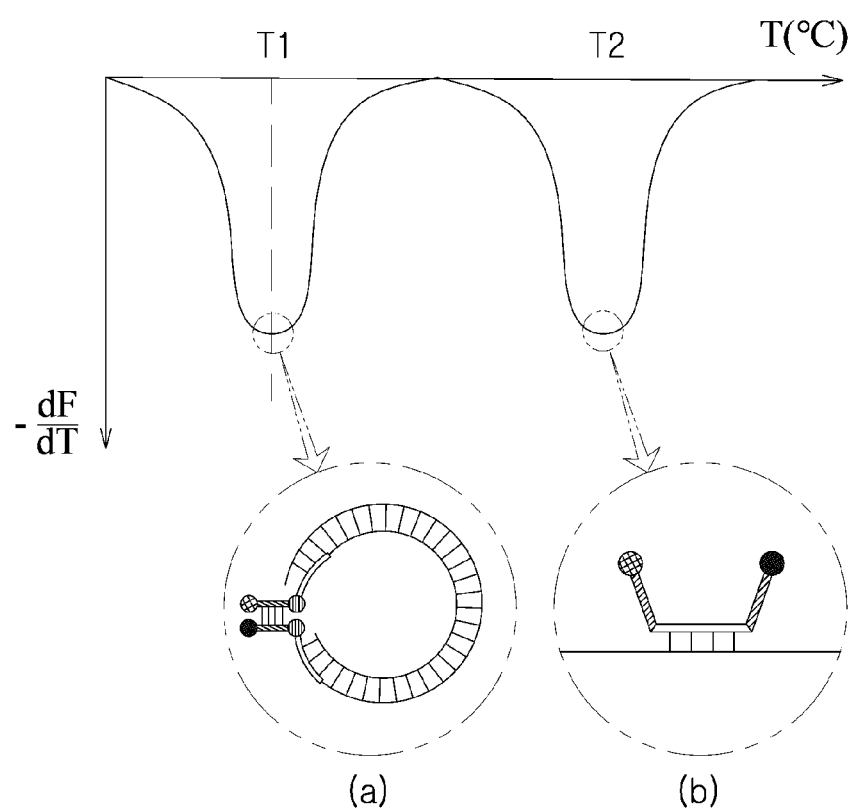
FIG. 50 is a graph of between temperature and a negative rate of change in fluorescence with respect to temperature according to an exemplary embodiment of the present application. F, fluorescence; T, temperature; dF/dT, the rate of change in fluorescence with respect to temperature; T1, dissociation peak value related to the nucleic acid complex pair: T2, dissociation peak value related to the probe complex.

Referring to FIG. 50, according to an exemplary embodiment of the present application, on the graph of the negative rate of change in fluorescence with respect to temperature/temperature, the maximum points may be shown at temperatures T1 and T2. Alternatively, according to an exemplary embodiment of the present application, on the graph of the negative rate of change in fluorescence with respect to temperature/temperature, the minimum points may be shown at temperatures T1 and T2. Alternatively, according to an exemplary embodiment of the present application, on the graph of the negative rate of change in fluorescence with respect to temperature/temperature, the maximum point may be shown at the temperature T1, and the minimum point may be shown at the temperature T2.

In a specific example, on the graph of the negative rate of change in fluorescence with respect to temperature/temperature, T1 at which the minimum point is shown may be a dissociation peak value related to the nucleic acid complex pair 10 (see FIG. 50(*a*)). Here, the nucleic acid complex pair 10 may be designed to perform signal quencher-type linkage. On the graph of the negative rate of change in fluorescence with respect to temperature/temperature, T2 at which the minimum point is shown may be a dissociation peak value related to the probe complex 610 (see FIG. 50(*b*)). Here, the probe complex 610 may be designed to perform signal emission-type linkage.

In a more specific example, 40, 45 and 50° C. are assigned as the dissociation peak values related to the multiple types of nucleic acid complex pairs 10, 15 different kinds of nucleic acid complex pairs 10, each of which is labeled with a total of five fluorescent materials, are designed, 55, 60 and 65° C. are assigned as the dissociation peak values related to the multiple types of the probe complexes 610, and 15 different kinds of probe complexes 610, each of which is labeled with a total of five fluorescent materials, are designed, and then PCR for unit cells (UC) including the nucleic acid complex pairs 10 and the probe complexes 610 may be performed.

Here, when the primer related to the probe complex 610 is a nucleic acid complex pair 10, the dissociation peak value of 45° C. and the dissociation peak value of 60° C. are detected in a fluorescent channel corresponding to FAM, it can be confirmed that there is a target nucleic acid corresponding to Target ID 101 in Table 1 in the unit cell (UC).

Here, when the primer related to the probe complex 610 is not a nucleic acid complex pair 10, and the dissociation peak value of 45° C. and the dissociation peak value of 60° C. are detected in the fluorescent channel corresponding to FAM, it can be confirmed that there area target nucleic acid corresponding to Target ID 1 and a target nucleic acid corresponding to Target ID21, shown in Table 1, in the unit cell (UC).

2.6.2.4 Experimental Example #5 for Probe Complex 610 and Nucleic Acid Complex Pair 10 According to First Exemplary Embodiment According to an exemplary embodiment of the present application, the presence of a target nucleic acid using the probe complex 610 and the nucleic acid complex pair 10 may be confirmed.

FIG. 51 is a set of graphs illustrating the result obtained by an experiment for confirming at least four kinds of target nucleic acids present in a unit cell (UC) according to an exemplary embodiment of the present application.

In the progression of this experiment, Tris-HCl (pH 9.0), a salt (KCl), $MaCl_2$, a dNTP mixture, a protein stabilizer, a PCR enhancer (macromolecules), and fast hot-start Taq DNA polymerase were introduced into a tube (or well) of a PCT plate.

Separate primers associated with the first nucleic acid complex pair 10 and the probe complex 610 were introduced into a first tube of the PCR plate.

The first nucleic acid complex pair 10 consisted of a first nucleic acid complex 110 and a second nucleic acid complex 120. 0.5 pmol/Rxn of the first nucleic acid complex 110 was introduced, and 8 pmol/Rxn of the second nucleic acid complex 120 was introduced.

The first nucleic acid complex 110 was formed by sequentially connecting a first label 113, a first tag 112, a first linker 114 and a first determinant 111, wherein the first label 113 was FAM, the first tag 112 was AAAAAAAAAA (SEQ ID NO: 5), the first linker 114 was Spacer 18, and the first determinant 111 was AGGTAAACGCTCCTCTGAA (SEQ ID NO: 6).

The second nucleic acid complex 120 was formed by sequentially forming a second label 123, a second tag 122, a second linker 124 and a second determinant 121, wherein the second label 123 was a quencher molecule (Iowa Black@ FQ (Iowa Black@ Quenchers)), the second tag 122 was TTTTTTTTTT (SEQ ID NO: 7), the second linker 124 was Spacer 18, and the second determinant 121 was GCGAGTTACGAAGACAAAA (SEQ ID NO: 8).

The probe complex 610 was formed by sequentially connecting a first label 612, a determinant 611 and a second label 613. 2 pmol/Rxn of the probe complex 610 was introduced. The first label 612 was a quencher molecule (Iowa Black® FQ (Iowa Black@ Quenchers)), the determinant 611 was CACTCATATACAGC (SEQ ID NO: 27), and the second label 613 was FAM.

A forward primer and a reverse primer, which are associated with the probe complex 610, were provided. 0.5 pmol/Rxn of the forward primer was introduced, and 8 pmol/Rxn of the reverse primer was introduced.

The forward primer related to the probe complex 610 was AGCTCCTATTGCCAACGTA (SEQ ID NO: 10), and the reverse primer was GTGTGGAGCATCTTGTAATC (SEQ ID NO: 28).

A temperature of a tube into which the nucleic acid complex pair 10, the probe complex 610, and the forward primer and the reverse primer, which are related to the probe complex 610, were introduced was adjusted, and thus PCR was performed for the solution in the tube. As shown in FIG. 29, after the temperature of the tube was maintained at 95° C. for approximately 10 minutes, and a sequence of a thermal denaturation step (S2000×95° C., 10 sec), an annealing step (S3000) (50° C., 40 sec) and a polymerization step (S4000) (60° C., 20 sec) was set as one cycle, and repeatedly performed for 40 cycles. In this experiment, Bio-Rad CFX96 (Permit Number 10-205) was used.

Afterward, a dissociation curve for the tube described above was obtained, and as shown in FIG. 51, a graph of fluorescence according to a temperature and a graph of the negative rate of change in fluorescence with respect to temperature/temperature were then obtained.

In the graph of the negative rate of change in fluorescence with respect to temperature/temperature, related to a dissociation peak value of the nucleic acid complex pair 10, the minimum value was confirmed at 23.5° C. Therefore, it can be confirmed that a target nucleic acid related to the nucleic acid complex pair 10 was present in a unit cell (UC).

On the graph of the negative rate of change in fluorescence with respect to temperature/temperature, related to the dissociation peak value of the probe complex 610, the maximum value was confirmed at 43.5° C. Therefore, it can be confirmed that there is a target nucleic acid related to the probe complex 610 in a unit cell (UC).

As a result, by obtaining the graph of the negative rate of change in fluorescence with respect to temperature/temperature and based on whether a dissociation peak value was detected at a specific temperature, the presence of a target nucleic acid of the nucleic acid complex pair 10 and the presence of a target nucleic acid of the probe complex 610 may be confirmed.

Figure 52:
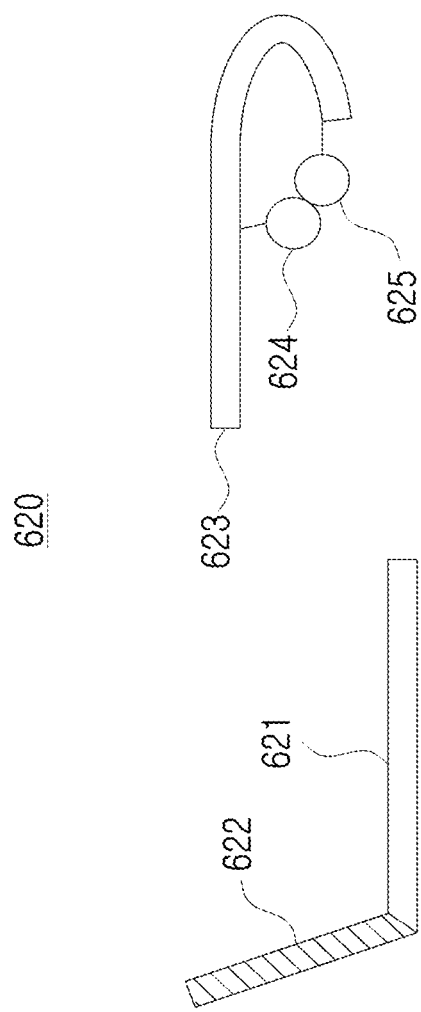
FIG. 52 is a diagram illustrating a probe complex 620 that includes a first probe analog including a determinant 621 and a first pairing part 622 and a second probe analog including a second pairing part 623, a first label 624 and a second label 625 according to the second exemplary embodiment of the present application.

2.6.3 Probe Complex 620 According to Second Exemplary Embodiment 2.6.3.1 Configuration of Probe Complex 620 According to Second Exemplary Embodiment FIG. 52 is a diagram illustrating a probe complex 620 according to a second exemplary embodiment of the present application.

The probe complex 620 according to the second exemplary embodiment of the present application may consist of a first probe analog and a second probe analog, which are physically distinguished.

The first probe analog may include a determinant 621 and a first pairing part 622. The first probe analog may be embodied by connecting the first pairing part 622 to the determinant 621. The second probe analog may include a second pairing part 623, a first label 624 and a second label 625.

The determinant 621 may include a unit molecule of a nucleic acid and/or a unit molecule of a nucleic acid analog. Examples of the unit molecule of the nucleic acid may be represented by Formulas 1 and 2. Examples of the unit molecule of the nucleic acid analog may be represented by Formulas 3 to 9.

The first pairing part 622 may include a unit molecule of a nucleic acid and/or a unit molecule of a nucleic acid analog. The second pairing part 623 may include a unit molecule of a nucleic acid and/or a unit molecule of a nucleic acid analog. As described above, examples of the unit molecule of the nucleic acid may be represented by Formulas 1 and 2. Examples of the unit molecule of the nucleic acid analog may be represented by Formulas 3 to 9.

The first label 624 may be an energy donor. The first label 624 may be a molecule emitting energy. An example of the energy donor may be FAM, JOE, TET, HEX, VIC, Oregon Green®, TAMRA, ROX, Cyanine-3, Cyanine-3.5, Cyanine-5, Cyanine-5.5, Aequorin or a cyan fluorescent protein (CFP).

The second label 625 may be an energy acceptor. The second label 625 may be a molecule accepting energy. An example of the energy acceptor may be a Black Hole quencher (BHQ), a green fluorescent protein (GFP) or a yellow fluorescent protein (YFP).

The first probe analog may be embodied by connecting the determinant 621 and the first pairing part 622. The first probe analog according to an exemplary embodiment of the present application may be embodied by bonding the first pairing part 622 to the determinant 621.

The second probe analog may be embodied by connecting the second pairing part 623, the first label 624 and the second label 625. The second probe analog according to an exemplary embodiment of the present application may be embodied by bonding the first label 624 and the second label 625 to the second pairing part 623.

The determinant 621 may include a region complementarily binding to a specific base sequence. The determinant 621 may include a region complementarily binding to at least a part of a target nucleic acid to be detected. The sentence "the determinant 621 includes a region complementarily binding to at least a part of a target nucleic acid" may mean that at least a partial region of the determinant 621 corresponds to at least one property of electrical, chemical and physical properties, and is linked to at least a part of the target nucleic acid to be detected.

The determinant 621 may complementarily bind to a probe-binding region (PR). The determinant 621 may specifically bind to the probe-binding region (PR). Here, the "probe-binding region (PR)" may mean a specific base sequence complementarily binds to the determinant 621.

The first pairing part 622 may be separated from the determinant 621 when an amplification product for a target nucleic acid including the probe-binding region (PR) is produced. The first pairing part 622 may be separated from the determinant 621 when amplification is performed in a region adjacent to the probe-binding region (PR) by initiating the production of the amplification product for a target nucleic acid including the probe-binding region (PR).

The first pairing part 622 may be separated from the determinant 621 by the action of a DNA polymerase. The first pairing part 622 may be cut and separated from the determinant 621 by the action of a DNA polymerase. In one example, the separation of the first pairing part 622 from the determinant 621 may be caused by the exonuclease activity of a DNA polymerase.

The first pairing part 622 may complementarily bind to the second pairing part 623. The probe complex 620 according to an exemplary embodiment of the present application may be embodied such that the first pairing part 622 and the second pairing part 623 are complementary bound. The first pairing part 622 may include a base sequence complementary to the second pairing part 623. The second pairing part 623 may include a base sequence complementary to the first pairing part 622.

The first pairing part 622 may bind to the second pairing part 623 and thus serve as a primer. The first pairing part 622 may bind to the second pairing part 623 and thus serve as a primer. In other words, when the first pairing part 622 binds to at least a partial region of the second pairing part 623, using the first pairing part 622 as a starting point, a nucleotide may be extended at the 3' end of the second pairing part 623 to have a base sequence complementary to the second pairing part 623.

The first label 624 and the second label 625 may include a region in which linkage is performed. The first label 625 may include a region donating energy. The second label 625 may include a region accepting energy.

The linkage between the first label 624 and the second label 625 may vary depending on a distance between them. When the first label 624 and the second label 625 are linked, compared to before the first label 624 and the second label 625 are linked, an optical characteristic of a unit cell detected by an optical device may be changed.

In a specific example, when the first label 624 and the second label 625 are linked, light emitted from the first label 624 may be absorbed by the second label 625. In another specific example, when the first label 624 and the second label 625 are linked, the wavelength band and intensity of light emitted from the first label 624 may be changed due to the second label 625.

According to an exemplary embodiment of the present application, the first label 624 and the second label 625 may be linked while being self-aggregated.

According to an exemplary embodiment of the present application, when the first pairing part 622 complementarily binds to the second pairing part 623, linkage may not be performed due to a long distance between the first label 624 and the second label 625. In other words, when the first pairing part 622 complementarily binds to the second pairing part 623, a nucleotide binds to a partial region to which the first pairing part 622 does not bind, thereby spacing the first label 624 and the second label 625.

Therefore, whether the first pairing part 622 is complementarily bound to the second pairing part 623 may be determined by the linkage between the first label 624 and the second label 625 according to whether the polymerization step (S4000) was performed after binding.

In the step of obtaining a dissociation curve (S6000), the binding between the sequence complementary to at least a part of the base sequences of 1) the second pairing part 623 and 2) the second pairing part 623 at a specific temperature may be dissociated. The complementary bonds between single strands including 1) the second pairing part 623 and 2) the first pairing part 622 may be dissociated at a specific temperature.

At a specific temperature in which the second pairing part 623 is thermally denatured into single strands, linkage between the first label 624 and the second label 625 may be performed. When the second pairing part 623 is thermally denatured into single strands, the second pairing part 623 is self-aggregated to cause the first label 624 and the second label 625 to become closer, resulting in initiation of the linkage between the first label 624 and the second label 625.

2.6.3.2 Operation of Probe Complex 620 According to Second Exemplary Embodiment The probe complex 620 according to the second exemplary embodiment of the present application may be used in PCR to detect a target nucleic acid.

Specifically, the probe complex 620 according to the second exemplary embodiment may be provided to a unit cell (UC). In addition to the probe complex, at least one of enzymes involved in polymerization (e.g., polymerase), base fragments (e.g., deoxynucleotide triphosphate (dNTP)), coenzymes involved in PCR (e.g., $MgCl_2$, $MgSO_4$), and buffers for providing optimum pH and/or salt concentrations in PCR may be further included in the unit cell (UC).

A thermal denaturation step (S2000), an annealing step (S3000) and a polymerization step (S4000) may be sequentially performed on the solution in the unit cell (UC) by adjusting the temperature of the unit cell (UC).

When the linkage between the determinant 621 and the first pairing part 622 is dissociated in the annealing step (S3000), the first pairing part 622 may complementarily bind to the second pairing part 623.

In the polymerization step (S4000), using the first pairing part 622 as a starting point, a nucleotide may be extended to have a base sequence complementary to a base sequence in at least a partial region of the second pairing part 623.

The stabilization step (S5000) and the step of obtaining a dissociation curve (S6000) may be performed on the PCR-completed unit cell (UC). A graph of the negative rate of change in fluorescence with respect to temperature/temperature may be obtained based on the obtained dissociation curve. On the graph of the negative rate of change in fluorescence with respect to temperature/temperature, a dissociation peak value may be confirmed.

The dissociation peak value may be related to a temperature at which a probe binding to the second pairing part 623 (that is, DNA strand including the first pairing part 622) is dissociated from the second pairing part 623, and thus the second pairing part 623 becomes a single strand. To an extreme degree, the probe binding to the second pairing part 623 (that is, DNA strand including the first pairing part 622) may correspond to a temperature at which the second pairing part 623 is dissociated from the second pairing part 623 and thus becomes a single strand.

In detection of multiple types of target nucleic acids using the multiple types of probe complex 620, the multiple types of probe complex 620 may be designed to have different dissociation peak values by adjusting the length and base sequence of the second pairing part 623.

The kind of a target nucleic acid present in a sample may be identified by confirming the kind of the probe complex 620 corresponding to a dissociation peak value confirmed by analyzing the graph obtained in the step of obtaining a dissociation curve (S6000). The target nucleic acid may be a sequence corresponding to a probe-binding region (PR). The target nucleic acid may be a sequence including the probe-binding region (PR).

In short, in the method of detecting the presence of a target nucleic acid using the probe complex 620, when a fluorescence value according to a temperature is detected for a unit cell (UC), a specific temperature at which a fluorescence value increases or decreases may be confirmed, and therefore, the presence of a target nucleic acid may be confirmed. In the method of detecting the presence of a target nucleic acid using the probe complex 620, based on a fluorescence value according to a temperature for the unit cell (UC), a graph of the negative rate of fluorescence according to temperature/temperature may be obtained, and the presence of a target nucleic acid may be confirmed based on the presence of a dissociation peak value.

2.6.3.3 Method of Detecting Target Nucleic Acid Using Probe Complex 620 and Nucleic Acid Complex Pair 10 According to Second Exemplary Embodiment To detect a target nucleic acid using a probe complex 620 and a nucleic acid complex pair 10 according to an exemplary embodiment of the present application, a unit cell (UC) may be subjected to a thermal denaturation step (S2000), an annealing step (S3000), a polymerization step (S4000), a stabilization step (S5000) and a step of obtaining a dissociation curve (S6000). A sequence of the thermal denaturation step (S2000), the annealing step (S3000) and the polymerization step (S4000) is set as one cycle, and may be repeatedly performed for more than one cycle.

At least one kind of nucleic acid complex pair 10 and at least one kind of probe complex 620 may be provided to a unit cell (UC).

When multiple types of probe complexes 620 are provided to a unit cell (UC) according to an exemplary embodiment of the present application, the multiple types of probe complexes 620 may be designed to have different binding forces between single strands, each including a second pairing part 623 and a first pairing part 622, of each probe complex 620. In a specific example, when the multiple types of probe complexes 620 are provided to a unit cell (UC), the multiple types of probe complexes 620 may be designed to have different temperatures at which the binding between single strands, each including the second pairing part 623 and the first pairing part 622, of each probe complex 620 is dissociated.

When multiple types of nucleic acid complex pairs 10 are provided to a unit cell (UC) according to an exemplary embodiment of the present application, the multiple types of nucleic acid complex pair 10 may be designed to have different bond dissociation forces between a first tag 112 and a second tag 122. In a specific example, when the multiple types of nucleic acid complex pair 10 are provided to a unit cell (UC), the multiple types of nucleic acid complex pair 10 may be designed to have different dissociation peak values based on the number of bases, the kinds of bases, and the kinds of unit nucleic acids according to complementary bonds between the first tag 112 and the second tag 122.

Enzymes, base fragments, coenzymes, and/or buffers, which are used in PCR, may be further provided to the unit cell (UC). A PCR kit that can be provided to the unit cell (UC) may include the probe complex 620 according to the first exemplary embodiment, the nucleic acid complex pair 10, and at least one of enzymes, base fragments, coenzymes and buffers, which are used in PCR.

The PCR kit according to an exemplary embodiment of the present application may include a probe complex 610 according to the first exemplary embodiment, a probe complex 620 according to the second exemplary embodiment, the nucleic acid complex pair 10, and at least one of enzymes, base fragments, coenzymes and buffers, which are used in PCR.

In one example, when there are a total of six dissociation peak values that can be detected by an optical device, the PCR kit may include two kinds of probe complexes 610 according to the first exemplary embodiment, corresponding to two dissociation peak values, respectively, two kinds of probe complexes 620 according to the second exemplary embodiment, corresponding to two dissociation peak values, respectively, and two kinds of nucleic acid complex pairs 10, corresponding to two dissociation peak values, respectively.

The PCR kit may be embodied in the form in which a composition including at least one material (e.g., a container containing a composition including one kind of nucleic acid complex pair 10) is contained in one container, and multiple containers (e.g., a container containing a composition having one kind of nucleic acid complex pair 10 and a container containing a composition having a different kind of nucleic acid complex pair 10) are contained in one package. The PCR kit may be embodied in the form of a composition including at least one material, and sold in one container. The PCR kit may be embodied in the form in which at least one material is dried, and sold in one container.

Figure 53:
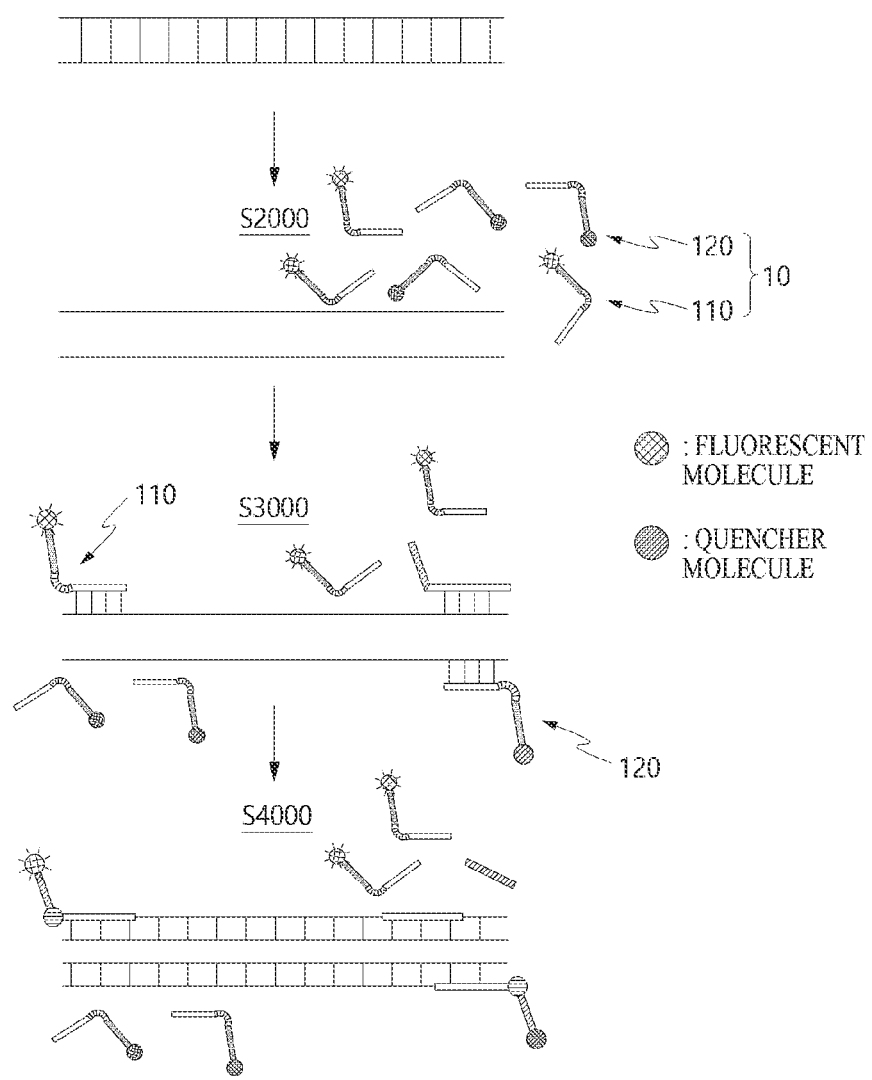
FIGS. 53 and 54 are diagrams illustrating a PCR of a solution provided in a unit cell (UC) including a probe complex 620 as shown in FIG. 52 and a nucleic acid complex pair 10 that includes a first nucleic acid complex 110 and a second nucleic acid complex 120 as shown in FIG. 32 according to an exemplary embodiment of the present application.
Figure 54:
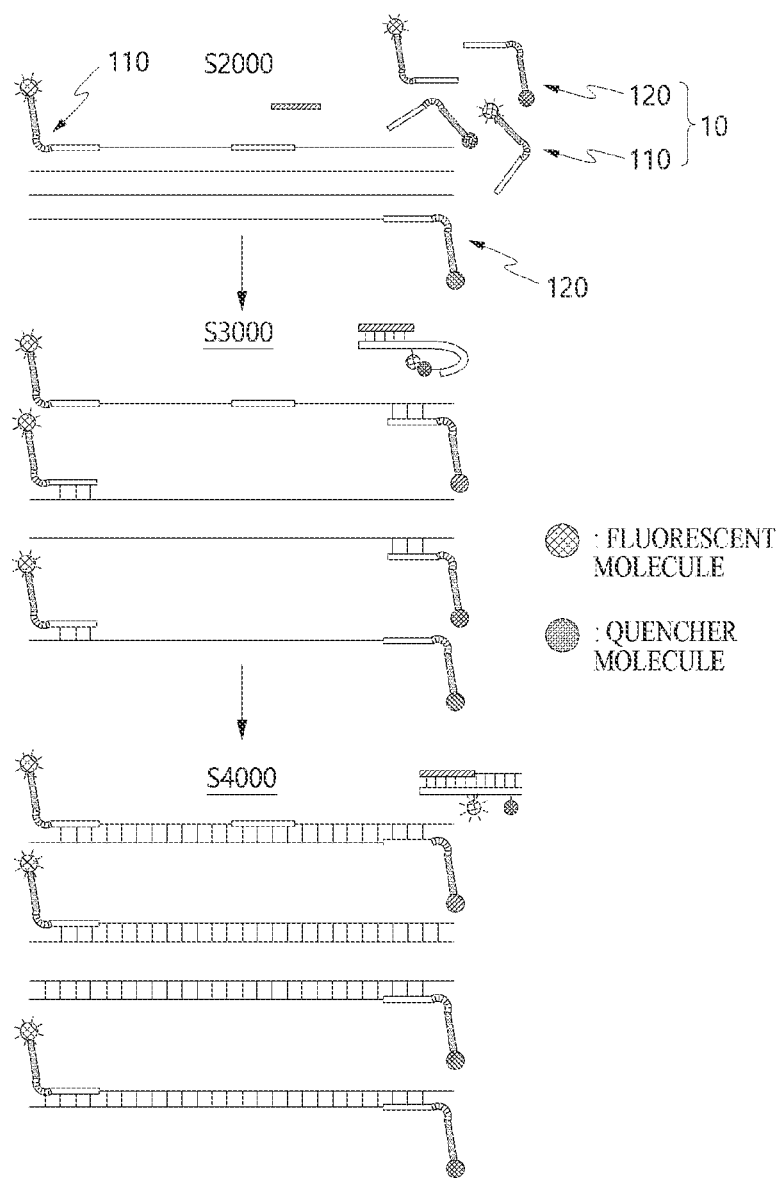

FIGS. 53 and 54 are diagrams illustrating PCR of a solution provided to a unit cell (UC) including a probe complex 620 and a nucleic acid complex pair 10 according to an exemplary embodiment of the present application.

According to an exemplary embodiment of the present application, PCR using the probe complex 620 and the nucleic acid complex pair 10 may be performed according to an asymmetric or symmetric PCR method.

Hereinafter, PCR according to a symmetric method will be described. In the PCR according to a symmetric method, there are almost the same amounts of the first nucleic acid complex 110 and the second nucleic acid complex 120 in a unit cell (UC). In PCR according to a symmetric method, in a unit cell (UC), a ratio of the first nucleic acid complex 110 and the second nucleic acid complex 120 may be 1:1.

In the thermal denaturation step (S2000), double-stranded DNA may be separated into single-stranded DNA by adjusting the temperature of the unit cell (UC). In the thermal denaturation step (S2000), the double-stranded DNA including a first target base sequence corresponding to a first determinant 111 of the first nucleic acid complex 110, a second target base sequence corresponding to a second determinant 121 of the second nucleic acid complex 120, and/or a probe-binding region (PR) may be separated into two single strands of DNA.

In the annealing step (S3000), the first nucleic acid complex 110, the second nucleic acid complex 120 and/or a first probe analog may bind to at least a partial region of DNA separated into single-stranded DNA. Specifically, the first nucleic acid complex 110 may complementarily bind to a first target base sequence. The second nucleic acid complex 120 may complementarily bind to a second target base sequence. The first probe analog may complementarily bind to the probe-binding region (PR).

In the polymerization step (S4000), using the first determinant 111 as a starting point, an amplification product for a first strand including the first target base sequence to which the first determinant 111 binds may be produced. In the polymerization step (S4000), using the second determinant 121 as a starting point, an amplification product for a second strand including the second target base sequence to which the second determinant 121 binds may be produced.

According to an exemplary embodiment of the present application, when the first determinant 111 or the second determinant 121 is used as a primer related to the probe complex 620, a base sequence of at least a part of the first probe analog may be separated from the probe-binding region (PR).

In a specific example, when the first determinant 111 or the second determinant 121 is used as a primer related to the probe complex 620, using the first determinant 111 or the second determinant 121 as a starting point, after the initiation of an amplification product for the first strand or second strand, the first pairing part 622 may be separated from the determinant 621 at the time of production of an amplification product for a base sequence adjacent to the region to which a first probe analog binds.

According to an exemplary embodiment of the present application, even when the first determinant 111 or the second determinant 121 is not used as a primer related to the probe complex 620, in the probe complex 620 to which the probe-binding region (PR) binds, the first pairing part 622 may be separated from the determinant 621 at the time of the production of the amplification product for a nucleic acid including a probe-binding region (PR) due to the initiation of a primer related to the probe complex 620 in a region adjacent to the probe complex 620 in the polymerization step (S4000).

After one cycle of PCR, in the thermal denaturation step (S2000), the double-stranded DNA in the unit cell (UC) maybe separated into single-stranded DNA. Here, the double-stranded DNA including at least one nucleic acid complex 1 formed in the polymerization step (S4000) may also be separated into two single strands of DNA.

After one cycle of PCR, in the thermal denaturation step (S2000), the first pairing part 622 may flow in the unit cell (UC). After one cycle of PCR, in the thermal denaturation step (S2000), the first pairing part 622 separated from the determinant 621 may flow in the unit cell (UC).

After one cycle of PCR, in the annealing step (S3000), the first nucleic acid complex 110 or the second nucleic acid complex 120 may bind to a first target base sequence and/or a second target base sequence of the single strand of the unit cell. In some cases, the first nucleic acid complex 110 may bind to single-stranded DNA including the second nucleic acid complex 120. The second nucleic acid complex 120 may bind to single-stranded DNA including the first nucleic acid complex 110.

After one cycle of PCR, in the annealing step (S3000), the first pairing part 622 may bind to a second probe analog of the probe complex 620 in the unit cell (UC). The first pairing part 622 flowing in the unit cell (UC) may bind to a second pairing part 623 of the second probe analog of the probe complex 620. When the first pairing part 622 binds to the second pairing part 623, the first pairing part 622 may serve as a primer.

After one cycle of PCR, in the polymerization step (S4000), using the first determinant 111 as a starting point, an amplification product for a nucleic acid including the second determinant 121 may be produced. After one cycle of PCR, in the polymerization step (S4000), using the second determinant 121 as a starting point, an amplification product for a nucleic acid including the first determinant 111 may be produced.

In addition, after one cycle of PCR, in the polymerization step (S4000), using the first pairing part 622 as a starting point, a nucleotide may be extended to have a base sequence complementary to at least a part of the base sequence of the second pairing part 623.

As a nucleotide is extended to have a base sequence complementary to at least a part of the base sequence of the second pairing part 623, the extended polynucleotide may form a double-stranded construct with the second pairing part 623. When the second pairing part 623 is a double-stranded construct, linkage between the first label 624 and the second label 625 may not be performed.

In the solution included in the unit cell (UC) that has been subjected to at least two cycles of PCR, a nucleic acid construct including the first nucleic acid complex 110 and the second nucleic acid complex 120, a nucleic acid construct including the first nucleic acid complex 110, a nucleic acid construct including the second nucleic acid complex 120, and a nucleic acid construct not including the first nucleic acid complex 110 and the second nucleic acid complex 120 may flow.

After PCR is completed, the stabilization step (S5000) may be performed. In the stabilization step (S5000), complementary binding between a first tag 112 and a second tag 122 of the nucleic acid construct including the first nucleic acid complex 110 and the second nucleic acid complex 120 may be performed.

In addition, in the stabilization step (S5000), the bond between the extended polynucleotide and the second pairing part 623 may be induced to have a base sequence complementary to at least a part of the base sequence of the second pairing part 623. In the stabilization step (S5000), the bond between 1) the polymer nucleotide extended to have a base sequence complementary to at least a part of the base sequence of the second pairing part 623 and the first pairing part 622, and 2) the second pairing part 623 may be induced.

Figure 55:
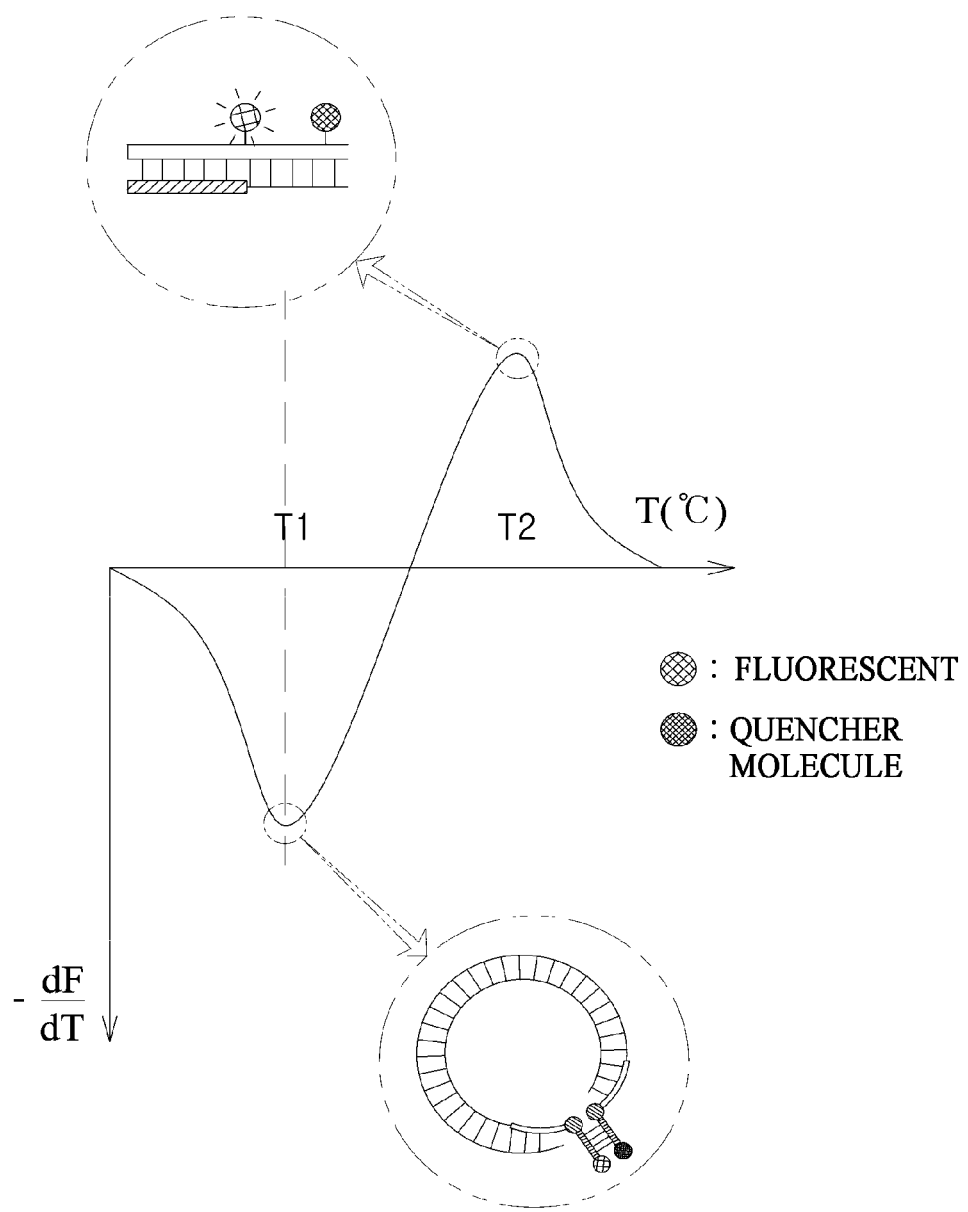
FIG. 55 is a diagram illustrating a graph of between temperature and a negative rate of change in fluorescence with respect to temperature according to an exemplary embodiment of the present application. T, temperature; dF/dT, the rate of change in fluorescence with respect to temperature; T1, dissociation peak value related to the nucleic acid complex pair; T2, dissociation peak value related to the probe complex.

Referring to FIG. 55, according to an exemplary embodiment of the present application, on a graph of the negative rate of change in fluorescence with respect to temperature/temperature, the maximum points may be shown at temperatures T1 and T2. Alternatively, according to an exemplary embodiment of the present application, on the graph of the negative rate of change in fluorescence with respect to temperature/temperature, the minimum points may be shown at the temperatures T1 and T2. Alternatively, according to an exemplary embodiment of the present application, on the graph of the negative rate of change in fluorescence with respect to temperature/temperature, the minimum point may be shown at the temperature T1, and the maximum point may be shown at the temperature T2.

In a specific example, on the graph of the negative rate of change in fluorescence with respect to temperature/temperature, T1 at which the minimum point is shown may be a dissociation peak value related to the nucleic acid complex pair 10 (see FIG. 50(*a*)). Here, the nucleic acid complex pair 10 may be designed to perform signal quencher-type linkage. On the graph of the negative rate of change in fluorescence with respect to temperature/temperature, T2 at which the minimum point is shown may be a dissociation peak value related to the probe complexes 620 (see FIG. 50(*b*)). Here, the probe complex 620 may be designed to perform signal quencher-type linkage.

3. Application #3 of Nucleic Acid Complex Pair 10—PCR Clamping & Tagging 3.1 Configuration of Nucleic Acid Complex Pair 10

According to an exemplary embodiment of the present application, a nucleic acid complex pair 10 may include a first nucleic acid complex 110 and a second nucleic acid complex 120.

The first nucleic acid complex 110 according to an exemplary embodiment of the present application may include at least a first determinant 111 and a first tag 112. The first nucleic acid complex 110 according to an exemplary embodiment of the present application may include a first determinant 111, a first tag 112, a first label 113 and a first linker 114.

The second nucleic acid complex 120 according to an exemplary embodiment of the present application may include at least a second determinant 121 and a second tag 122. The second nucleic acid complex 120 according to an exemplary embodiment of the present application may include a second determinant 121, a second tag 122, a second label 123 and a second linker 124.

The first determinant 111 may be a forward primer or reverse primer, which initiates PCR When the first determinant 111 is a forward primer, the second determinant 121 may be a reverse primer. When the first determinant 111 is a reverse primer, the second determinant 121 may be a forward primer.

The first determinant 111 and the second determinant 121 may react with a related target nucleic acid. As a more specific example, the first determinant 111 may react with a target nucleic acid related to a first disease, and the second determinant 111 may react with the target nucleic acid related to the first disease.

Specific operations and components of the first determinant 111 and the second determinant 121 have been described in 1.1.1.3.2 Primers, and thus duplicated descriptions will be omitted.

The first tag 112 may be a single-stranded material including a nucleic acid and/or nucleic acid analog. The first tag 112 maybe a probe for PCR clamping.

The base sequence of the first tag 112 may have at least one difference from that of the first determinant 111. The base sequence of the first tag 112 maybe designed by substituting or deleting a partial base sequence of the base sequence of the first determinant 111. The base sequence of the first tag 112 may have at least one difference from that of the second determinant 121. The base sequence of the first tag 112 may be designed by substituting or deleting a partial base sequence of the base sequence of the second determinant 121.

Detailed descriptions thereof have been provided in 1.1.2.3.2 Probes for PCR clamping, and thus duplicated descriptions will be omitted.

The first tag 112 may react with a first target base sequence of the first determinant 111 and a similar base sequence thereof, or a second target base sequence of the second determinant 121 and a similar base sequence thereof. In one example, the first tag 112 may be used as a probe for PCR clamping for a similar base sequence of the first target base sequence of the first determinant 111. In another example, the first tag 112 may be used as a probe for PCR clamping for a similar base sequence of the second target base sequence of the second determinant 121.

The second tag 122 may complementary bind to the first tag 112. The second tag 122 may complementary bind to the first tag 112 to cause the first label 113 and the second label 123 to become closer.

The first label 113 and the second label 123 may perform a linked action. Based on whether the first tag 112 binds to the second tag 122, the first label 113 and the second label 123 may perform a linked action.

The linker 400 may be a compound having a predetermined length. The linker 400 may be a blocker for PCR. The detailed descriptions thereof have been described in 3.1.1.3.1 Blocker for PCR, and thus duplicated descriptions will be omitted.

3.1 Operation of Nucleic Acid Complex Pair 10

The nucleic acid complex pair 10 according to an exemplary embodiment of the present application may be subjected to PCR to confirm whether there is a target nucleic acid related to the nucleic acid complex pair 10 in a unit cell (UC).

Specifically, when at least two cycles of a thermal denaturation step (S2000), an annealing step (S3000) and a polymerization step (S4000) are performed, a nucleic acid construct including the nucleic acid complex pair 10 may be formed.

Afterward, when the stabilization step (S5000) is performed, the nucleic acid construct including the nucleic acid complex pair 10 may have a secondary structure. When complementary bonds between the first tag 112 and the second tag 122 of the nucleic acid complex pair 10 are formed, a linked action between the first label 113 and the second label 123 may be performed.

And then, when a fluorescence value of a unit cell (UC) is detected by varying the temperature of the unit cell (UC) in a step of obtaining a dissociation curve (S6000), and a graph of the negative rate of change in fluorescence according to temperature/temperature is obtained, the maximum point or the minimum point may be confirmed at a temperature corresponding to a dissociation peak value of the nucleic acid complex pair 10. A target nucleic acid related to the nucleic acid complex pair 10 in the unit cell (UC) may be confirmed according to whether the maximum or minimum point was confirmed at the temperature corresponding to the dissociation peak value.

In this regard, the presence of a target nucleic acid may be detected by the PCR method disclosed in 1.3.2 Operation of nucleic acid complex pair 10 for target detection and the multiplex PCR method disclosed in 2.3 Operation of nucleic acid complex pair 10.

At the same time, in the annealing step (S3000), the first tag 112 may complementarily bind to a similar base sequence of the first determinant 111 or the second determinant 121. When the first tag 112 complementarily binds to a similar base sequence of the first determinant 111 or the second determinant 121, the first determinant 111 or the second determinant 121 may be mismatched to the similar base sequence to prevent non-specific bonding.

In addition, in the polymerization step (S4000), the first tag 112 complementarily binding to a similar base sequence of the first determinant 111 or the second determinant 121 may prevent the amplification of the similar base sequence. In a specific example, as the first tag 112 may complementarily bind to the similar base sequence, and the first linker 114 connected with the first tag 112 prevents the extension of a nucleotide at the 3' end of the first tag, the production of an amplification product for a nucleic acid including the similar base sequence may be prevented.

This has been described in detail in 1.2.2 Operation of nucleic acid complex 1, and thus duplicated descriptions will be omitted.

Therefore, by using the nucleic acid complex pair 10 according to an exemplary embodiment of the present application, the amplification of a nucleic acid including the similar base sequence in a unit cell may be prevented, an amplification product for the nucleic acid including the similar base sequence may be formed, and the presence of the nucleic acid including a target base sequence in a sample may be confirmed.

As a result, by using the nucleic acid complex pair 10 according to an exemplary embodiment of the present application, a more highly sensitive target nucleic acid can be detected.

4. Application #4 of Nucleic Acid Complex Pair 10—Digital PCR 4.1 General of Digital PCR According to an exemplary embodiment of the present application, the nucleic acid complex pair 10 may be used in digital PCR. The digital PCR may have an advantage of achievement of more sensitive and accurate diagnosis, by performing general PCR in each unit cell (UC) for a solution included in unit cells (UC) (e.g., tubes) subjected to PCR, which is previously divided into hundreds to tens of thousands of portions.

4.2 Application of Nucleic Acid Complex Pair 10 for Providing Primer Pair

Figure 56:
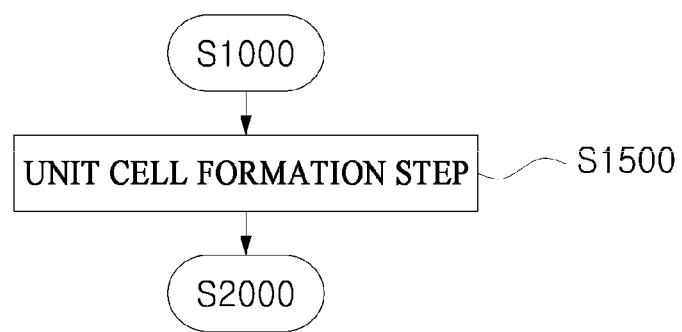
FIG. 56 is a diagram illustrating a step of preparing a sample when a nucleic acid complex pair 10 is used for digital PCR according to an exemplary embodiment of the present application.

FIG. 56 is a diagram illustrating the step of preparing a sample when the nucleic acid complex pair 10 is used for digital PCR according to an exemplary embodiment of the present application.

According to an exemplary embodiment of the present application, a step of forming a unit cell (UC) (S1500) may be performed in such a manner that a solution including the nucleic acid complex pair 10 is distributed to be suitable for digital PCR.

However, since the solution including the nucleic acid complex pair 10 is subsequently distributed into unit cells (UC) suitable for digital PCR, the first nucleic acid complex 110 and the second nucleic acid complex 120 may be uniformly distributed in each cell (UC).

Specifically, more of the first nucleic acid complex 110 may be distributed to a first unit cell (UC) than the second nucleic acid complex 120, more of the second nucleic acid complex 120 may be distributed to a second unit cell (UC) than the first nucleic acid complex 110, or neither the first nucleic acid complex 110 nor the second nucleic acid complex 120 may be distributed to a third unit cell (UC). Here, a sample such as a primer for PCR is already consumed or cannot be reused, but the presence of absence of a target nucleic acid cannot be precisely confirmed.

To solve this, before forming a unit cell (UC) for digital PCR, a step of pairing the nucleic acid complex pair 10 (S1000) may be performed. In other words, for digital PCR, the complementary bond between the first tag 112 and the second tag 122 of the nucleic acid complex pair 10 may be induced.

In the pairing step (S1000), the complementary bond between the first tag 112 and the second tag 122 of the nucleic acid complex pair 10 may be induced by adjusting the temperature of the solution contained in each tube. The temperature of the solution in the pairing step (S1000) may be less than 40° C. The detailed descriptions of the pairing step (S1000) have been provided in 1.1 Application of nucleic acid complex pair 10 for providing a primer pair.

In a specific exemplary embodiment, the first nucleic acid complex 110 may include at least the forward primer and the first pairing part 112, and the second nucleic acid complex 120 may at least include the reverse primer and the second pairing part 122.

The solution including the nucleic acid complex pair 10 may be subjected to the pairing step (S1000) which induces complementary bond between the first tag 112 and the second pairing part 122 before formation of a unit cell (UC) (S1500).

As a result, a relatively highly distribution of a proportion of one of the forward primer or reverse primer to one unit cell (UC) may be prevented. Ultimately, when the nucleic acid complex pair 10 in which the first tag 112 and the second tag 122 complementarily bind to form a pair is distributed to a unit cell (UC), it is possible to perform distribution to have a 1:1 ratio of the forward primer and a reverse primer per unit cell (UC).

4.3 Application of Nucleic Acid Complex Pair 10 to Detect Target Nucleic Acid 4.3.1 Structure of Nucleic Acid Complex Pair 10

At least one kind of nucleic acid complex pair 10 used for digital PCR may be similar to at least one kind of nucleic acid complex pair 10 used for general PCR described above. In other words, for digital PCR, nucleic acid complex pairs 10 according to some exemplary embodiments disclosed in the present application may be used.

The configurations, materials, examples and operations of the nucleic acid complex pairs 10 according to some exemplary embodiments of the specification have already been described in detail. Therefore, it is clearly shown that the nucleic acid complex pair 10 already disclosed with regard to digital PCR can be used, and duplicated descriptions will be omitted.

In addition, when there is a configuration or operation changed when the nucleic acid complex pair 10 is used for digital PCR and/or other exemplary embodiments, configurations or operations changed in the corresponding exemplary embodiment will be described in detail.

4.3.2 Operation of Nucleic Acid Complex Pair 10

When the presence of a target nucleic acid in a unit cell (UC) is confirmed using the nucleic acid complex pair 10 according to an exemplary embodiment of the present application in digital PCR, a step of forming a unit cell (UC) using a solution including the nucleic acid complex pair 10 (S1500) may be performed before PCR.

FIG. 57 is a set of diagrams illustrating a unit cell (UC) in digital PCR according to an exemplary embodiment of the present application.

Specific aspects for forming a unit cell (UC) using the solution including the nucleic acid complex pair 10 may vary according to whether a method of performing digital PCR is a well type or a droplet type.

According to an exemplary embodiment of the present application, for digital PCR, a unit cell (UC) may be formed in such a manner that the solution including the nucleic acid complex pair 10 is distributed in a plate having a plurality of wells (see FIG. 57(*a*)). In the solution including the nucleic acid complex pair 10, at least one of an enzyme involved in polymerization (e.g., polymerase), a base fragment (e.g., deoxynucleotide triphosphate (dNTP)), a coenzyme involved in PCR (e.g., $MgCl_2$ or $MgSO_4$), a buffer for providing optimal pH and/or salt concentrations for PCR may be further included.

According to an exemplary embodiment of the present application, the solution including the nucleic acid complex pair 10 may be sequentially distributed to wells. In one example, unit cells (UC) may be formed in such a manner that a sample is first distributed to wells, the nucleic acid complex pair 10 is sequentially distributed to the wells, and an enzyme used in PCR is finally distributed to the wells.

According to another exemplary embodiment of the present application, the solution including the nucleic acid complex pair 10 may be simultaneously distributed to wells. In one example, unit cells (UC) may be formed in such a manner that a sample, the nucleic acid complex pair 10 and an enzyme-containing mixed solution used for PCR are distributed to wells.

A method of distributing the solution to wells may vary. In one example, the solution or the like may be distributed to wells by a method using a microfluidic channel. In another example, the solution or the like may be distributed to wells in such a manner that a solution is plated on a plate having a form in which the tops of wells are open.

According to an exemplary embodiment of the present application, for digital PCR, unit cells (UC) may be formed in such a manner that the solution including the nucleic acid complex pair 10 is formed in a droplet (see FIG. 57(*b*)). In the solution including the nucleic acid complex pair 10, at least one of an enzyme involved in polymerization (e.g., polymerase), a base fragment (e.g., deoxynucleotide triphosphate (dNTP)), a coenzyme involved in PCR (e.g., $MgCl_2$ or $MgSO_4$), a buffer for providing optimal pH and/or salt concentrations for PCR may be further included.

According to an exemplary embodiment of the present application, a first droplet is formed by distributing a solution including a sample in a droplet with a size of tens of nL to tens of pL, a second droplet is formed by distributing a solution including the nucleic acid complex pair 10 in a droplet with a size of tens of nL to tens of pL, and a third droplet is formed by distributing a solution including an enzyme required for PCR in a droplet with a size of tens of nL to tens of pL, and then a unit cell (UC) may be formed by combining at least the first droplet, the second droplet and the third droplet.

Alternatively, a first droplet may be formed by distributing a first solution including the nucleic acid complex pair 10 in a droplet with a size of tens of nL to tens of pL, and a second droplet may be formed by distributing a second solution including the nucleic acid complex pair 10 in a droplet with a size of tens of nL to tens of pL, and thus a unit cell (UC) may be formed by combining at least the first droplet and the second droplet.

Alternatively, the solutions including a sample, the nucleic acid complex pair 10 and an enzyme required for PCR may be distributed in a droplet with a size of tens of nL to tens of pL, thereby forming a unit cell (UC).

For the digital PCR using the nucleic acid complex pair 10 according to an exemplary embodiment of the present application, PCR may be performed for the solution included in the unit cell (UC). For the digital PCR using the nucleic acid complex pair 10 according to an exemplary embodiment of the present application, a thermal denaturation step (S2000), an annealing step (S3000) and a polymerization step (S4000) for the solution including the unit cell (UC) may be performed.

For digital PCR using the nucleic acid complex pair 10 according to an exemplary embodiment of the present application, a sequence of the thermal denaturation step (S2000), the annealing step (S3000) and the polymerization step (S4000) for the solution included in the unit cell (UC) is set as one cycle, and may be repeatedly performed for more than one cycle.

A stabilization step (S5000) and a step of obtaining a dissociation curve (S6000) for the solution included in the unit cell (UC) may be performed. The S2000 to S6000 described above may be similar to S2000 to S6000 in general (or real-time) PCR which have been described above.

Figure 58:
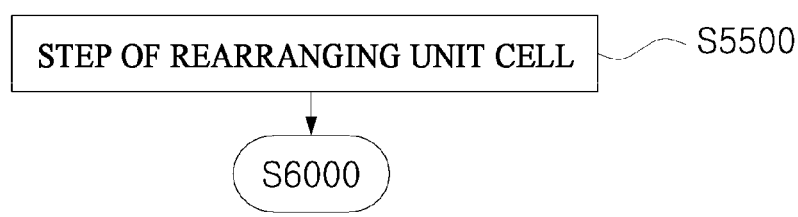
FIG. 58 is a diagram illustrating an operation in digital PCR using a nucleic acid complex pair 10 according to an exemplary embodiment of the present application.

FIG. 58 is a diagram illustrating an operation in digital PCR using a nucleic acid complex pair 10 according to an exemplary embodiment of the present application.

According to an exemplary embodiment of the present application, a step of rearranging a plurality of unit cells (UC) in which PCR is completed (5500) may be performed.

Specifically, in the well-type digital PCR, the temperature of the solution included in the unit cell (UC)(at least, including a sample and the nucleic acid complex pair 10) may be adjusted by adjusting the temperature of a plate having a plurality of wells. The temperature of the plate may be adjusted by adjusting the temperature of the thermocycler implemented in a region where the plate is disposed.

However, in the droplet-type digital PCR, it may be difficult to perform a step of obtaining a dissociation curve (S6000) in a current digital PCR apparatus for detecting a fluorescence value of a unit cell (UC) moving through a microfluidic channel.

To solve this, in the droplet-type PCR, a step of rearranging a unit cell (UC) may be performed in such a manner that a plurality of unit cells (UC) are uniformly divided into microfluidic lanes (LN), using a plate in which microfluidic lanes (LN) are formed.

FIG. 59 is a set of diagrams illustrating a method of performing the step of obtaining a dissociation curve (S6000) in digital PCR according to an exemplary embodiment of the present application.

In the plate for obtaining a dissociation curve according to an exemplary embodiment of the present application, a plurality of microfluidic lanes (LN) may be formed (see FIG. 59(a)). A plurality of unit cells (UC) may be uniformly divided into microfluidic lanes (LN) of the plate with the plurality of lanes (LN). The plate for obtaining a dissociation curve according to an exemplary embodiment of the present application may have one microfluidic lane (LN)(see FIG. 59(b)). A plurality of unit cells (UC) may be arranged in a line on the plate having one microfluidic lane (LN).

The plate for obtaining a dissociation curve according to an exemplary embodiment of the present application may have a microfluidic lane (LN) having a size large enough to hold a droplet of a first unit cell (UC). The dimension of at least one microfluidic lane (LN) may be determined based on the radius of the droplet of the first unit cell (UC). In addition, when determining the dimension of the at least one microfluidic lane (LN), it can be considered that the radius of the droplet may be changed according to a volume, a temperature or a pressure.

As a result, according to an exemplary embodiment of the present application, in digital PCR using the nucleic acid complex pair 10, a dissociation curve for each unit cell (UC) may be obtained, and a dissociation peak value may be confirmed based on information on the obtained dissociation curve.

Therefore, according to the nucleic acid complex pair 10 disclosed in the present application and an operation in digital PCR using the nucleic acid complex pair 10, the presence of a target nucleic acid may be confirmed also in the digital PCR method.

In addition, when a method of detecting a plurality of target nucleic acids using multiple kinds of nucleic acid complex pairs 10 disclosed in the present application is applied to digital PCR, the presence of multiple kinds of target nucleic acids in a unit cell (UC) can be confirmed also in a digital PCR method.

In other words, even when multiple kinds of nucleic acid complex pairs 10 including labels detected with the same fluorescence (or the same signal) are used, the presence of multiple kinds of target nucleic acids per fluorescent channel can be confirmed in a digital PCR method.

<PCR Instrument 2000>

According to an exemplary embodiment of the present application, a PCR instrument 2000 may be used to perform PCR for at least one unit cell (UC) in a loaded plate. According to an exemplary embodiment of the present application, by using the PCR instrument 2000, a graph of fluorescence according to a temperature for at least one unit cell (UC) in the loaded plate may be obtained. According to an exemplary embodiment of the present application, by using the PCR instrument 2000, the graph of the negative rate of change in fluorescence according to temperature/temperature for at least one unit cell (UC) in a loaded plate may be obtained, and a dissociation peak value may be confirmed. According to an exemplary embodiment of the present application, by using the PCR instrument 2000, a dissociation peak value for at least one unit cell (UC) in a loaded plate may be confirmed, and the presence of at least one kind of target nucleic acid included in a unit cell (UC) may be confirmed.

Figure 60:
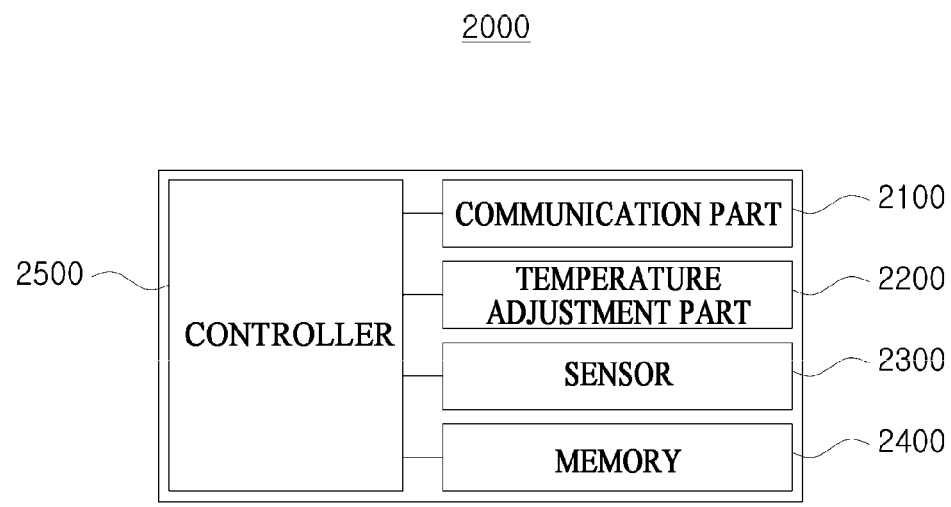
FIG. 60 is a block diagram of a PCR instrument 2000 according to an exemplary embodiment of the present application.

FIG. 60 is a block diagram of the PCR instrument 2000 according to an exemplary embodiment of the present application.

The PCR instrument 2000 may include a communication part 2100, a temperature adjustment part 2200, a sensor 2300, a memory 2400 and a controller 2500.

The communication part 2100 may be used to allow the PCR instrument 2000 to transmit/receive necessary data with an external device.

The communication part 2100 may perform wireless communication. The communication part 2100 may transmit/receive data by at least one wireless communication method among Wifi, Bluetooth, ZigBee, WiGig, RFID, radio frequency identification, infrared data association (IrDA), ultra wideband (UWB) and WiHD.

The communication part 2100 may include a wired communication module. For example, the communication part 2100 may transmit/receive data by at least one communication method among a USB method, a serial method and a parallel method.

The temperature adjustment part 2200 may serve to adjust the temperature of a PCR plate loaded in the PCR instrument 2000.

According to an exemplary embodiment of the present application, the temperature adjustment part 2200 may include a heating agent and/or a coolant. In a specific example, the temperature adjustment part 2200 may include a thermoelectric element that can perform both heating and cooling.

The sensor 2300 may serve to detect fluorescence for at least one unit cell (UC) of the PCR plate loaded in the PCR instrument 2000. According to an exemplary embodiment of the present application, the sensor 2300 may include a filter that converts the wavelength band of light and a light detector to detect the characteristics of light emitted when light with a specific wavelength is incident.

Alternatively, the sensor 2300 may serve to detect full-wavelength optical characteristics, and output optical characteristics per a corresponding wavelength band.

The optical instrument according to an exemplary embodiment of the present application may be a PCR instrument 2000 including the sensor 2300.

The memory 2400 may store all kinds of data required for the PCR instrument 2000.

The memory may include at least one type of storage medium among a flash memory-type, a hard disk-type, a multimedia card micro-type and card-type memories (e.g., SD or XD memory, etc.), a random access memory (RAM), a static random access memory (SRAM), a read-only memory (ROM), an electrically erasable programmable read-only memory (EEPROM), a programmable read-only memory (PROM), a magnetic memory, a magnetic disk and an optical disk.

The controller 2500 may control the overall operation of the PCR instrument 2000. The controller 2500 may perform calculation and processing of all kinds of information, and control the operation of components of the PCR instrument 2000.

The controller 2500 may be implemented as a computer or a similar device thereto depending on hardware, software or a combination thereof. In one example, the controller 2400 may be provided in the form of an electronic circuit such as a CPU chip serving a control function by processing an electrical signal as hardware, and the form of a program for driving a hardware controller as software.

Figure 61:
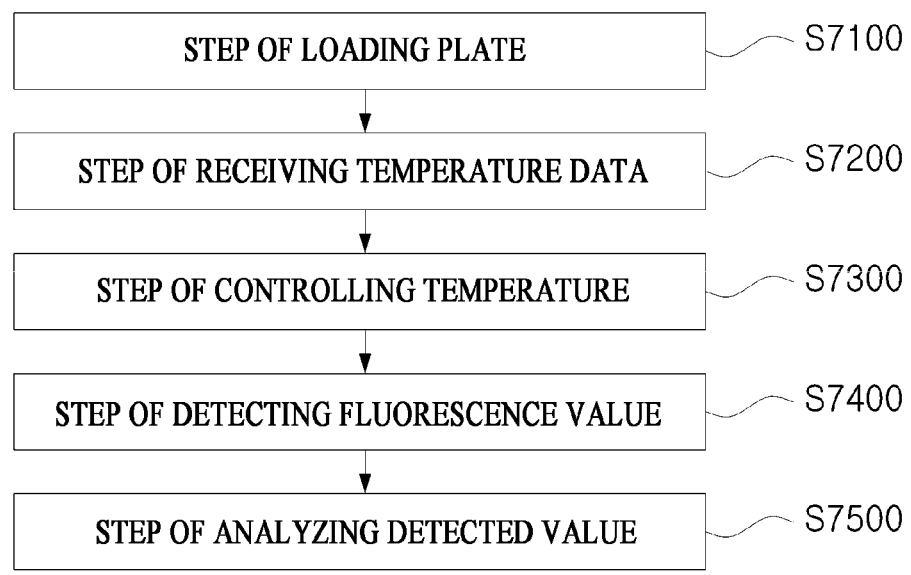
FIG. 61 is a flow chart illustrating an operation (S7000) of a PCR instrument 2000 according to an exemplary embodiment of the present application.

FIG. 61 is a flow chart illustrating an operation (S7000) of the PCR instrument 2000 according to an exemplary embodiment of the present application.

The PCR instrument 2000 may be subjected to a step of loading a plate (S7100), a step of receiving temperature data (S7200), a step of controlling a temperature (S7300), a step of detecting a fluorescence value (S7400), and a step of analyzing the detected value (S7500). Each of the above-described steps may be omitted or repeated, and other additional operations can be performed.

The step of loading a plate (S7100) may be performed in such a manner that a PCR plate provided to a plate loading part of the PCR instrument 2000 is introduced into a reaction region in the PCR instrument 2000.

According to an exemplary embodiment of the present application, when the plate is loaded into the PCR instrument 2000, the plate and the temperature adjustment part 2200 may be in physical contact with each other, and a reaction environment of the plate may be adjusted by the PCR instrument 2000.

The step of receiving temperature data (S7200) may be performed in such a manner that at least one piece of data on a thermal denaturation temperature, an annealing temperature, a polymerization temperature, a temperature in the stabilization step, and a temperature in the step of obtaining a dissociation curve is input.

According to an exemplary embodiment of the present application, the PCR instrument 2000 may receive data on the temperature and temperature-maintaining time in each step to perform PCR. The PCR instrument 2000 may receive data on the temperature and temperature-maintaining time in each step to perform PCR using an input interface formed outside of the PCR instrument 2000. Alternatively, data on the temperature and temperature-maintaining time in each step to perform PCR may be input using the communication part 2100 of the PCR instrument 2000.

According to another exemplary embodiment of the present application, the PCR instrument 2000 may store the data on the temperature and temperature-maintaining time in each step to perform PCR in the memory 2400.

The temperature adjustment part 2200 of the PCR instrument 2000 may control the temperature of at least one unit cell (UC) of the loaded plate. When PCR progresses by controlling a temperature, the PCR instrument 2000 may detect a fluorescence value (S7400). In the step of detecting a fluorescence value, to obtain a fluorescence value of at least one unit cell (UC) of the loaded plate according to a temperature, the temperature of at least one unit cell (UC) may be simultaneously adjusted.

According to an exemplary embodiment of the present application, the controller 2500 of the PCR instrument 2000 may analyze the detected value obtained in S7400. The controller 2500 of the PCR instrument 2000 may analyze a fluorescence value according to the temperature obtained in S7400.

The step of analyzing the detected value (S7500) may include a step of converting a graph of fluorescence according to a temperature into a graph of the negative rate of change in fluorescence according to temperature/temperature. The step of analyzing the detected value (S7500) may include a step of confirming a dissociation peak value on the converted graph of the negative rate of change in fluorescence according to temperature/temperature. The step of analyzing the detected value (S7500) may include a step of outputting a target nucleic acid corresponding to a dissociation peak value confirmed on the converted graph of the negative rate of change in fluorescence according to temperature/temperature.

As above, the configurations and features of the present application have been described with reference to exemplary embodiments according to the present application. However, the present application is not limited thereto, and it is obvious to those of ordinary skill in the art that the embodiments can be easily altered and modified into various forms within the spirit and range of the present application, and thus the alterations or modifications are included in the accompanying claims.

SEQUENCE LISTING FREE TEXT

SEQ ID NO: 1 is an artificial sequence.
SEQ ID NO: 2 is a primer sequence for *Neisseria gonorrhoeae*.
SEQ ID NO: 3 is an artificial sequence.
SEQ ID NO: 4 is a primer sequence for *Neisseria gonorrhoeae*.
SEQ ID NO: 5 is an artificial sequence.
SEQ ID NO: 6 is a primer sequence for *Chlamydia trachomatis*.
SEQ ID NO: 7 is an artificial sequence.
SEQ ID NO: 8 is a primer sequence for *Chlamydia trachomatis*.
SEQ ID NO: 9 is an artificial sequence.
SEQ ID NO: 10 is a primer sequence for *Mycoplasma hominis*.
SEQ ID NO: 11 is an artificial sequence.
SEQ ID NO: 12 is a primer sequence for *Mycoplasma hominis*.
SEQ ID NO: 13 is an artificial sequence.
SEQ ID NO: 14 is a primer sequence for *Human papillomavirus* type 16.
SEQ ID NO: 15 is an artificial sequence.
SEQ ID NO: 16 is a primer sequence for *Human papillomavirus* type 16.
SEQ ID NOs: 17 to 26 are artificial sequences.
SEQ ID NO: 27 is a primer sequence for *Mycoplasma hominis*.
SEQ ID NO: 28 is a primer sequence for *Mycoplasma hominis*.

What is claimed is:

1. A kit for a multiplexing PCR, the kit comprising:
a first nucleic acid complex pair including a first nucleic acid complex and a second nucleic acid complex, wherein the first nucleic acid complex includes a first determinant, a first tag and a first label, and the second nucleic acid complex includes a second determinant, a second tag and a second label; and
a second nucleic acid complex pair including a third nucleic acid complex and a fourth nucleic acid complex, wherein the third nucleic acid complex includes a third determinant, a third tag and a third label, and the fourth nucleic acid complex includes a fourth determinant, a fourth tag and a fourth label,
wherein the first label is one of a first fluorophore-first quencher pair, and the second label is the other of the first fluorophore-first quencher pair,
wherein a fluorescence intensity emitted from the first fluorophore is adjusted by the first quencher when the first tag complementarily binds to the second tag,
wherein the third tag has a binding portion which complementarily binds to the fourth tag,
wherein the third label is one of a second fluorophore-second quencher pair, and the fourth label is the other of the second fluorophore-second quencher pair,
wherein a fluorescence intensity emitted from the second fluorophore is adjusted by the second quencher when the third tag complementarily binds to the fourth tag,
wherein a wavelength band of light emitted from the first fluorophore is substantially the same as a wavelength band of light emitted from the second fluorophore, and
wherein a length of the binding portion of the first tag is longer than a length of the binding portion of the third tag.

2. The kit for a multiplexing PCR of claim 1,
wherein a complementary binding between the first tag and the second tag is dissociated at a first disassociation temperature, and a complementary binding between the third tag and the fourth tag is dissociated at a second disassociation temperature, and
wherein the first disassociation temperature is higher than the second disassociation temperature.

3. The kit for a multiplexing PCR of claim 1,
wherein a base sequence of the binding portion of the first tag is different from a base sequence of the binding portion of the third tag.

4. The kit for a multiplexing PCR of claim 1,
wherein the first tag has a non-binding portion which does not bind to the second tag, and the third tag has a non-binding portion which does not bind to the fourth tag.

5. The kit for a multiplexing PCR of claim 1,
wherein the first label and the second label are configured to interact with each other at a first predetermined condition, and the third label and the fourth label are configured to interact with each other at a second predetermined condition,
wherein when the first quencher is located within a first effective linkage distance from the first fluorophore, the first predetermined condition is satisfied, and
wherein when the second quencher is located within a second effective linkage distance from the second fluorophore, the second predetermined condition is satisfied.

6. The kit for a multiplexing PCR of claim 5,
wherein a wavelength of an optical signal caused by the interaction between the first and the second labels is the same as a wavelength of an optical signal caused by the interaction between the third and fourth labels.

7. The kit for a multiplexing PCR of claim 5,
wherein a wavelength of an optical signal caused by the interaction between the first and the second labels is different from a wavelength of an optical signal caused by the interaction between the third and fourth labels.

8. The kit for a multiplexing PCR of claim 5,
wherein the first label is configured to emit a light of a first predetermined wavelength and the second label is configured to quench the light emitted from the first label, and
wherein the third label is configured to emit a light of a second predetermined wavelength and the fourth label is configured to quench the light emitted from the third label.

9. The kit for a multiplexing PCR of claim 8,
wherein the first predetermined wavelength is the same as the second predetermined wavelength.

10. The kit for a multiplexing PCR of claim 5,
wherein the first label is located between the first determinant and the first tag,
wherein the second label is located between the second determinant and the second tag,
wherein the third label is located between the third determinant and the third tag, and
wherein the fourth label is located between the fourth determinant and the fourth tag.

11. The kit for a multiplexing PCR of claim 5,
wherein the first label is located between the first determinant and the first tag,
wherein the second tag is located between the second determinant and the second label,
wherein the third label is located between the third determinant and the third tag, and
wherein the fourth tag is located between the fourth determinant and the fourth label.

12. The kit for a multiplexing PCR of claim 5,
wherein the first tag is located between the first determinant and the first label,
wherein the second tag is located between the second determinant and the second label,
wherein the third tag is located between the third determinant and the third label, and
wherein the fourth tag is located between the fourth determinant and the fourth label.

13. The kit for a multiplexing PCR of claim 1,
wherein the first tag is the same as the third tag, and
wherein the second tag is different from the fourth tag.

14. The kit for a multiplexing PCR of claim 1,
wherein the first target is associated with a first disease and the second target is associated with a second disease different from the first disease.

15. The kit for a multiplexing PCR of claim 5,
wherein the forward primer of the first target is corresponding to a first sequence of the first target,
wherein the reverse primer of the first target is corresponding to a second sequence of the first target,
wherein a distance between the first sequence and the second sequence at the first target is longer than the first threshold distance,
wherein the forward primer of the second target is corresponding to a third sequence of the second target,
wherein the reverse primer of the second target is corresponding to a fourth sequence of the second target, and
wherein a distance between the third sequence and the fourth sequence at the second target is longer than the second threshold distance.

16. The kit for a multiplexing PCR of claim 15,
wherein the distance between the first sequence and the second sequence at the first target is defined as a number of base pairs between the first sequence and the second sequence at the first target, and
wherein the distance between the third sequence and the fourth sequence at the second target is defined as a number of base pairs between the third sequence and the fourth sequence at the second target.

17. The kit for a multiplexing PCR of claim 16,
wherein the first effective linkage distance is determined by a physical property of the first fluorophore and a property of the first quencher, and
wherein the second effective linkage distance is determined by a physical property of the second fluorophore and a property of the second quencher.

* * * * *

SEQUENCE LISTING

<160> NUMBER OF SEQ ID NOS: 40

<210> SEQ ID NO 1
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1 aaaaaaaa                                                                 8

<210> SEQ ID NO 2
<211> LENGTH: 19
<212> TYPE: DNA
<213> ORGANISM: Neisseria gonorrhoeae

<400> SEQUENCE: 2
tacgcctgct actttcacg                                                     19

<210> SEQ ID NO 3
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 tttttttt                                                                 8

<210> SEQ ID NO 4
<211> LENGTH: 22
<212> TYPE: DNA
<213> ORGANISM: Neisseria gonorrhoeae

<400> SEQUENCE: 4
atatttaagg gcataatttc cg                                                 22

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aaaaaaaaaa                                                               10

<210> SEQ ID NO 6
<211> LENGTH: 19
<212> TYPE: DNA
<213> ORGANISM: Chlamydia trachomatis

<400> SEQUENCE: 6
aggtaaacgc tcctctgaa                                                     19

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 7
tttttttttt                                                           10

<210> SEQ ID NO 8
<211> LENGTH: 19
<212> TYPE: DNA
<213> ORGANISM: Chlamydia trachomatis

<400> SEQUENCE: 8
gcgagttacg aagacaaaa                                                 19

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aaccttggga                                                           10

<210> SEQ ID NO 10
<211> LENGTH: 19
<212> TYPE: DNA
<213> ORGANISM: Mycoplasma hominis

<400> SEQUENCE: 10
agctcctatt gccaacgta                                                 19

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tcccaaggtt                                                           10

<210> SEQ ID NO 12
<211> LENGTH: 19
<212> TYPE: DNA
<213> ORGANISM: Mycoplasma hominis

<400> SEQUENCE: 12
aatctttgtg tggagcatc                                                 19

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
accgcgcggg                                                           10

<210> SEQ ID NO 14
<211> LENGTH: 19
<212> TYPE: DNA
<213> ORGANISM: Human papillomavirus type 16
```

```
<400> SEQUENCE: 14
tggagataca cctacattg                                           19

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cccgcgcggt                                                     10

<210> SEQ ID NO 16
<211> LENGTH: 20
<212> TYPE: DNA
<213> ORGANISM: Human papillomavirus type 16

<400> SEQUENCE: 16
gctggaccat ctatttcatc                                          20

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aaaaaaaacc tt                                                  12

<210> SEQ ID NO 18
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ccacacaaag att                                                 13

<210> SEQ ID NO 19
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19 cccgcgcg                                                        8

<210> SEQ ID NO 20
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20 cgcgcggg                                                        8
```

```
<210> SEQ ID NO 21
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21 cgcgcg                                                                   6

<210> SEQ ID NO 22
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggtgtatctc ca                                                           12

<210> SEQ ID NO 23
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23 aaaaaa                                                                   6

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24 tatgcccttta aatat                                                       15

<210> SEQ ID NO 25
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25 gtaactcgc                                                                9

<210> SEQ ID NO 26
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26 aaccttgg                                                                 8
```

-continued

```
<210> SEQ ID NO 27
<211> LENGTH: 14
<212> TYPE: DNA
<213> ORGANISM: Mycoplasma hominis

<400> SEQUENCE: 27
cactcatata cagc                                                       14

<210> SEQ ID NO 28
<211> LENGTH: 20
<212> TYPE: DNA
<213> ORGANISM: Mycoplasma hominis

<400> SEQUENCE: 28
gtgtggagca tcttgtaatc                                                 20

<210> SEQ ID NO 29
<211> LENGTH: 17
<212> TYPE: DNA
<213> ORGANISM: Unknown
<220> FEATURE:
<223> OTHER INFORMATION: Description of Unknown:
      Determinant 100 sequence

<400> SEQUENCE: 29
aaacggctca aattttt                                                    17

<210> SEQ ID NO 30
<211> LENGTH: 17
<212> TYPE: DNA
<213> ORGANISM: Unknown
<220> FEATURE:
<223> OTHER INFORMATION: Description of Unknown:
      Determinant 100 binding sequence

<400> SEQUENCE: 30
aaaaatttga gccgttt                                                    17

<210> SEQ ID NO 31
<211> LENGTH: 11
<212> TYPE: DNA
<213> ORGANISM: Unknown
<220> FEATURE:
<223> OTHER INFORMATION: Description of Unknown:
      Determinant 100 binding sequence

<400> SEQUENCE: 31
aaaaatttga g                                                          11

<210> SEQ ID NO 32
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gaacgccatc                                                            10

<210> SEQ ID NO 33
<211> LENGTH: 13
<212> TYPE: DNA
<213> ORGANISM: Unknown
<220> FEATURE:
<223> OTHER INFORMATION: Description of Unknown:
```

Determinant 100 sequence

<400> SEQUENCE: 33
tacgaatgcc atc                                                      13

<210> SEQ ID NO 34
<211> LENGTH: 13
<212> TYPE: DNA
<213> ORGANISM: Unknown
<220> FEATURE:
<223> OTHER INFORMATION: Description of Unknown:
      Determinant 100 binding sequence

<400> SEQUENCE: 34
gatggcattc gta                                                      13

<210> SEQ ID NO 35
<211> LENGTH: 10
<212> TYPE: DNA
<213> ORGANISM: Unknown
<220> FEATURE:
<223> OTHER INFORMATION: Description of Unknown:
      Tag 200 binding sequence

<400> SEQUENCE: 35
cttgcggtag                                                          10

<210> SEQ ID NO 36
<211> LENGTH: 13
<212> TYPE: DNA
<213> ORGANISM: Unknown
<220> FEATURE:
<223> OTHER INFORMATION: Description of Unknown:
      Tag 200 binding sequence

<400> SEQUENCE: 36
atgcttgcgg tag                                                      13

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cccccaaaaa                                                          10

<210> SEQ ID NO 38
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tttttggggg                                                          10

<210> SEQ ID NO 39
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 39
ccaaaaaccc                                                          10

<210> SEQ ID NO 40
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gggtttttgg                                                          10
```